United States Patent [19]
Wicnienski et al.

[11] Patent Number: 5,821,363
[45] Date of Patent: Oct. 13, 1998

[54] ANTINEOPLASTIC USE AND PHARMACEUTICAL COMPOSITIONS CONTAINING THEM

[75] Inventors: Nancy A. Wicnienski, Kalamazoo; Robert C. Kelly, Augusta; Peter G. M. Wuts, Kalamazoo, all of Mich.

[73] Assignee: Pharmacia & Upjohn Company, Kalamazoo, Mich.

[21] Appl. No.: 676,370

[22] PCT Filed: Jan. 26, 1995

[86] PCT No.: PCT/US95/00551

§ 371 Date: Jul. 23, 1996

§ 102(e) Date: Jul. 23, 1996

[87] PCT Pub. No.: WO95/20582

PCT Pub. Date: Aug. 3, 1995

Related U.S. Application Data

[63] Continuation-in-part of Ser. No. 189,235, Jan. 28, 1994, abandoned.

[51] Int. Cl.[6] ............... C07D 263/04; C07D 413/12; C07D 305/14
[52] U.S. Cl. ............... 548/215; 549/510; 549/511
[58] Field of Search ............... 549/510, 511; 548/215

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,876,399 | 10/1989 | Holton et al. | 568/817 |
| 4,924,011 | 5/1990 | Deals et al. | 549/510 |
| 4,924,012 | 5/1990 | Colin et al. | 549/510 |
| 4,942,184 | 7/1990 | Hangwitz et al. | 514/449 |
| 4,960,790 | 10/1990 | Sstella et al. | 514/449 |
| 5,015,744 | 5/1991 | Holton | 549/510 |
| 5,059,699 | 10/1991 | Kingston et al. | 549/511 |
| 5,136,060 | 8/1992 | Holton | 549/510 |
| 5,157,049 | 10/1992 | Hangwitz et al. | 514/449 |
| 5,227,400 | 7/1993 | Holton et al. | 514/444 |
| 5,248,796 | 9/1993 | Chen et al. | 549/510 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,380,751 | 1/1995 | Chen et al. | 514/449 |
| 5,476,954 | 12/1995 | Bourzat et al. | 549/510 |
| 5,532,388 | 7/1996 | Bouchard et al. | 549/510 |
| 5,550,261 | 8/1996 | Bouchard et al. | 549/510 |
| 5,571,917 | 11/1996 | Bouchard et al. | 544/369 |
| 5,576,450 | 11/1996 | Bouchard et al. | 549/510 |
| 5,580,997 | 12/1996 | Bouchard et al. | 549/510 |
| 5,580,998 | 12/1996 | Bouchard et al. | 549/510 |
| 5,587,493 | 12/1996 | Bouchard et al. | 549/510 |
| 5,599,942 | 2/1997 | Bouchard et al. | 548/215 |
| 5,637,723 | 6/1997 | Commercon et al. | 548/215 |

FOREIGN PATENT DOCUMENTS

| | | | |
|---|---|---|---|
| 0 253 738 | 7/1987 | European Pat. Off. | C07D 305/14 |
| 0 253 739 | 7/1987 | European Pat. Off. | C07D 305/14 |
| 0 366 841 | 11/1988 | European Pat. Off. | F16C 5/00 |
| 0 400 971 | 5/1990 | European Pat. Off. | C07D 205/08 |
| 0 414 610 A1 | 8/1990 | European Pat. Off. | C07C 233/83 |
| 0 428 376 A1 | 11/1990 | European Pat. Off. | C07D 265/04 |
| 0 524 093 A1 | 7/1992 | European Pat. Off. | C07D 305/14 |
| 0 534 708 A1 | 9/1992 | European Pat. Off. | C07D 405/12 |
| 0 534 709 A1 | 9/1992 | European Pat. Off. | C07D 305/14 |
| 0 558 959 A1 | 2/1993 | European Pat. Off. | C07D 305/14 |
| 0 577 082 A1 | 6/1993 | European Pat. Off. | A61K 31/335 |
| 0 577 083 A1 | 6/1993 | European Pat. Off. | C07D 305/14 |
| 0 600 517 A1 | 12/1993 | European Pat. Off. | C07D 305/14 |
| WO 90/10443 | 9/1990 | WIPO | C07D 305/00 |
| WO 91/13053 | 9/1991 | WIPO | C07C 229/34 |
| WO 91/13066 | 9/1991 | WIPO | C07D 303/48 |
| WO 91/17976 | 11/1991 | WIPO | C07C 235/84 |
| WO 91/17977 | 11/1991 | WIPO | C07C 235/84 |
| WO 93/16060 | 8/1993 | WIPO | C07D 305/14 |
| WO 94/07876 | 4/1994 | WIPO | C07D 305/14 |
| WO 94/07877 | 4/1994 | WIPO | C07D 305/14 |
| WO 94/07878 | 4/1994 | WIPO | C07D 305/14 |
| WO 94/07879 | 4/1994 | WIPO | C07D 305/14 |
| WO 94/10169 | 5/1994 | WIPO | C07D 413/12 |
| WO 94/13654 | 6/1994 | WIPO | C07D 305/14 |

OTHER PUBLICATIONS

IUPAC Commission on the Nomenclature of Organic Chemistry (CNOC), Nomenclature of Organic Chemistry. Section F: natural Products and Related Compounds, Eur. J. Biochem. 86, 1–8 (1978).

Blechert, Siegfried and Kleine–Klausing, Andrea, Synthesis of a Biologically Active Taxol Analogue, Angew. Chem. Int. Ed. Engl. 30 (1991) No. 4, 412–414.

Castro, Bertrand R., Replacement of Alcoholic Hydroxyl Groups By Halogens and Other Nucleophiles Via Oxyphosphonium Intermediates, 29, pp. 1–162 (1983).

Chaudhary, Ashok G, Rimoldi, John M., Kingston, David G.I., Modified Taxols. 10. Preparation of 7–Deoxytaxol, A Highly Bioactive Taxol Derivative, and Interconversion of Taxol and 7–epi–Taxol[1], J. Org. Chem., 58, 3798–3799 (1993).

(List continued on next page.)

*Primary Examiner*—Ba K. Trinh
*Attorney, Agent, or Firm*—William G. Jameson

[57] ABSTRACT

This invention provides 7-deoxy-$\Delta^{12,13}$-iso-taxol of formula (I) which are useful for the treatment of the same cancers for which taxol has been shown active.

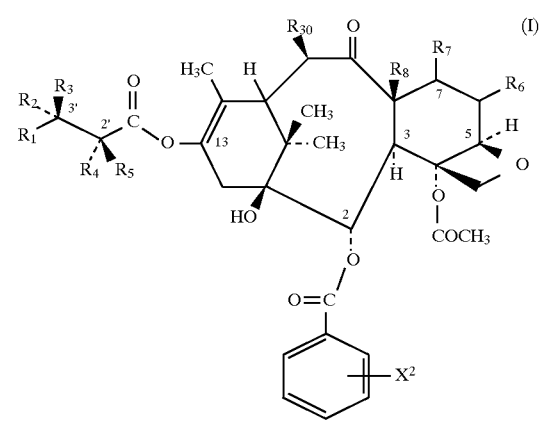

23 Claims, No Drawings

OTHER PUBLICATIONS

Bouchard et al, CA 121:205130, 1994 (WO 9412485).

Chen, Shu–Hui, Huang, Stella and Farina, Vittorio, On The Reaction of Taxol With Dast, Tetrahedron Letters, vol. 35, No. 1, pp. 41–44, (1994).

Chen, Shu–Hui; Huang, Stella; Wei, Jianmei; Farina, Vittorio; Serendipitous Synthesis of a Cyclopropane–Containing Taxol Analog via Anchimeric Participation of an Unactivated Angular Methyl Group; Advance ACS Abstracts, vol. 1., No. 2, Jul. 15, 1993.

Chaudhary, AG; Gharpure, MM; Rimoldi, JM; Chordia MD; Gunatilaka, AA Leslie; Kingston, David GI; Unexpectedly Facile Hydrolysis of the 2–Benzoate Group of Taxol and Syntheses of Analogs with Increased Activities, J. Am. Chem. Soc. 1994, 116, 4097–4098.

Chen, Shu–Hui; Huang, Stella; Wei, Jianmei; Farina, Vittorio; Serendipitous Synthesis of a Cyclopropane–Containing Taxol Analog via Anchimeric articipation of an Unactivated Angular Methyl Group, J. Org. Chem. 1993, 58, 4520–4521.

Commercon, A; Bezard, D; Beranrd, F; Bourzat, JD; Improved Protection and Esterification of a Precursor of the Taxotere® and Taxol Side Chains, Tetrahedron Letters, No. 36, pp. 5185–5188, 1992.

Denis, Jean–Joel, Greene, Andrew E., A Highly Efficient, Practical Approach to Natural Taxol, J. Am. Chem. Soc., 110, 5917–5919 (1988).

Denis, J–N., Correa, A., Greene, A.E., An Improved Synthesis of the Taxol Side Chain and of RP 56976, J. Org. Chem., 1990, 55, 1957–1957.

Didier, Eric, Fouque, Elie, Taillepied, Isabelle and Commercon, Alain, 2–Monosubstituted–1,3–Oxazolidines as Improved Protective Groups of N–Boc–Phenylisoserine in Docetaxel Preparation, Tetrahedron Letters 35(15):2349–352 (1994).

Gaskin, Felicia, Cantor, Charles R., Turbidimetric Studies of the in Vitro Assembly and Disassembly of Porcine Neurotubules, J. Mol. Biol. 89, 737–758 (1974).

Georg, G.I., Cheruvallath, Z. S., Himes, R.H., Mejillano, M.R., BioMed. Chem. Lett. 1992, 2, 295.

Guenard, Daniel; Gueritte–Voegelein, Francoise; Potier, Pierre; Taxol and Taxotere: Discovery, Chemistry, and Structure–Activity Relationships, Acc. Chem. Res. 1993, 26, 160–167.

Kingston, David GI, The Chemistry of Taxol, Pharmac. Ther., vol. 52, pp. 1–34, 1991.

Klein, Larry L., Maring, Clarence J., Li, Leping, Yeung, Clinton M., Thomas Sheela A., Grampovnik, David J., Plattner, Jacob J., Henry Rodger F., Synthesis of Ring B–Rearranged Taxane Analogs, J. Org. Chem. 59, 2370–2373 (1994).

Li, Li H., Kuentzel, Sandra L., Murch, Lana L., Pschigoda, Loraine M., Krueger, William C., Comparative Biological and Biochemical Effects of Nogalamycin and Its Analogs on L1210 Leukemia, Cancer Research 39, 4816–4822 (Dec. 1979).

Magri, Neal F., Kingston, David G.I., Modified Taxols. 2.[1] Oxidation Products of Taxol, J. Org. Chem. 51, 797–802 (1986).

Magri, Neal F., Kingston, David G.I., Modified Taxols, 4. [1]Synthesis and Biological Activity of Taxols Modified in the Side Chain, Journal of Natural Products, vol. 51, No. 2, pp. 298–306 Mar.–Apr. 1988.

Mangatal, L., Adeline, M.–T., Guenard, D., Gueritte–Vogelein, F., Potier, P., Application of the Vicinal Oxyamination Reaction With Asymmetric Induction To The Hemisynthesis of Taxol and Analogues, Tetrahedron 1989, vol. 45, No. 13, 4177–4190.

Monsarrat, Bernard, Mariel, Eric, Cros, Suzie, Gares, Michele, Guenard, Daniel, Gueritte–Voegelein, Francoise, Wright, Michel, Taxol Metabolism Isolation and Identification of Three Major Metabolites of Taxol in Rat Bile, Drug Metabolism and Disposition, vol. 18, No. 6, pp. 895–901, 1990.

Mathew, Abraham E., Mejillano, Magdalena R., Nath, Jyoti P., Himes, Richard H., Stella, Valentino J., Synthesis and Evaluation of Some Water–soluble Products and Derivatives of Taxol with Antitumor Activity, J. Med. Chem. 35, 145–151 (1992).

Ojima, Iwao, Zucco, Martine, Duclos, Oliver, Kuduk, Scott D., Sun, Chung Ming, Park, Young Hoon, N–Acyl–3–Hydroxy–βLactams as Key Intermediates for Taxotere and its Analogs, Bioorganic & Medicinal Chemistry Letters, vol. 3, No. 11 2479–2482 (1993).

Ojima, I: Habus, I; Zhao, M; Efficient and Practical Asymmetric Synthesis of the Taxol C–13 Side Chain, N–Benzoyl–(2R,3S)–3–phenylisoserine, and Its Analogues via Chiral 3–Hydroxy–4–aryl–β–lactams, J. Org. Chem., 1991, 56 1681–1683.

Ringel, Israel and Horwitz, Susan Band, Taxol is Converted to 7–Epitaxol, a Biologically Active Isomer, in Cell Culture Medium, The Journal of Pharmacology and Experimental Theapeutics, vol. 242, 692–698 (1987).

Rowinsky, Eric K.; Donehower, Ross C; The Clinicial Pharmacology and Use of Antimicrotubule Agents in Cancer Chemotherapeutics, Pharmac. Ther. vol. 52, pp. 35–84, 1991.

Samaranayake, Gamini; Magri, Neal F; Jitrangsri, Chote; Kingston, David GI; Modified Taxols. 5.Reaction of Taxol with Electrophilic Reagents and Preprearation of a Rearranged Taxol Derivative with Tubulin Assembly Activity, J. Org. Chem. 1991, 56, 5114–5119.

Senilh, V., Gueritte–Vogelein, F., Guenard, D., Colin, M., Potier, P., C.R. Acad. Sc. Paris t. 299, Serie II, No. 15, 1039–1043 (1984).

Slichenmyer, William J; Von Hoff, Daniel D; Taxol: a new and effective anti–cancer drug, Anti–Cancer Drugs, vol. 2, 1991, pp. 519–530.

TIPS, Apr. 1992, vol. 13 pp. 134–136, Mechanism of action of taxol.

Kingston, David GI; Chaudhary, Ashok G; Gunatilaka, AA Leslie; Middleton, Mark L; Synthesis of Taxol from Baccatin III via an Oxazoline Intermediate, Tetrahedron Letters 35, No. 26, pp. 4483–4484 (1994).

Nicolaou, KC; Riemer, C; Kerr, MA; Rideout, D; Wrasidlo, W; Nature 364:464–66 (1993).

Chen, Shu–Hui; Farina, Vittori; Wei, Jian–Mei; Long, Byron; Fairchild, Craig; Mamber, Stephen W; Kadow, John F; Vyas, Dolatrai; Doyle, Terrence W; Structure–Activity Relationships of Taxol®: Synthesis and Biological Evaluation of C2 Taxol Analogs, Bioorganic & Medical Chemistry Letters, vol. 4, No. 3, 479–82, 1994.

ANTINEOPLASTIC USE AND PHARMACEUTICAL COMPOSITIONS CONTAINING THEM

This application is a 371 of PCT/US95/00531 filed Jan. 26, 1995 which is a continuation-in-part of U.S. Ser. No. 08/189,235 filed Jan. 28, 1994, now abandoned.

BACKGROUND OF THE INVENTION

Taxol is a member of the taxane family of diterpenes, having the structure shown below:

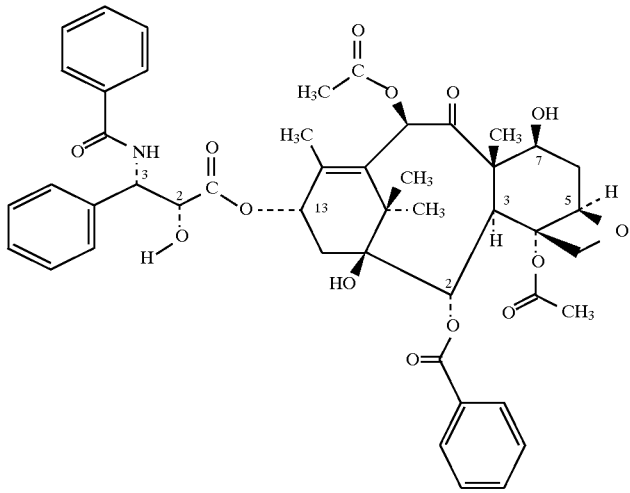

The numbering system shown for taxol is that recommended by IUPAC (IUPAC, Commission on the Nomenclature of Organic Chemistry, 1978).

The chemistry of the potent anticancer diterpenoid taxol and analogs thereof is reviewed, with an emphasis on isolation and analysis, structural modifications, partial synthesis, and structure-activity relationships by David G. I. Kingston, The Chemistry of Taxol, Pharmac. Ther., Vol 52, pp 1–34, 1991.

The clinical pharmacology of taxol is reviewed by Eric K. Rowinsky and Ross C. Donehower, The Clinical Pharmacology and Use of Antimicrotubule Agents in Cancer Chemotherapeutics, Pharmac. Ther., Vol 52, pp 35–84, 1991. Clinical and preclinical studies with taxol are reviewed by William J. Slichenmyer and Daniel D. Von Hoff, Taxol: A New and Effective Anti-cancer Drug, Anti-Cancer Drugs, Vol. 2, pp 519–530, 1991.

Taxol and analogs thereof are the subject of various patents including, for example, U.S. Pat. Nos. 4,814,470; 4,857,653; 4,942,184; 4,924,011; 4,924,012; 4,960,790; 5,015,744; 5,157,049; 5,059,699; 5,136,060; 4,876,399; 5,227,400, 5,248,796 as well as PCT Publication No. WO 92/09589, European Patent Application 90305845.1 (Publication No. A2 0 400 971), 90312366.9 (Publication No. A1 0 428 376), 89400935.6 (Publication No. A1 0 366 841) and 90402333.0 (Publication No. 0 414 610 A1), 87401669.4 (A1 0 253 739), 92308608.6 (A1 0 534 708), 92308609.4 (A1 534 709) and PCT Publication Nos. WO 91/17977, WO 91/17976, WO 91/13066, WO 91/13053.

Various processes for the preparation of taxol (and intermediates and analogs thereof) are described in Tetrahedron Letters, 1992, 33, 5185; J. Org. Chem., 1991, 56, 1681 and J. Org. Chem., 1991, 56, 5114 as well as WO 94/07876, WO 94/07877, WO 94/07878 and WO 94/07879. See also U.S. Pat. No. 4,924,011 (and Reissue Patent 34,277, dated 8 Jun. 1993) as well as Tetrahedron Letters 35, 4483 (1994).

Chen et al., Serendipitous Synthesis of a Cyclopropane-Containing Taxol Analog via Anchimeric Participation of an Unactivated Angular Methyl Group, Advance ACS Abstracts, Vol 1, No. 2., Jul. 15, 1993 reported the treatment of a 7-epi taxol derivative with DAST in dichloromethane led to an unexpected reaction involving participation of the C-19 methyl group and clean formation of a cyclopropane ring. See also J. Org. Chem., 1993, 58, 4520 (Aug. 13, 1993) and U.S. Pat. No. 5,254,580 (granted 19 Oct. 1993).

U.S. Pat. No. 5,248,796 (granted 28 Sep. 1993) relates to 10-desacetoxy-11,12-dihydrotaxol-10,12(18)-diene derivatives and the preparation of 10-desacetoxytaxol.

EP Application 0 558 959 A1 discloses various phosphonooxy and carbonate 2' taxol derivatives of taxol with increased water solubility.

Water-soluble pro-taxol analogs are disclosed in Nicolaou, K. C.; Riemer, C.; Kerr, M. A.; Rideout, D.; Wrasidlo, W., Nature 364:464–66 (1993).

C-2 substituted benzoate analogs of taxol and their synthesis is described in J. Am. Chem. Soc. 1994, 116, 4097–98 and Bioorganic & Medical Chemistry Letters, Vol. 4, No. 3, 479–82, 1994.

SUMMARY OF THE INVENTION

This invention provides $\Delta^{12,13}$-iso-taxol analogs of Formula I:

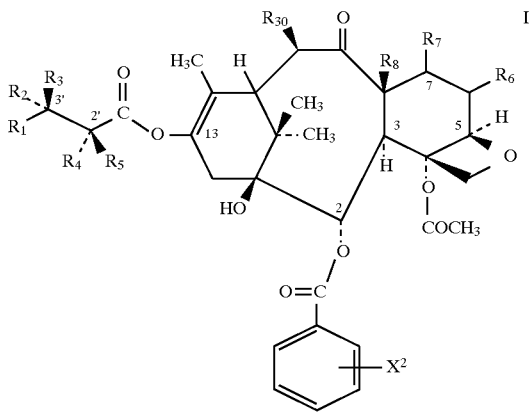

The compounds of Formula I are useful for the treatment of the same cancers for which taxol has been shown active, including human ovarian cancer, breast cancer, and malignant melanoma as well as lung cancer, gastric cancer, colon cancer, head and neck cancer, and leukemia.

CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)$H. Groups $R_i$ and $R_j$ would represent monovalent variable substituents if attached to the formula $CH_3$—$CH_2$—$C(R_i)$($R_j$)—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as taxol, these carbon atoms are designated as $C_i$, where "i" is the integer corresponding to the carbon atom number. For example, $C_6$ represents the 6 position or carbon atom number in the nucleus as traditionally designated by those skilled in the art.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N*$=$C(CH_3)$—CH=CCl—CH=$C*H$ with the convention that the atoms marked with an asterisk (*) are bonded to each other resulting in the formation of a ring. Likewise, the cyclic molecular fragment, 4-(ethyl)-1-piperazinyl can be represented by —$N*$—$(CH_2)_2$—$N(C_2H_5)$—$CH_2$—$C*H_2$. Similarly, 2-furyl can be represented by —$C*$—O—CH=CH—$C*H$= and 2-thienyl represented by —$C*$—S—CH=CH—$C*H$=.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other.

In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —$C(\alpha$-$R_{i-j})(\beta$-$R_{i-k})$—. For example, when the bivalent variable $R_6$, —$C(=R_6)$— is defined to consist of two monovalent variable substituents, the two monovalent variable substituents are $\alpha$-$R_{6-1}$:$\beta$-$R_{6-2}$, . . . $\alpha$-$R_{6-9}$:$\beta$-$R_{6-10}$, etc, giving —$C(\alpha$-$R_{6-1})(\beta$-$R_{6-2})$—, . . . —$C(\alpha$-$R_{6-9})(\beta$-$R_{6-10})$—, etc. Likewise, for the bivalent variable $R_{11}$, —$C(=R_{11})$—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated " . . . $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$) alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

The term "Boc" refers to C(O)O-t-butyl, "Troc" refers to C(O))CH$_2$CCl$_3$, TES refers to Si(Et)$_3$, Ph refers to phenyl, Ac refers to C(O)CH$_3$, and Bz refers to C(O)Ph.

DETAILED DESCRIPTION OF THE INVENTION

More specifically, this invention provides 7-deoxy-$\Delta^{12,13}$-iso-taxol analogs of general Formula I

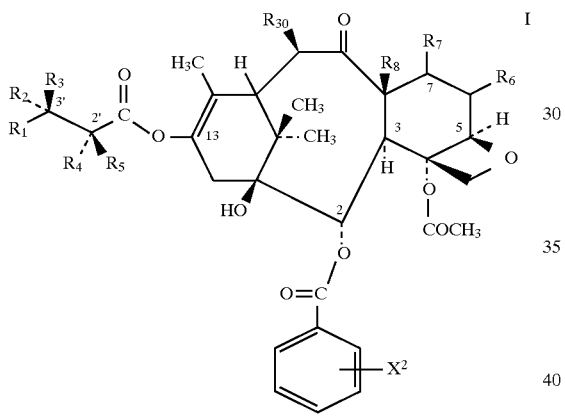

wherein:

$X^2$ is selected from the group consisting of
- —H
- —$C_1$–$C_4$ alkyl,
- —$C_1$–$C_3$ alkoxy (preferably —OCH$_3$),
- halo (preferably —Cl),
- —$C_1$–$C_3$ alkylthio,
- -trifluoromethyl,
- —$C_2$–$C_6$ dialkylamino,
- benzyloxymethyl,
- cyano,
- azide (N$_3$),
- or nitro;

$R_1$ is selected from the group consisting of
- —CH$_3$,
- —C$_6$H$_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro,
- -2-furyl, 2-thienyl, 1-naphthyl, 2-naphthyl or 3,4-methylenedioxyphenyl;

$R_2$ is selected from the group consisting of —H, —NHC(O)H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)C$_3$–C$_8$cycloalkyl, —NHC(O)OC(CH$_2$CH$_3$)$_2$CH$_3$, —NHC(O)OC(CH$_3$)$_2$CH$_2$Cl, —NHC(O)OC(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$ or —NHC(O)NHC(CH$_3$)$_3$, $R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$X$^-$ where n is 1–3, R'$_4$ is —H or —$C_1$–$C_4$alkyl, R'$_5$ is —H, —$C_1$–$C_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH], —OC(O)(CH$_2$)$_n$NR$^2$R$^3$ [where n is 1–3, R$^2$ is —H or —$C_1$–$C_3$alkyl and R$^3$—H or —$C_1$–$C_3$alkyl], —OC(O)CH(R")NH$_2$ [where R" is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3^-$Y$^+$, —OC(O)CH$_2$CH$_2$C(O)NHCH$_2$CH$_2$CH$_2$SO$_3^-$Y$^+$ wherein Y$^+$ is Na$^+$ or N$^+$(Bu)$_4$, —OC(O)CH$_2$CH$_2$C(O)OCH$_2$CH$_2$OH;

$R_5$ is —H or —OH, with the overall proviso that when $R_5$ is —OH, $R_4$ is —H and with the further proviso that when $R_5$ is —H, $R_4$ is other than —H;

$R_6$ is —H:—H when $R_7$ is $\alpha$-$R_{71}$:$\beta$-$R_{72}$ where one of $R_{71}$ and $R_{72}$ is —H and the other of $R_{71}$ and $R_{72}$ is —X$_7$ where X$_7$ is halo or azido (—N$_3$) and R$_8$ is —CH$_3$;

$R_6$ is —H:—H when $R_7$ is $\alpha$-H:$\beta$-$R_{74}$ where $R_{74}$ and R$_8$ are taken together to form a cyclopropyl ring;

$R_6$ is $R_{65}$:$R_{66}$ when $R_7$ is $R_{75}$:$R_{76}$ where one of $R_{65}$ and $R_{66}$ is taken together with one of $R_{75}$ and $R_{76}$ to form a second bond between the carbon atoms to which they are attached and the other of $R_{65}$ and $R_{66}$ is —H, and the other of $R_{75}$ and $R_{76}$ is —H and where R$_8$ is —CH$_3$;

$R_6$ is —H:—H when $R_7$ is α-$R_{81}$:β-$R_{82}$ where one of $R_{81}$ and $R_{82}$ is —H and the other of $R_{81}$ and $R_{82}$ is —OH or —H and $R_8$ is —CH$_3$;

$R_6$ is —H:—H when $R_7$ is α-$R_{91}$:β-$R_{92}$ where one of $R_{91}$ and $R_{92}$ is —H and the other of $R_{91}$ and $R_{92}$ is —W where W is selected from the group consisting of —OC(O)H, —O—C$_1$–C$_6$alkyl, —O—C$_3$–C$_6$cycloalkyl, —O—(CH$_2$)$_n$phenyl where n is 1–6, —O—C(O)C$_1$–C$_{10}$alkyl, —O—C(O)phenyl, —O—C(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)naphthyl, —O—C(O)naphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Ophenyl, —O—C(O)Ophenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Onaphthyl, —O—C(O)Onaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OC$_1$–C$_{10}$alkyl, —O—C(O)NHC$_1$–C$_{10}$alkyl, —O—C(O)NHphenyl, —O—C(O)NHphenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)NHnaphthyl, —O—C(O)NHnaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OCH$_2$CHCl$_2$, —O—C(O)OCH$_2$CCl$_3$, —OSi(R$^{16}$)$_3$ [where R$^{16}$, being the same or different, is selected from C$_1$–C$_6$alkyl or cyclo(C$_5$–C$_8$)alkyl], —O—CH$_2$—O—C$_1$–C$_6$alkyl, —O—CH$_2$—O—(CH$_2$)$_n$phenyl where $_n$ is 1–3, —O—CH$_2$—O—(CH$_2$)$_n$phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro and where $_n$ is 1–3, —O—CH$_2$—O—CH$_2$—CX$_q$H$_{3-q}$ where $_q$=0–3 and X is halogen, and R$_8$ is —CH$_3$;

$R_{30}$ is —H, OH, or —OC(O)CH$_3$; and pharmaceutically acceptable salts thereof when the compound contains either an acidic or basic functional group.

A preferred embodiment of the subject invention is compounds of Formula I where $R_1$ is phenyl or phenyl substituted with halo, $R_2$ is —NHC(O)C$_6$H$_5$, $R_3$ and $R_5$ are —H, $R_4$ is —OH, and $R_{30}$ is —OH or —OC(O)CH$_3$. Another preferred embodiment of the subject invention is compounds of Formula I where $R_1$ is preferably phenyl or phenyl substituted with halo, $R_2$ is —NHC(O)OC(CH$_3$)$_3$, $R_3$ and $R_5$ are —H, $R_4$ is —OH, and $R_{30}$ is —H or —COCH$_3$. A preferred embodiment of the subject invention is compounds of Formula I where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

An embodiment of the subject invention are compounds of Formula I where $R_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro or $R_2$ is selected from the group consisting of —H, —NHC(O)H, —NHC(O)C$_1$–C$_{10}$alkyl (preferably —NHC(O)C$_4$–C$_6$alkyl), —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro.

An embodiment of the subject invention are compounds of Formula I where $X^2$ is —H.

An embodiment of the subject invention are compounds of Formula I where $X^2$ is —H;

$R_1$ is selected from the group consisting of
 —CH$_3$,
 —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, -2-furyl, 2-thienyl, 1-naphthyl, 2-naphthyl or 3,4-methylenedioxyphenyl;

$R_2$ is selected from the group consisting of —H, —NHC(O)H, —NHC(O)C$_1$–C$_{10}$alkyl (preferably —NHC(O)C$_4$–C$_6$alkyl), —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl, —NHC(O)OC(CH$_2$CH$_3$)$_2$CH$_3$, —NHC(O)OC(CH$_3$)$_2$CH$_2$Cl, —NHC(O)OC(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$ or —NHC(O)NHC(CH$_3$)$_3$;

$R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$X$^-$ where n is 1–3, R'$_4$ is —H or —C$_1$–C$_4$alkyl, R'$_5$ is —H, —C$_1$–C$_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is NH$_3$, (HOC$_2$H$_4$)$_3$N, N(CH$_3$)$_3$, CH$_3$N(C$_2$H$_4$)$_2$NH, NH$_2$ $(CH_2)_6NH_2$, N-methylglucamine, NaOH or KOH], —OC(O)(CH$_2$)$_n$NR$^2$R$^3$ [where n is 1–3, R$^2$ is —H or —C$_1$–C$_3$alkyl and R$^3$—H or —C$_1$–C$_3$alkyl], —OC(O)CH(R")NH$_2$ [where R" is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3^-$Y$^+$, —OC(O)CH$_2$CH$_2$C(O)NHCH$_2$CH$_2$CH$_2$SO$_3^-$Y$^+$ wherein Y$^+$ is Na$^+$ or N$^+$(Bu)$_4$, —OC(O)CH$_2$CH$_2$C(O)OCH$_2$CH$_2$OH;

R$_5$ is —H or —OH, with the overall proviso that when R$_5$ is —OH, R$_4$ is —H and with the further proviso that when R$_5$ is —H, R$_4$ is other than —H;

R$_6$ is —H:—H when R$_7$ is α-R$_{71}$:β-R$_{72}$ where one of R$_{71}$ and R$_{72}$ is —H and the other of R$_{71}$ and R$_{72}$ is —X$_7$ where X$_7$ is halo or azido (—N$_3$) and R$_8$ is —CH$_3$;

R$_6$ is —H:—H when R$_7$ is α-H:β-R$_{74}$ where R$_{74}$ and R$_8$ are taken together to form a cyclopropyl ring;

R$_6$ is R$_{65}$:R$_{66}$ when R$_7$ is R$_{75}$:R$_{76}$ where one of R$_{65}$ and R$_{66}$ is taken together with one of R$_{75}$ and R$_{76}$ to form a second bond between the carbon atoms to which they are attached and the other of R$_{65}$ and R$_{66}$ is —H, and the other of R$_{75}$ and R$_{76}$ is —H and where R$_8$ is —CH$_3$;

R$_6$ is —H:—H when R$_7$ is α-R$_{81}$:β-R$_{82}$ where one of R$_{81}$ and R$_{82}$ is —H and the other of R$_{81}$ and R$_{82}$ is —OH or —H and R$_8$ is —CH$_3$;

R$_6$ is —H:—H when R$_7$ is α-R$_{91}$:β-R$_{92}$ where one of R$_{91}$ and R$_{92}$ is —H and the other of R$_{91}$ and R$_{92}$ is —W where W is selected from the group consisting of —OC(O)H, —O—C$_1$–C$_6$alkyl, —O—C$_3$–C$_6$cycloalkyl, —O—(CH$_2$)$_n$phenyl where n is 1–6, —O—C(O)C$_1$–C$_{10}$alkyl, —O—C(O)phenyl, —O—C(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)naphthyl, —O—C(O)naphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Ophenyl, —O—C(O)Ophenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Onaphthyl, —O—C(O)Onaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OC$_1$–C$_{10}$alkyl, —O—C(O)NHC$_1$–C$_{10}$alkyl, —O—C(O)NHphenyl, —O—C(O)NHphenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)NHnaphthyl, —O—C(O)NHnaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OCH$_2$CHCl$_2$, —O—C(O)OCH$_2$CCl$_3$, —OSi(R$^{16}$)$_3$ [where R$^{16}$ is C$_1$–C$_6$alkyl], —O—CH$_2$—O—C$_1$–C$_6$alkyl, —O—CH$_2$—O—(CH$_2$)$_n$phenyl where $_n$ is 1–3, —O—CH$_2$—O—(CH$_2$)$_n$phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro and where $_n$ is 1–3, —O—CH$_2$—O—CH$_2$—CX$_q$H$_{3-q}$ where $_q$=0–3 and X is halogen, and R$_8$ is —CH$_3$;

R$_{30}$ is —H, OH, or —OC(O)CH$_3$; and pharmaceutically acceptable salts thereof when the compound contains either an acidic or basic functional group.

A further embodiment of the subject invention are compounds of Formula I where X$^2$ is in the ortho, meta or para-position (preferably meta or para, more preferably the meta position) and is selected from the group consisting of —C$_1$–C$_4$ alkyl, —C$_1$–C$_3$ alkoxy (preferably —OCH$_3$), halo (preferably —Cl), —C$_1$–C$_3$ alkylthio, trifluoromethyl, —C$_2$–C$_6$ dialkylamino, benzyloxymethyl, cyano, azide (N$_3$), or nitro.

A still further embodiment of the subject invention are compounds of Formula I where X$^2$ is in the ortho, meta or para-position (preferably meta or para, more preferably the meta position) and is selected from the group consisting of —N$_3$, —CN, —OCH$_3$ or —Cl. A still further embodiment of the subject invention are compounds of Formula I where X$^2$ is in the ortho, meta or para-position (preferably meta or para, more preferably the meta position) and is selected from the group consisting of —N$_3$, —CN, —OCH$_3$ or —Cl and R$_1$ is phenyl or phenyl substituted with halo, R$_2$ is —NHC(O)C$_6$H$_5$, R$_3$ and R$_5$ are —H, R$_4$ is —OH, and R$_{30}$ is —OH or —OC(O)CH$_3$.

A further embodiment of the subject invention are compounds of Formula I where X$^2$ is in the ortho, meta or para-position (preferably meta or para, more preferably the meta position) and is selected from the group consisting of —N$_3$, —CN, —OCH$_3$ or —Cl and R$_1$ is preferably phenyl or phenyl substituted with halo, R$_2$ is —NHC(O)OC(CH$_3$)$_3$, R$_3$ and R$_5$ are —H, R$_4$ is —OH, and R$_{30}$ is —H or —COCH$_3$.

A preferred embodiment of the subject invention is compounds of Formula I where X$^2$ is —H and R$_1$ is phenyl or phenyl substituted with halo, R$_2$ is —NHC(O)C$_6$H$_5$, R$_3$ and R$_5$ are —H, R$_4$ is —OH, and R$_{30}$ is —OH or —OC(O)CH$_3$. Another preferred embodiment of the subject invention is compounds of Formula I where X$^2$ is —H and R$_1$ is preferably phenyl or phenyl substituted with halo, R$_2$ is —NHC(O)OC(CH$_3$)$_3$, R$_3$ and R$_5$ are —H, R$_4$ is —OH, and R$_{30}$ is —H or —COCH$_3$. A preferred embodiment of the subject invention is compounds of Formula I where X$^2$ is —H and R$_1$ is preferably phenyl or phenyl substituted with halo, R$_2$ is —NHC(O)NHC(CH$_3$)$_3$, R$_3$ and R$_5$ are —H, R$_4$ is —OH, and R$_{30}$ is —OH or —OCOCH$_3$.

An embodiment of the subject invention are compounds of Formula I where X$^2$ is —H and R$_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro and R$_2$ is selected from the group consisting of —H, —NHC(O)H, —NHC(O)C$_1$–C$_{10}$alkyl (preferably —NHC(O)C$_4$–C$_6$alkyl), —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro.

This invention also provides $\Delta^{12,13}$-iso-taxol analogs of general Formula IIa Formula Va
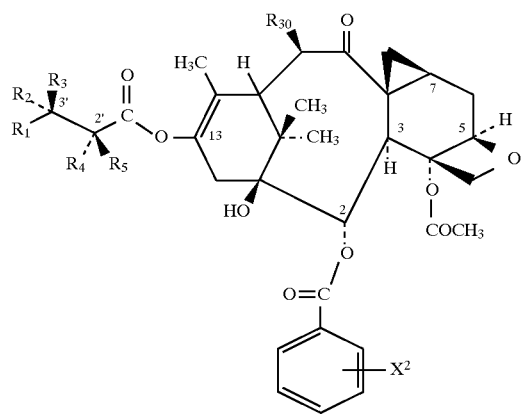
and Formula IIIa
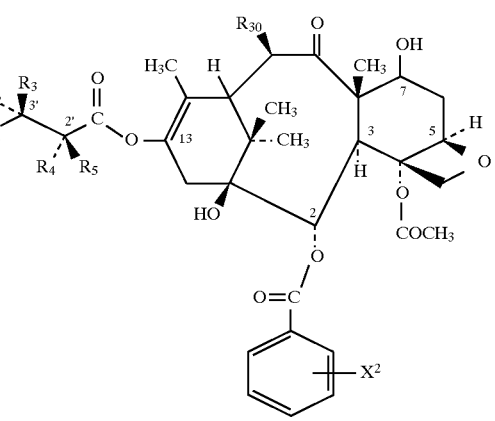
and Formula VIa
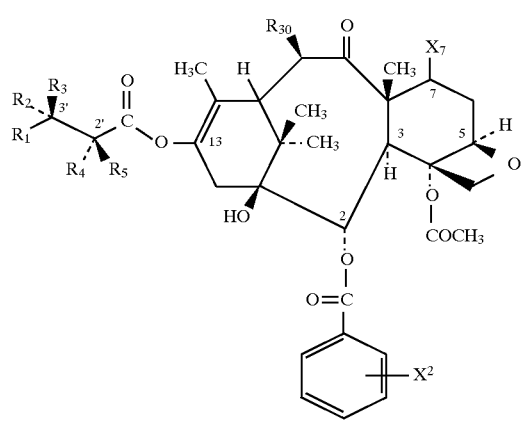
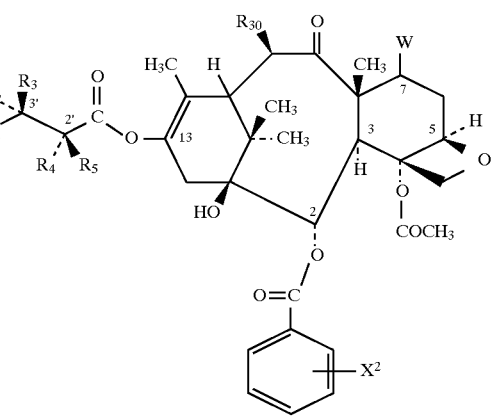
wherein
$X_7$ is selected from the group consisting of —F, —Br, —Cl, —I, or —$N_3$; and wherein W, $R_1$, $R_2$, $R_3$, $R_4$, $R_5$, $R_{30}$ and $X^2$ are as defined above.
This invention also provides $\Delta^{12,13}$-iso-taxol analogs of general Formula II
and Formula IVa
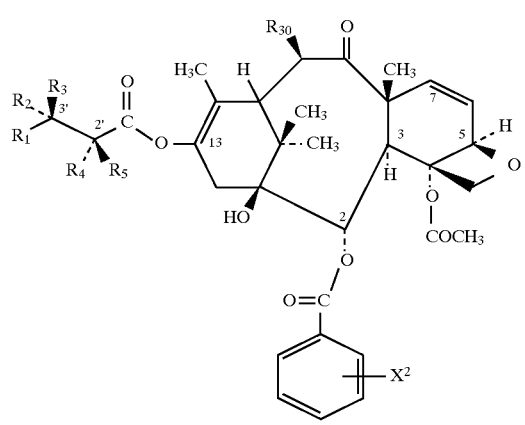
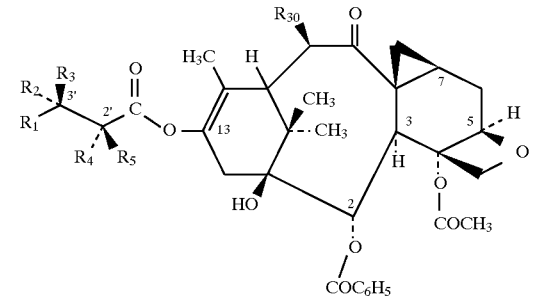

and Formula III

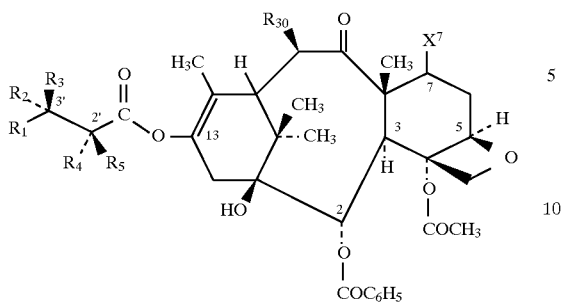

and Formula IV

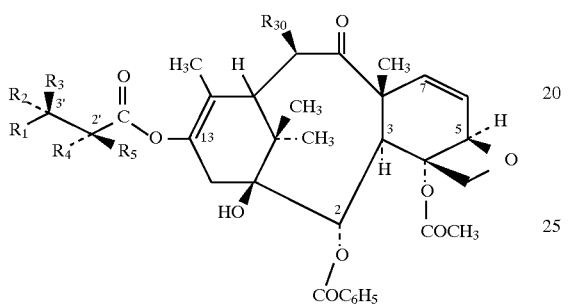

Formula V

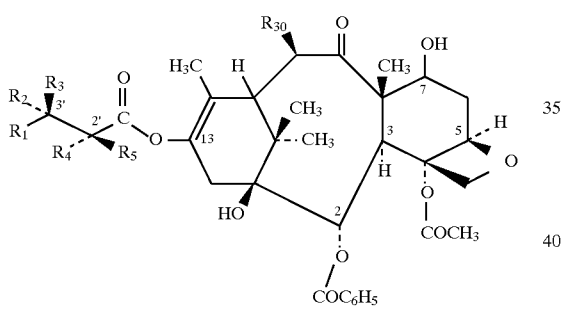

and Formula VI

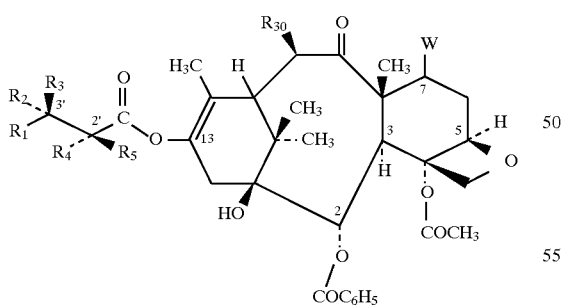

wherein

X$_7$ is selected from the group consisting of —F, —Br, —Cl, —I, or —N$_3$; and wherein W, R$_1$, R$_2$, R$_3$, R$_4$, R$_5$ and R$_{30}$ are as defined above.

An embodiment of the present invention are 7-deoxy-7β, 8β-methano-Δ$^{12,13}$-iso-taxol analogs of general Formula II (or IIa) wherein:

R$_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro;

R$_2$ is selected from the group consisting of —H, —NHC(O)C$_1$–C$_{10}$alkyl (preferably —NHC(O)C$_4$–C$_6$alkyl), —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl;

R$_3$ is selected from the group consisting of —H, —NHC(O)phenyl or —NHC(O)OC(CH$_3$)$_3$, with the overall proviso that one of R$_2$ and R$_3$ is —H but R$_2$ and R$_3$ are not both —H;

R$_4$ is —H or selected from the group consisting of —OH, —OAc (—OC(O)CH$_3$), —OC(O)OCH$_2$C(Cl)$_3$, —OCOCH$_2$CH$_2$NH$_3$$^+$HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$X$^-$ where n is 1–3, R'$_4$ is —H or —C$_1$–C$_4$alkyl, R'$_5$ is —H, —C$_1$–C$_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH], —OC(O) (CH$_2$)$_n$NR$^2$R$^3$ [where n is 1–3, R$^2$ is —H or —C$_1$–C$_3$alkyl and R$^3$—H or —C$_1$–C$_3$alkyl], —OC(O)CH(R")NH$_2$ [where R" is selected from the group consisting of —H, —CH$_3$, —CH$_2$CH (CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3$$^-$Y$^+$, —OC(O)CH$_2$CH$_2$C(O)NHCH$_2$CH$_2$CH$_2$SO$_3$$^-$Y$^+$ wherein Y$^+$ is Na$^+$ or N$^+$(Bu)$_4$, —OC(O)CH$_2$CH$_2$C(O)OCH$_2$CH$_2$OH;

R$_5$ is —H or —OH, with the overall proviso that when R$_5$ is —OH, R$_4$ is —H and with the further proviso that when R$_5$ is —H, R$_4$ is other than —H;

R$_{30}$ is —H, —OH, or —O—C(O)CH$_3$; and pharmaceutically acceptable salts thereof when the compound contains either an acidic or basic functional group.

A preferred embodiment of the subject invention is compounds of Formula II (or IIa) where R$_1$ is phenyl or phenyl substituted with halo, R$_2$ is —NHC(O)C$_6$H$_5$, R$_3$ and R$_5$ are —H, and R$_{30}$ is —C(O)CH$_3$. Another preferred embodiment of the subject invention is compounds of Formula II (or IIa) where R$_1$ is preferably phenyl or phenyl substituted with halo, R$_2$ is —NHC(O)OC(CH$_3$)$_3$, and R$_3$, R$_5$ and R$_{30}$ are —OH. A further preferred embodiment of the subject invention is compounds of Formula II (or IIa) where $R_1$ is preferably phenyl or phenyl substituted with halo, $R_2$ is —NHC(O)OC(CH$_3$)$_3$, and $R_3$ and $R_5$ are —H, and $R_{30}$ is —OC(O)CH$_3$. Another preferred embodiment of the subject invention is compounds of Formula I where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

Additional preferred embodiments of Formula II include:

The compound according to Formula II, namely 7-deoxy-7β,8β-methano-Δ$^{12,13}$-iso-taxol;

The compound according to Formula II, namely 2'-[{(2,2,2-trichloroethyl)oxy}carbonyl]-7-deoxy-7β,8β-methano-Δ$^{12,13}$-iso-taxol;

The compound according to Formula II, namely 10-acetyl-7-deoxy-7β,8β-methano-Δ$^{12,13}$-iso-taxotere; and The compound according to Formula II, namely N-debenzoyl-n-(t-butyl)aminocarbonyl-7-deoxy-7β,8β-methano-Δ$^{12,13}$-iso-taxol.

A preferred embodiment of the subject invention are compounds of Formula II (or IIa) where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

Another embodiment of the present invention are 7-halo-Δ$^{12,13}$-iso-taxol analogs of general Formula III (or IIIa) wherein:

$X_7$ is selected from the group consisting of —F, —Br, —Cl, —I, or —N$_3$;

$R_1$ is selected from the group consisting of —CH$_3$, —C$_6$H$_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro;

$R_2$ is selected from the group consisting of —H, —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH$_3$)=CHCH$_3$, —NHC(O)OC(CH$_3$)$_3$, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl;

$R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH and pharmaceutically acceptable salts thereof, —CO(CH$_2$)$_3$COOH and pharmaceutically acceptable salts thereof, and —OC(O)—Z—C(O)—R' [where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$X$^-$ where n is 1–3, R'$_4$ is —H or —C$_1$–C$_4$alkyl, R'$_5$ is —H, —C$_1$–C$_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH], —OC(O)(CH$_2$)$_n$NR$^2$R$^3$ [where n is 1–3, R$^2$ is —H or —C$_1$–C$_3$alkyl and R$^3$ —H or —C$_1$–C$_3$alkyl], —OC(O)CH(R")NH$_2$ [where R" is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$], the residue of the amino acid proline, —OC(O)CH=CH$_2$, —C(O)CH$_2$CH$_2$C(O)NHCH$_2$CH$_2$SO$_3^-$Y$^+$, —OC(O)CH$_2$CH$_2$C(O)NHCH$_2$CH$_2$SO$_3^-$Y$^+$ wherein Y$^+$ is Na$^+$ or N$^+$(Bu)$_4$, —OC(O)CH$_2$CH$_2$C(O)OCH$_2$CH$_2$OH;

$R_5$ is —H or —OH, with the overall proviso that when $R_5$ is —OH, $R_4$ is —H and with the further proviso that when $R_5$ is —H, $R_4$ is other than —H;

$R_{30}$ is —H, —OH or —OC(O)CH$_3$; and pharmaceutically acceptable salts thereof when the compound contains either an acidic or basic functional group.

The compounds of Formula III (or IIIa) include both the 7-α and 7-β configuration of the 7-halo substitution. Halo refers to —F, —Br, —Cl, —I, or N$_3$.

In compounds of Formula III (or IIIa): $X_7$ is preferably —F, and $R_3$ and $R_5$ are preferably —H, and $R_1$ is preferably phenyl or phenyl substituted with halo.

A preferred embodiment of the subject invention are compounds of Formula III (or IIIa) where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

Additional preferred embodiments of Formula III (or IIIa) include:

A compound according to Formula III (or IIIa) wherein $R_4$ is —H and $R_5$ is —OH;

A compound according to Formula III (or (IIIa) wherein $R_4$ is other than —H and $R_5$ is —H;

A compound according to Formula III (or IIIa) wherein $R_3$ is —H, and $R_1$ is Ph or substituted phenyl;

A compound according to Formula III (or IIIa) wherein $X_7$ is —F;

A compound according to Formula III (or IIIa) wherein $X_7$ is -α—F;

A compound according to Formula III (or IIIa) wherein $X_7$ is —F and $R_4$ is other than —H and $R_5$ is —H;

A compound according to Formula III (or IIIa) wherein $X_7$ is —F, $R_3$ is —H, and $R_1$ is Ph or substituted phenyl;

A compound according to Formula III selected from the group consisting of 7-deoxy-7-fluoro-Δ$^{12,13}$-iso-taxol and 2'-[{(2,2,2-trichloroethyl)oxy}carbonyl]-7-deoxy-7-fluoro-Δ$^{12,13}$-iso-taxol; and A compound according to Formula III, namely N-debenzoyl-N-(t-butyl)aminocarbonyl-7-deoxy-7-fluoro-Δ$^{12,13}$-iso-taxol.

An additional preferred embodiment of Formula III are compounds selected from the group consisting of 7-deoxy-7α-fluoro-Δ$^{12,13}$-iso-taxol, 7-deoxy-7β-fluoro-Δ$^{12,13}$-iso-taxol, 2'-[{(2,2,2-trichloroethyl)-oxy}carbonyl]-7-deoxy-7α-fluoro-Δ$^{12,13}$-iso-taxol and 2'-[{(2,2,2-trichloroethyl)-oxy}carbonyl]-7-deoxy-7β-fluoro-Δ$^{12,13}$-iso-taxol.

Another embodiment of the present invention are $\Delta^{6,7}$-$\Delta^{12,13}$-iso-taxol analogs of general Formula IV (or IVa) wherein:

$R_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro;

$R_2$ is selected from the group consisting of —H, —NHC(O)H, —NHC(O)C$_1$–C$_{10}$alkyl, —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro or —NHC(O)C$_3$–C$_8$ cycloalkyl; and $R_3$, $R_4$, $R_5$ and $R_{30}$ are as defined above.

A preferred embodiment of the present invention are $\Delta^{6,7}$-$\Delta^{12,13}$-iso-taxol analogs of general Formula IV (or IVa) where $R_1$ is phenyl or phenyl substituted with halo, $R_2$ is —NHC(O)C$_6$H$_5$, $R_3$ and $R_5$ are —H, and $R_{30}$ is —OC(O)CH$_3$. Another preferred embodiment of the subject invention is compounds of Formula IV (or IVa) where $R_1$ is preferably phenyl or phenyl substituted with halo, $R_2$ is —NHC(O)OC(CH$_3$)$_3$, and $R_3$ and $R_5$ are —H, and $R_{30}$ is —OH.

Another preferred embodiment of the subject invention are compounds of Formula IV (or IVa) where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

Preferred embodiments of Formula IV include:

A compound according to Formula IV, namely 7-deoxy-$\Delta^{6,7}$-$\Delta^{12,13}$-iso-taxol;

A compound according to Formula IV, namely 2'-[{(2,2,2-trichloroethyl)oxy}carbonyl]-7-deoxy-$\Delta^{6,7}$-$\Delta^{12,13}$-iso-taxol; and A compound according to Formula IV, namely 10-acetyl-7-deoxy-$\Delta^{6,7}$-$\Delta^{12,13}$-iso-taxotere; and A compound according to Formula IV, namely N-debenzoyl-N-(t-butyl)aminocarbonyl-7-deoxy-$\Delta^{6,7}$-$\Delta^{12,13}$-iso-taxol.

A preferred embodiment of the subject invention is compounds of Formula V (or Va) where $R_1$ is phenyl or phenyl substituted with halo, $R_2$ is —NHC(O)C$_6$H$_5$, $R_3$ and $R_5$ are —H, and $R_{30}$ is —C(O)CH$_3$.

Another preferred embodiment of the subject invention is compounds of Formula V (or Va) where $R_1$ is preferably phenyl or phenyl substituted with halo, $R_2$ is —NHC(O)OC(CH$_3$)$_3$, and $R_3$, $R_5$ and $R_{30}$ are —H. A further preferred embodiment of the subject invention is compounds of Formula II where $R_1$ is preferably phenyl or phenyl substituted with halo, $R_2$ is —NHC(O)OC(CH$_3$)$_3$, and $R_3$ and $R_5$ are —H, and $R_{30}$ is —C(O)CH$_3$. Another preferred embodiment of the subject invention is compounds of Formula I where $R_1$ is preferably phenyl or phenyl substituted with halo, $R_2$ is —NHC(O)NHC(CH$_3$)$_3$, $R_3$ and $R_5$ are —H, $R_4$ is —OH, and $R_{30}$ is —OH or —OCOCH$_3$.

A further embodiment of the present invention are iso-taxol analogs of general Formula V (or Va) wherein:

$R_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro;

$R_2$ is selected from the group consisting of —H, —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl; and $R_3$, $R_4$, $R_5$ and $R_{30}$ are as defined above.

The compounds of Formula V (or Va) include both the 7-α and 7-β configuration of the 7-hydroxy substitution.

An embodiment of the present invention are 7-deoxy-7-W-$\Delta^{12,13}$-iso-taxol analogs of general Formula VI (and VIa) wherein:

$R_1$ is selected from the group consisting of —CH$_3$, —C$_6$H$_5$ or phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro;

$R_2$ is selected from the group consisting of —H, —NHC(O)C$_1$–C$_{10}$alkyl (preferably —NHC(O)C$_4$–C$_6$alkyl), —NHC(O)phenyl, —NHC(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, hydroxy or nitro, —NHC(O)C(CH$_3$)=CHCH$_3$, —NHC(O)OC(CH$_3$)$_3$, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —NHC(O)C$_3$–C$_8$cycloalkyl;

$R_3$ is selected from the group consisting of —H, —NHC(O)phenyl or —NHC(O)OC(CH$_3$)$_3$; with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3^+$ HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R' [where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$X$^-$ where n is 1–3, R'$_4$ is —H or —C$_1$–C$_4$alkyl, R'$_5$ is —H, —C$_1$–C$_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is $NH_3$, $(HOC_2H_4)_3N$, $N(CH_3)_3$, $CH_3N(C_2H_4)_2NH$, $NH_2(CH_2)_6NH_2$, N-methylglucamine, NaOH or KOH], —OC(O) $(CH_2)_nNR^2R^3$ [where n is 1–3, $R^2$ is —H or —$C_1$–$C_3$alkyl and $R^3$—H or —$C_1$–$C_3$alkyl], —OC(O)CH(R")$NH_2$ [where R" is selected from the group consisting of —H, —$CH_3$, —$CH_2CH(CH_3)_2$, —CH($CH_3$)$CH_2CH_3$, —CH($CH_3$)$_2$, —$CH_2$phenyl, —$(CH_2)_4NH_2$, —$CH_2CH_2COOH$, —$(CH_2)_3NHC(=NH)NH_2$], the residue of the amino acid proline, —OC(O)CH=$CH_2$, —C(O)$CH_2CH_2$C(O)NH$CH_2CH_2SO_3^-Y^+$, —OC(O)$CH_2CH_2$C(O)NH$CH_2CH_2CH_2SO_3^-Y^+$ wherein $Y^+$ is $Na^+$ or $N^+(Bu)_4$, —OC(O)$CH_2CH_2$C(O)OC$H_2CH_2$OH;

$R_5$ is —H or —OH, with the overall proviso that when $R_5$ is —OH, $R_4$ is —H and with the further proviso that when $R_5$ is —H, $R_4$ is other than —H;

$R_{30}$ is —H, —OH or —OC(O)$CH_3$; and pharmaceutically acceptable salts thereof when the compound contains either an acidic or basic functional group.

Another embodiment of the present invention are 7-deoxy-7-W-$\Delta^{12,13}$-iso-taxol analogs of general Formula VI (and VIa) wherein:

$R_1$ is selected from the group consisting of —$CH_3$, —$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro;

$R_2$ is selected from the group consisting of —H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C($CH_3$)=CH$CH_3$, —NHC(O)OC($CH_3$)$_3$, —$NH_2$, —NHSO$_2$-4-methylphenyl, —NHC(O)$(CH_2)_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)$CH_2$C($CH_3$)$_3$, —NHC(O)C($CH_3$)$_3$, —NHC(O)OC$_1$–$C_{10}$alkyl, —NHC(O)NHC$_1$–$C_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl; and W is selected from the group consisting of
propionyl;
O-(2,2-dichloroethyl)carbonate;
O-(2-chloroethyl)carbonate;
O-methyl;
O-propyl;
O-allyl;
O-methoxymethyl;
O-ethoxymethyl;
O-methoxyethoxymethyl;
O-benzyloxymethyl;
O-(2,2,2-trichloroethoxy)methyl;
O-(2,2,2-trichloroethoxy)methoxymethyl; and $R_3$, $R_4$, $R_5$ and $R_{30}$ are as defined above.

A further preferred embodiment of the present invention are 7-deoxy-7-W-$\Delta^{12,13}$-iso-taxol analogs of general Formula VI wherein:

$R_1$ is selected from the group consisting of —$CH_3$, —$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro;

$R_2$ is selected from the group consisting of —H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C($CH_3$)=CH$CH_3$, —NHC(O)OC($CH_3$)$_3$, —$NH_2$, —NHSO$_2$-4-methylphenyl, —NHC(O)$(CH_2)_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)$CH_2$C($CH_3$)$_3$, —NHC(O)C($CH_3$)$_3$, —NHC(O)OC$_1$–$C_{10}$alkyl, —NHC(O)NHC$_1$–$C_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl;

W is selected from the group consisting of
O-ethoxymethyl;
O-methoxyethoxymethyl;
O-benzyloxymethyl;
O-(2,2,2-trichloroethoxy)methyl;
O-(2,2,2-trichloroethoxy)methoxymethyl; and $R_3$, $R_4$, $R_5$ and $R_{30}$ are as defined above.

A preferred embodiment of the subject invention is compounds of Formula VI where $R_1$ is phenyl or phenyl substituted with halo, $R_2$ is —NHC(O)$C_6H_5$, $R_3$ and $R_5$ are —H, and $R_{30}$ is —C(O)$CH_3$. Another preferred embodiment of the subject invention is compounds of Formula VI where $R_1$ is preferably phenyl or phenyl substituted with halo, $R_2$ is —NHC(O)OC($CH_3$)$_3$, and $R_3$, $R_5$ and $R_{30}$ are —H. A further preferred embodiment of the subject invention is compounds of Formula VI where $R_1$ is preferably phenyl or phenyl substituted with halo, $R_2$ is —NHC(O)OC($CH_3$)$_3$, and $R_3$ and $R_5$ are —H, and $R_{30}$ is —OC(O)$CH_3$. Another preferred embodiment of the subject invention is compounds of Formula VI where $R_1$ is preferably phenyl or phenyl substituted with halo, $R_2$ is —NHC(O)NHC($CH_3$)$_3$, $R_3$ and $R_5$ are —H, $R_4$ is —OH, and $R_{30}$ is —OH or —OCOCH$_3$.

In compounds of Formula VI, W is preferably selected from the group consisting of
propionyl;
O-(2,2-dichloroethyl)carbonate;
O-(2-chloroethyl)carbonate;
O-methyl;
O-propyl;
O-allyl;
O-methoxymethyl;
O-ethoxymethyl;
O-methoxyethoxymethyl;
O-benzyloxymethyl;
O-(2,2,2-trichloroethoxy)methyl;
O-(2,2,2-trichloroethoxy)methoxymethyl; and more preferably
O-methoxymethyl;
O-ethoxymethyl;
O-methoxyethoxymethyl;
O-benzyloxymethyl;
O-(2,2,2-trichloroethoxy)methyl; and
O-(2,2,2-trichloroethoxy)methoxymethyl.

Examples of —NHC(O)$C_1$–$C_{10}$alkyl include —NHC(O)-n-pentyl and —NHC(O)CH($CH_3$)$CH_2CH_3$.

Examples of $C_1$–$C_6$ alkyl include straight and branched alkyl chains, including for example methyl, ethyl, isopropyl, t-butyl, isobutyl and 2-methyl-pentyl.

Examples of $C_1$–$C_3$ alkoxy are methoxy, ethoxy, propoxy and isomeric forms thereof Halo refers to —F, —Br, —Cl or I, or $N_3$.

Examples of Formula II compounds of this invention include:

2'-[{(2,2,2-trichloroethyl)oxy}carbonyl]-7-deoxy-7β,8β-methano-$\Delta^{12,13}$-iso-taxol;
7-deoxy-7β,8β-methano-$\Delta^{12,13}$-iso-taxol;
2'-succinyl-7-deoxy-7β,8β-methano-$\Delta^{12,13}$-iso-taxol;
2'-(β-alanyl)-7-deoxy-7β,8β-methano-$\Delta^{12,13}$-iso-taxol formate;
2'-glutaryl-7-deoxy-7β,8β-methano-$\Delta^{12,13}$-iso-taxol;
2'-[-C(O)(CH$_2$)$_3$C(O)NH(CH$_2$)$_3$N(CH$_3$)$_2$]-7-deoxy-7β,8β-methano-$\Delta^{12,13}$-iso-taxol;
2'-(β-sulfopropionyl)-7-deoxy-7β,8β-methano-$\Delta^{12,13}$-iso-taxol;
2'-(2-sulfoethylamido)succinyl-7-deoxy-7β,8β-methano-$\Delta^{12,13}$-iso-taxol;
2'-(3-sulfopropylamido)succinyl-7-deoxy-7β,8β-methano-$\Delta^{12,13}$-iso-taxol;
2'-(triethylsilyl)-7-deoxy-7β,8β-methano-$\Delta^{12,13}$-iso-taxol;
2'-(t-butyldimethylsilyl)-7-deoxy-7β,8β-methano-$\Delta^{12,13}$-iso-taxol;
2'-(N,N-diethylaminopropionyl)-7-deoxy-7β,8β-methano-$\Delta^{12,13}$-iso-taxol;
2'-(N,N-dimethylglycyl)-7-deoxy-7β,8β-methano-$\Delta^{12,13}$-iso-taxol;
2'-(glycyl)-7-deoxy-7β,8β-methano-$\Delta^{12,13}$-iso-taxol;
2'-(L-alanyl)-7-deoxy-7β,8β-methano-$\Delta^{12,13}$-iso-taxol;
2'-(L-leucyl)-7-deoxy-7β,8β-methano-$\Delta^{12,13}$-iso-taxol;
2'-(L-isoleucyl)-7-deoxy-7β,8β-methano-$\Delta^{12,13}$-iso-taxol;
2'-(L-valyl)-7-deoxy-7β,8β-methano-$\Delta^{12,13}$-iso-taxol;
2'-(L-phenylalanyl)-7-deoxy-7β,8β-methano-$\Delta^{12,13}$-iso-taxol;
2'-(L-prolyl)-7-deoxy-7β,8β-methano-$\Delta^{12,13}$-iso-taxol;
2'-(L-lysyl)-7-deoxy-7β,8β-methano-$\Delta^{12,13}$-iso-taxol;
2'-(L-glutamyl)-7-deoxy-7β,8β-methano-$\Delta^{12,13}$-iso-taxol;
2'-(L-arginyl)-7-deoxy-7β,8β-methano-$\Delta^{12,13}$-iso-taxol;
7-deoxy-7β,8β-methano-$\Delta^{12,13}$-iso-taxotere;
10-acetyl-7-deoxy-7β,8β-methano-$\Delta^{12,13}$-iso-taxotere;
N-debenzoyl-N-tetrahydrofuran-3-yloxycarbonyl-7-deoxy-7β,8β-methano-$\Delta^{12,13}$-iso-taxol;
N-debenzoyl-N-(1-adamantoyl)-7-deoxy-7β,8β-methano-$\Delta^{12,13}$-iso-taxol;
N-debenzoyl-N-phenylaminocarbonyl-7-deoxy-7β,8β-methano-$\Delta^{12,13}$-iso-taxol;
N-debenzoyl-N-t-butylaminocarbonyl-7-deoxy-7β,8β-methano-$\Delta^{12,13}$-iso-taxol;
N-debenzoyl-N-(1-methyl-1-cyclohexylanoyl)-7-deoxy-7β,8β-methano-$\Delta^{12,13}$-iso-taxol;
N-debenzoyl-N-(1-phenyl-1-cyclopentanoyl)-7-deoxy-7β,8β-methano-$\Delta^{12,13}$-iso-taxol;
N-debenzoyl-N-phthalimido-7-deoxy-7β,8β-methano-$\Delta^{12,13}$-iso-taxol;
N-debenzoyl-N-t-butylaminothiocarbonyl-7-deoxy-7β,8β-methano-$\Delta^{12,13}$-iso-taxol;
N-debenzoyl-N-t-amyloxycarbonyl-7-deoxy-7β,8β-methano-$\Delta^{12,13}$-iso-taxol;
N-debenzoyl-N-neopentyloxycarbonyl-7-deoxy-7β,8β-methano-$\Delta^{12,13}$-iso-taxol;
N-debenzoyl-N-(2-chloro-1,1-dimethylethyl)oxycarbonyl-7-deoxy-7β,8β-methano-$\Delta^{12,13}$-iso-taxol;
N-debenzoyl-N-(3-methyl-3-pentyl)oxycarbonyl-7-deoxy-7β,8β-methano-$\Delta$12,13-iso-taxol;
3'-desphenyl-3'-(2-furyl)-7-deoxy-7β,8β-methano-$\Delta^{12,13}$-iso-taxol;
3'-desphenyl-3'-(2-thienyl)-7-deoxy-7β,8β-methano-$\Delta^{12,13}$-iso-taxol;
3'-desphenyl-3'-(1-naphthyl)-7-deoxy-7β,8β-methano-$\Delta^{12,13}$-iso-taxol;
3'-desphenyl-3'-(2-naphthyl)-7-deoxy-7β,8β-methano-$\Delta^{12,13}$-iso-taxol;
3'-desphenyl-3'-(4-methoxyphenyl)-7-deoxy-7β,8β-methano-$\Delta^{12,13}$-iso-taxol;
3'-desphenyl-3'-(4-chlorophenyl)-7-deoxy-7β,8β-methano-$\Delta^{12,13}$-iso-taxol;
3'-desphenyl-3'-(4-bromophenyl)-7-deoxy-7β,8β-methano-$\Delta^{12,13}$-iso-taxol;
3'-desphenyl-3'-(3,4methylenedioxyphenyl)-7-deoxy-7β,8β-methano-$\Delta^{12,13}$-iso-taxol;
3'-desphenyl-3'-(3,4-dimethoxyphenyl)-7-deoxy-7β,8β-methano-$\Delta^{12,13}$-iso-taxol;
3'-desphenyl-3'-(4-nitrophenyl)-7-deoxy-7β,8β-methano-$\Delta^{12,13}$-iso-taxol;
3'-desphenyl-3'-(4-fluorophenyl)-7-deoxy-7β,8β-methano-$\Delta^{12,13}$-iso-taxol;
N-debenzoyl-N-(4-bromobenzoyl)-7-deoxy-7β,8β-methano-$\Delta^{12,13}$-iso-taxol;
N-debenzoyl-N-(4-methylbenzoyl)-7-deoxy-7β,8β-methano-$\Delta^{12,13}$-iso-taxol;
N-debenzoyl-N-(4-t-butylbenzoyl)-7-deoxy-7β,8β-methano-$\Delta^{12,13}$-iso-taxol;
N-debenzoyl-N-(4-methoxybenzoyl)-7-deoxy-7β,8β-methano-$\Delta^{12,13}$-iso-taxol;
N-debenzoyl-N-(4-fluorobenzoyl)-3'-desphenyl-3'-(4-fluorophenyl)-7-deoxy-7β,8β-methano-$\Delta^{12,13}$-iso-taxol;
N-debenzoyl-N-(4-fluorobenzoyl)-7-deoxy-7β,8β-methano-$\Delta^{12,13}$-iso-taxol;
N-debenzoyl-N-(4-methylbenzoyl)-3'-desphenyl-3'-(4-chlorophenyl)-7-deoxy-7β,8β-methano-$\Delta^{12,13}$-iso-taxol;
N-debenzoyl-N-(4-chlorobenzoyl)-3'-desphenyl-3'-(4-fluorophenyl)-7-deoxy-7β,8β-methano-$\Delta^{12,13}$-iso-taxol;
N-debenzoyl-N-(4-bromobenzoyl)-3'-desphenyl-3'-(4-fluorophenyl)-7-deoxy-7β,8β-methano-$\Delta^{12,13}$-iso-taxol;
N-debenzoyl-N-(4-methylbenzoyl)-3'-desphenyl-3'-(4-fluorophenyl)-7-deoxy-7β,8β-methano-$\Delta^{12,13}$-iso-taxol;
N-debenzoyl-N-(4-fluorobenzoyl)-3'-desphenyl-3'-(4-methoxyphenyl)-7-deoxy-7β,8β-methano-$\Delta^{12,13}$-iso-taxol;
N-debenzoyl-N-(4-methylbenzoyl)-3'-desphenyl-3'-(4-methoxyphenyl)-7-deoxy-7β,8β-methano-$\Delta^{12,13}$-iso-taxol;
N-debenzoyl-N-(4-fluorobenzoyl)-3'-desphenyl-3'-(4-chlorophenyl)-7-deoxy-7β,8β-methano-$\Delta^{12,13}$-iso-taxol;
N-debenzoyl-N-(4-chlorobenzoyl)-3'-desphenyl-3'-(4-chlorophenyl)-7-deoxy-7β,8β-methano-$\Delta^{12,13}$-iso-taxol;
N-debenzoyl-N-(4-bromobenzoyl)-3'-desphenyl-3'-(4-chlorophenyl)-7-deoxy-7β,8β-methano-$\Delta^{12,13}$-iso-taxol;
N-debenzoyl-N-(4-t-butylbenzoyl)-3'-desphenyl-3'-(4-chlorophenyl)-7-deoxy-7β,8β-methano-$\Delta^{12,13}$-iso-taxol;
N-debenzoyl-N-(4-t-butylbenzoyl)-3'-desphenyl-3'-(4-fluorophenyl)-7-deoxy-7β,8β-methano-$\Delta^{12,13}$-iso-taxol;
N-debenzoyl-N-(4-chlorobenzoyl)-3'-desphenyl-3'-(4-methoxyphenyl)-7-deoxy-7β,8β-methano-$\Delta^{12,13}$-iso-taxol;
N-debenzoyl-N-(4-bromobenzoyl)-3'-desphenyl-3'-(4-methoxyphenyl)-7-deoxy-7β,8β-methano-$\Delta^{12,13}$-iso-taxol;
N-debenzoyl-N-(4-t-butylbenzoyl)-3'-desphenyl-3'-(4-methoxyphenyl)-7-deoxy-7β,8β-methano-$\Delta^{12,13}$-iso-taxol;
N-debenzoyl-N-(4-methoxybenzoyl)-3'-desphenyl-3'-(4-methoxyphenyl)-7-deoxy-7β,8β-methano-$\Delta^{12,13}$-iso-taxol;
N-debenzoyl-N-(t-butyl)aminocarbonyl-7-deoxy-7β,8β-methano-$\Delta^{12,13}$-iso-taxol; and
pharmaceutically acceptable salts thereof when the compound contains either an acidic or basic functional group.

Examples of Formula III compounds of this invention include:

2'-[{(2,2,2-trichloroethyl)oxy}carbonyl]-7-deoxy-7-fluoro-$\Delta^{12,13}$-iso-taxol;
7-deoxy-7-fluoro-$\Delta^{12,13}$-iso-taxol;
2'-succinyl-7-deoxy-7-fluoro-$\Delta^{12,13}$-iso-taxol;
2'-(β-alanyl)-7-deoxy-7-fluoro-$\Delta^{12,13}$-iso-taxol formate;
2'-glutaryl-7-deoxy-7-fluoro-$\Delta^{12,13}$-iso-taxol;
2'-[-C(O)(CH$_2$)$_3$C(O)NH(CH$_2$)$_3$N(CH$_3$)$_2$]-7-deoxy-7-fluoro-$\Delta^{12,13}$-iso-taxol;
2'-(β-sulfopropionyl)-7-deoxy-7-fluoro-$\Delta^{12,13}$-iso-taxol;
2'-(2-sulfoethylamido)succinyl-7-deoxy-7-fluoro-$\Delta^{12,13}$-iso-taxol;
2'-(3-sulfopropylamido)succinyl-7-deoxy-7-fluoro-$\Delta^{12,13}$-iso-taxol;
2'-(triethylsilyl)-7-deoxy-7-fluoro-$\Delta^{12,13}$-iso-taxol;
2'-(t-butyldimethylsilyl)-7-deoxy-7-fluoro-$\Delta^{12,13}$-iso-taxol;
2'-(N,N-diethylaminopropionyl)-7-deoxy-7-fluoro-$\Delta^{12,13}$-iso-taxol;
2'-(N,N-dimethylglycyl)-7-deoxy-7-fluoro-$\Delta^{12,13}$-iso-taxol;
2'-(glycyl)-7-deoxy-7-fluoro-$\Delta^{12,13}$-iso-taxol;
2'-(L-alanyl)-7-deoxy-7-fluoro-$\Delta^{12,13}$-iso-taxol;
2'-(L-leucyl)-7-deoxy-7-fluoro-$\Delta^{12,13}$-iso-taxol;
2'-(L-isoleucyl)-7-deoxy-7-fluoro-$\Delta^{12,13}$-iso-taxol;
2'-(L-valyl)-7-deoxy-7-fluoro-$\Delta^{12,13}$-iso-taxol;
2'-(L-phenylalanyl)-7-deoxy-7-fluoro-$\Delta^{12,13}$-iso-taxol;
2'-(L-prolyl)-7-deoxy-7-fluoro-$\Delta^{12,13}$-iso-taxol;
2'-(L-lysyl)-7-deoxy-7-fluoro-$\Delta^{12,13}$-iso-taxol;
2'-(L-glutamyl)-7-deoxy-7-fluoro-$\Delta^{12,13}$-iso-taxol;
2'-(L-arginyl)-7-deoxy-7-fluoro-$\Delta^{12,13}$-iso-taxol;
7-deoxy-7-fluoro-$\Delta^{12,13}$-iso-taxotere;
10-acetyl-7-deoxy-7-fluoro-$\Delta^{12,13}$-iso-taxotere;
N-debenzoyl-N-tetrahydropyran-4-yloxycarbonyl-7-deoxy-7-fluoro-$\Delta^{12,13}$-iso-taxol;
N-debenzoyl-N-pivaloyl-7-deoxy-7-fluoro-$\Delta^{12,13}$-iso-taxol;
N-debenzoyl-N-n-hexylaminocarbonyl-7-deoxy-7-fluoro-$\Delta^{12,13}$-iso-taxol;
N-debenzoyl-N-t-butylaminocarbonyl-7-deoxy-7-fluoro-$\Delta^{12,13}$-iso-taxol;
N-debenzoyl-N-(1-methyl-1-cyclohexylanoyl)-7-deoxy-7-fluoro-$\Delta^{12,13}$-iso-taxol;
N-debenzoyl-N-(1-phenyl-1-cyclopentanoyl)-7-deoxy-7-fluoro-$\Delta^{12,13}$-iso-taxol;
N-debenzoyl-N-phthalimido-7-deoxy-7-fluoro-$\Delta^{12,13}$-iso-taxol;
N-debenzoyl-N-t-butylaminothiocarbonyl-7-deoxy-7-fluoro-$\Delta^{12,13}$-iso-taxol;
N-debenzoyl-N-t-amyloxycarbonyl-7-deoxy-7-fluoro-$\Delta^{12,13}$-iso-taxol;
N-debenzoyl-N-neopentyloxycarbonyl-7-deoxy-7-fluoro-$\Delta^{12,13}$-iso-taxol;
N-debenzoyl-N-(2-chloro-1,1-dimethylethyl)oxycarbonyl-7-deoxy-7-fluoro-$\Delta^{12,13}$-iso-taxol;
N-debenzoyl-N-(3-methyl-3-pentyl)oxycarbonyl-7-deoxy-7-fluoro-$\Delta^{12,13}$-iso-taxol;
3'-desphenyl-3'-(2-furyl)-7-deoxy-7-fluoro-$\Delta^{12,13}$-iso-taxol;
3'-desphenyl-3'-(2-thienyl)-7-deoxy-7-fluoro-$\Delta^{12,13}$-iso-taxol;
3'-desphenyl-3'-(1-naphthyl)-7-deoxy-7-fluoro-$\Delta^{12,13}$-iso-taxol;
3'-desphenyl-3'-(2-naphthyl)-7-deoxy-7-fluoro-$\Delta^{12,13}$-iso-taxol;
3'-desphenyl-3'-(4-methoxyphenyl)-7-deoxy-7-fluoro-$\Delta^{12,13}$-iso-taxol;
3'-desphenyl-3'-(4-chlorophenyl)-7-deoxy-7-fluoro-$\Delta^{12,13}$-iso-taxol;
3'-desphenyl-3'-(4-bromophenyl)-7-deoxy-7-fluoro-$\Delta^{12,13}$-iso-taxol;
3'-desphenyl-3'-(3,4-methylenedioxyphenyl)-7-deoxy-7-fluoro-$\Delta^{12,13}$-iso-taxol;
3'-desphenyl-3'-(3,4-dimethoxyphenyl)-7-deoxy-7-fluoro-$\Delta^{12,13}$-iso-taxol;
3'-desphenyl-3'-(4-nitrophenyl)-7-deoxy-7-fluoro-$\Delta^{12,13}$-iso-taxol;
3'-desphenyl-3'-(4-fluorophenyl)-7-deoxy-7-fluoro-$\Delta^{12,13}$-iso-taxol;
N-debenzoyl-N-(4-bromobenzoyl)-7-deoxy-7-fluoro-$\Delta^{12,13}$-iso-taxol;
N-debenzoyl-N-(4-methylbenzoyl)-7-deoxy-7-fluoro-$\Delta^{12,13}$-iso-taxol;
N-debenzoyl-N-(4-t-butylbenzoyl)-7-deoxy-7-fluoro-$\Delta^{12,13}$-iso-taxol;
N-debenzoyl-N-(4-methoxybenzoyl)-7-deoxy-7-fluoro-$\Delta^{12,13}$-iso-taxol;
N-debenzoyl-N-(4-fluorobenzoyl)-3'-desphenyl-3'-(4-fluorophenyl)-7-deoxy-7-fluoro-$\Delta^{12,13}$-iso-taxol;
N-debenzoyl-N-(4-fluorobenzoyl)-7-deoxy-7-fluoro-$\Delta^{12,13}$-iso-taxol;
N-debenzoyl-N-(4-methylbenzoyl)-3'-desphenyl-3'-(4-chlorophenyl)-7-deoxy-7-fluoro-$\Delta^{12,13}$-iso-taxol;
N-debenzoyl-N-(4-chlorobenzoyl)-3'-desphenyl-3'-(4-fluorophenyl)-7-deoxy-7-fluoro-$\Delta^{12,13}$-iso-taxol;
N-debenzoyl-N-(4-bromobenzoyl)-3'-desphenyl-3'-(4-fluorophenyl)-7-deoxy-7-fluoro-$\Delta^{12,13}$-iso-taxol;
N-debenzoyl-N-(4-methylbenzoyl)-3'-desphenyl-3'-(4-fluorophenyl)-7-deoxy-7-fluoro-$\Delta^{12,13}$-iso-taxol;
N-debenzoyl-N-(4-fluorobenzoyl)-3'-desphenyl-3'-(4-methoxyphenyl)-7-deoxy-7-fluoro-$\Delta^{12,13}$-iso-taxol;
N-debenzoyl-N-(4-methylbenzoyl)-3'-desphenyl-3'-(4-methoxyphenyl)-7-deoxy-7-fluoro-$\Delta^{12,13}$-iso-taxol;
N-debenzoyl-N-(4-fluorobenzoyl)-3'-desphenyl-3'-(4-chlorophenyl)-7-deoxy-7-fluoro-$\Delta^{12,13}$-iso-taxol;
N-debenzoyl-N-(4-chlorobenzoyl)-3'-desphenyl-3'-(4-chlorophenyl)-7-deoxy-7-fluoro-$\Delta^{12,13}$-iso-taxol;
N-debenzoyl-N-(4-bromobenzoyl)-3'-desphenyl-3'-(4-chlorophenyl)-7-deoxy-7-fluoro-$\Delta^{12,13}$-iso-taxol;
N-debenzoyl-N-(4t-butylbenzoyl)-3'-desphenyl-3'-(4-chlorophenyl)-7-deoxy-7-fluoro-$\Delta^{12,13}$-iso-taxol;
N-debenzoyl-N-(4t-butylbenzoyl)-3'-desphenyl-3'-(4-fluorophenyl)-7-deoxy-7-fluoro-$\Delta^{12,13}$-iso-taxol;
N-debenzoyl-N-(4-chlorobenzoyl)-3'-desphenyl-3'-(4-methoxyphenyl)-7-deoxy-7-fluoro-$\Delta^{12,13}$-iso-taxol;
N-debenzoyl-N-(4-bromobenzoyl)-3'-desphenyl-3'-(4-methoxyphenyl)-7-deoxy-7-fluoro-$\Delta^{12,13}$-iso-taxol;
N-debenzoyl-N-(4-t-butylbenzoyl)-3'-desphenyl-3'-(4-methoxyphenyl)-7-deoxy-7-fluoro-$\Delta^{12,13}$-iso-taxol;
N-debenzoyl-N-(4-methoxybenzoyl)-3'-desphenyl-3'-(4-methoxyphenyl)-7-deoxy-7-fluoro-$\Delta^{12,13}$-iso-taxol; and
pharmaceutically acceptable salts thereof when the compound contains either an acidic or basic functional group.

Examples of Formula IV compounds of this invention include:

2'-{[(2,2,2-trichloroethyl)oxy]carbonyl}-7-deoxy-$\Delta^{6,7}$-$\Delta^{12,13}$-iso-taxol;
7-deoxy-$\Delta^{6,7}$-$\Delta^{12,13}$-iso-taxol;
N-desbenzoyl-N-benzyloxycarbonyl-2'-{[(2,2,2-trichloroethyl)oxy]carbonyl}-7-deoxy-$\Delta^{6,7}$-$\Delta^{12,13}$-iso-taxol;
N-desbenzoyl-N-benzyloxycarbonyl-7-deoxy-$\Delta^{6,7}$-$\Delta^{12,13}$-iso-taxol;
2'-succinyl-7-deoxy-$\Delta^{6,7}$-$\Delta^{12,13}$-iso-taxol;
2'-(β-alanyl)-7-deoxy-$\Delta^{6,7}$-$\Delta^{12,13}$-iso-taxol formate;
2'-glutaryl-7-deoxy-$\Delta^{6,7}$-$\Delta^{12,13}$-iso-taxol;
2'-[—C(O)(CH$_2$)$_3$C(O)NH(CH$_2$)$_3$N(CH$_3$)$_2$]-7-deoxy-$\Delta^{6,7}$-$\Delta^{12,13}$-iso-taxol;

2'-(β-sulfopropionyl)-7-deoxy-$\Delta^{6,7}$-$\Delta^{12,13}$-iso-taxol;
2'-(2-sulfoethylamido)succinyl-7-deoxy-$\Delta^{6,7}$-$\Delta^{12,13}$-iso-taxol;
2'-(3-sulfopropylamido)succinyl-7-deoxy-$\Delta^{6,7}$-$\Delta^{12,13}$-iso-taxol;
2'-(triethylsilyl)-7-deoxy-$\Delta^{6,7}$-$\Delta^{12,13}$-iso-taxol;
2'-(t-butyldimethylsilyl)-7-deoxy-$\Delta^{6,7}$-$\Delta^{12,13}$-iso-taxol;
2'-(N,N-diethylaminopropionyl)-7-deoxy-$\Delta^{6,7}$-$\Delta^{12,13}$-iso-taxol;
2'-(N,N-dimethylglycyl)-7-deoxy-$\Delta^{6,7}$-$\Delta^{12,13}$-iso-taxol;
2'-(glycyl)-7-deoxy-$\Delta^{6,7}$-$\Delta^{12,13}$-iso-taxol;
2'-(L-alanyl)-7-deoxy-$\Delta^{6,7}$-$\Delta^{12,13}$-iso-taxol;
2'-(L-leucyl)-7-deoxy-$\Delta^{6,7}$-$\Delta^{12,13}$-iso-taxol;
2'-(L-isoleucyl)-7-deoxy-$\Delta^{6,7}$-$\Delta^{12,13}$-iso-taxol;
2'-(L-valyl)-7-deoxy-$\Delta^{6,7}$-$\Delta^{12,13}$-iso-taxol;
2'-(L-phenylalanyl)-7-deoxy-$\Delta^{6,7}$-$\Delta^{12,13}$-iso-taxol;
2'-(L-prolyl)-7-deoxy-$\Delta^{6,7}$-$\Delta^{12,13}$-iso-taxol;
2'-(L-lysyl)-7-deoxy-$\Delta^{6,7}$-$\Delta^{12,13}$-iso-taxol;
2'-(L-glutamyl)-7-deoxy-$\Delta^{6,7}$-$\Delta^{12,13}$-iso-taxol;
2'-(L-arginyl)-7-deoxy-$\Delta^{6,7}$-$\Delta^{12,13}$-iso-taxol;
7-deoxy-$\Delta^{6,7}$-$\Delta^{12,13}$-iso-taxotere;
10-acetyl-7-deoxy-$\Delta^{6,7}$-$\Delta^{12,13}$-iso-taxotere;
N-debenzoyl-N-(1-methyl-1-cyclohexylanoyl)-7-deoxy-$\Delta^{6,7}$-$\Delta^{12,13}$-iso-taxol;
N-debenzoyl-N-(1-phenyl-1-cyclopentanoyl)-7-deoxy-$\Delta^{6,7}$-$\Delta^{12,13}$-iso-taxol;
N-debenzoyl-N-phthalimido-7-deoxy-$\Delta^{6,7}$-$\Delta^{12,13}$-iso-taxol;
N-debenzoyl-N-t-butylaminothiocarbonyl-7-deoxy-$\Delta^{6,7}$-$\Delta^{12,13}$-iso-taxol;
N-debenzoyl-N-t-amyloxycarbonyl-7-deoxy-$\Delta^{6,7}$-$\Delta^{12,13}$-iso-taxol;
N-debenzoyl-N-neopentyloxycarbonyl-7-deoxy-$\Delta^{6,7}$-$\Delta^{12,13}$-iso-taxol;
N-debenzoyl-N-(2-chloro-1,1-dimethylethyl)oxycarbonyl-7-deoxy-$\Delta^{6,7}$-$\Delta^{12,13}$-iso-taxol;
N-debenzoyl-N-(3-methyl-3-pentyl)oxycarbonyl-7-deoxy-$\Delta^{6,7}$-$\Delta^{12,13}$-iso-taxol;
3'-desphenyl-3'-(2-furyl)-7-deoxy-$\Delta^{6,7}$-$\Delta^{12,13}$-iso-taxol;
3'-desphenyl-3'-(2-thienyl)-7-deoxy-$\Delta^{6,7}$-$\Delta^{12,13}$-iso-taxol;
3'-desphenyl-3'-(1-naphthyl)-7-deoxy-$\Delta^{6,7}$-$\Delta^{12,13}$-iso-taxol;
3'-desphenyl-3'-(2-naphthyl)-7-deoxy-$\Delta^{6,7}$-$\Delta^{12,13}$-iso-taxol;
3'-desphenyl-3'-(4-methoxyphenyl)-7-deoxy-$\Delta^{6,7}$-$\Delta^{12,13}$-iso-taxol;
3'-desphenyl-3'-(4-chlorophenyl)-7-deoxy-$\Delta^{6,7}$-$\Delta^{12,13}$-iso-taxol;
3'-desphenyl-3'-(4-bromophenyl)-7-deoxy-$\Delta^{6,7}$-$\Delta^{12,13}$-iso-taxol;
3'-desphenyl-3'-(3,4-methylenedioxyphenyl)-7-deoxy-$\Delta^{6,7}$-$\Delta^{12,13}$-iso-taxol;
3'-desphenyl-3'-(3,4-dimethoxyphenyl)-7-deoxy-$\Delta^{6,7}$-$\Delta^{12,13}$-iso-taxol;
3'-desphenyl-3'-(4-nitrophenyl)-7-deoxy-$\Delta^{6,7}$-$\Delta^{12,13}$-iso-taxol;
3'-desphenyl-3'-(4-fluorophenyl)-7-deoxy-$\Delta^{6,7}$-$\Delta^{12,13}$-iso-taxol;
N-debenzoyl-N-(4-bromobenzoyl)-7-deoxy-$\Delta^{6,7}$-$\Delta^{12,13}$-iso-taxol;
N-debenzoyl-N-(4-methylbenzoyl)-7-deoxy-$\Delta^{6,7}$-$\Delta^{12,13}$-iso-taxol;
N-debenzoyl-N-(4t-butylbenzoyl)-7-deoxy-$\Delta^{6,7}$-$\Delta^{12,13}$-iso-taxol;
N-debenzoyl-N-(4-methoxybenzoyl)-7-deoxy-$\Delta^{6,7}$-$\Delta^{12,13}$-iso-taxol;
N-debenzoyl-N-(4-fluorobenzoyl)-3'-desphenyl-3'-(4-fluorophenyl)-7-deoxy-$\Delta^{6,7}$-$\Delta^{12,13}$-iso-taxol;
N-debenzoyl-N-(4-fluorobenzoyl)-3'-desphenyl-3'-(4-chlorophenyl)-7-deoxy-$\Delta^{6,7}$-$\Delta^{12,13}$-iso-taxol;
N-debenzoyl-N-(4-methylbenzoyl)-3'-desphenyl-3'-(4-chlorophenyl)-7-deoxy-$\Delta^{6,7}$-$\Delta^{12,13}$-iso-taxol;
N-debenzoyl-N-(4-chlorobenzoyl)-3'-desphenyl-3'-(4-fluorophenyl)-7-deoxy-$\Delta^{6,7}$-$\Delta^{12,13}$-iso-taxol;
N-debenzoyl-N-(4-bromobenzoyl)-3'-desphenyl-3'-(4-fluorophenyl)-7-deoxy-$\Delta^{6,7}$-$\Delta^{12,13}$-iso-taxol;
N-debenzoyl-N-(4-methylbenzoyl)-3'-desphenyl-3'-(4-fluorophenyl)-7-deoxy-$\Delta^{6,7}$-$\Delta^{12,13}$-iso-taxol;
N-debenzoyl-N-(4-fluorobenzoyl)-3'-desphenyl-3'-(4-methoxyphenyl)-7-deoxy-$\Delta^{6,7}$-$\Delta^{12,13}$-iso-taxol;
N-debenzoyl-N-(4-methylbenzoyl)-3'-desphenyl-3'-(4-methoxyphenyl)-7-deoxy-$\Delta^{6,7}$-$\Delta^{12,13}$-iso-taxol;
N-debenzoyl-N-(4-fluorobenzoyl)-3'-desphenyl-3'-(4-chlorophenyl)-7-deoxy-$\Delta^{6,7}$-$\Delta^{12,13}$-iso-taxol;
N-debenzoyl-N-(4-chlorobenzoyl)-3'-desphenyl-3'-(4-chlorophenyl)-7-deoxy-$\Delta^{6,7}$-$\Delta^{12,13}$-iso-taxol;
N-debenzoyl-N-(4-bromobenzoyl)-3'-desphenyl-3'-(4-chlorophenyl)-7-deoxy-$\Delta^{6,7}$-$\Delta^{12,13}$-iso-taxol;
N-debenzoyl-N-(4-t-butylbenzoyl)-3'-desphenyl-3'-(4-chlorophenyl)-7-deoxy-$\Delta^{6,7}$-$\Delta^{12,13}$-iso-taxol;
N-debenzoyl-N-(4-t-butylbenzoyl)-3'-desphenyl-3'-(4-fluorophenyl)-7-deoxy-$\Delta^{6,7}$-$\Delta^{12,13}$-iso-taxol;
N-debenzoyl-N-(4-chlorobenzoyl)-3'-desphenyl-3'-(4-methoxyphenyl)-7-deoxy-$\Delta^{6,7}$-$\Delta^{12,13}$-iso-taxol;
N-debenzoyl-N-(4-bromobenzoyl)-3'-desphenyl-3'-(4-methoxyphenyl)-7-deoxy-$\Delta^{6,7}$-$\Delta^{12,13}$-iso-taxol;
N-debenzoyl-N-(4-t-butylbenzoyl)-3'-desphenyl-3'-(4-methoxyphenyl)-7-deoxy-$\Delta^{6,7}$-$\Delta^{12,13}$-iso-taxol;
N-debenzoyl-N-(4methoxybenzoyl)-3'-desphenyl-3'-(4-methoxyphenyl)-7-deoxy-$\Delta^{6,7}$-$\Delta^{12,13}$-iso-taxol;
N-debenzoyl-N-(t-butyl)aminocarbonyl-7-deoxy-$\Delta^{6,7}$-$\Delta^{12,13}$-iso-taxol; and
pharmaceutically acceptable salts thereof when the compound contains either an acidic or basic functional group.

Examples of Formula V compounds of this invention include:
2'-[{(2,2,2-trichloroethyl)oxy}carbonyl]-$\Delta^{12,13}$-iso-taxol;
$\Delta^{12,13}$-iso-taxol;
2'-succinyl-$\Delta^{12,13}$-iso-taxol;
2'-(β-alanyl)-$\Delta^{12,13}$-iso-taxol formate;
2'-glutaryl-$\Delta^{12,13}$-iso-taxol;
2'-[—C(O)(CH$_2$)$_3$C(O)NH(CH$_2$)$_3$N(CH$_3$)$_2$]-$\Delta^{12,13}$-iso-taxol;
2'-(β-sulfopropionyl)-$\Delta^{12,13}$-iso-taxol;
2'-(2-sulfoethylamido)succinyl-$\Delta^{12,13}$-iso-taxol;
2'-(3-sulfopropylamido)succinyl-$\Delta^{12,13}$-iso-taxol;
2'-(triethylsilyl)-$\Delta^{12,13}$-iso-taxol;
2'-(t-butyldimethylsilyl)-$\Delta^{12,13}$-iso-taxol;
2'-(N,N-diethylaminopropionyl)-$\Delta^{12,13}$-iso-taxol;
2'-(N,N-dimethylglycyl)-$\Delta^{12,13}$-iso-taxol;
2'-(glycyl)-$\Delta^{12,13}$-iso-taxol;
2'-(L-alanyl)-$\Delta^{12,13}$-iso-taxol;
2'-(L-leucyl)-$\Delta^{12,13}$-iso-taxol;
2'-(L-isoleucyl)-$\Delta^{12,13}$-iso-taxol;
2'-(L-valyl)-$\Delta^{12,13}$-iso-taxol;
2'-(L-phenylalanyl)-$\Delta^{12,13}$-iso-taxol;
2'-(L-prolyl)-$\Delta^{12,13}$-iso-taxol;
2'-(L-lysyl)-$\Delta^{12,13}$-iso-taxol;
2'-(L-glutamyl)-$\Delta^{12,13}$-iso-taxol;
2'-(L-arginyl)-$\Delta^{12,13}$-iso-taxol;
$\Delta^{12,13}$-iso-taxotere;
10-acetyl-$\Delta^{12,13}$-iso-taxotere;
N-debenzoyl-N-tetrahydropyran-4-yloxycarbonyl-$\Delta^{12,13}$-iso-taxol;
N-debenzoyl-N-pivaloyl-$\Delta^{12,13}$-iso-taxol;
N-debenzoyl-N-n-hexylaminocarbonyl-$\Delta^{12,13}$-iso-taxol;
N-debenzoyl-N-(1-methyl-1-cyclohexylanoyl)-$\Delta^{12,13}$-iso-taxol;

N-debenzoyl-N-(1-phenyl-1-cyclopentanoyl)-$\Delta^{12,13}$-iso-taxol;
N-debenzoyl-N-phthalimido-$\Delta^{12,13}$-iso-taxol;
N-debenzoyl-N-t-butylaminothiocarbonyl-$\Delta^{12,13}$-iso-taxol;
N-debenzoyl-N-t-amyloxycarbonyl-$\Delta^{12,13}$-iso-taxol;
N-debenzoyl-N-neopentyloxycarbonyl-$\Delta^{12,13}$-iso-taxol;
N-debenzoyl-N-(2-chloro-1,1-dimethylethyl)oxycarbonyl-$\Delta^{12,13}$-iso-taxol;
N-debenzoyl-N-(3-methyl-3-pentyl)oxycarbonyl-$\Delta^{12,13}$-iso-taxol;
3'-desphenyl-3'-(2-furyl)-$\Delta^{12,13}$-iso-taxol;
3'-desphenyl-3'-(2-thienyl)-$\Delta^{12,13}$-iso-taxol;
3'-desphenyl-3'-(1-naphthyl)-$\Delta^{12,13}$-iso-taxol;
3'-desphenyl-3'-(2-naphthyl)-$\Delta^{12,13}$-iso-taxol;
3'-desphenyl-3'-(4-methoxyphenyl)-$\Delta^{12,13}$-iso-taxol;
3'-desphenyl-3'-(4-chlorophenyl)-$\Delta^{12,13}$-iso-taxol;
3'-desphenyl-3'-(4-bromophenyl)-$\Delta^{12,13}$-iso-taxol;
3'-desphenyl-3'-(3,4-methylenedioxyphenyl)-$\Delta^{12,13}$-iso-taxol;
3'-desphenyl-3'-(3,4-dimethoxyphenyl)-$\Delta^{12,13}$-iso-taxol;
3'-desphenyl-3'-(4-nitrophenyl)-$\Delta^{12,13}$-iso-taxol;
3'-desphenyl-3'-(4-fluorophenyl)-$\Delta^{12,13}$-iso-taxol;
N-debenzoyl-N-(4-bromobenzoyl)-$\Delta^{12,13}$-iso-taxol;
N-debenzoyl-N-(4-methylbenzoyl)-$\Delta^{12,13}$-iso-taxol;
N-debenzoyl-N-(4-t-butylbenzoyl)-$\Delta^{12,13}$-iso-taxol;
N-debenzoyl-N-(4-methoxybenzoyl)-$\Delta^{12,13}$-iso-taxol;
N-debenzoyl-N-(4-fluorobenzoyl)-3'-desphenyl-3'-(4-fluorophenyl)-$\Delta^{12,13}$-iso-taxol;
N-debenzoyl-N-(4-fluorobenzoyl)-$\Delta^{12,13}$-iso-taxol;
N-debenzoyl-N-(4-methylbenzoyl)-3'-desphenyl-3'-(4-chlorophenyl)-$\Delta^{12,13}$-iso-taxol;
N-debenzoyl-N-(4-chlorobenzoyl)-3'-desphenyl-3'-(4-fluorophenyl)-$\Delta^{12,13}$-iso-taxol;
N-debenzoyl-N-(4-bromobenzoyl)-3'-desphenyl-3'-(4-fluorophenyl)-$\Delta^{12,13}$-iso-taxol;
N-debenzoyl-N-(4-methylbenzoyl)-3'-desphenyl-3'-(4-fluorophenyl)-$\Delta^{12,13}$-iso-taxol;
N-debenzoyl-N-(4-fluorobenzoyl)-3'-desphenyl-3'-(4-methoxyphenyl)-$\Delta^{12,13}$-iso-taxol;
N-debenzoyl-N-(4-methylbenzoyl)-3'-desphenyl-3'-(4-methoxyphenyl)-$\Delta^{12,13}$-iso-taxol;
N-debenzoyl-N-(4-fluorobenzoyl)-3'-desphenyl-3'-(4-chlorophenyl)-$\Delta^{12,13}$-iso-taxol;
N-debenzoyl-N-(4-chlorobenzoyl)-3'-desphenyl-3'-(4-chlorophenyl)-$\Delta^{12,13}$-iso-taxol;
N-debenzoyl-N-(4-bromobenzoyl)-3'-desphenyl-3'-(4-chlorophenyl)-$\Delta^{12,13}$-iso-taxol;
N-debenzoyl-N-(4-t-butylbenzoyl)-3'-desphenyl-3'-(4-chlorophenyl)-$\Delta^{12,13}$-iso-taxol;
N-debenzoyl-N-(4-t-butylbenzoyl)-3'-desphenyl-3'-(4-fluorophenyl)-$\Delta^{12,13}$-iso-taxol;
N-debenzoyl-N-(4-chlorobenzoyl)-3'-desphenyl-3'-(4-methoxyphenyl)-$\Delta^{12,13}$-iso-taxol;
N-debenzoyl-N-(4-bromobenzoyl)-3'-desphenyl-3'-(4-methoxyphenyl)-$\Delta^{12,13}$-iso-taxol;
N-debenzoyl-N-(4-t-butylbenzoyl)-3'-desphenyl-3'-(4-methoxyphenyl)-$\Delta^{12,13}$-iso-taxol;
N-debenzoyl-N-(4-methoxybenzoyl)-3'-desphenyl-3'-(4-methoxyphenyl)-$\Delta^{12,13}$-iso-taxol;
N-debenzoyl-N-(t-butyl)aminocarbonyl-$\Delta^{12,13}$-iso-taxol; and
pharmaceutically acceptable salts thereof when the compound contains either an acidic or basic functional group.

Additional preferred embodiments of the invention include:

7-deoxy-7β,8β-methano-$\Delta^{12,13}$-iso-taxotere; N-de-(t-butyloxycarbonyl)-N-(t-butyl)aminocarbonyl-7-deoxy-7β,8β-methano-$\Delta^{12,13}$-iso-taxotere; 7-deoxy-7-fluoro-$\Delta^{12,13}$-iso-taxotere; N-de-(t-butyloxycarbonyl)-N-(t-butyl)aminocarbonyl-7-deoxy-7-fluoro-$\Delta^{12,13}$-iso-taxotere; 7-deoxy-$\Delta^{6,7}$-$\Delta^{12,13}$-iso-taxotere; and N-de-(t-butyloxycarbonyl)-N-(t-butyl)aminocarbonyl-7-deoxy-$\Delta^{6,7}$-$\Delta^{12,13}$-iso-taxotere.

Examples of Formula IIa compounds of the invention include:

2-debenzoyl-2-(m-cyanobenzoyl)-7-deoxy-7β,8β-methano-$\Delta^{12,13}$-iso-taxol;
2-debenzoyl-2-(m-cyanobenzoyl)-2'-[{(2,2,2-trichloroethyl)oxy}carbonyl]-7-deoxy-7β,8β-methano-$\Delta^{12,13}$-iso-taxol;
2-debenzoyl-2-(m-cyanobenzoyl)-10-acetyl-7-deoxy-7β,8β-methano-$\Delta^{12,13}$-iso-taxotere;
2-debenzoyl-2-(m-cyanobenzoyl)-N-debenzoyl-N-(t-butyl)aminocarbonyl-7-deoxy-7β,8β-methano-$\Delta^{12,13}$-iso-taxol;
2-debenzoyl-2-(m-methoxybenzoyl)-7-deoxy-7β,8β-methano-$\Delta^{12,13}$-iso-taxol;
2-debenzoyl-2-(m-methoxybenzoyl)-2'-[{(2,2,2-trichloroethyl)oxy}carbonyl]-7-deoxy-7β,8β-methano-$\Delta^{12,13}$-iso-taxol;
2-debenzoyl-2-(m-methoxybenzoyl)-10-acetyl-7-deoxy-7β,8β-methano-$\Delta^{12,13}$-iso-taxotere;
2-debenzoyl-2-(m-methoxybenzoyl)-N-debenzoyl-N-(t-butyl)aminocarbonyl-7-deoxy-7β,8β-methano-$\Delta^{12,13}$-iso-taxol;
2-debenzoyl-2-(m-chlorobenzoyl)-7-deoxy-7β,8β-methano-$\Delta^{12,13}$-iso-taxol;
2-debenzoyl-2-(m-chlorobenzoyl)-2'-[{(2,2,2-trichloroethyl)oxy}carbonyl]-7-deoxy-7β,8β-methano-$\Delta^{12,13}$-iso-taxol;
2-debenzoyl-2-(m-chlorobenzoyl)-10-acetyl-7-deoxy-7β,8β-methano-$\Delta^{12,13}$-iso-taxotere;
2-debenzoyl-2-(m-chlorobenzoyl)-N-debenzoyl-N-(t-butyl)aminocarbonyl-7-deoxy-7β,8β-methano-$\Delta^{12,13}$-iso-taxol;
2-debenzoyl-2-(m-azidobenzoyl)-7-deoxy-7β,8β-methano-$\Delta^{12,13}$-iso-taxol;
2-debenzoyl-2-(m-azidobenzoyl)-2'-[{(2,2,2-trichloroethyl)oxy}carbonyl]-7-deoxy-7β,8β-methano-$\Delta^{12,13}$-iso-taxol;
2-debenzoyl-2-(m-azidobenzoyl)-10-acetyl-7-deoxy-7β,8β-methano-$\Delta^{12,13}$-iso-taxotere;
2-debenzoyl-2-(m-azidobenzoyl)-N-debenzoyl-N-(t-butyl)aminocarbonyl-7-deoxy-7β,8β-methano-$\Delta^{12,13}$-iso-taxol;
2-debenzoyl-2-(p-cyanobenzoyl)-7-deoxy-7β,8β-methano-$\Delta^{12,13}$-iso-taxol;
2-debenzoyl-2-(p-cyanobenzoyl)-2'-[{(2,2,2-trichloroethyl)oxy}carbonyl]-7-deoxy-7β,8β-methano-$\Delta^{12,13}$-iso-taxol;
2-debenzoyl-2-(p-cyanobenzoyl)-10-acetyl-7-deoxy-7β,8β-methano-$\Delta^{12,13}$-iso-taxotere;
2-debenzoyl-2-(p-cyanobenzoyl)-N-debenzoyl-N-(t-butyl)aminocarbonyl-7-deoxy-7β,8β-methano-$\Delta^{12,13}$-iso-taxol;
2-debenzoyl-2-(p-methoxybenzoyl)-7-deoxy-7β,8β-methano-$\Delta^{12,13}$-iso-taxol;
2-debenzoyl-2-(p-methoxybenzoyl)-2'-[{(2,2,2-trichloroethyl)oxy}carbonyl]-7-deoxy-7β,8β-methano-$\Delta^{12,13}$-iso-taxol;
2-debenzoyl-2-(p-methoxybenzoyl)-10-acetyl-7-deoxy-7β,8β-methano-$\Delta^{12,13}$-iso-taxotere;
2-debenzoyl-2-(p-methoxybenzoyl)-N-debenzoyl-N-(t-butyl)aminocarbonyl-7-deoxy-7β,8β-methano-$\Delta^{12,13}$-iso-taxol;
2-debenzoyl-2-(p-chlorobenzoyl)-7-deoxy-7β,8β-methano-$\Delta^{12,13}$-iso-taxol;
2-debenzoyl-2-(p-chlorobenzoyl)-2'-[{(2,2,2-trichloroethyl)oxy}carbonyl]-7-deoxy-7β,8β-methano-$\Delta^{12,13}$-iso-taxol;
2-debenzoyl-2-(p-chlorobenzoyl)-10-acetyl-7-deoxy-7β,8β-methano-$\Delta^{12,13}$-iso-taxotere;

2-debenzoyl-2-(p-chlorobenzoyl)-N-debenzoyl-N-(t-butyl)
aminocarbonyl-7-deoxy-7β,8β-methano-Δ$^{12,13}$-iso-taxol;
2-debenzoyl-2-(p-azidobenzoyl)-7-deoxy-7β,8β-methano-
Δ$^{12,13}$-iso-taxol;
2-debenzoyl-2-(p-azidobenzoyl)-2'-[{(2,2,2-trichloroethyl)
oxy}carbonyl]-7-deoxy-7β,8β-methano-Δ$^{12,13}$-iso-taxol;
2-debenzoyl-2-(p-azidobenzoyl)-10-acetyl-7-deoxy-7β,8β-
methano-Δ$^{12,13}$-iso-taxotere; and
2-debenzoyl-2-(p-azidobenzoyl)-N-debenzoyl-N-(t-butyl)
aminocarbonyl-7-deoxy-7β,8β-methano-Δ$^{12,13}$-iso-taxol.
Examples of Formula IIIa compounds of the invention include:
2-debenzoyl-2-(m-cyanobenzoyl)-7-deoxy-7-fluoro-Δ$^{12,13}$-
iso-taxol;
2-debenzoyl-2-(m-cyanobenzoyl)-2'-[{(2,2,2-
trichloroethyl)oxy}carbonyl]-7-deoxy-7-fluoro-Δ$^{12,13}$-
iso-taxol;
2-debenzoyl-2-(m-cyanobenzoyl)-N-debenzoyl-N-(t-butyl)
aminocarbonyl-7-deoxy-7-fluoro-Δ$^{12,13}$-iso-taxol;
2-debenzoyl-2-(m-methoxybenzoyl)-7-deoxy-7-fluoro-
Δ$^{12,13}$-iso-taxol;
2-debenzoyl-2-(m-methoxybenzoyl)-2'-[{(2,2,2-
trichloroethyl)oxy}carbonyl]-7-deoxy-7-fluoro-Δ$^{12,13}$-
iso-taxol;
2-debenzoyl-2-(m-methoxybenzoyl)-N-debenzoyl-N-(t-
butyl)aminocarbonyl-7-deoxy-7-fluoro-Δ$^{12,13}$-iso-taxol;
2-debenzoyl-2-(m-chlorobenzoyl)-7-deoxy-7-fluoro-Δ$^{12,13}$-
iso-taxol;
2-debenzoyl-2-(m-chlorobenzoyl)-2'-[{(2,2,2-
trichloroethyl)oxy}carbonyl]-7-deoxy-7-fluoro-Δ$^{12,13}$-
iso-taxol;
2-debenzoyl-2-(m-chlorobenzoyl)-N-debenzoyl-N-(t-butyl)
aminocarbonyl-7-deoxy-7-fluoro-Δ$^{12,13}$-iso-taxol;
2-debenzoyl-2-(m-azidobenzoyl)-7-deoxy-7-fluoro-Δ$^{12,13}$-
iso-taxol;
2-debenzoyl-2-(m-azidobenzoyl)-2'-[{(2,2,2-trichloroethyl)
oxy}carbonyl]-7-deoxy-7-fluoro-Δ$^{12,13}$-iso-taxol;
2-debenzoyl-2-(m-azidobenzoyl)-N-debenzoyl-N-(t-butyl)
aminocarbonyl-7-deoxy-7-fluoro-Δ$^{12,13}$-iso-taxol;
2-debenzoyl-2-(p-cyanobenzoyl)-7-deoxy-7-fluoro-Δ$^{12,13}$-
iso-taxol;
2-debenzoyl-2-(p-cyanobenzoyl)-2'-[{(2,2,2-trichloroethyl)
oxy}carbonyl]-7-deoxy-7-fluoro-Δ$^{12,13}$-iso-taxol;
2-debenzoyl-2-(p-cyanobenzoyl)-N-debenzoyl-N-(t-butyl)
aminocarbonyl-7-deoxy-7-fluoro-Δ$^{12,13}$-iso-taxol;
2-debenzoyl-2-(p-methoxybenzoyl)-7-deoxy-7-fluoro-
Δ$^{12,13}$-iso-taxol;
2-debenzoyl-2-(p-methoxybenzoyl)-2'-[{(2,2,2-
trichloroethyl)oxy}carbonyl]-7-deoxy-7-fluoro-Δ$^{12,13}$-
iso-taxol;
2-debenzoyl-2-(p-methoxybenzoyl)-N-debenzoyl-N-(t-
butyl)aminocarbonyl-7-deoxy-7-fluoro-Δ$^{12,13}$-iso-taxol;
2-debenzoyl-2-(p-chlorobenzoyl)-7-deoxy-7-fluoro-Δ$^{12,13}$-
iso-taxol;
2-debenzoyl-2-(p-chlorobenzoyl)-2'-[{(2,2,2-trichloroethyl)
oxy}carbonyl]-7-deoxy-7-fluoro-Δ$^{12,13}$-iso-taxol;
2-debenzoyl-2-(p-chlorobenzoyl)-N-debenzoyl-N-(t-butyl)
aminocarbonyl-7-deoxy-7-fluoro-Δ$^{12,13}$-iso-taxol;
2-debenzoyl-2-(p-azidobenzoyl)-7-deoxy-7-fluoro-Δ$^{12,13}$-
iso-taxol;
2-debenzoyl-2-(p-azidobenzoyl)-2'-[{(2,2,2-trichloroethyl)
oxy}carbonyl]-7-deoxy-7-fluoro-Δ$^{12,13}$-iso-taxol;
2-debenzoyl-2-(p-azidobenzoyl)-N-debenzoyl-N-(t-butyl)
aminocarbonyl-7-deoxy-7-fluoro-Δ$^{12,13}$-iso-taxol;
2-debenzoyl-2-(m-cyanobenzoyl)-10-acetyl-7-deoxy-7-
fluoro-Δ$^{12,13}$-iso-taxotere;
2-debenzoyl-2-(m-methoxybenzoyl)-10-acetyl-7-deoxy-7-
fluoro-Δ$^{12,13}$-iso-taxotere;
2-debenzoyl-2-(m-chlorobenzoyl)-10-acetyl-7-deoxy-7-
fluoro-Δ$^{12,13}$-iso-taxotere;
2-debenzoyl-2-(p-chlorobenzoyl)-10-acetyl-7-deoxy-7-
fluoro-Δ$^{12,13}$-iso-taxotere;
2-debenzoyl-2-(p-cyanobenzoyl)-10-acetyl-7-deoxy-7-
fluoro-$^{12,13}$-iso-taxotere;
2-debenzoyl-2-(p-azidobenzoyl)-10-acetyl-7-deoxy-7-
fluoro-Δ$^{12,13}$-iso-taxotere; and
2-debenzoyl-2-(m-azidobenzoyl)-10-acetyl-7-deoxy-7-
fluoro-Δ$^{12,13}$-iso-taxotere.
Examples of Formula IVa compounds of the invention include:
2-debenzoyl-2-(m-cyanobenzoyl)-7-deoxy-Δ$^{6,7}$-Δ$^{12,13}$-iso-
taxol;
2-debenzoyl-2-(m-cyanobenzoyl)-2'-[{(2,2,2-
trichloroethyl)oxy}carbonyl]-7-deoxy-Δ$^{6,7}$-Δ$^{12,13}$-iso-
taxol;
2-debenzoyl-2-(m-cyanobenzoyl)-10-acetyl-7-deoxy-Δ$^{6,7}$-
Δ$^{12,13}$-iso-taxotere;
2-debenzoyl-2-(m-cyanobenzoyl)-N-debenzoyl-N-(t-butyl)
aminocarbonyl-7-deoxy-Δ$^{6,7}$-Δ$^{12,13}$-iso-taxol;
2-debenzoyl-2-(m-methoxybenzoyl)-7-deoxy-Δ$^{6,7}$-Δ$^{12,13}$-
iso-taxol;
2-debenzoyl-2-(m-methoxybenzoyl)-2'-[{(2,2,2-
trichloroethyl)oxy}carbonyl]-7-deoxy-Δ$^{6,7}$-Δ$^{12,13}$-iso-
taxol;
2-debenzoyl-2-(m-methoxybenzoyl)-10-acetyl-7-deoxy-
Δ$^{6,7}$-Δ$^{12,13}$-iso-taxotere;
2-debenzoyl-2-(m-methoxybenzoyl)-N-debenzoyl-N-(t-
butyl)aminocarbonyl-7-deoxy-Δ$^{6,7}$-Δ$^{12,13}$-iso-taxol;
2-debenzoyl-2-(m-chlorobenzoyl)-7-deoxy-Δ$^{6,7}$-Δ$^{12,13}$-iso-
taxol;
2-debenzoyl-2-(m-chlorobenzoyl)-2'-[{(2,2,2-
trichloroethyl)oxy}carbonyl]-7-deoxy-Δ$^{6,7}$-Δ$^{12,13}$-iso-
taxol;
2-debenzoyl-2-(m-chlorobenzoyl)-10-acetyl-7-deoxy-Δ$^{6,7}$-
Δ$^{12,13}$-iso-taxotere;
2-debenzoyl-2-(m-chlorobenzoyl)-N-debenzoyl-N-(t-butyl)
aminocarbonyl-7-deoxy-Δ$^{6,7}$-Δ$^{12,13}$-iso-taxol;
2-debenzoyl-2-(m-azidobenzoyl)-7-deoxy-Δ$^{6,7}$-Δ$^{12,13}$-iso-
taxol;
2-debenzoyl-2-(m-azidobenzoyl)-2'-[{(2,2,2-trichloroethyl)
oxy}carbonyl]-7-deoxy-Δ$^{6,7}$-Δ$^{12,13}$-iso-taxol;
2-debenzoyl-2-(m-azidobenzoyl)-10-acetyl-7-deoxy-Δ$^{6,7}$-
Δ$^{12,13}$-iso-taxotere;
2-debenzoyl-2-(m-azidobenzoyl)-N-debenzoyl-N-(t-butyl)
aminocarbonyl-7-deoxy-Δ$^{6,7}$-Δ$^{12,13}$-iso-taxol;
2-debenzoyl-2-(p-cyanobenzoyl)-7-deoxy-Δ$^{6,7}$-Δ$^{12,13}$-iso-
taxol;
2-debenzoyl-2-(p-cyanobenzoyl)-2'-[{(2,2,2-trichloroethyl)
oxy}carbonyl]-7-deoxy-Δ$^{6,7}$-Δ$^{12,13}$-iso-taxol;
2-debenzoyl-2-(p-cyanobenzoyl)-10-acetyl-7-deoxy-Δ$^{6,7}$-
Δ$^{12,13}$-iso-taxotere;
2-debenzoyl-2-(p-cyanobenzoyl)-N-debenzoyl-N-(t-butyl)
aminocarbonyl-7-deoxy-Δ$^{6,7}$-Δ$^{12,13}$-iso-taxol;
2-debenzoyl-2-(p-methoxybenzoyl)-7-deoxy-Δ$^{6,7}$-Δ$^{12,13}$-
iso-taxol;
2-debenzoyl-2-(p-methoxybenzoyl)-2'-[{(2,2,2-
trichloroethyl)oxy}carbonyl]-7-deoxy-Δ$^{6,7}$-Δ$^{12,13}$-iso-
taxol;
2-debenzoyl-2-(p-methoxybenzoyl)-10-acetyl-7-deoxy-
Δ$^{6,7}$-Δ$^{12,13}$-iso-taxotere;
2-debenzoyl-2-(p-methoxybenzoyl)-N-debenzoyl-N-(t-
butyl)aminocarbonyl-7-deoxy-Δ$^{6,7}$-Δ$^{12,13}$-iso-taxol;
2-debenzoyl-2-(p-chlorobenzoyl)-7-deoxy-Δ$^{6,7}$-Δ$^{12,13}$-iso-
taxol;
2-debenzoyl-2-(p-chlorobenzoyl)-2'-[{(2,2,2-trichloroethyl)
oxy}carbonyl]-7-deoxy-Δ$^{6,7}$-Δ$^{12,13}$-iso-taxol;

2-debenzoyl-2-(p-chlorobenzoyl)-10-acetyl-7-deoxy-$\Delta^{6,7}$-$\Delta^{12,13}$-iso-taxotere;
2-debenzoyl-2-(p-chlorobenzoyl)-N-debenzoyl-N-(t-butyl)aminocarbonyl-7-deoxy-$\Delta^{6,7}$-$\Delta^{12,13}$-iso-taxol;
2-debenzoyl-2-(p-azidobenzoyl)-7-deoxy-$\Delta^{6,7}$-$\Delta^{12,13}$-iso-taxol;
2-debenzoyl-2-(p-azidobenzoyl)-2'-[{(2,2,2-trichloroethyl)oxy}carbonyl]-7-deoxy-$\Delta^{6,7}$-$\Delta^{12,13}$-iso-taxol;
2-debenzoyl-2-(p-azidobenzoyl)-10-acetyl-7-deoxy-$\Delta^{6,7}$-$\Delta^{12,13}$-iso-taxotere; and
2-debenzoyl-2-(p-azidobenzoyl)-N-debenzoyl-N-(t-butyl)aminocarbonyl-7-deoxy-$\Delta^{6,7}$-$\Delta^{12,13}$-iso-taxol.

Examples of Formula Va compounds of the invention include:
2-debenzoyl-2-(m-cyanobenzoyl)-7-deoxy-$\Delta^{12,13}$-iso-taxol;
2-debenzoyl-2-(m-cyanobenzoyl)-2'-[{(2,2,2-trichloroethyl)oxy}carbonyl]-7-deoxy-$\Delta^{12,13}$-iso-taxol;
2-debenzoyl-2-(m-cyanobenzoyl)-10-acetyl-7-deoxy-$\Delta^{12,13}$-iso-taxotere;
2-debenzoyl-2-(m-cyanobenzoyl)-N-debenzoyl-N-(t-butyl)aminocarbonyl-7-deoxy-$\Delta^{12,13}$-iso-taxol;
2-debenzoyl-2-(m-methoxybenzoyl)-7-deoxy-$\Delta^{12,13}$-iso-taxol;
2-debenzoyl-2-(m-methoxybenzoyl)-2'-[{(2,2,2-trichloroethyl)oxy}carbonyl]-7-deoxy-$\Delta^{12,13}$-iso-taxol;
2-debenzoyl-2-(m-methoxybenzoyl)-10-acetyl-7-deoxy-$\Delta^{12,13}$-iso-taxotere;
2-debenzoyl-2-(m-methoxybenzoyl)-N-debenzoyl-N-(t-butyl)aminocarbonyl-7-deoxy-$\Delta^{12,13}$-iso-taxol;
2-debenzoyl-2-(m-chlorobenzoyl)-7-deoxy-$\Delta^{12,13}$-iso-taxol;
2-debenzoyl-2-(m-chlorobenzoyl)-2'-[{(2,2,2-trichloroethyl)oxy}carbonyl]-7-deoxy-$\Delta^{12,13}$-iso-taxol;
2-debenzoyl-2-(m-chlorobenzoyl)-10-acetyl-7-deoxy-$\Delta^{12,13}$-iso-taxotere;
2-debenzoyl-2-(m-chlorobenzoyl)-N-debenzoyl-N-(t-butyl)aminocarbonyl-7-deoxy-$\Delta^{12,13}$-iso-taxol;
2-debenzoyl-2-(m-azidobenzoyl)-7-deoxy-$\Delta^{12,13}$-iso-taxol;
2-debenzoyl-2-(m-azidobenzoyl)-2'-[{(2,2,2-trichloroethyl)oxy}carbonyl]-7-deoxy-$\Delta^{12,13}$-iso-taxol;
2-debenzoyl-2-(m-azidobenzoyl)-10-acetyl-7-deoxy-$\Delta^{12,13}$-iso-taxotere;
2-debenzoyl-2-(m-azidobenzoyl)-N-debenzoyl-N-(t-butyl)aminocarbonyl-7-deoxy-$\Delta^{12,13}$-iso-taxol;
2-debenzoyl-2-(p-cyanobenzoyl)-7-deoxy-$\Delta^{12,13}$-iso-taxol;
2-debenzoyl-2-(p-cyanobenzoyl)-2'-[{(2,2,2-trichloroethyl)oxy}carbonyl]-7-deoxy-$\Delta^{12,13}$-iso-taxol;
2-debenzoyl-2-(p-cyanobenzoyl)-10-acetyl-7-deoxy-$\Delta^{12,13}$-iso-taxotere;
2-debenzoyl-2-(p-cyanobenzoyl)-N-debenzoyl-N-(t-butyl)aminocarbonyl-7-deoxy-$\Delta^{12,13}$-iso-taxol;
2-debenzoyl-2-(p-methoxybenzoyl)-7-deoxy-$\Delta^{12,13}$-iso-taxol;
2-debenzoyl-2-(p-methoxybenzoyl)-2'-[{(2,2,2-trichloroethyl)oxy}carbonyl]-7-deoxy-$\Delta^{12,13}$-iso-taxol;
2-debenzoyl-2-(p-methoxybenzoyl)-10-acetyl-7-deoxy-$\Delta^{12,13}$-iso-taxotere;
2-debenzoyl-2-(p-methoxybenzoyl)-N-debenzoyl-N-(t-butyl)aminocarbonyl-7-deoxy-$\Delta^{12,13}$-iso-taxol;
2-debenzoyl-2-(p-chlorobenzoyl)-7-deoxy-$\Delta^{12,13}$-iso-taxol;
2-debenzoyl-2-(p-chlorobenzoyl)-2'-[{(2,2,2-trichloroethyl)oxy}carbonyl]-7-deoxy-$\Delta^{12,13}$-iso-taxol;
2-debenzoyl-2-(p-chlorobenzoyl)-10-acetyl-7-deoxy-$\Delta^{12,13}$-iso-taxotere;
2-debenzoyl-2-(p-chlorobenzoyl)-N-debenzoyl-N-(t-butyl)aminocarbonyl-7-deoxy-$\Delta^{12,13}$-iso-taxol;
2-debenzoyl-2-(p-azidobenzoyl)-7-deoxy-$\Delta^{12,13}$-iso-taxol;
2-debenzoyl-2-(p-azidobenzoyl)-2'-[{(2,2,2-trichloroethyl)oxy}carbonyl]-7-deoxy-$\Delta^{12,13}$-iso-taxol;
2-debenzoyl-2-(p-azidobenzoyl)-10-acetyl-7-deoxy-$\Delta^{12,13}$-iso-taxotere; and
2-debenzoyl-2-(p-azidobenzoyl)-N-debenzoyl-N-(t-butyl)aminocarbonyl-7-deoxy-$\Delta^{12,13}$-iso-taxol.

The present invention also provides a process for preparing oxazolidines of Formula 5

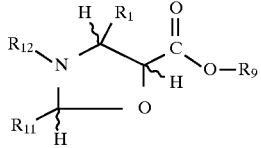

in which
$R_1$ is as defined above;
$R_9$ is selected from $C_1$–$C_6$alkyl;
$R_{11}$ is phenyl substituted with —$(OC_1$–$C_2$alkyl$)_n$ where n is 1 to 3;
$R_{12}$ is selected from the group consisting of —C(O)H, —C(O)$C_1$–$C_{10}$alkyl (preferably —C(O)$C_4$–$C_6$alkyl), —C(O)phenyl, —C(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —C(O)C(CH$_3$)=CHCH$_3$, —C(O)OC(CH$_3$)$_3$, —C(O)OCH$_2$phenyl, —SO$_2$-4-methylphenyl, —C(O)(CH$_2$)$_3$COOH, —C(O)-4-(SO$_3$H)phenyl, —C(O)-1-adamantyl, —C(O)O-3-tetrahydrofuranyl, —C(O)O-4-tetrahydropyranyl, —C(O)CH$_2$C(CH$_3$)$_3$, —C(O)C(CH$_3$)$_3$, —C(O)OC$_1$–C$_{10}$alkyl, —C(O)NHC$_1$–C$_{10}$alkyl, —C(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, or —C(O)$C_3$–$C_8$cycloalkyl, —C(O)C(CH$_2$CH$_3$)$_2$CH$_3$, —C(O)C(CH$_3$)$_2$CH$_2$Cl, —C(O)C(CH$_3$)$_2$CH$_2$CH$_3$, —C(O)-1-phenyl-1-cyclopentyl, —C(O)-1-methyl-1-cyclohexyl, —C(S)NHC(CH$_3$)$_3$, —NHC(O)NHC(CH$_3$)$_3$ or —C(O)NHPh;

which comprises reacting a hydroxy-amine of Formula 3

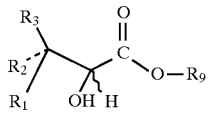

in which $R_1$ and $R_3$ are as defined above and $R_2$ is selected from the group consisting of —NHC(O)H, —NHC(O)$C_1$–$C_{10}$alkyl (preferably —NHC(O)$C_4$–$C_6$alkyl), —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NHSO$_2$-4-methylphenyl, —NHC(O)(CH$_2$)$_3$COOH, —NHC(O)-4-(SO$_3$H)phenyl, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–C$_{10}$alkyl, —NHC(O)NHC$_1$–C$_{10}$alkyl, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, or —NHC(O)$C_3$–$C_8$cycloalkyl, —NHC(O)C(CH$_2$CH$_3$)$_2$CH$_3$, —NHC(O)C(CH$_3$)$_2$CH$_2$Cl, —NHC(O)C(CH$_3$)$_2$CH$_2$CH$_3$, —NHC(O)-1-phenyl-1-cyclo-pentyl, —NHC(O)-1-methyl-1-cyclohexyl, —NHC(S)NHC(CH$_3$)$_3$, —NHC(O)NHC(CH$_3$)$_3$ or —NHC(O)NHPh;

with (1) an electron rich benzaldehyde of Formula 4A

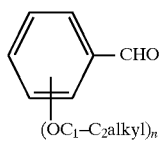

or (2) an electron rich acetal of Formula 4

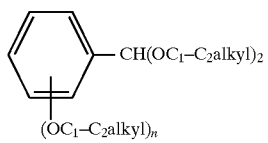

where n is 1–3.

In addition, the present invention provides a process of preparing

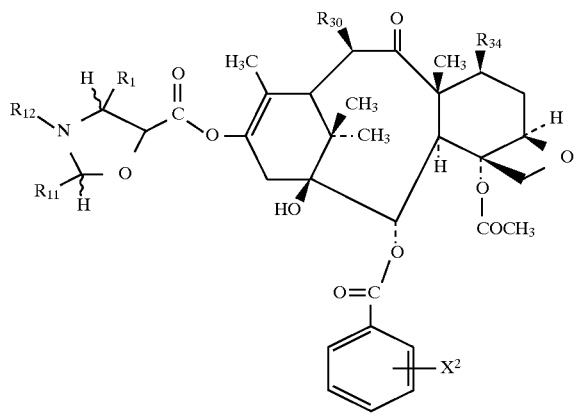

which comprises reacting an oxazolidine free acid of Formula 7

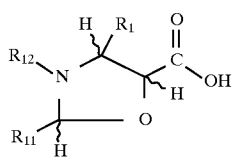

with a baccatin compound of Formula 8

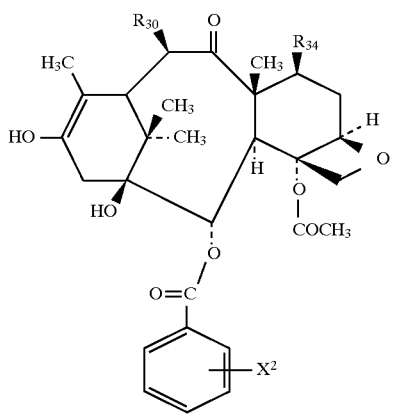

in the presence of a dehydrating agent. Wherein $R_{30}$ and $R_{34}$, being the same or different, are selected from the group consisting of —OC(O)C$_1$–C$_6$alkyl, —OC(O)OC$_1$–C$_6$alkyl, —OC(O)OCH$_2$CX$_3$ where X is Halo, —OC(O)OCH$_2$CH$_2$Si(R$_{20}$)$_3$ (where R$_{20}$ is C$_1$–C$_6$alkyl, or —OSi(R$_{16}$)$_3$ [where R$_{16}$, being the same or different, is selected from C$_1$–C$_6$alkyl or cyclo(C$_5$–C$_8$)alkyl]; and X$_2$, R$_{11}$ and R$_{12}$ are as defined above.

The present invention also provides a process of preparing

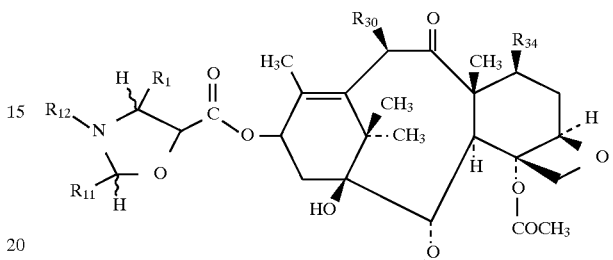

which comprises reacting an oxazolidine free acid of Formula 7

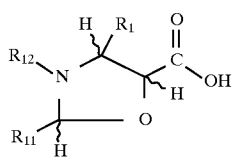

with a baccatin compound of Formula 8'

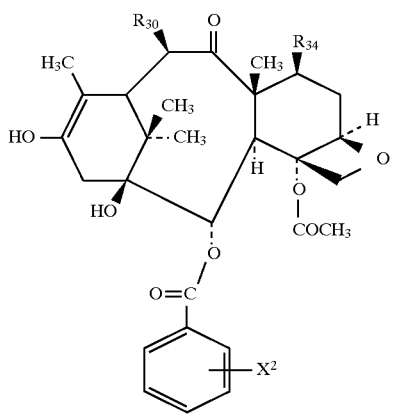

in the presence of a dehydrating agent. Wherein $R_{30}$ and $R_{34}$, being the same or different, are selected from the group consisting of —OC(O)C$_1$–C$_6$alkyl, —OC(O)OC$_1$–C$_6$alkyl, —OC(O)OCH$_2$CX$_3$ where X is Halo, —OC(O)OCH$_2$CH$_2$Si(R$_{20}$)$_3$ (where R$_{20}$ is C$_1$–C$_6$alkyl or —OSi(R$_{16}$)$_3$ [where R$_{16}$, being the same or different, is selected from C$_1$–C$_6$alkyl or cyclo(C$_5$–C$_8$)alkyl]; and X$_2$, R$_{11}$ and R$_{12}$ are as defined above.

A further embodiment of the subject invention are the novel compounds of Formula 8

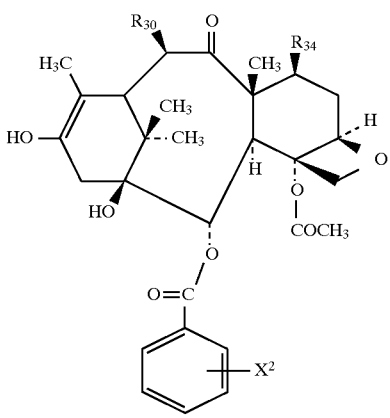

where $R_{34}$ is selected from 2-(3-methylbutyl)dimethylsilyl-O-, (n-butyl)$_3$silyl-O-, 2-(2-methylethyl)diethylsilyl-O-, cyclohexyldimethylsilyl-O-, cycloheptyldimethylsilyl-O-.

A further embodiment of the subject invention are the novel compounds of Formula 8'

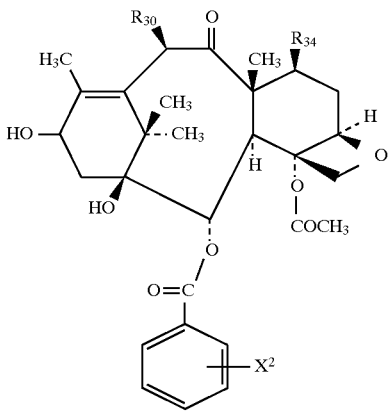

where $R_{34}$ is selected from 2-(3-methylbutyl)dimethylsilyl-O-, (n-butyl)$_3$silyl-O-, 2-(2-methylethyl)diethylsilyl-O-, cyclohexyldimethylsilyl-O-, cycloheptyldimethylsilyl-O-.

The compounds of the present invention are prepared by the method(s) as shown in Charts 1 through 7 and 46. Generally the compounds of this invention are prepared from a protected baccatin analog with a free 13-hydroxyl such as compound iii of Charts 1 & 2 or compound xvii of Chart 7 by oxidation to give the 13 keto-baccatins v or xviii. The respective enones are then reduced with activated zinc or by electrolytic reduction, or by other metal reductions such as sodium or aluminum amalgam, chromium(II) salts or other reductions of the correct reducing potential. The resulting enols vi of Chart 3 and xix of Chart 7 are coupled to a protected side chain precursor by one of several methods. Most favorably the coupling of the enols vi or xix may be accomplished by the method described in PCT/US93/11827 (Case 4809.P CP); see page 24, line 14 as well as Preparation Nos. 8, 11, 13, 16, 22, 28 and 60.

Thus, the enols vi or xix are condensed with a protected isoserinyl carboxylic acid such as vii in the presence of a dehydrating agent such as dicyclohexyl carbodiimide, or other carbodiimide, carbonyl diimidazole, 2,2-dipyridyl carbonate, alkyl or aryl sulfonyl chloride or sulfonic anhydride or other dehydrating agent known in the art for the preparation of esters to give the protected taxol analog viii or xi. The enols vi or xix may be also condensed with a side chain precursor by methods described in the literature (see: Kingston, D. G. I. *Pharmac. Ther.,* 1991, 52, 1–34; Commercon, A.; Bézard, D.; Bernard, F.; Bourzat, J. D. *Tetrahedron Lett.,* 1992, 33, 5185; Georg, G. I.; Cheruvallath, Z. S.; Himes, R. H.; Mejillano, M. R. *BioMed. Chem. Lett.* 1992, 2, 295; Kingston, D. G. I.; Molinero, A. A.; Rimoldi, J. M. *Prog. Chem. Org. Nat. Prod.,* 1993, 61, pp 1–206). The resultant protected taxol analog viii or xi may then be deprotected to taxol analogs such as ix and xii.

More specifically, the compounds of this invention may be prepared as shown in Charts 1, 2 and 3. Thus, 10-deacetyl baccatin III (i, Chauviere, G.; Guenard, D.; Picot, F.; Senihl, V.; Potier, P. C. R. *Acad. Sc. Paris, Serie II,* 1981, 93, 501.) may be selectively protected at the 7-position, for example with a carbonate, ester or silyl protecting group to give a protected baccatin (ii). The 7 protected baccatin (ii) may then be protected at the 10 position with a carbonate or ester group to give iii. If the 10 protecting group is acetate then the compound iii is a 7 protected derivative of baccatin III. The same 10 acetyl derivative is available as shown in Chart 2. Thus, a 10 protected baccatin, particularly where the 10 protecting group is acetyl, is baccatin III (iv). Protection of iv in the same manner as protection of ii from Chart 1, gives compound iii, particularly where, $R^{10}$ is acetate. The 13-hydroxyl group of compound iii, may be oxidized to the give the ketone v. The oxidation may be accomplished with manganese dioxide in aprotic solvents such as methylene chloride, tetrahydrofuran, dioxane, chloroform, toluene, or alkanes such as hexane, pentane, or heptane. The reaction may be run at 0° C. to 60° C., though most readily at room temperature. The oxidation may be carried out with other oxidizing agents, such as chromium trioxide in pyridine, pyridinium dichromate, pyridinium chlorochromate, potassium permanganate, tetrapropylammonium perruthenate, Dess-Martin periodinane, or other oxidant known in the art. As shown in Chart 3, the ketone v may be reduced to the enol vi. This reduction is readily accomplished with zinc metal activated by washing successively with 1N hydrochloric acid, water, ethanol and ether. The reduction is carried out in acetic acid at 25° C., and is over in 2 to 4 hours. The reaction may be run at 0° C. for 24 to 48 hours or at up to 70° C. for 10 to 20 minutes. The reaction may also be run in aqueous acetic acid, methanol containing ammonium chloride, or in water miscible solvents such as tetrahydrofuran or dioxane containing acetic acid, formic acid, or other carboxylic acid, or aqueous acid such as hydrochloric, sodium bisulfate, or phosphoric acid. The reduction also may be carried out electrolytically in solvents such as methanol, pyridine, tetrahydrofuran, or dioxane with a carbon or platinum electrode and with the electrolytic potential set just high enough to carry out the reduction. The reduction may also be accomplished with other metals such as sodium or aluminum amalgam, or with chromium (II) salts. The enol vi is readily coupled with an oxazolidinecarboxylic acid vii in a solvent such as toluene, xylene, tetrahydrofuran, dioxane, or the like in the presence of a dehydrating agent such as dicyclohexylcarbodiimide, or other carbodiimide, carbonyl diimidazole, 2,2-dipyridyl carbonate, alkyl or aryl sulfonyl chloride or sulfonic anhydride or other dehydrating agent known in the art for the preparation of esters in the presence of a catalyst such as 4-dimethylaminopyridine or tri-n-butyl phosphine to give the protected enol ester viii. When the $R^{14}$ protecting group on position 7 has a different selectivity from $R^{10}$ and is removable by mild acid or by hydrogenolysis then the protected enol ester viii may be converted to the deprotected $\Delta^{12,13}$-isotaxol analog ix. For example if $R^{14}$ is a silyl group such as trimethyl or triethyl silyl and $R^{10}$ is acetate; then treatment of protected enol ester viii with mild acid such as 80% acetic acid-water for 4 to 110 hours at 10° C. to 60° C. gives the $\Delta^{12,13}$-isotaxol analog ix. Alternatively, the deprotection may be accomplished with mild acid such as 0.1N hydrochloric acid in methanol or ethanol, or with other acids such as trifluoroacetic, methanesulfonic or other acid in alcoholic and mixed alcoholic and aqueous solvents. If the protecting group $R^{14}$ is removable by hydrogenation, such as a benzyloxymethyl ether, then conversion of protected enol ester viii to the deprotected $\Delta^{12,13}$-isotaxol analog ix may be accomplished by hydrogenation in solvents such as methanol, ethanol, ethyl acetate, tetrahydrofuran, or the like in the presence of a hydrogenolysis catalyst such as palladium metal, palladium on carbon, Raney nickel, or the like.

The compounds of this invention include $\Delta^{12,13}$-iso taxol analogs with modification on the 6,7-, 7-, and 7,8-positions as shown in Charts 4 through 7. Thus, selective deprotection of $R^{14}$ of structure viii gives the 7-hydroxy compound x. If $R^{14}$ in compound viii is for example trichloroethyl carbonate and $R^{10}$ is an ester or ether, then reduction with zinc in a mildly acid medium such as acetic acid-water, methanol, ethanol, or other alcoholic solvent acidified with hydrochloric acid or ammonium chloride gives the 7-hydroxy compound x. If $R^{14}$ in compound viii is for example a silyl ether such trimethyl or triethyl silyl and $R^{10}$ is an ester or ether or carbonate, then treatment with tetra-n-butyl ammonium fluoride or pyridine-hydrofluoride or triethyl ammonium hydrofluoride in solvents such as tetrahydrofuran, dioxane, or alcoholic solvents such as methanol or ethanol gives the 7-hydroxy compound x.

Compound xi where $R^6$ and $R^7$ taken together are a double bond and $R^8$ is methyl, a protected 7-deoxy-$\Delta^{6,7}$-$\Delta^{12,13}$-isotaxol analog, is most favorably prepared from x by conversion of the 7-hydroxyl group of compound x to the triflate followed by elimination. Thus, treatment of 7-hydroxy compound x with trifluoromethanesulfonic anhydride in methylene chloride, 1,2-dichloroethane, chloroform, or other suitable aprotic solvent, in the presence of a base such as pyridine, 2-methyl pyridine, 2,6-dimethyl pyridine or 2,4,6-trimethyl pyridine or other suitable base at a temperature of −20° C. to 60° C. for 10 minutes to 10 hours gives the trifluoromethanesulfonate of alcohol x. Treatment of this trifluoromethanesulfonate with 1,8-diazabicyclo [5.4.0]undec-7-ene, 1,5-diazabicyclo[4.3.0]non-5-ene or other strong amine base in tetrahydrofuran, dioxane, or other suitable aprotic solvent at 0° C. to 90° C. for 10 minutes to 10 hours gives the $\Delta^{6,7}$-compound of structure xi. The elimination of the trifluoromethanesulfonate of compound x can also be accomplished with other strong bases such lithium, potassium, or sodium hexamethyl disilazane, lithium diethyl, or di-isopropyl amide, sodium or potassium t-butoxide or other strong base in a suitable solvent such as tetrahydrofuran, dioxane, t-butyl alcohol or the like at −80° C. to 90° C. for 10 minutes to 5 hours.

Compound xi where $R^6$ is hydrogen and $R^7$ and $R^8$ taken together are 7β,8β-methano, a protected 7-deoxy-7β,8β-methano-$\Delta^{12,13}$-isotaxol analog, can also be prepared from the trifluoromethanesulfonate of alcohol x. Thus, treatment of trifluoromethanesulfonate of compound x with sodium azide, sodium chloride, sodium sulfate, potassium azide, potassium chloride, potassium sulfate or other salt, in aqueous tetrahydrofuran, aqueous dioxane, aqueous methanol, or aqueous ethanol, or other water and water miscible solvent combinations at 0° C. to 90° C. for 20 minutes to 48 hours. Alternatively, a triflate x may be treated with 10 to 500 fold weight excess of silica gel either by slow elution on chromatography or in a batch mode in a solvent such as toluene, THF, dioxane, methylene chloride, ethyl acetate, DMF, DMA, or other solvent for 1 hour to 200 hours at room temperature.

Compound xi where $R^6$ is hydrogen and $R^7$ is fluoride and $R^8$ is methyl, a protected 7-deoxy-7-fluoro-$\Delta^{12,13}$-isotaxol analog, is most favorably prepared from alcohol x by reaction with a reagent such as diethylaminosulfur trifluoride (DAST), dimethylaminosulfur trifluoride (methylDAST), bis(dimethylamino)sulfur difluoride, bis (diethylamino)sulfur difluoride, or (diethylamino) (dimethylamino)sulfur difluoride. The preferred method for this conversion is with DAST or methylDAST. The reaction with DAST or methylDAST is carried out in an aprotic solvent such as methylene chloride ($CH_2Cl_2$), chloroform ($CHCl_3$), fluorotrichloromethane (Freon 11®), ethylene glycol dimethyl ether (glyme), 2-methoxyethyl ether (diglyme), pyridine, hydrocarbons such as pentane, hexane, or isooctane, tetrahydrofuran (THF), benzene, toluene, xylene. The preferred solvent is methylene chloride. The reaction may be performed in a range of temperature from −100° C. to 100° C. or above. Generally, the reaction is begun under conditions of low temperature, e.g., −78° C., and then is allowed to proceed at a higher temperature, e.g., 25° C. The reaction is quenched with water, the crude product is isolated by standard extraction methods, and is purified by standard chromatographic methods and/or by crystallization.

Compound xi where $R^6$ and $R^7$ taken together are a double bond and $R^8$ is methyl, a protected 7-deoxy-$\Delta^{6,7}$-$\Delta^{12,13}$-isotaxol analog, may also be prepared by reaction of alcohol x with a reagent such as diethylaminosulfur trifluoride (DAST), dimethylaminosulfur trifluoride (methylDAST), bis(dimethylamino)sulfur difluoride, bis (diethylamino)sulfur difluoride, or (diethylamino) (dimethylamino)sulfur difluoride as described above.

Compound xi where $R^6$ is hydrogen and $R^7$ and $R^8$ taken together are 7β,8β-methano, a protected 7-deoxy-7β,8β-methano-$\Delta^{12,13}$-isotaxol analog, may also be prepared by reaction of alcohol x with a reagent such as diethylaminosulfur trifluoride (DAST), dimethylaminosulfur trifluoride (methylDAST), bis(dimethylamino)sulfur difluoride, bis (diethylamino)sulfur difluoride, or (diethylamino) (dimethylamino)sulfur difluoride as described above.

A protected $\Delta^{12,13}$-isotaxol analog xi of Chart 4 may be converted to a $\Delta^{12,13}$-isotaxol analog xii by deprotection. Thus, reaction of oxazolidine xi with a mild acid in an aqueous or alcoholic solvent gives the 13-isoserinyl-$\Delta^{12,13}$-baccatin III ($\Delta^{12,13}$-isotaxol analog) xii. More specifically, treatment of oxazolidine xi with mild acid such as 80% acetic acid-water for 4 to 110 hours at 10° C. to 60° C. gives the $\Delta^{12,13}$-isotaxol analog xii. Alternatively, the deprotection may be accomplished with mild acid such as 0.1N hydrochloric acid in methanol or ethanol, or with other acids such as trifluoroacetic, methanesulfonic or other acid in alcoholic and mixed alcoholic and aqueous solvents. Also the oxazolidine of xi is removable by hydrogenation. Thus, hydrogenation of oxazolidine xi in solvents such as methanol, ethanol, ethyl acetate, tetrahydrofuran, or the like in the presence of a hydrogenolysis catalyst such as palladium metal, palladium on carbon, Raney nickel, or the like gives $\Delta^{12,13}$-isotaxol analog xii.

$\Delta^{12,13}$-Isotaxol analogs xiii of Chart 5 where $R^{14}$ is a carbonate, carbamate, ether, ester or silyl ether may be prepared by selective cleavage of the oxazolidine of viii. Thus, as described above, reaction of oxazolidine viii with a mild acid in an aqueous or alcoholic solvent gives the 13-isoserinyl-$\Delta^{12,13}$-baccatin III ($\Delta^{12,13}$-isotaxol analog) xiii. More specifically, treatment of oxazolidine viii with mild acid such as 80% acetic acid-water for 4 to 110 hours at 10° C. to 60° C. gives the $\Delta^{12,13}$-isotaxol analog xiii. Alternatively, the deprotection may be accomplished with mild acid such as 0.1N hydrochloric acid in methanol or ethanol, or with other acids such as trifluoroacetic, methanesulfonic or other acid in alcoholic and mixed alcoholic and aqueous solvents. Also the oxazolidine of viii is removable by hydrogenation. Thus, hydrogenation of oxazolidine viii in solvents such as methanol, ethanol, ethyl acetate, tetrahydrofuran, or the like in the presence of a hydrogenolysis catalyst such as palladium metal, palladium on carbon, Raney nickel, or the like gives $\Delta^{12,13}$-isotaxol analog xiii.

The $\Delta^{12,13}$-isotaxol analog xv with $R^{17}$ as an ester, carbonate, carbamate, or ether of Chart 6 may be made from an oxazolidinyl 7-hydroxy-$\Delta^{12,13}$-isotaxol x by conversion to 7-substituted oxazolidine xiv followed by cleavage of the oxazolidine ring. Oxazolidine xiv, as a 7-ester, may be produced from oxazolidinyl 7-hydroxy-$\Delta^{12,13}$-isotaxol x by esterification with an acyl halide, acyl anhydride or carboxylic acid and a dehydrating agent as is known in the art. Oxazolidine xiv, as a 7-carbonate, may be produced from an oxazolidinyl 7-hydroxy-$\Delta^{12,13}$-isotaxol x by reaction with an alkoxy chloroformate or alkoxy carbonate anhydride as is known in the art. Oxazolidine xiv, as a 7-carbonate, may also be prepared from an oxazolidinyl 7-hydroxy-$\Delta^{12,13}$-isotaxol x by reaction with phosgene, diphosgene, triphosgene or p-nitrophenyl chloroformate followed by reaction of the intermediate chloroformate or p-nitrophenyl carbonate with an alcohol as is known in the art. Oxazolidine xiv, as a 7-carbamate, may be prepared from an oxazolidinyl 7-hydroxy-$\Delta^{12,13}$-isotaxol x by reaction with a alkyl or aryl isocyanate as is known in the art. Oxazolidine xiv, as a 7-carbamate, may also be prepared from a 7-hydroxy-$\Delta^{12,13}$-isotaxol x by reaction of a carbonate as prepared above with an amine as is known in the art. Oxazolidine xiv, as a 7-carbamate, may also be prepared from a 7-hydroxy-$\Delta^{12,13}$-isotaxol x by reaction with phosgene, diphosgene, triphosgene or p-nitrophenyl chloroformate and reaction of the intermediate chloroformate or p-nitrophenyl carbonate with an amine as is known in the art. Oxazolidine xiv, as a 7-alkoxymethyl or aryloxymethyl ether, may be prepared from a 7-hydroxy-$\Delta^{12,13}$-isotaxol x by reaction with a chloromethyl alkyl or chloromethylaryl ether as is known in the art. Oxazolidine xiv, as a 7-alkyl or aryl ether may be prepared from a 7-hydroxy-$\Delta^{12,13}$-isotaxol x by reaction with a base such as sodium hydride, potassium hydride or lithium diethyl, or diisopropyl amide, sodium or potassium hexamethyldisilazane or other strong base in a solvent such as tetrahydrofuran, dioxane, dimethoxy ethane, or other such solvent at −78° C. to 60° C. in the presence of an alkyl halide such as methyl iodide, ethyl iodide, benzyl chloride, allyl chloride or bromide of the like for 10 minutes to 48 hours to give oxazolidine xiv as a 7-alkoxy or arylxoymethyl ether. Oxazolidine xiv, as a 7-alkyl or aryl ether may also be prepared from a 7-hydroxy-$\Delta^{12,13}$-isotaxol 10 by reaction with a diazo alkane or aryl diazo compound in the presence of a transition metal catalyst such as rhodium, ruthenium or palladium in an aprotic solvent such as THF, dioxane, or DMF at a temperature of −20° C. to 150° C.

A 7-substituted oxazolidine xiv, as a 7 ester, carbonate, carbamate, or ether of Chart 6 as prepared above may be deprotected to a $\Delta^{12,13}$-isotaxol analog xv by the deprotection procedures as described for the conversion of oxazolidine viii to $\Delta^{12,13}$-isotaxol analog xiii of Chart 5.

A baccatin III analog xvi of Chart 7 may be converted to a baccatin III analog of structure xvii where $R^6$ and $R^7$ when taken together are a double bond and $R^8$ is methyl, or where $R^6$ is hydrogen and $R^7$ and $R^8$ when taken together are 7β,8β-methano, or where $R^6$ is hydrogen, $R^7$ is fluoro and $R^8$ is methyl may be prepared as described above and shown in Chart 4 for the conversion of 7-hydroxy compound x to the respective 7-deoxy-$\Delta^{6,7}$-$\Delta^{12,13}$-isotaxol analog, 7-deoxy-7β,8β-methano-$\Delta^{12,13}$-isotaxol analog, or the 7-deoxy-fluoro-$\Delta^{12,13}$-isotaxol analog xi. A 13-hydroxy baccatin analog xvii may be oxidized to the 13 keto baccatin analog xviii in the same manner as described above and shown in Chart 2 for the oxidation of a 13-hydroxy baccatin analog iii to a 13-keto-baccatin analog v. A 13-keto baccatin analog xviii may be reduced to a $\Delta^{12,13}$-iso-baccatin analog xix as described above and shown in Chart 3 for the reduction of a 13-keto baccatin analog v to a $\Delta^{12,13}$-isobaccatin analog vi. A $\Delta^{12,13}$-isobaccatin analog xix may be converted to a protected $\Delta^{12,13}$-isotaxol analog xi as described above and shown in Chart 3 for the conversion of a $\Delta^{12,13}$-isobaccatin analog vi to a protected $\Delta^{12,13}$-isotaxol analog viii. A protected $\Delta^{12,13}$-isotaxol analog xi of Chart 7 may be converted to a $\Delta^{12,13}$-isotaxol analog xii as described above and shown in Chart 4.

The compounds of Formula I where $X^2$ is other than —H, can be prepared by the methods disclosed in J. Am. Chem. Soc. 1994, 116, 4097–98 and Bioorganic & Medical Chemistry Letters, Vol. 4, No. 3, 479–82, 1994; and Tetrahedron Lett. 1994, 35, 8931 which are incorporated herein by reference.

Alternatively, the compounds of this invention (Formula I)

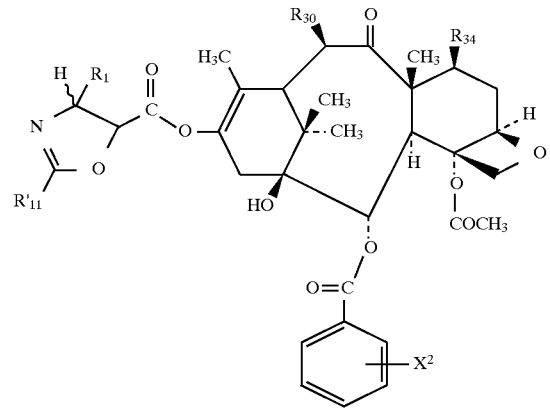

which comprises reacting an oxazoline free acid of Formula 7'

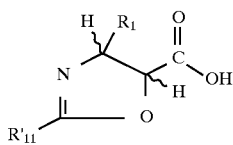

with a baccatin compound of Formula 8

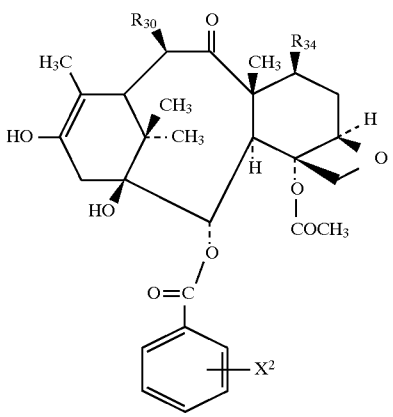

in the presence of a dehydrating agent;

wherein $R_{30}$ and $R_{34}$, being the same or different, are selected from the group consisting of —OC(O)$C_1$–$C_6$alkyl, —OC(O)O$C_1$–$C_6$alkyl, —OC(O)OCH$_2$CX$_3$ where X is Halo, —OC(O)OCH$_2$CH$_2$Si(R$_{20}$)$_3$ (where $R_{20}$ is $C_1$–$C_6$alkyl), or —OSi(R$_{16}$)$_3$ [where $R_{16}$, being the same or different, is selected from $C_1$–$C_6$alkyl or cyclo($C_5$–$C_8$)alkyl];

$X^2$ is selected from the group consisting of

—H,

—$C_1$–$C_4$ alkyl,

—$C_1$–$C_3$ alkoxy, halo,

—$C_1$–$C_3$ alkylthio,

-trifluoromethyl,

—$C_2$–$C_6$ dialkylamino, benzyloxymethyl, cyano, azide (N$_3$), or nitro;

$R_1$ is selected from the group consisting of
 —CH$_3$,
 —$C_6$H$_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-naphthyl, 2-naphthyl or 3,4-methylenedioxyphenyl; and $R'_{11}$ is selected from the group consisting of
 —$C_1$–$C_{10}$alkyl,
 -phenyl,
 -phenyl substituted with one, 2 or 3 $C_1$–$C_4$ alkyl, $C_1$–$C_3$ alkoxy, halo, $C_1$–$C_3$ alylthio, trifluoromethyl, $C_2$–$C_6$ dialkylamino, hydroxy or nitro,
 -1-adamantyl,
 -3-tetrahydrofuranyl,
 -4-tetrahydropyranyl, or
 —CH$_2$C(CH)$_3$.

Another aspect of this invention is the process of preparing

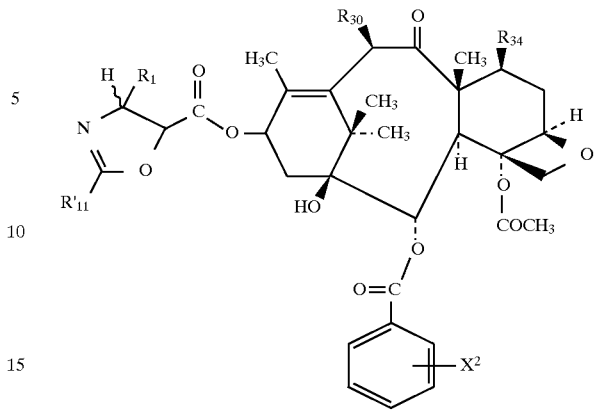

which comprises reacting an oxazoline free acid of Formula 7'

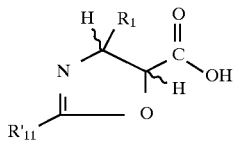

with a baccatin compound of Formula 8'

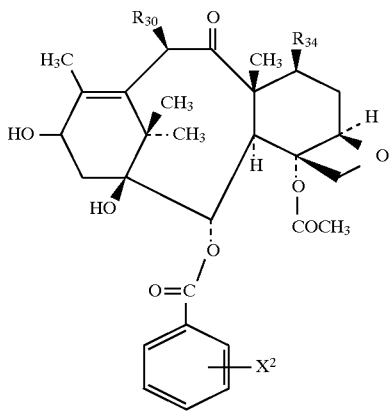

in the presence of a dehydrating agent;

wherein $R_{30}$ and $R_{34}$, being the same or different, are selected from the group consisting of —OC(O)$C_1$–$C_6$alkyl, —OC(O)O$C_1$–$C_6$alkyl, —OC(O)OCH$_2$CX$_3$ where X is Halo, —OC(O)OCH$_2$CH$_2$Si(R$_{20}$)$_3$ (where $R_{20}$ is $C_1$–$C_6$alkyl), or —OSi(R$_{16}$)$_3$ [where $R_{16}$, being the same or different, is selected from $C_1$–$C_6$alkyl or cyclo($C_5$–$C_8$)alkyl];

$X^2$ is selected from the group consisting of

—H,

—$C_1$–$C_4$ alkyl,

—$C_1$–$C_3$ alkoxy, halo,

—$C_1$–$C_3$ alkylthio,

-trifluoromethyl,

—$C_2$–$C_6$ dialkylamino, benzyloxymethyl, cyano, azide (N$_3$), or nitro;

$R_1$ is selected from the group consisting of

—$CH_3$,
—$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-naphthyl, 2-naphthyl or 3,4-methylenedioxyphenyl; and $R'_{11}$ is selected from the group consisting of
- —$C_1$–$C_{10}$alkyl,
- -phenyl,
- -phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro,
- -1-adamantyl,
- -3-tetrahydrofuranyl,
- 4-tetrahydropyranyl, or
- —$CH_2C(CH_3)_3$.

General procedure for the coupling of oxazoline acid to silyl protected Baccatin III followed by deprotection is provided Part A: The oxazoline acid slurried in toluene is treated with 0.5–1 equivalents of a dehydrating agent such as a carbodiimide and allowed to react. The resulting solution is then treated with a catalytic amount of dimethylaminopyridine or a similar catalyst and the protected baccatin III. When TLC shows the reaction to be complete. The slurry is filtered to remove the urea, poured into aqueous sodium bicarbonate solution and extracted with methyl t-butyl ether. Concentration and purification by chromatography affords the coupled ester.

Part B: The ester from above is combined with methanol and treated with HCl. The solution is refluxed until TLC shows the reaction to be complete. The reaction mixture is quenched with sodium bicarbonate solution and stirred at rt to effect O to N acyl migration. Isolation with Ethyl acetate and chromatography affords taxol.

Silylation of 10-DAB (79)

10-DAB (79) and pyridine are combined in a ratio of 3 mL pyridine to 1 g 10-DAB and treated with 5 equivalents of the silyl chloride at room temperature. The solution is stirred at room temperature until HPLC indicates the reaction is complete. Upon completion of the reaction, the solution is poured into water and the product is isolated with a suitable solvent, usually ethyl acetate or methyl t-butyl ether. The organic layers are dried over magnesium sulfate and concentrated to afford the silyl derivative (80).

EXAMPLE 1

Preparation of 13-keto-7-TES-baccatin III (2)

A 5 g (7.13 mM) quantity of 7-TES-baccatin III (1, Denis, J. N.; Greene, A. E. *J. Am. Chem. Soc.* 1988, 110, 5917) is dissolved in 75 mL of methylene chloride and the resultant solution is treated with 5 g (57.5 mM) of manganese dioxide. The mixture is stirred with a magnetic stirrer for 19 hr at which time TLC indicates no starting material left. The reaction is then filtered through celite and the filtrate concentrated under vacuum giving 13-keto-7-TES-baccatin III.

TLC(silica gel GF): SM $R_f$=0.,24 product $R_f$=0.50, in (1:2) ethyl acetate-hexane.

Proton NMR($CDCl_3$,TMS): $\delta$8.08(d, 2H), 7.47–7.63(m, 3H), 6.59(s, 1H), 5.70(d, 1H), 4.93(d, 1H), 4.48(m, 1H), 4.31(d, 1H), 4.12(d, 1H), 3.91(d, 1H), 2.95(d, 1H), 2.65(d, 1H), 2.55(m, 1H), 2.23(s, 3H), 2.19(s, 3H), 2.18(s, 3H), 1.88(m, 1H), 1.67(s, 3H), 1.28(s, 3H), 1.19(s, 3H), 0.92(m, 9H), 0.58(m, 6H).

Carbon NMR($CDCl_3$,TMS): $\delta$199.95, 198.07, 169.85, 168.64, 166.53, 152.75, 139.96, 133.67, 129.76, 128.46, 83.65, 80.25, 78.20, 75.89, 75.77, 72.59, 71.98, 59.16, 45.94, 43.15, 42.18, 36.90, 32.74, 21.44, 20.56, 17.94, 13.25, 9.30, 6.46, 4.96.

EXAMPLE 1A

13-Keto-7-TES-baccatin III (2)

A slurry of activated manganese (IV) oxide (14.7 g, Aldrich) in $CH_2Cl_2$ (80 mL) is treated with a solution of 7-TES-baccatin (7.14 g) in $CH_2Cl_2$ (320 mL) added from a dropping funnel over a 5 minute period. The reaction is stirred at room temperature for 4 hours. TLC (30% acetone/hexane and 50% EtOAc/hexane) indicates that the reaction is complete. The mixture is filtered to remove the solids and further rinsed with $CH_2Cl_2$. The combined filtrates are evaporated to dryness and subjected to high vacuum to yield 13-Keto-7-TES-baccatin III as a white solid (6.81 g, 96% yield): Tlc: Silica gel; 50% EtOAc/hexane; starting material Rf=0.41, ketone 2 Rf=0.59.

$^1$H NMR ($CDCl_3$, TMS), $\delta$8.07 (m, 2H), 7.63 (m, 1H), 7.50 (m, 2H), 6.59 (s, 1H), 5.70 (d, J=6.8 Hz, 1H), 4.93 (d, J=9.5 Hz, 1H), 4.48 (m, 1H), 4.33 (d, J=8.4, 1H), 4.12 (d, J=8.4 Hz, 1H), 3.92 (d, J=6.7 Hz, 1H), 2.96 (d, J=19.9 Hz, 1H), 2.66 (d, J=20.0 Hz, 1H), 2.55 (m, 1H), 2.23 (s, 3H), 2.194 (s, 3H), 2.188 (s, 3H), 1.88 (m, 1H), 1.85 (s, 1H), 1.67 (s, 3H), 1.28 (s, 3H), 1.19 (s, 3H), 0.92 (t, J=7.8 Hz, 9H), 0.59 (q, J=7.6 Hz, 6H).

EXAMPLE 2

Preparation of 7-TES-$\Delta^{12,13}$-iso-baccatin III (3)

Zinc dust (2.82 g, 43.1 mg-atom) is sequentially washed with dilute HCl, water (6×), methanol (6×) and ether (3×), decanting the liquid each time. The zinc is dried under vacuum. A solution of 13-keto-7-TES-baccatin III (2, 0.498 g, 0.71 mM) in acetic acid (4 mL) is treated with the activated zinc. The reaction is stirred under nitrogen at room temperature 4 hours. The reaction is diluted with ethyl acetate, filtered through diatomaceous earth. Evaporation of the filtrate followed by dilution with toluene and re-evaporation 7-TES-$\Delta^{12,13}$-iso-baccatin III.

Proton NMR ($CDCl_3$, TMS): $\delta$0.53 (m, 6H); 0.89 (m, 9H); 1.11 (s, 3H); 1.14 (s, 3H); 1.61 (s, 3H); 1.82 (s, 3H); 1.87 (m, 1H); 2.09 (d, 1H, J=18.0 Hz); 2.18 (s, 3H); 2.33 (s, 3H); 2.30–2.58 (m, 2H); 2.74 (d, 1H, J=18.0 Hz); 4.14 (d, 1H, J=5.3 Hz); 4.25 (d, 1H, J=8.4 Hz); 4.37 (m, 1H); 4.39 (d, 1H, J=8.4 Hz); 4.37 (s, 1H); 4.93 (dd, 1H); 5.48 (dd, 1H); 5.91 (s, 1H); 7.48 (m, 2H); 7.61 (m, 1H); 8.08 (m, 2H).

Carbon NMR ($CDCl_3$, TMS): 5.36, 6.69, 9.08, 12.75, 18.75, 21.18, 23.14, 29.89, 32.43, 37.17, 38.59, 39.66. 56.52, 59.09, 73.05, 73.36, 75.56, 76.82, 80.92, 84.50, 102.44, 128.53, 129.03, 129.90, 133.57, 146.02, 166.57, 168.83, 170.82, 205.52.

Elem. Anal. Calc'd for $C_{37}H_{52}O_{11}Si_1$: 63.41% C, 7.48% H.

Found: 63.31%C, 7.45% H.

IR(Nujol): 981, 1112, 1241, 1281, 1375, 1454, 1687, 1716, 1725, 1741, 3402, 3508 $cm^{-1}$.

EXAMPLE 2A

7-Triethylsilyl-12,13-isobaccatin III (3)

A solution of 13-keto-7-TES-baccatin III (2) (7.90 g, 11.3 mmol) in degassed HOAc (80 mL, argon) is placed in a 250 mL three neck round bottom flask equipped with an air powered stirrer. The solution is purged with nitrogen and then activated zinc dust (82 g) added in one portion as a dry powder. The reaction is stirred vigorously. The starting material is consumed after two hours by tlc evidence (50% EtOAc/hexane). The reaction is worked up by dilution with EtOAc (degassed with argon). The reaction mixture is filtered through Celite under a nitrogen atmosphere. The flask and filter cake are rinsed well with degassed EtOAc. The combined filtrates are evaporated at a reduced pressure. Degassed toluene is added to the residue and re-evaporated.

The addition and evaporation of toluene is repeated until the HOAc is gone (two more times). The vacuum on the evaporator is released and replaced each time with nitrogen. A white solid is obtained which is placed under high vacuum (0.02 Torr) overnight to yield 7.57 g (96%) of 7-Triethylsilyl-12,13-isobaccatin III.

$^1$H NMR (CDCl$_3$,TMS), δ8.08 (d, 2H, J=7.1 Hz), 7.61 (t, 1H, J=7.5, Hz), 7.49 (t, 2H, J=7.5 Hz), 5.92 (s, 1H), 5.49 (d, 1H, J=5.3 Hz), 4.93 (m, 1H), 4.40 (d, 1H, J=8.1 Hz), 4.37 (m, 1H), 4.26 (d, 1H, J=8.5 Hz), 4.14 (d, 1H, J=5.3 Hz), 2.75 (d, 1H, J=18.0 Hz), 2.54–2.46 (m, 1H), 2.41 (m, 1H), 2.33 (s, 3H), 2.17 (s, 3H), 2.07 (m, 1H,), 1.89 (m, 1H), 1.81 (s, 3H), 1.14 (s, 3H), 1.11 (s, 3H), 0.89 (m, 9H), 0.52 (m, 6H).

EXAMPLE 3

Preparation of 7-TES-Δ$^{12,13}$-iso-baccatin III-13-(4S,5R)-N-Boc-2-(2,4-dimethoxyphenyl)-4-phenyl-5-oxazolidinecarboxylic acid ester (5)

(4S,5R)-N-Boc-2-(2,4-dimethoxyphenyl)-4-phenyl-5-oxazolidinecarboxylic acid (4a,b) is prepared from the side chain salt as follows. The (4S,5R)-N-Boc-2-(2,4-dimethoxyphenyl)-4-phenyl-5-oxazolidinecarboxylic acid potassium salt (1.5 mM) is suspended in ethyl acetate, and the solution washed twice with 5% aqueous sodium bisulfate, once with brine, dried and evaporated. The carboxylic acid is treated with methylene chloride (2 mL), 4-dimethylaminopyridine (48 mg), a solution of the 7-TES-Δ$^{12,13}$-iso-baccatin III (3, 0.492 g, 0.702 mM) in toluene (5 mL) plus methylene chloride (8 mL), and 1,3-dicyclohexylcarbodiimide (0.316 g, 1.53 mM). The solution is stirred under an inert atmosphere 2.5 h. The reaction is diluted with ethyl acetate and washed with aqueous sodium bisulfate and aqueous bicarbonate plus brine. The layers are filtered and separated, and the organic layer dried and evaporated. The product is purified by silica gel chromatography in acetone-hexane mixtures. 7-TES-Δ$^{12,13}$-iso-baccatin III-13-(4S,5R)-N-Boc-2-(2,4-dimethoxyphenyl)-4-phenyl-5-oxazolidinecarboxylic acid ester (5a,b) is obtained.

Proton NMR (CDCl$_3$, TMS): δ0.54 (m); 0.89 (m); 1.05 (s); 1.57 (s); 1.87 (m); 2.15 (s); 2.16 (s); 2.19 (s); 2.50 (m); 3.82 (s); 3.86 (s); 3.89 (s); 4.35 (m); 4.88 (m); 5.30 (m); 5.50 (2d); 5.88 (s); 5.99 (s); 6.50 (m); 7.35–7.65 (m); 8.02 (m).

Separation of 5a & 5b

The reaction is carried out as above with 7-TES-Δ$^{12,13}$-iso-baccatin III (3, 0.5 g, 0.71 mM) and the crude product obtained after aqueous extraction is chromatographed over an E. Merck size B medium pressure chromatography column eluted with (20-80) acetone-n-hexane (300 mL), (25-75) acetone-n-hexane (300 mL), and (30-70) acetone-n-hexane (300 mL), collecting fractions of 15 mL. Fractions 24–28 are found by TLC to contain a 50-50 mixture of less and more polar isomers of 7-TES-Δ$^{12,13}$-iso-baccatin III-13-(4S,5R)-N-Boc-2-(2,4-dimethoxyphenyl)-4-phenyl-5-oxazolidinecarboxylic acid ester (5a & 5b, 355 mg). Fractions 1–4, 15–23, and 29 are combined, evaporated and found to contain impure 5a and 5b. This mixture is rechromatographed over an E. Merck size B medium pressure chromatography column eluted with (25-75) ethyl acetate-n-hexane (200 mL), (30-70) ethyl acetate-n-hexane (500 mL), and (40-60) ethyl acetate-n-hexane (500 mL), collecting fractions of 15 mL. The less polar isomer of 7-TES-Δ$^{12,13}$-iso-baccatin III-13-(4S,5R)-N-Boc-2-(2,4-dimethoxyphenyl)-4-phenyl-5-oxazolidinecarboxylic acid ester (5a) is found in fractions 25–30 and the more polar isomer of 7-TES-Δ$^{12,13}$-iso-baccatin III-13-(4S,5R)-N-Boc-2-(2,4-dimethoxyphenyl)-4-phenyl-5-oxazolidinecarboxylic acid ester (5b) is found in fractions 31–39.

Less polar isomer 7-TES-Δ$^{12,13}$-iso-baccatin III-13-(4S,5R)-N-Boc-2-(2,4-dimethoxyphenyl)-4-phenyl-5-oxazolidinecarboxylic acid ester (5a)

TLC (silica gel GF): (30-70) ethyl acetate-hexane; R$_f$: 0.50.

Proton NMR (CDCl$_3$, TMS): δ0.47–0.63 (q, 6H); 0.84–0.99 (t, 9H); 1.24 (s, 9H); 2.16 (s, 3H); 2.19 (s, 3H); 3.81 (s, 3H); 3.86 (s, 3H); 4.24–4.30 (d, 1H); 4.35–4.42 (d, 1H); 4.42–4.50 (q, 1H); 4.83–4.93 (d, 1H); 4.97 (s, 1H); 5.35–5.50 (d, 1H); 5.51–5.58 (d, 1H); 6.00 (s, 1H); 6.39–6.46 (dd, 1H); 6.48–6.53 (d, 1H); 6.72 (s, 1H); 7.10–7.19 (d, 1H); 7.29–7.65 (m, 8H); 8.00–8.11 (d, 2H).

More polar isomer 7-TES-Δ$^{12,13}$-iso-baccatin III-13-(4S,5R)-N-Boc-2-(2,4-dimethoxyphenyl)-4-phenyl-5-oxazolidinecarboxylic acid ester (5b)

TLC (silica gel GF): (30-70) ethyl acetate-hexane; R$_f$: 0.37.

Proton NMR (CDCl$_3$, TMS): δ0.45–0.59 (q, 6H); 0.83–0.96 (t, 9H); 1.05 (s, 9H); 2.16 (s, 3H); 3.69–3.75 (d, 1H); 3.82 (s, 3H); 3.90 (s, 3H); 4.18–4.25 (d, 1H); 4.30–4.36 (d, 1H); 4.27–4.43 (m, 1H); 4.56–4.64 (bd, 1H); 4.80–4.86 (d, 1H); 5.25–5.33 (d, 1H); 5.45–5.51 (d, 1H); 5.88 (s, 1H); 6.36–6.45 (dd, 1H); 6.45–6.54 (d, 1H); 7.30–7.68 (m, 9H); 8.00–8.06 (d, 2H).

EXAMPLE 4

Preparation of 7-TES-13-(N-Boc-β-phenyl isoserinyl)-Δ$^{12,13}$-iso-baccatin III (6)

7-TES-Δ$^{12,13}$-iso-baccatin III-13-(4S,5R)-N-Boc-2-(2,4-dimethoxyphenyl)-4-phenyl-5-oxazolidinecarboxylic acid ester (5a,b 355 mg 0.319 mM) is stirred at room temperature and under nitrogen in 8 mL acetic acid-2 mL water. The reaction is followed by TLC and after 24 hours the more polar isomer 5b has all reacted while there some of the less polar isomer 5a still remains. The reaction is diluted with 100 mL ethyl acetate and washed with 50 mL 1N sodium hydroxide and 3 times with 50 mL 5% sodium bicarbonate. The organic layer is dried over sodium sulfate and evaporated under vacuum. The crude product is chromatographed over an E. Merck size B prepacked silica gel column. Fractions of 10 mL are collected, analyzing them by TLC. The column is eluted with (20-80) acetone-n-hexane (800 mL), (30-70) acetone-n-hexane (300 mL), (40-60) acetone-n-hexane (300 mL). Fractions 22–36 are found to contain 7-TES-13-(N-Boc-β-phenyl isoserinyl)-Δ$^{12,13}$-iso-baccatin III (6) as a mixture. Fractions 59–63 are found to contain 13-(N-Boc-β-phenyl isoserinyl)-Δ$^{12,13}$-iso-baccatin III (7). The residue from evaporation of fractions 22–36 is rechromatographed over an E. Merck size B prepacked silica gel column eluted with (5-95) acetone-toluene. Fractions 30–60 are found to contain 7-TES-13-(N-Boc-β-phenyl isoserinyl)-Δ$^{12,13}$-iso-baccatin III (6)

TLC (silica gel GF): (10-90) acetone-toluene; R$_f$: 0.31

Proton NMR (CDCl$_3$, TMS): δ0.48–0.61 (q, 6H); 0.84–0.96 (t, 9H); 1.14 (s, 3H); 1.23 (s, 9H); 1.26 (s, 3H); 1.62 (s, 3H); 1.84–1.98 (t, 1H); 2.03–2.15 (d, 1H); 2.17 (s, 3H); 2.83–2.94 (d, 1H); 3.18–3.25 (d, 1H); 3.82–3.89 (d, 1H); 4.26–4.34 (d, 1H); 4.38–4.45 (d, 1H); 4.36–4.48 (m, 1H); 4.67–4.74 (d, 1H); 4.89–4.97 (d, 1H); 5.40 (s, 1H); 5.53–5.57 (d, 1H); 5.97 (s, 1H); 7.13–7.63 (m, 9H); 8.08–8.17 (d, 2H).

Mass spectrum: (M+H)+ measured at 964.4547; theory for C$_{51}$H$_{69}$NO$_{15}$Si+H is 964.4514.

EXAMPLE 5

Preparation of 13-(N-Boc-β-phenyl isoserinyl)-$\Delta^{12,13}$-iso-baccatin III (7)

7-TES-$\Delta^{12,13}$-iso-baccatin III-13-(4S,5R)-N-Boc-2-(2,4-dimethoxyphenyl)-4-phenyl-5-oxazolidinecarboxylic acid ester (5a,b; 0.69 g, 0.62 mM) is stirred in a mixture of acetic acid (16 mL) and water (4 mL) at room temperature under an inert atmosphere 4 days. The reaction is diluted with ethyl acetate and washed multiple times with water and aqueous sodium bicarbonate. The organic layer is dried over anhydrous sodium sulfate and evaporated. The product is chromatographed on silica gel 60 (230–400 mesh) in acetone-hexane mixtures and 13-(N-Boc-β-phenyl isoserinyl)-$\Delta^{12,13}$-isobaccatin III is obtained.

Proton NMR (CDCl$_3$, TMS): δ1.06 (s, 3H); 1.22 (s, 9H); 1.30 (s, 3H); 1.92 (m, 1H); 2.08 (d, 1H, J=19 Hz); 2.23 (s, 3H); 2.51 (m, 1H); 2.57 (s, 3H); 2.76 (s, 1H); 2.92 (d, 1H, J=19 Hz); 3.21 (bs, 1H); 3.52 (d, 1H, J=4 Hz); 3.71 (d, 1H, J=6 Hz); 4.33 (d, 1H, J=8 Hz); 4.36 (m, 1H); 4.42 (d, 1H, J=8 Hz); 4.70 (d, 1H); 4.94 (dd, 1H); 5.40 (m, 1H); 5.48 (s, 1H); 5.58 (d, 1H, J=6 Hz); 7.30–7.67 (m, 8H); 8.13 (d, 2H, J=7 Hz).

Carbon NMR (CDCl$_3$, TMS): 9.12, 14.38, 19.97, 21.07, 22.65, 28.13, 29.78, 32.73, 35.30, 38.78, 39.53. 55.72, 57.94, 71.54, 73.57, 73.71, 77.66, 77.77, 80.19, 81.05, 84.58, 121.90, 126.56, 128.04, 128.74, 128.89, 128.95, 130.27, 133.67, 138.52, 143.33, 155.16, 166.77, 170.74, 170.90, 172.04, 206.64.

Mass Spectrum (FAB): Calc'd for $C_{45}H_{55}N_1O_{15}$: 850.3650 Found: 850.3650

Major ions at 794, 594, 105.

EXAMPLE 6

Preparation of 7-TES-13-(N-Boc-β-phenyl isoserinyl)-$\Delta^{12,13}$-iso-baccatin III (6) and 13-(N-Boc-β-phenyl isoserinyl)-$\Delta^{12,13}$-iso-baccatin III (7)

Less polar isomer 7-TES-$\Delta^{12,13}$-iso-baccatin III-13-(4S, 5R)-N-Boc-2-(2,4-dimethoxyphenyl)-4-phenyl-5-oxazolidinecarboxylic acid ester (5a, 50 mg, 0.045 mM) is treated with 0.5 mL 0.1N HCl in MeOH with stirring at room temperature under nitrogen. The reaction is followed by TLC, starting material being found to be consumed in 30 minutes. The reaction mixture is partitioned between ethyl acetate-5% sodium bicarbonate. The organic layer is separated, dried over sodium acetate and evaporated under vacuum. The crude product is chromatographed over an E. Merck size A prepacked silica gel column, eluting with a gradient of (10-90) acetone-toluene to (20-80) acetone-toluene. Fractions of 5 mL are collected, analyzing them by TLC. Fractions 4–14 are found to contain 7-TES-13-(N-Boc-β-phenyl isoserinyl)-$\Delta^{12,13}$-iso-baccatin III (6) and fractions 18–28 are found to contain 13-(N-Boc-β-phenyl isoserinyl)-$\Delta^{12,13}$-iso-baccatin III (7). The data for 6 and 7 are comparable to those described in examples 4 and 5.

EXAMPLE 7

Preparation of 10-deacetyl-13-(N-Boc-β-phenyl isoserinyl)-$\Delta^{12,13}$-iso-baccatin III (8)

13-(N-Boc-β-phenyl isoserinyl)-$\Delta^{12,13}$-iso-baccatin III (7, 25 mg 0.029 mM) is stirred at room temperature under nitrogen in 1 mL 95% ethanol. To this is added 2 drops anhydrous hydrazine. Most of the starting material is reacted after 5 minutes, as indicated by TLC. After 1 hour, the reaction is partitioned between methylene chloride-water. The layers are separated and the water layer re-extracted with methylene chloride. The organic layers are combined, dried over sodium sulfate and evaporated under vacuum. The crude product is purified by chromatography over an E. Merck size A prepacked silica gel column. The column is eluted with (40-60) acetone-hexane, collecting 3mL fractions. The fractions are analyzed by TLC and pure product found in fractions 16–23, which are combined and evaporated, leaving 10-deacetyl-13-(N-Boc-β-phenyl isoserinyl)-$\Delta^{12,13}$-iso-baccatin III (8) as a solid.

TLC (silica gel GF): 40–60 acetone-hexane; Rf: 0.28.

Proton NMR (CDCl$_3$, TMS): d 1.02 (s, 3H); 1.23 (s, 9H); 1.25 (s, 3H); 1.68 (s, 3H); 1.71 (s, 3H); 2.57 (s, 3H); 3.38 (bs, 1H); 3.76–3.82 (d, 1H); 4.16 (bs, 1H); 4.39–4.46 (d, 1H); 4.50–4.56 (bd, 1H); 4.56–4.63 (bd, 1H); 4.70 (bs, 1H); 4.90–4.97 (d, 1H); 5.33–5.44 (bd, 1H); 5.44–5.54 (bd, 1H); 5.52–5.59 (d, 1H); 7.30–7.45 (m, 5H); 7.45–7.56 (t, 2H); 7.56–7.66 (t, 1H); 8.09–8.18 (d, 2H).

EXAMPLE 8

2'-Troc-13-(N-Boc-β-phenyl isoserinyl)-$\Delta^{12,13}$-iso-baccatin III (9)

A solution of 13-(N-Boc-β-phenyl isoserinyl)-$\Delta^{12,13}$-iso-baccatin III (7, 0.104 g, 0.12 mmole) and dry pyridine (0.6 mL) in methylene chloride (10 mL) is cooled to −20° C. under a nitrogen atmosphere. 2,2,2-Trichloroethyl chloroformate (20 μL, 0.032 g, 0.015 mmole) is added in one portion to the solution. The reaction is examined after 1 hr by TLC, which shows that no reaction has occurred. Additional 2,2,2-trichloroethyl chloroformate (20 μL, 0.15 mmole) is added and the reaction stirred for an additional 1.75 hr. Although TLC indicates incomplete reaction (about 1:1 starting material and product) at this point, the reaction is quenched and worked up by washing with ice cold 0.1N HCl (2×), saturated NaHCO$_3$, and with H$_2$O. The organic layer is dried (NaSO$_4$), filtered, and evaporated to give a residual mixture (0.139 g). The mixture is chromatographed over silica gel (one E. Merck size B Lobar column) using CH$_2$Cl$_2$ to apply the material to the column and 50% EtOAc-hexane to elute the column. Fractions of 8 mL volume are collected. Later fractions (42–60) contain starting material while earlier fractions (20–25) contained 2'-Troc-13-(N-Boc-β-phenyl isoserinyl)-$\Delta^{12,13}$-iso-baccatin III (9).

Proton NMR (CDCl$_3$, TMS): δ8.13 (d, 2H, J=7.3 Hz), 7.59 (t, 1H, J=7.3 Hz), 7.30–7.52 (m, 7H), 5.66 (d, 1H, J=10.0 Hz), 5.58 (d, 1H, J=5.7 Hz, H$_2$), 5.45–5.53 (m, 3H), 4.96 (dd, 1 H, J=3.2, 9.6 Hz, H$_5$), 4.71 (s, 2H, troc-CH$_2$—), 4.42 (d, 1H, J=8.8 Hz, H$_{20a}$), 4.39 (m, 1H, H$_7$), 4.34 (d, 1H, J=8.6 Hz, H$_{20b}$), 3.71 (d, 1H, J=5.7 Hz, H$_3$), 2.94 (d, 1H, J=19.0 Hz, H$_{14a}$), 2.76 (s, 1H, H$_{11}$), 2.61 (s, 3H, —CH$_3$), 2.53 (7 lines, 1H, J$_{H7}$=6.2, J$_{H5}$=9.5, J$_{gem}$=15.0 Hz, H$_{6a}$), 2.23 (s, 3H, —CH$_3$), 2.17 (d, 1H, J=19.3 Hz, H$_{14b}$), 1.93 (7 lines, 1H, J$_{H7}$=11.3, J$_{H5}$=3.3, J$_{gem}$=14.6 Hz, H$_{6b}$), 1.67 (—CH$_3$), 1.64 (—CH$_3$), 1.28 (s, 3H, —CH$_3$), 1.22 (s, 9H, —CMe$_3$), 1.05 (s, 3H, —CH$_3$).

EXAMPLE 9

Preparation of $\Delta^{12,13}$-iso-baccatin III-13-(4S,5R)-N-Boc-2-(2,4-dimethoxyphenyl)-4-phenyl-5-oxazolidinecarboxylic acid ester (10a)

The less polar isomer of 7-TES-$\Delta^{12,13}$-iso-baccatin III-13-(4S,5R)-N-Boc-2-(2,4-dimethoxyphenyl)-4-phenyl-5-oxazolidinecarboxylic acid ester (5a, 45 mg, 0.041 mM) is dissolved in 1 mL dry THF with stirring at room temperature and under nitrogen. To this is added tetrabutyl ammonium fluoride trihydrate (15 mg, 0.041 mM). The reaction is followed by TLC and is mostly complete in one hour. The reaction mixture is partitioned between ethyl acetate-5% sodium bicarbonate. The organic layer is dried over sodium sulfate and evaporated under vacuum. The crude product is purified by chromatography over an E. Merck size A prepacked silica gel column. The column is eluted with (40-60) ethyl acetate-hexane and (60-40) ethyl acetate-hexane. Fractions of 5 mL are collected, analyzing them by TLC. The major product spot is found in fractions 12–18, which upon combining and evaporating under vacuum leaves $\Delta^{12,13}$-iso-baccatin III-13-(4S,5R)-N-Boc-2-(2,4-dimethoxyphenyl)-4-phenyl-5-oxazolidinecarboxylic acid ester (10a) as a solid.

TLC (silica gel GF): (40-60) ethyl acetate-hexane; $R_f$: 0.44.

Proton NMR (CDCl$_3$, TMS): δ1.07 (s, 3H); 1.25 (s, 9H); 1.33 (s, 3H); 1.62 (s, 3H); 1.70 (s, 3H); 2.17 (s, 3H); 2.24 (s, 3H); 3.51–3.56 (d, 1H); 3.68–3.75 (d, 1H); 3.82 (s, 3H); 3.88 (s, 3H); 4.28–4.36 (d, 1H); 4.38–4.44 (d, 1H); 4.36–4.47 (m, 1H); 4.86–4.96 (dd, 1H); 4.99 (s, 1H); 5.33–5.41 (d, 1H); 5.50 (s, 1H); 5.56–5.63 (d, 1H); 6.40–6.46 (dd, 1H); 6.50–6.54 (d, 1H); 6.72 (s, 1H); 7.09–7.16 (d, 1H); 7.33–7.68 (m, 8H); 8.01–8.10 (d, 2H).

Mass spectrum: (M+H)$^+$ at 998. Other ions at 942, 898, 384, 284, 105, 57.

EXAMPLE 10
Preparation of 7-Troc-$\Delta^{12,13}$-iso-baccatin III-13-(4S,5R)-N-Boc-2-(2,4-dimethoxyphenyl)-4-phenyl-5-oxazolidinecarboxylic acid ester (11a)

$\Delta^{12,13}$-Iso-baccatin III-13-(4S,5R)-N-Boc-2-(2,4-dimethoxyphenyl)-4-phenyl-5-oxazolidinecarboxylic acid ester (10a, 81 mg, 0.081 mM) is stirred under nitrogen at room temperature in 1 mL dry pyridine. To this is added 140 μL trichloroethyl chloroformate in 200 μL methylene chloride. The reaction is left to go overnight. TLC the next day shows no starting material left.

The reaction mixture is partitioned between methylene chloride-1N HCl. The layers are separated and the water layer re-extracted with methylene chloride. The organic layers are combined, dried over sodium sulfate and evaporated under vacuum. The crude product is chromatographed over an E. Merck size A prepacked silica gel column, eluting with (30-70) ethyl acetate-hexane. Fractions of 5 mL are collected, analyzing them by TLC. 7-Troc-$\Delta^{12,13}$-iso-baccatin III-13-(4S,5R)-N-Boc-2-(2,4-dimethoxyphenyl)-4-phenyl-5-oxazolidinecarboxylic acid ester (11a) is found in fractions 9–15, which upon combining and evaporating under vacuum leaves a solid.

TLC (silica gel GF): (30-70) ethyl acetate-hexane; $R_f$: 0.14

Proton NMR (CDCl$_3$, TMS): δ1.10 (s, 3H); 1.26 (s, 9H); 1.32 (s, 3H); 1.77 (s, 3H); 2.16 (s, 3H); 2.19 (s, 3H); 3.82 (s, 3H); 3.86 (s, 3H); 3.92–3.98 (d, 1H); 4.24–4.34 (d, 1H); 4.36–4.44 (d, 1H); 4.54–4.63 (d, 1H); 4.85–4.94 (d, 1H); 4.85–4.94 (m, 1H); 4.99 (bs, 1H); 5.26–5.36 (m, 1H); 5.36–5.44 (s, 1H); 5.54–5.60 (d, 1H); 5.63 (s, 1H); 6.38–6.46 (dd, 1H); 6.48–6.53 (dd, 1H); a6.72 (s, 1H); 7.10–7.18 (d, 1H); 7.34–7.66 (m, 8H); 8.01–8.10 (d, 2H).

EXAMPLE 11
Preparation of 7-Troc-13-(N-Boc-β-phenyl isoserinyl)-$\Delta^{12,13}$-iso-baccatin III (12)

7-Troc-$\Delta^{12,13}$-iso-baccatin III-13-(4S,5R)-N-Boc-2-(2,4-dimethoxyphenyl)-4-phenyl-5-oxazolidinecarboxylic acid ester (11a, 82 mg, 0.07 mM) is treated at room temperature with stirring under nitrogen with 800 μL 0.1N HCl in methanol. The reaction is followed by TLC and is mostly complete after 1 hour. The reaction mixture is partitioned between ethyl acetate-5% sodium bicarbonate. The layers are separated and the water layer re-extracted with ethyl acetate. The organic layers are combined, dried over sodium sulfate and evaporated under vacuum. The crude product is Chromatographed over an E. Merck size A prepacked silica gel column, eluting with a gradient of (30-70) ethyl acetate-hexane to (40-60) ethyl acetate-hexane. Fractions of 5 mL are collected, analyzing them by TLC. The product is found in fractions 11–17 which upon combining and evaporating under vacuum give 7-Troc-13-(N-Boc-β-phenyl isoserinyl)-$\Delta^{12,13}$-iso-baccatin III (12) as a solid.

TLC (silica gel GF): (30-70) ethyl acetate-hexane; $R_f$: 0.14

Proton NMR (CDCl$_3$, TMS): δ1.08 (s, 3H); 1.25 (s, 9); 1.29 (s, 3H); 1.77 (s, 3H); 1.90–2.03 (t, 1H); 2.14 (s, 3H); 2.59 (s, 3H); 3.30–3.36 (d, 1H); 3.90–3.99 (d, 1H); 4.26–4.33 (d, 1H); 4.39–4.47 (d, 1H); 4.54–4.63 (d, 1H); 4.72 (bs, 1H); 4.86–4.93 (d, 1H); 4.90–4.98 (d, 1H); 5.23–5.33 (q, 1H); 5.34–5.51 (q, 1H); 5.52–5.60 (d, 1H); 5.62 (s, 1H); 7.30–7.45 (m, 5H); 7.45–7.55 (t, 2H); 7.55–7.65 (t, 1H); 8.08–8.17 (d, 1H).

EXAMPLE 12
2'-Troc-13-(N-Boc-β-phenyl isoserinyl)-7-deoxy-7-fluoro-$\Delta^{12,13}$-iso-baccatin III (13), 2'-Troc-13-(N-Boc-β-phenyl isoserinyl)-7-deoxy-7b,8b-methano-$\Delta^{12,13}$-iso-baccatin III (14), and 2'-Troc-13-(N-Boc-β-phenyl isoserinyl)-7-deoxy-$\Delta^{6,7}$-$\Delta^{12,13}$-iso-baccatin III (15)

Dimethylaminosulfur trifluoride (methylDAST, 8 μL, 0.011 g, 0.08 mmol) is added to a cold (−78° C. bath) solution of 2'-Troc-13-(N-Boc-β-phenyl isoserinyl)-$\Delta^{12,13}$-iso-baccatin III (9, 0.050 g, 0.048 mmol) in CH$_2$Cl$_2$ (4 mL) under a N$_2$ atmosphere. The cooling bath is removed and after 1.75 hr, TLC indicates an incomplete reaction. The solution is again cooled to −78° C. and additional methyl-DAST (12 μL) is added. The cooling bath is removed and a TLC after 1.25 hr indicates complete reaction. The reaction is quenched with H$_2$O and diluted with CH$_2$Cl$_2$. The layers are separated and the organic layer washed with water. The aqueous layers are combined and back extracted with CH$_2$Cl$_2$. The combined CH$_2$Cl$_2$ extracts are dried (Na$_2$SO$_4$), filtered, and concentrated to give a white solid. This solid is chromatographed over silica gel (two E. Merck size A Lobar columns) using a solution in CH$_2$Cl$_2$ to apply the material to the column and using first 5% CH$_3$CN—CH$_2$Cl$_2$ (115 fractions) and then 10% CH$_3$CN—CH$_2$Cl$_2$ for elution of the column. Fractions of 3 mL volume are collected through fraction 100 and fractions of 8 mL volume are collected thereafter. Fractions 56–98 contained 2'-Troc-13-(N-Boc-β-phenyl isoserinyl)-7-deoxy-$\Delta^{6,7}$-$\Delta^{12,13}$-iso-baccatin III (15);

Proton NMR (CDCl$_3$, TMS): δ8.18 (d, 2H, J=7.1 Hz), 7.60 (t, 1H, J=7.3 Hz), 7.50 (t, 2H, J=7.5 Hz), 7.30–7.45 (m, 5H), 6.10 (dd, 1H, J=5.1, 9.9 Hz, H$_6$), 6.04 (d, 1H, J=9.8 Hz, H$_7$), 5.73 (d, 1H, J=5.6 Hz, H$_2$), 5.66 (d, 1H, J=10.1 Hz), 5.50 (2H), 5.18 (s, 1H, H$_{10}$), 5.14 (d, 1H, J=5.0 Hz, H$_5$), 4.70 (s, 2H, troc-CH$_2$—), 4.55 (d, 1H, J=8.3 Hz, H$_{20a}$), 4.35 (d, 1H, J=8.3 Hz, H$_{20b}$), 3.68 (d, 1H, J=5.6 Hz, H$_3$), 2.97 (d, 1H, J=19.1 Hz, H$_{14a}$), 2.75 (s, 1H, H$_{11}$), 2.64 (s, 3H, —CH$_3$), 2.19 (s, 3H, —CH$_3$), 2.11 (d, 1H, J=19.3 Hz, H$_{14b}$), 1.75 (s, 3H, —CH$_3$), 1.58 (s, —CH$_3$), 1.30 (s, 3H, —CH$_3$), 1.20 (s, 9H, —CMe$_3$), 1.04 (s, 3H, —CH$_3$);

Fractions 106–124 contain a mixture of which 2'-Troc-13-(N-Boc-β-phenyl isoserinyl)-7-deoxy-7b,8b-methano-$\Delta^{12,13}$-iso-baccatin III (14) was the major component.

Proton NMR (CDCl$_3$, TMS): δ8.18 (d, 2H, J=7.2 Hz), 7.58 (t, 1H, J=7.3 Hz), 7.49 (t, 2H, J=7.4 Hz), 7.30–7.45 (m, 5H), 5.65 (m, 2H, H$_2$, H$_2$'), 5.48 (m, 2H, —NH—, H$_3$'), 5.22 (d, 1H, J=2.0 Hz, H$_{10}$), 4.80 (d, 1H, J=3.2 Hz, H$_5$), 4.70 (s, 2H, troc-CH$_2$—), 4.43 (d, 1H, J=8.7 Hz, H$_{20a}$), 4.11 (d, 1H, J=8.6 Hz, H$_{20b}$), 3.87 (d, 1H, J=6.7 Hz, H$_3$), 2.96 (d, 1H, J=19.2 Hz, H$_{14a}$), 2.75 (s, 1H, H$_{11}$), 2.58 (s, 3H, —CH$_3$), 2.46 (dt, 1H, J=4.4, 16.1 Hz, H$_{6a}$), 2.17 (s, 3H, —CH$_3$), 2.15 (m, 3H, H$_{6b}$, H$_{19a}$, H$_{20b}$), 1.68 (m, H$_{19b}$), 1.63 (s, 3H, —CH$_3$), 1.31 (m, H$_7$), 1.13 (s, 3H, —CH$_3$), 1.13 (s, 9H, —CMe$_3$), 1.12 (s, 3H, —CH$_3$).

Carbon NMR(CDCl$_3$, TMS): δ203.5, 169.7, 167.3, 164.8, 154.7, 153.2, 144.4, 137.1, 133.6, 130.3, 129.1, 129.0, 128.7, 128.3, 126.3, 123.1, 85.1, 80.4, 79.0, 78.6, 78.4, 77.2, 75.6, 55.0, 54.1, 39.7, 36.6, 32.9, 32.4, 30.2, 28.9, 28.0, 25.8, 22.4, 21.1, 20.8, 14.2, 12.8.

The minor component in this mixture is compound 2'-Troc-13-(N-Boc-β-phenyl isoserinyl)-7-deoxy-7-fluoro-Δ$^{12,13}$-iso-baccatin III (13), which was identified in the following experiment after removal of the 2'-troc protecting group and separation from the 7β,8β-methano analog 13-(N-Boc-β-phenyl isoserinyl)-7-deoxy-7b,8b-methano-Δ$^{12,13}$-iso-baccatin III (17, in Example 13).

EXAMPLE 13
13-(N-Boc-β-phenyl iserinyl)-7-deoxy-7-fluoro-Δ$^{12,13}$-iso-baccatin III (16, and 13-(N-Boc-β-phenyl isoserinyl)-7-deoxy-7β,8β-methano-Δ$^{12,13}$-iso-baccatin III (17)

A solution of the 1:9 mixture of 2'-Troc-13-(N-Boc-β-phenyl isoserinyl)-7-deoxy-7-fluoro-Δ$^{12,13}$-iso-baccatin III (13) and 2'-Troc-13-(N-Boc-β-phenyl isoserinyl)-7-deoxy-7β,8β-methano-Δ$^{12,13}$-iso-baccatin III (14) from the example 12 (0.029 g, 0.029 mmol) in CH$_3$OH-HOAc (9:1) is stirred with activated Zn dust (0.074 g) under a N$_2$ atmosphere at room temperature. After 4 hr, a small amount of starting material remains; additional Zn dust (0.025 g) is added and stirring continued for another hour. The mixture is filtered to remove solids and the filtrate evaporated under reduced pressure giving a residue which is dissolved in CH$_2$Cl$_2$ and washed twice with H$_2$O. The aqueous extracts are back extracted with CH$_2$Cl$_2$ and the combined organic extracts dried (Na$_2$SO$_4$), filtered, and evaporated to yield a white solid residue (0.027 g). This residue is chromatographed over silica gel (two E. Merck size A Lobar columns, 3.5 mL fractions) by application to the column in CH$_2$Cl$_2$ solution and elution of the column with 40% EtOAc-hexane. Fractions 41–58 contain pure 13-(N-Boc-β-phenyl isoserinyl)-7-deoxy-7β,8β-methano-Δ$^{12,13}$-iso-baccatin III (17), 66%;

Proton NMR (CDCl$_3$, TMS): δ8.19 (d, 2H, J=7.2 Hz), 7.29–7.62 (m, 8H), 5.62 (d, 1H, 6.7 Hz, H$_2$), 5.41 (s, 2H, —NH—, H$_3$'), 5.22 (d, 1H, J=2.0 Hz, H$_{10}$), 4.79 (d, 1H, J=3.1 Hz, H$_5$), 4.69 (d, 1H, J=3.8 Hz, H$_2$'), 4.42 (d, 1H, J=8.7 Hz, H$_{20a}$), 4.09 (d, 1H, J=8.8 Hz, H$_{20b}$), 3.87 (d, 1H, J=6.7 Hz, H$_3$), 2.96 (d, 1H, J=19.3 Hz, H$_{14a}$), 2.75 (s, 1H, H$_{11}$), 2.56 (s, 3H, —CH$_3$), 2.45 (dt, 1H, J=4.3, 16.1 Hz, H$_{6a}$) 2.17 (s, —CH$_3$), 2.05–2.21 (m, 3H, H$_{6b}$, H$_{14b}$, H$_{19a}$), 1.72 (t, 1H, J=6.2 Hz, H$_{19b}$), 1.58 (s, 3H, —CH$_3$), 1.33 (s, 3H, —CH$_3$), 1.13 (s, 12H, —CMe$_3$, —CH$_3$).

mass spectrum: found 832.3529, C$_{45}$H$_{53}$NO$_{14}$+H requires 832.3544, 776, 732, 551, 73, 57 m/z.

Fractions 62–75 contained 13-(N-Boc-β-phenyl isoserinyl)-7-deoxy-7-fluoro-Δ$^{12,13}$-iso-baccatin III (16);

Proton NMR (CDCl$_3$, TMS): δ8.13 (d, 2H, J=7.2 Hz), 7.60 (t, 1H), 7.49 (t, 2H), 7.30–7.42 (m, 5H), 5.87 (d, 1H, J=6.1 Hz, H$_2$), 5.54 (d, 1H, J=5.8 Hz, H$_3$'), 5.41 (m, 2H, —NH—, H$_{10}$), 5.11 (d, 1H, J=7.2 Hz, H$_5$), 4.71 (m, 1H, H$_2$'), 4.58 (d, 1H, J=47 Hz, H$_7$), 4.49 (d, 1H, J=8.4 Hz, H$_{20a}$), 4.36 (d, 1H, J=8.5 Hz, H$_{20b}$), 4.11 (d, 1H, J=5.6 Hz, H$_3$), 2.92 (d, 1H, J=19 Hz, H$_{14a}$), 2.74 (s, 1H, H$_{11}$), 2.59 (s, 3H, —CH$_3$), 2.20 (s, 3H, —CH$_3$), 2.10 (d, 1H, J=19 Hz, H$_{14b}$), 1.64 (s, 3H, —CH$_3$), 1.27 (s, 9H, —CMe$_3$), 1.08 (s, 3H, —CH$_3$).

mass spectrum: found 852.3597, C$_{45}$H$_{54}$FNO$_{14}$+H requires 852.3606, 832, 796, 752, 692, 180, 105, 57 m/z.

EXAMPLE 14
13-(N-Boc-β-phenyl isoserinyl)-7-deoxy-Δ$^{6,7}$-Δ$^{12,13}$-iso-baccatin III (18)

A solution of 2'-Troc-13-(N-Boc-β-phenyl isoserinyl)-7-deoxy-Δ$^{6,7}$-Δ$^{12,13}$-iso-baccatin III (15, 0.0080 g, 0.0079 mmol) in 9:1 CH$_3$OH-HOAc (2 mL) is stirred with activated Zn dust (0.020 g) under N$_2$ at room temperature for 3 hr after which additional Zn dust (0.050 g) is added and stirring continued another 1.25 hr. The mixture is filtered to remove solids, the filtrate is evaporated, the residue is dissolved in CH$_2$Cl$_2$ and the solution washed with saturated aq NaHCO$_3$ and twice with H$_2$O. The combined aqueous washes are back extracted with CH$_2$Cl$_2$. The combined CH$_2$Cl$_2$ extracts are dried (Na$_2$SO$_4$), filtered, and evaporated to give a white solid (0.008 g). The solid is chromatographed over silica gel (two E. Merck size A Lobar columns, 3 mL fractions) using a solution in CH$_2$Cl$_2$ for application to the column and 40% EtOAc-hexane for elution of the column. Pure 13-(N-Boc-β-phenyl isoserinyl)-7-deoxy-Δ$^{6,7}$-Δ$^{12,13}$-iso-baccatin III (18) is eluted in fractions 31–51.

Proton NMR (CDCl$_3$, TMS): δ8.18 (d, 2H, J=7.2 Hz), 7.61 (t, 1H, J=7.3 Hz), 7.50 (m, 2H), 7.30–7.44 (m, 5H), 6.09 (dd, 1H, J=5.1, 9.9 Hz, H$_6$), 6.05 (d, 1H, J=9.8 Hz, H$_7$), 5.73 (d, 1H, J=5.5 Hz, H$_2$), 5.40 (s, 2H, —NH—, H$_3$'), 5.18 (s, 1H, H$_{10}$), 5.13 (d, 1H, J=5.1 Hz, H$_5$), 4.70 (m, 1H, H$_2$'), 4.55 (d, 1H, J=8.3 Hz, H$_{20a}$), 4.34 (d, 1H, J=8.4 Hz, H$_{20b}$), 3.68 (d, 1H, J=5.4 Hz, H$_3$), 2.97 (d, 1H, J=18.9 Hz, H$_{14a}$), 2.74 (s, 1H, H$_{11}$), 2.61 (s, 3H, —CH$_3$), 2.20 (s, 3H, —CH$_3$), 2.09 (d, 1H, J=18.0 Hz, H$_{14b}$), 1.75 (s, 3H, —CH$_3$), 1.52 (s, 3H, —CH$_3$), 1.32 (s, 1H, —CH$_3$), 1.20 (s, 9H, —CMe$_3$), 1.05 (s, 3H, —CH$_3$).

mass spectrum: found 832.3579, C$_{45}$H$_{53}$NO$_{14}$+H requires 832.3544, 776, 732, 180, 105, 57 m/z.

EXAMPLE 15
Baccatin-III-7-O-triflate (20)

A solution of baccatin-III (5.25 g, 8.93 mmoles) in CH$_2$Cl$_2$ (21 mL) and pyridine (18.1 mL) is cooled in a −30° C. bath. Trifluoromethanesulfonic anhydride (3.76 mL, 6.31 g, 22.3 mmoles) is added and the resulting mixture is stirred and allowed to warm to room temperature over a period of an hour. The reaction is complete after 4 hrs; saturated aq NH$_4$Cl (50 mL) is added and the mixture is extracted with CH$_2$Cl$_2$. The organic extract is washed successively with 1M aq NaHSO$_4$ (50 mL), saturated aq NaHCO$_3$ (2×50 mL), saturated aq NaCl, and dried (Na$_2$SO$_4$), filtered, and concentrated under reduced pressure. Care is taken not to warm the solution greater than 40° C. during removal of the solvent. A pale yellow solid is obtained which is flash chromatographed over silica gel (6" silica gel in a 75 mm column, 125 mL fractions). The material is applied to the column in a CH$_2$Cl$_2$ solution and the column eluted with 5% CH$_3$CN—CH$_2$Cl$_2$. Fractions 19–35 contain the desired 7-O-triflate (20) which is a solid.

Proton NMR (CDCl$_3$, TMS): δ8.10 (d, 2H, J=7.2 Hz), 7.63 (t, 1H, J=7.4 Hz), 7.49 (t, 2H, J=7.6 Hz), 6.63 (s, 1H, H$_{10}$), 5.68 (d, 1H, J=7.0 Hz, H$_2$), 5.52 (dd, 1H, J=7.5, 10.1 Hz, H$_7$), 4.94 (d, 1H, J=8.4 Hz, H$_5$), 4.86 (m, 1H, H$_{13}$), 4.35 (d, 1H, J=8.4 Hz, H$_{20a}$), 4.15 (d, 1H, J=8.4 Hz, H$_{20b}$), 4.01 (d, 1H, J=7.0 Hz, H$_3$), 2.87 (5 lines, H$_{14a}$), 2.30 (s, 3H, —CH$_3$), 2.20 (s, 3H, —CH$_3$), 2.10–2.30 (m, H$_{6a}$, H$_{6b}$, H$_{14b}$), 1.87 (s, 3H, —CH$_3$), 1.59 (s, 3H, —CH$_3$), 1.19 (s, 3H, —CH$_3$), 1.05 (s, 3H, —CH$_3$).

EXAMPLE 16
Δ$^{6,7}$-Baccatin-III (21)

A solution of baccatin-III-7-O-triflate (20, 0.97 g, 1.35 mmoles) and 1,8-diazabicyclo[5.4.0]undec-7-ene (1.01 mL, 1.03 g, 6.76 mmoles) in THF (6 mL) is stirred at room temperature for 1 hr, at 50° C. for 2.5 hr, and at reflux temperature for 3 hr, after which reaction is complete.

EtOAc is added and the solution washed with saturated aq NaHCO$_3$ and with saturated aq NaCl. The organic layer is dried (Na$_2$SO$_4$), filtered, and evaporated under reduced pressure. The residue (0.876 g) is flash chromatographed over silica gel (6" silica gel in a 45 mm column) using a solution in CH$_2$Cl$_2$ (1 mL) for application to the column. The column is eluted with 10% CH$_3$CN—CH$_2$Cl$_2$ (1 L), 15% CH$_3$CN—CH$_2$Cl$_2$ (0.5 L), and with 20% CH$_3$CN—CH$_2$Cl$_2$ (0.5 L). Fractions containing the desired material are detected by TLC and are combined to give $\Delta^{6,7}$-Baccatin-III (21).

Proton NMR (CDCl$_3$, TMS): δ8.14 (d, 2H, J=7.2 Hz), 7.63 (t, 1H, J=7.3 Hz), 7.50 (t, 2H, J=7.6 Hz), 6.24 (s, 1H, H$_{10}$), 6.07 (dd, 1H, J=5.7, 9.9 Hz, H$_6$), 5.87 (d, 1H, J=9.9 Hz, H$_7$), 5.80 (d, 1H, J=6.6 Hz, H$_2$), 5.12 (d, 1H, J=5.5 Hz, H$_5$), 4.87 (m, 1H, H$_{13}$), 4.43 (d, 1H, J=8.1 Hz, H$_{20a}$), 4.29 (d, 1H, J=8.1 Hz, H$_{20b}$), 4.10 (d, 1H, J=6.6 Hz, H$_3$), 2.31 (s, 3H, —CH$_3$), 2.20–2,31 (m, 2H, H$_{14a,b}$), 2.24 (s, 3H, —CH$_3$), 1.97 (s, 3H, —CH$_3$), 1.85 (s, 3H, —CH$_3$), 1.12 (s, 6H, 2-CH$_3$).

Carbon NMR (CDCl$_3$, TMS): δ205.6, 170.3, 169.7, 167.0, 145.5, 139.8, 133.7, 132.6, 130.1, 129.4, 128.6, 126.2, 81.2, 81.0, 78.7, 76.4, 75.5, 67.9, 55.5, 42.7, 41.7, 39.0, 30.9, 26.3, 22.7, 21.0, 20.9, 20.2, 15.0.

EXAMPLE 17
Preparation of $\Delta^{6,7}$-13-keto-baccatin III (22)

$\Delta^{6,7}$-Baccatin III (100 mg, 0.17 mM) is dissolved in 2 mL CH$_2$Cl$_2$ and 300 mg activated MnO$_2$ added. TLC shows no starting material left after 18 hr at which point the reaction is filtered through Celite and concentrated in vacuo leaving $\Delta^{6,7}$-13 keto-baccatin III (22).

Proton NMR (CDCl$_3$, TMS): δ1.19 (s,3H); 1.24 (s,3H); 1.81 (s,3H); 2.03 (s,3H); 2.19 (s,3H); 2.28 (s,3H); 2.67 (d,1H); 3.01 (d,1H); 4.22 (m,2H); 4.45 (d,1H); 5.09 (d,1H); 5.87 (m,2H); 6.09 (dd,1H); 6.32 (s,1H); 7.50 (m,2H); 7.64 (m,1H); 8.10 (d,2H)

Mass Spectrum (FAB): Calc'd for C$_{31}$H$_{35}$O$_{10}$: 567.2230; Found: 567.216

EXAMPLE 18
Preparation of $\Delta^{6,7}$-$\Delta^{12,13}$-iso-baccatin III (23)

$\Delta^{6,7}$-13-keto-baccatinIII (22, 90 mg, 0.16 mM) is dissolved in 750 μL HOAc and HOAc and 560 mg activated Zn is added. TLC shows no starting material after 1 hr at which point the reaction is filtered through Celite and concentrated in vacuo leaving $\Delta^{6,7}$-$\Delta^{12,13}$-iso-baccatin III (23).

Proton NMR (CDCl$_3$, TMS): δ1.02 (s,3H); 1.14 (s,3H); 1.56 (s,3H); 1.72 (s,3H); 2.18 (s,3H); 2.35 (s,3H); 3.83 (d,1H); 4.32 (d,1H); 4.52 (d,1H); 5.09 (s,1H); 5.14 (d,1H); 5.66 (d,1H); 6.05 (m,2H); 7.49 (m,2H); 7.62 (m,1H); 8.11 (d,2H)

Mass Spectrum: [M+H]$^+$=569; C$_{31}$H$_{37}$O$_{10}$ requires 569, other ions at m/z 105

EXAMPLE 19
Preparation of 7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24a,b)

Crude (4S,5R)-N-Boc-2-(2,4-dimethoxyphenyl)-4-phenyl-5-oxazolidine carboxylic acid potassium salt (116 mg, 0.25 mM) is partitioned between CH$_2$Cl$_2$ and 5% NaHSO$_4$ solution. The layers are separated and the aqueous layer extracted with EtOAc. The combined organic layers are filtered through anhydrous sodium sulfate and concentrated in vacuo leaving 112 mg of (4S,5R)-N-Boc-2-(2,4-dimethoxyphenyl)-4-phenyl-5-oxazolidinecarboxylic acid (4a,b). $\Delta^{6,7}$-$\Delta^{12,13}$-iso-baccatin III (23, 94 mg, 0.16 mM) is dissolved in 1 mL toluene. All of the (4S,5R)-N-Boc-2-(2, 4-dimethoxyphenyl)-4-phenyl-5-oxazolidinecarboxylic acid (4a,b) is added in a solution of CH$_2$Cl$_2$. To the solution is added DCC (60 mg, 0.29 mM) and DMAP (10 mg, 0.08 mM). After stirring overnight the reaction is filtered through Celite. The filtrate is concentrated in vacuo and chromatographed over an E. Merck size A silica column in 10% EtOAc:Toluene. The column is eluted with 10% EtOAc:Toluene (25 mL), 15% EtOAc:Toluene (40 mL), 20% EtOAc:Toluene (100 mL), and 25% EtOAc:Toluene (50 mL) collecting 3 mL fractions. The less polar isomer 7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24a) is found in fractions 27–37. The more polar isomer 7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24b) is found in fractions 44–54.

Data for less polar isomer 7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24a)

Proton NMR (CDCl$_3$, TMS): δ1.00 (s,3H); 1.16 (s); 1.18 (s); 1.26 (s,3H); 1.66 (s, 3H); 2.11 (s,3H); 2.13 (s,3H); 2.21 (m,1H); 2.77 (d,1H); 3.60 (d,1H); 3.73 (s,3H); 3.77 (s,3H); 4.25 (d,1H); 4.46 (d,1H); 4.90 (br s,1H); 5.05 (br s,1H); 5.11 (s,1H); 5.27 (br s,1H); 5.65 (d,1H); 5.99 (m,2H); 6.33 (dd,1H); 6.41 (d,1H); 6.65 (s,1H); 7.31 (m); 7.46 (m,3H); 7.56 (m,1H); 8.04 (d,2H)

Data for more polar isomer 7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24b)

Proton NMR (CDCl$_3$, TMS): δ1.04 (s); 1.27 (s); 1.69 (s,3H); 2.17 (s,3H); 2.67 (m,1H); 3.56 (d,1H); 3.80 (s,3H); 3.84 (m); 3.88 (s,3H); 4.26 (d,1H); 4.47 (d,1H); 4.59 (d,1H); 5.03 (d,1H); 5.08 (s,1H); 5.27 (d,1H); 5.67 (d,1H); 6.00 (m,2H); 6.48 (d,2H); 7.40 (br s); 7.50 (m,2H); 7.64 (m,1H); 8.06 (d,2H)

EXAMPLE 20
Preparation of 13-(N-Boc-β-phenyl isoserinyl)-7-deoxy-$\Delta^{6,7}$-$\Delta^{12,13}$-iso-baccatin III (18)

7-deoxy-$\Delta^{6,7}$-$\Delta^{12,13}$-iso-baccatin III-13-(4S,5R)-N-Boc-2-(2,4-dimethoxyphenyl)-4-phenyl-5-oxazolidinecarboxylic acid ester (24b, 36 mg, 0.037 mM) is dissolved in 800 μL methanol and 200 μL acetic acid added. After stirring for 17 hrs. TLC shows the reaction is approximately 50% complete and no further change is seen after 20 hrs. Thus, another 400 μL methanol and 100 μL acetic acid is added. An additional 150 mL acetic acid is added after 41 hrs. After 48 hrs. the reaction is partitioned between 5% NaHCO$_3$, brine, and EtOAc. The layers are separated and the aqueous re-extracted using EtOAc. The combined organic layers are filtered through Na$_2$SO$_4$ and concentrated in vacuo. The residue is chromatographed over 4 gm of silica gel packed in 25% EtOAc:Toluene. The column was eluted with 20% EtOAc:Toluene (20 mL), 25% EtOAc:Toluene (40 mL), and 33% EtOAc:Toluene (24 mL) collecting 2 mL fractions. 13-(N-Boc-β-phenyl isoserinyl)-7-deoxy-$\Delta^{6,7}$-$\Delta^{12,13}$-iso-baccatin III (18) is found in fractions 19–33. Mixed fractions 14–18 are rechromatographed over 1 gm of silica gel packed in 20% EtOAc:Toluene. The column was eluted with 20% EtOAc:Toluene (10 mL), 33% EtOAc:Toluene (6 mL), and 50% EtOAc:Toluene (6 mL) collecting 0.5 mL fractions. 13-(N-Boc-β-phenyl isoserinyl)-7-deoxy-$\Delta^{6,7}$-$\Delta^{12,13}$-iso-baccatin III (18) is found if fractions 25–34. The physical data are consistent with those from example 14.

EXAMPLE 21
Preparation of N-(t-butylaminocarbonyl)-β-phenyl isoserine methyl ester (26)

(2R,3S)-β-phenyl-isoserine methyl ester (4.35g, 22 mM) is dissolved in 100 ML dry THF and the flask cooled to 0° C. To the solution is added t-butyl isocyanate (2.8 mL, 25 mM). TLC after 15 minutes shows some starting material left so another 0.5 mL of the isocyanate is added. TLC after 1 hour shows no starting material so the solvent is concentrated in vacuo.

Proton NMR (CDCl$_3$, TMS): δ1.27 (s, 9H); 3.43 (d, 1H); 3.81 (s, 3H); 4.34 (br s, 1H); 4.48 (m, 1H); 5.27 (m, 1H); 5.32 (m, 1H); 7.29 (m, 2H); 7.34 (m, 3H)

Mass spectrum (FAB-High Res.) Theory for C$_{15}$H$_{22}$N$_2$O$_4$+H: 295.1658 Found: 295.1663

EXAMPLE 22
Preparation of (4S,5R)-N-(t-butylaminocarbonyl)2-(2,4-dimethoxyphenyl)-4-phenyl-5-oxazolidinecarboxylic acid methyl ester (28a & b)

N-t-butyl-β-phenyl-isoserine methyl ester (26, 68 mg, 0.23 mM) is dissolved in 5 mL dry THF and the solution treated with 2,4-dimethoxy benzaldehyde dimethyl acetal (70 mg, 0.33 mM) and pyridinium p-toluenesulfonate (6 mg, 0.02 mM) and the solution warmed to reflux. Approximately 2 mL solvent is boiled away 3 times in a 45 minute period replenishing with 2 mL of fresh THF at which time TLC shows no starting material. The solvent is concentrated in vacuo and chromatographed over 7 gm of silica gel packed in 1:3 EtOAc:Hexane. The column is eluted with 80 mL 1:3 EtOAc:Hexane, 45 mL 1:2 EtOAc:Hexane, 30 mL 2:3 EtOAc:Hexane, and 30 mL 1:1 EtOAc:Hexane collecting 3 mL fractions.

A less polar isomer, (4S,5R)-N-(t-butylaminocarbonyl)2-(2,4-dimethoxyphenyl)-4-phenyl-5-oxazolidinecarboxylic acid methyl ester (28a) was found in fractions 21–31.

A more polar isomer, (4S,5R)-N-(t-butylaminocarbonyl)2-(2,4-dimethoxyphenyl)-4-phenyl-5-oxazolidinecarboxylic acid methyl ester (28b) was found in fractions 33–42.

Less Polar Product 28a

Proton NMR (CDCl$_3$, TMS): δ1.19 (s, 9H); 3.82 (s, 3H); 3.85 (s, 3H); 3.89 (s, 3H); 4.68 (br s, 1H); 4.88 (d, 1H); 5.52 (d, 1H); 6.46 (m); 6.70 (s, 1H); 7.25–7.50 (m)

Mass spectrum (FAB-High Res.): Theory for C$_{24}$H$_{31}$N$_2$O$_6$+H: 443.2182 Found: 443.2172

More Polar Product 28b

Proton NMR (CDCl$_3$, TMS): δ0.99 (m, 9H); 3.53 (m, 3H); 3.81 (m, 3H); 3.88 (m, 3H); 4.05 (m, 1H); 4.55 (m, 1H); 5.45 (m, 1H); 6.48 (m, 2H); 6.79 (m, 1H); 7.25–7.50 (m)

Mass spectrum (FAB-High Res.): Theory for C$_{24}$H$_{31}$N$_2$O$_6$+H: 443.2182 Found: 443.2180

EXAMPLE 23
Preparation of (4S,5R)-N-(t-butylaminocarbonyl)-2-(2,4-dimethoxyphenyl)-4-phenyl-5-oxazolidinecarboxylic acid potassium salt (29a)

(4S,5R)-N-(t-butylaminocarbonyl)-2-(2,4-dimethoxyphenyl)-4-phenyl-5-oxazolidinecarboxylic acid methyl ester (Example No. 22, 28a, 6.27 g, 14.2 mM) is stirred at room temperature under nitrogen in methanol (50 mL). To this is added a solution of potassium carbonate (2.50 g, 18.1 mM) in water (6 mL). After 6 hours the reaction is evaporated under reduced pressure to remove the methanol and the residue freeze dried. There is obtained a quantitative yield of (4S,5R)-N-Boc-2-(2,4-dimethoxyphenyl)-4-phenyl-5-oxazolidinecarboxylic acid potassium salt (29a) admixed with potassium carbonate salts as a powder.

Proton NMR (DMSO-d$_6$, TMS): Δ1.10 (s, 9H); 3.77 (s, 3H); 4.17 (d, 1H, J=2.3 Hz); 4.70 (bs, 1H); 5.16 (d, 1H, J=2.3 Hz); 6.50 (s+m, 2H); 6.60 (d, 1H); 7.14–7.42 (m, 6H);.

EXAMPLE 23A
Preparation of (4S,5R)-N-(t-butylaminocarbonyl)-2-(2,4-dimethoxyphenyl)-4-phenyl-5-oxazolidinecarboxylic acid potassium salt (29b)

(4S,5R)-N-(t-butylaminocarbonyl)-2-(2,4-dimethoxyphenyl)-4-phenyl-5-oxazolidinecarboxylic acid methyl ester (Example No. 22, 28b, 0.98 g, 2.2 mM) is stirred at room temperature under nitrogen in methanol (50 mL). To this is added a solution of potassium carbonate (0.39 g, 2.5 mM) in water (1.1 mL). After 5 hours the reaction is evaporated under reduced pressure to remove the methanol and the residue freeze dried. There is obtained a quantitative yield of (4S,5R)-N-Boc-2-(2,4-dimethoxyphenyl)-4-phenyl-5-oxazolidinecarboxylic acid potassium salt (29b) admixed with potassium carbonate salts as a powder.

Proton NMR (DMSO-d$_6$, TMS): δ0.81 (s, 9H); 3.80 (s, 3H); 3.85 (s, 3H); 3.92 (d, 1H, J=6.4 Hz); 4.86 (bs, 1H); 5.16 (d, 1H, J=6.4 Hz); 6.43 (s, 1H); 6.56 (m, 2H); 7.30–7.47 (m, 6H);.

EXAMPLE 24
Preparation of (4S,5R)-N-(t-butylaminocarbonyl)-2-(2,4-dimethoxyphenyl)-4-phenyl-5-oxazolidinecarboxylic acid (30a)

(4S,5R)-N-Boc-2-(2,4-dimethoxyphenyl)-4-phenyl-5-oxazolidinecarboxylic acid potassium salt (29a, example 23) is partitioned between methylene chloride and water containing 0.9 mL 1N HCl. The layers are separated and the aqueous layer reextracted with methylene chloride. The organic layers are combined, dried over sodium sulfate and evaporated. This leaves (4S,5R)-N-Boc-2-(2,4-dimethoxyphenyl)-4-phenyl-5-oxazolidinecarboxylic acid (30a) as a solid.

EXAMPLE 25
Preparation of 7-TES-Δ$^{12,13}$-iso-baccatin III-13-(4S,5R)-N-(t-butylaminocarbonyl)-2-(2,4-dimethoxyphenyl)-4-phenyl-5-oxazolidinecarboxylic acid ester (31a)

(4S,5R)-N-(t-butylaminocarbonyl)-2-(2,4-dimethoxyphenyl)-4-phenyl-5-oxazolidinecarboxylic acid (3 mM, Preparation No. 24, 30a) is dissolved in 20 mL methylene chloride (11 mL)-toluene (5 mL). To this is added 7-TES-Δ$^{12,13}$-iso-baccatin III (1.0 g, 1.4 mM, 3, example 2), 4-dimethylaminopyridine (93 mg, 0.76 mM), and 1,3-dicyclohexylcarbodiimide (0.63 g, 3.1 mM) and the reaction mixture stirred for 3 h under a nitrogen atmosphere. The reaction is diluted with toluene and filtered. The filtrate is washed with 1N hydrochloric acid, 5% aqueous sodium bicarbonate, and brine. The organic solution is dried over anhydrous sodium sulfate and evaporated. The product is purified by column chromatography on silica gel 60 in acetone-hexane mixtures. Concentration of the fractions found to contain product by TLC give 7-TES-Δ$^{12,13}$-iso-baccatin III-13-(4S,5R)-N-(t-butylaminocarbonyl)-2-(2,4-dimethoxyphenyl)-4-phenyl-5-oxazolidinecarboxylic acid ester (31a) as a solid.

Proton NMR (CDCl$_3$, TMS): δ0.54 (m, 6H); 0.90 (m, 12H); 1.16 (s, 3H); 1.17 (s, 9H); 1.80 (s, 3H); 1.89 (m, 1H); 2.15 (s, 3H); 2.18 (s, 3H); 2.30 (d, 1H); 2.50 (m, 2H); 2.78 (d, 1H); 3.83 (s, 3H); 3.85 (d, 1H); 3.91 (s, 3H); 4.28 (d, 1H); 4.38 (d, 1H); 4.43 (m, 1H); 4.64 (bs, 1H); 4.88 (m, 1H); 5.04 (d, 1H); 5.55 (m, 1H); 5.65 (d, 1H); 5.99 (s, 1H); 6.49 (m, 2H); 6.74 (s, 1H); 7.22 (d, 1H); 7.34–7.68 (m, 8H); 8.07 (m, 2H).

Carbon NMR (CDCl$_3$, TMS): δ5.27, 6.55, 8.99, 13.83, 14.11, 18.92, 20.90, 22.30, 28.79, 29.67, 32.86, 36.94, 38.75, 39.63, 50.59, 55.13, 55.28, 56.42, 58.40, 62.81, 72.50, 73.15, 74.10, 76.88, 80.58, 84.28, 85.81, 98.11, 104.94, 117.48, 122.28, 126.75, 127.66, 128.41, 128.49, 128.76, 129.76, 133.43, 139.81, 142.87, 154.95, 158.14, 161.68, 166.32, 168.33, 168.55, 170.12, 204.76.

EXAMPLE 26

Preparation of 7-TES-13-(N-(t-butylaminocarbonyl)-β-phenyl isoserinyl)-$\Delta^{12,13}$-iso-baccatin III (32a) and 13-(N-(t-butylaminocarbonyl)-β-phenyl isoserinyl)-$\Delta^{12,13}$-iso-baccatin III (32b)

7-TES-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (31a, example 25, 0.102 g, 0.092 mM) is stirred in a mixture of acetic acid (4 mL) and water (1 mL) at room temperature under an inert atmosphere 65 h. The reaction is diluted with ethyl acetate and washed with 5% aqueous sodium bicarbonate. The organic layer is dried over anhydrous sodium sulfate and evaporated. The product is purified by column chromatography on silica gel 60 in (30-70) and (40-60) acetone-hexane. Fractions of 4 mL are collected. Concentration of fractions 13–22 gives 7-TES-13-(N-(t-butylaminocarbonyl)-β-phenyl isoserinyl)-$\Delta^{12,13}$-iso-baccatin III (32a). Concentration of fractions 35–40 gives 13-(N-(t-butylaminocarbonyl)-β-phenyl isoserinyl)-$\Delta^{12,13}$-iso-baccatin III (32b).

Data for 32a

Proton NMR (CDCl$_3$, TMS): δ0.53 (m, 6H); 0.89 (t, 9H); 1.13 (s, 12H); 1.24 (s, 4H); 1.57 (bs, 1H); 1.62 (s, 3H); 1.68 (s, 3H); 1.89 (m, 1H); 2.07 (d, 1H); 2.16 (s, 3H); 2.50 (m, 2H); 2.58 (s, 3H); 2.86 (d, 1H); 3.84 (d, 1H, J=5.6 Hz); 4.34 (m, 4H); 4.71 (d, 1H, J=2.9 Hz); 4.92 (dd, 1H); 5.03 (d, 1H, J=9.0 Hz); 5.53 (m, 2H); 5.97 (s, 1H); 7.28–7.68 (m, 8H); 8.11 (m, 2H).

Data for 32b

Proton NMR (CDCl$_3$, TMS): δ1.05 (s, 3H); 1.13 (s, 9H); 1.29 (s, 3H); 1.55 (s, 3H);1.62 (s, 3H); 1.65 (bs, 1H); 1.89 (m, 1H); 2.11 (d, 1H); 2.23 (s, 3H); 2.47 (m, 1H); 2.54 (s, 3H); 2.72 (bs, 1H); 2.87 (d, 1H); 3.58 (d, 1H); 3.68 (d, 1H); 4.10 (bs, 1H); 4.31(m, 2H); 4.39 (d, 1H); 4.62 (bs, 1H); 4.71 (d, 1H); 4.90 (dd, 1H); 5.44 (s+m, 2H); 5.57 (m, 2H); 7.36(m, 5H); 7.49 (m, 2H); 7.59 (m, 1H); 8.10 (d, 2H).

Carbon NMR (CDCl$_3$, TMS): δ9.07, 14.41, 19.80, 21.03, 23.19, 29.30, 29.81, 32.87, 35.30, 38.66, 39.50, 50.47, 55.75, 57.93, 71.66, 73.50, 74.70, 77.21, 77.64, 77.73, 81.09, 84.47, 121.69, 126.66, 127.93, 128.75, 128.86, 130.22, 133.69, 138.88, 143.26, 156.52, 166.63, 170.69, 171.33, 171.99 206.71.

Mass spectrum (FAB-High Res.) Theory for C$_{45}$H$_{56}$N$_2$O$_{14}$+H: 849.3809 Found: 849.3842

EXAMPLE 27

Preparation of $\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (33a)

7-TES-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (31a, preparation 26, 460 mg, 0.413 mM) is dissolved in acetonitrile (0.5 mL) and the solution treated with triethyl amine hydrofluoride (0.5 mL). The reaction is stirred at room temperature for 6 h. The reaction is then diluted with ethyl acetate and washed with 5% aqueous sodium bicarbonate, 5% aqueous sodium bisulfate and saturated brine. The organic layer is dried over sodium sulfate and evaporated under vacuum. The crude product is purified by chromatography over 50 g of HPLC grade silica gel eluting with 30% and 40% acetone in hexane. Fractions of 10 mL are collected, analyzing them by TLC. The major product spot is found in fractions 24–30, which upon combining and evaporating under vacuum leave of $\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (33a).

Proton NMR (CDCl$_3$, TMS): δ1.07 (s, 3H); 1.17 (s, 9H); 1.32 (s, 3H); 1.62 (s, 3H); 1.67 (s, 3H); 1.91 (m, 1H); 2.16 (s, 3H); 2.24 (s, 3H); 2.31 (d, 1H); 2.49 (m, 1H); 2.81 (m, 2H); 3.54 (d, 1H); 3.71 (d, 1H); 3.83 (s, 3H); 3.92 (s, 3H); 4.35 (m, 3H); 4.65(bs, 1H); 4.89 (m, 1H); 5.06 (d, 1H); 5.49 (bs, 1H); 5.58 (d, 1H); 5.67 (d, 1H); 6.47 (m, 1H); 6.53 (d, 1H); 6.73 (s, 1H); 7.20(d, 1H); 7.34–7.65 (m, 8H); 8.07 (m, 2H).

Carbon NMR (CDCl$_3$, TMS): δ9.14, 13.83, 14.39, 19.85, 21.09, 22.50, 29.12, 29.93, 31.8, 33.2, 35.35, 38.69, 39.60, 50.92, 55.45, 55.82, 57.99, 63.16, 71.60, 73.68, 77.37, 77.72, 80.96, 84.62, 86.27, 98.43, 105.27, 117.5, 121.81, 127.02, 128.02, 128.76, 128.83, 130.09, 133.79, 140.2, 143.21, 155.4, 158.4, 162.1, 166.6, 168.7, 170.56, 172.0, 206.74.

EXAMPLE 28

Preparation of 7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (34a)

A solution of $\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (33a, 63 mg, 0.063 mM) in CH$_2$Cl$_2$ (0.4 mL) and pyridine (0.15 mL) is cooled in a –78° C. bath. Trifluoromethanesulfonic anhydride (33 μL, 0.20 mM) is added resulting in the reaction solidifying. The reaction is warmed until it melts and then is re-cooled. After 1 h the reaction was warmed to room temperature and stirred 10 min. The reaction is poured into saturated aq NH$_4$Cl and the mixture is extracted with CH$_2$Cl$_2$. The organic extract is washed with 1M aq NaHSO$_4$ (50 mL), dried and concentrated under reduced pressure. The residue is chromatographed over silica gel (3 g), eluted with 30% acetone in hexane. Fractions of 1 mL are collected. Concentration of fractions 17,18 leaves 7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (34a).

Proton NMR (CDCl$_3$, TMS): δ1.11 (s, 3H); 1.17 (s, 9H); 1.77 (s, 6H); 2.20 (s, 3H); 2.21 (s, 3H); 2.34 (d, 1H); 2.68 (bs, 1H); 2.80 (d, 1H); 2.95 (m, 1H); 3.83 (s, 3H); 3.88 (m, 1H); 3.93 (s, 3H); 4.34 (d, 1H); 4.43 (d, 1H); 4.67 (bs, 1H); 4.86 (m, 1H); 5.05 (m, 1H); 5.53 (m, 1H); 5.60 (m, 1H); 5.88 (s, 1H); 6.47 (m, 1H); 6.53 (m, 1H); 6.72 (s, 1H); 7.20 (d, 1H); 7.30–7.70 (m, 8H); 8.07 (m, 2H).

Carbon NMR (CDCl$_3$, TMS): δ10.17, 14.12, 14.42, 19.71, 20.71, 22.36, 22.65, 29.10, 29.93, 31.59, 33.24, 38.75, 39.67, 50.93, 55.16, 55.44, 55.69, 57.57, 63.04, 72.95, 74.73, 77.20, 79.68, 80.87, 83.38, 85.86, 86.06, 98.38, 105.33, 117.61 122.78, 127.00, 127.98, 128.81, 130.09, 133.98, 140.17, 142.78, 155.29, 158.46, 162.06, 166.41, 168.91, 168.99, 170.90, 203.44.

EXAMPLE 29

Preparation of 7-deoxy-7β,8β-methano-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (35a)

A solution of 7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (34a, Example 28) in distilled dioxane is treated with an aqueous sodium azide solution. The reaction is refluxed under nitrogen one hour. The mixture is diluted with ethyl acetate and washed with water and brine, dried over anhydrous sodium sulfate, and evaporated. The product is purified by column chromatography on silica gel 60 in ethyl acetate-methylene chloride mixtures. Evaporation of the fractions found by TLC to contain the product gives 7-deoxy-7β,8β-methano-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (35a).

EXAMPLE 30
Preparation of 13-(N-(t-butylaminocarbonyl)-β-phenyl isoserinyl)-7-deoxy-7β,8β-methano-$\Delta^{12,13}$-iso-baccatin III (36)

Following the procedure of example 5, 7-deoxy-7β,8β-methano-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (35a) is stirred in a 4:1 mixture of acetic acid and water at room temperature under an inert atmosphere 4 days. The reaction is diluted with ethyl acetate and washed multiple times with water and aqueous sodium bicarbonate. The organic layer is dried over anhydrous sodium sulfate and evaporated. The product is chromatographed on silica gel 60 (230–400 mesh) in acetone-hexane mixtures. Evaporation of the fractions found to contain product by TLC leaves 13-(N-(t-butylaminocarbonyl)-β-phenyl isoserinyl)-7-deoxy-7β,8β-methano-$\Delta^{12,13}$-iso-baccatin III (36).

EXAMPLE 31
Preparation of 13-(N-(t-butylaminocarbonyl)-β-phenylisoserinyl)-7-deoxy-7β,8β-methano-$\Delta^{12,13}$-iso-baccatin III (36) and 13-(N-(t-butylaminocarbonyl)-β-phenylisoserinyl)-7-trifluoromethanesulfonyl-$\Delta^{12,13}$-iso-baccatin III (37)

A solution of $\Delta^{12,13}$-iso-baccatin III-13-[(4S,5R)-N-t-butylaminocarbonyl-(2,4-dimethoxyphenyl)-4-phenyl-5-oxazolidinecarboxylic acid ester]-7-triflate (0.20 g, 0.18 mM) in 2 mL of (80:20) acetic acid:methanol is stirred at room temperature for 1.3 hours. The reaction is diluted with ethyl acetate and washed with 5% aqueous sodium bicarbonate. The organic layer is dried over anhydrous sodium sulfate and concentrated. The crude product is chromatographed on silica gel 60 in acetone-hexane mixtures, resulting in partial conversion to 7,19-methano-13-(N-t-butylaminocarbonyl-β-phenylisoserinyl)-$\Delta^{12,13}$-iso-baccatin III. The products eluting from this column are re-chromatographed in ethyl acetate-methylene chloride mixtures to give 13-(N-(t-butylaminocarbonyl)-β-phenylisoserinyl)-7-trifluoromethanesulfonyl-$\Delta^{12,13}$-iso-baccatin III (37, 70 mg) and 13-(N-(t-butylaminocarbonyl)-β-phenylisoserinyl)-7-deoxy-7β,8β-methano-$\Delta^{12,13}$-iso-baccatin III (36, 41 mg).

Data for 13-(N-(t-butylaminocarbonyl)-β-phenylisoserinyl)-7-trifluoromethanesulfonyl-$\Delta^{12,13}$-iso-baccatin III (37)

Proton NMR (CDCl$_3$, TMS): δ1.09 (s); 1.11 (s); 1.17 (s); 1.24 (s); 1.76 (s); 2.1(m); 2.18 (s); 2.47 (s); 2.65 (m); 2.90 (m); 3.83 (d); 4.31(d); 4.43 (d); 4.73 (d); 4.88 (m); 5.32 (bs); 5.47(m); 5.58 (d); 5.85(s); 7.30–7.63 (m); 8.09 (d).

Carbon NMR (CDCl$_3$, TMS): δ10.09, 14.36, 19.69, 20.68, 22.62, 23.00, 29.13, 29.22, 29.73, 31.54, 33.01, 33.53, 38.67, 39.57, 50.68, 55.13, 55.41, 57.50, 72.79, 74.24, 74.66, 79.59, 83.30, 85.89, 122.70, 126.72, 127.99, 128.61, 128.81, 128.86, 130.22, 133.88, 138.65, 142.85, 156.47, 166.41, 168.98, 170.68, 171.16, 203.40.

Data for 13-(N-(t-butylaminocarbonyl)-β-phenylisoserinyl)-7-deoxy-7β,8β-methano-$\Delta^{12,13}$-iso-baccatin III (36)

Proton NMR (CDCl$_3$, TMS): δ1.04 (s, 9H); 1.12 (s); 1.31 (s+m); 1.55 (s); 1.73 (m); 2.17 (s+m); 2.41(m, 1H); 2.55 (s, 3H); 2.73 (bs, 1H); 2.91 (d, 1H); 3.86 (d, 1H); 4.09 (d, 1H); 4.29 (bs, 1H); 4.41 (d, 1H); 4.70 (d, 1H); 4.78 (m, 1H); 5.08 (d, 1H); 5.21 (d, 1H); 5.50 (m, 1H); 5.62 (d, 1H); 7.27–7.65 (m, 10H); 8.18 (m, 2H).

Carbon NMR (CDCl$_3$, TMS): δ12.80, 14.22, 20.86, 21.08, 22.44, 25.79, 28.77, 29.20, 30.09, 32.44, 32.81, 36.69, 39.70, 50.38, 55.03, 55.22, 74.39, 75.70, 78.29, 78.41, 78.87, 80.47, 85.15, 122.40, 126.65, 127.83, 128.77, 129.02, 130.38, 133.64, 139.15, 141.77, 156.19, 167.28, 169.76, 170.36, 171.02, 203.64.

EXAMPLE 32
Preparation of 13-(N-(t-butylaminocarbonyl)-β-phenyl isoserinyl)-7-deoxy-$\Delta^{6,7}$-$\Delta^{12,13}$-iso-baccatin III (38)

Following the procedure of Example 16, a solution of 13-(N-(t-butylaminocarbonyl)-β-phenyl isoserinyl)-7-trifluoromethanesulfonyl-$\Delta^{12,13}$-iso-baccatin III (37) and 1,8-diazabicyclo[5.4.0]undec-7-ene in THF is stirred at room temperature for 1 hr, at 50° C. for 2.5 hr, and at reflux temperature for 3 hr, after which reaction is complete. EtOAc is added and the solution washed with saturated aq NaHCO$_3$ and with saturated aq NaCl. The organic layer is dried (Na$_2$SO$_4$), filtered, and evaporated under reduced pressure. The residue is flash chromatographed over silica gel using a solution in CH$_2$Cl$_2$ for application to the column. The column is eluted with acetonitrile-methylene chloride mixtures. Fractions containing the desired material are detected by TLC and are combined to give 13-(N-(t-butylaminocarbonyl)-β-phenyl isoserinyl)-7-deoxy-$\Delta^{6,7}$-$\Delta^{12,13}$-iso-baccatin III (38).

EXAMPLE 33
Preparation of 7-deoxy-$\Delta^{6,7}$-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (39a)

Following the procedure of Example 16, a solution of 7-trifluoromethanesulfonyl-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (34a) and 1,8-diazabicyclo[5.4.0]undec-7-ene in THF are stirred at room temperature for 1 hr, at 50° C. for 2.5 hr, and at reflux temperature for 3 hr, after which reaction is complete. EtOAc is added and the solution washed with saturated aq NaHCO$_3$ and with saturated aq NaCl. The organic layer is dried (Na$_2$SO$_4$), filtered, and evaporated under reduced pressure. The column is eluted with acetonitrile-methylene chloride mixtures. Fractions containing the desired material are detected by TLC and are combined to give 7-deoxy-$\Delta^{6,7}$-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (39a).

EXAMPLE 34
Preparation of 13-[N-(t-butylaminocarbonyl)-β-phenyl isoserinyl]-7-deoxy-$\Delta^{6,7}$-$\Delta^{12,13}$-iso-baccatin III (38)

Following the procedure of Example 5, 7-deoxy-$\Delta^{6,7}$-$\Delta^{12,13}$-iso-baccatin III 13-(4S,5R)-N-(t-butylaminocarbonyl)-2-(2,4-dimethoxyphenyl)-4-phenyl-5-oxazolidinecarboxylic acid ester (39a) is stirred in a 4:1 mixture of acetic acid and water at room temperature under an inert atmosphere 4 days. The reaction is diluted with ethyl acetate and washed multiple times with water and aqueous sodium bicarbonate. The organic layer is dried over anhydrous sodium sulfate and evaporated. The product is chromatographed on silica gel 60 (230–400 mesh) in acetone-hexane mixtures. Evaporation of the fractions found to contain product by TLC leaves 13-[N-(t-butylaminocarbonyl)-β-phenyl isoserinyl]-7-deoxy-$\Delta^{6,7}$-$\Delta^{12,13}$-iso-baccatin III (38).

EXAMPLE 35
Preparation of 7-(O-ethoxymethyl)-$\Delta^{12,13}$-iso-baccatin III-13-(4S,5R)-N-Boc-2-(2,4-dimethoxyphenyl)-4-phenyl-5-oxazolidinecarboxylic acid ester (40a)

$\Delta^{12,13}$-Iso-baccatin III-13 (4S,5R)-N-Boc-2-(2,4-dimethoxyphenyl)-4-phenyl-5-oxazolidinecarboxylic acid ester (10a) is stirred at room temperature under nitrogen in methylene chloride and the solution treated with chloroethyl ethyl ether and diisopropylethyl amine. The reaction is stirred for 2 days, when it is complete as shown by TLC. The reaction is then partitioned between methylene chloride-water. The layers are separated and the water layer reextracted with methylene chloride. The organic layers are dried over sodium sulfate, combined and evaporated under vacuum. The crude product is chromatographed over silica gel, eluting with acetone-hexane mixtures. Fractions contain the product are found by TLC and are combined and evaporated under vacuum leaving 7-(O-ethoxymethyl)-$\Delta^{12,13}$-iso-baccatin III-13-(4S,5R)-N-Boc-2-(2,4-dimethoxyphenyl)-4-phenyl-5-oxazolidinecarboxylic acid ester (40a).

EXAMPLE 36
Preparation of 7-(O-ethoxymethyl)-13-(N-Boc-β-phenyl isoserinyl)-$\Delta^{12,13}$-iso-baccatin III (41)

Following the procedure of example 5, 7-(O-ethoxymethyl)-$\Delta^{12,13}$-iso-baccatin III-13-(4S,5R)-N-Boc-2-(2,4-dimethoxyphenyl)-4-phenyl-5-oxazolidinecarboxylic acid ester (40a) is stirred in a 4:1 mixture of acetic acid and water at room temperature under an inert atmosphere 4 days. The reaction is diluted with ethyl acetate and washed multiple times with water and aqueous sodium bicarbonate. The organic layer is dried over anhydrous sodium sulfate and evaporated. The product is chromatographed on silica gel 60 (230–400 mesh) in acetone-hexane mixtures. Evaporation of the fractions found to contain product by TLC leaves 7-(O-ethoxymethyl)-13-(N-Boc-β-phenyl isoserinyl)-$\Delta^{12,13}$-iso-baccatin III (41).

EXAMPLE 37
Preparation of 7-(O-ethoxymethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (42a)

$\Delta^{12,13}$-Iso-baccatin III-13 (4S,5R)-N-(t-butylaminocarbonyl)-2-(2,4-dimethoxyphenyl)-4-phenyl-5-oxazolidinecarboxylic acid ester (33a, 70 mg, 0.070 mM) is stirred at room temperature under nitrogen in 1 mL of methylene chloride and the solution treated with chloromethyl ethyl ether (32 μl, 0.35 mM) and diisopropylethyl amine (61 μl, 0.35 mM). After 1 hour the reaction is treated with additional diisopropylethyl amine (5 μl). The reaction is stirred for 2 days, when it is still incomplete as shown by TLC. Additional chloromethyl ethyl ether (15 μl) and diisopropylethyl amine (30 μl) is added and the reaction stirred an additional 12 days. The reaction is then partitioned between methylene chloride-water. The layers are separated and the water layer reextracted with methylene chloride. The organic layers are dried over sodium sulfate, combined and evaporated under vacuum. The crude product is chromatographed over silica gel (10 g), eluting with (10-90) acetone-toluene. Fractions of 3 mL are collected, analyzing them by TLC. Impure product is found in fractions 9–20. These are combined, evaporated under vacuum and the residue rechromatographed over an E Merck size A prepacked silica gel column eluting with (10-90) acetone-hexane. Fractions of 3 mL are collected. The product is found in fractions 10–15, which upon combining and evaporating under vacuum leave 7-ethoxymethyl-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (42a).

TLC (silica gel GF): (20-80) acetone-hexane; $R_f$: 0.59.

Proton NMR (CDCl$_3$, TMS): δ1.07–1.18 (t, 3H); 1.18 (s, 9H); 1.30 (s, 3H); 1.68 (s, 3H); 1.72 (s, 3H); 1.89–2.03 (m,1H); 2.16 (s, 3H); 2.19 (s, 3H); 2.26–2.39 (d, 1H); 2.64 (s, 1H); 2.73–2.85 (d, 1H); 2.84–2.96 (m, 1H);3.30–3.43 (m, 1H); 3.61–3.75 (m,1H); 3.83 (s, 3H); 3.86–3.92 (d, 1H); 3.92 (s, 3H); 4.00–4.10 (q, 1H); 4.25–4.34 (d, 1H); 4.36–4.44 (d, 1H); 4.60–4.74 (m, 3H) 4.84–4.93 (dd, 1H); 5.04–5.09 (d, 1H); 5.50–5.58 (d, 1H); 5.64–5.70 (d, 1H); 6.44–6.51 (dd, 1H); 6.51–6.56 (d, 1H); 6.75 (s, 1H); 7.16–7.24 (d, 1H); 7.32–7.57 (m 7H); 7.57–7.65 (t, 1H); 8.03–8.10 (d, 2H).

EXAMPLE 38
Preparation of 7-(O-ethoxymethyl)-13-(N-(t-butylaminocarbonyl)-β-phenyl isoserinyl)-$\Delta^{12,13}$-iso-baccatin III (43)

7-(O-ethoxymethyl)-$\Delta^{12,13}$-iso-baccatin III-13-(4S,5R)-N-(t-butylaminocarbonyl)-2-(2,4 -dimethoxyphenyl)-4-phenyl-5-oxazolidinecarboxylic acid ester (42a, 45 mg, 0.043 mM) is stirred in a mixture of acetic acid (1.5 mL) and water (0.5 mL) at room temperature. The reaction is followed by TLC and is complete in 3 hours. The reaction is then freeze-dried. The crude product is purified by HPLC over an E. Merck size A prepacked silica gel column, eluting with a gradient of (25-75) to (35-65) acetone-hexane. Fractions of 3 ml are collected, analyzing them by TLC. Product is found in fractions 7–11, which are combined and evaporated under vacuum to give 7-(O-ethoxymethyl)-13-(N-(t-butylamino-carbonyl)-β-phenyl isoserinyl)-$\Delta^{12,13}$-iso-baccatin III (43) as a solid.

TLC(silica gel 60): (30-70) acetone-hexane; Rf: 0.24

Proton NMR (CDCl$_3$; TMS): δ1.07–1.20 (m, 15H); 1.24 (s, 3H); 1.58 (s, 3H); 1.67 (s, 3H); 1.87–2.02 (t, 1H); 2.02–2.14 (d, 1H); 2.16 (s, 3H); 2.55 (s, 3H); 2.77–2.94 (m, 2H); 3.27–3.42 (m, 1H); 3.60–3.72 (m, 1H); 3.84–3.90 (d, 1H); 3.97–4.06 (dd, 1H); 4.24–4.31 (d, 1H); 4.37–4.44 (d, 1H); 4.54 (s, 1H);4.57–4.64 (d, 1H); 4.64–4.72 (m, 2H); 4.87–4.95 (dd, 1H); 5.27–5.35 (d, 1H); 5.42–5.49 (dd, 1H); 5.49–5.55 (d, 1H); 5.75 (s, 1H); 7.14–7.42 (m, 5H); 7.44–7.55 (t, 2H); 7.55–7.63 (t, 1H); 8.07–8.15 (d, 2H).

EXAMPLE 39
Preparation of 7-deoxy-7β,8β-methano-baccatin III (44)

A solution of 7-trifluoromethanesulfonyl-baccatin III (87 mg, 0.12 mM) in distilled dioxane (1.5 mL) is treated with an aqueous sodium azide solution (0.10 g, 1.5 mM NaN$_3$ in 0.30 mL water.) The reaction is refluxed under nitrogen one hour. The mixture is diluted with ethyl acetate and washed with water and brine, dried over anhydrous sodium sulfate, and evaporated. The product is purified by column chromatography on silica gel 60 in 25% ethyl acetate-methylene chloride. Evaporation of the fractions found by TLC to contain the product gives 7-deoxy-7β,8β-methano-baccatin III (44) as crystals.

Proton NMR (CDCl$_3$, TMS): δ1.10 (s, 3H); 1.22 (s, 3H); 1.35 (m, 1H); 1.64 (m, 1H); 1.78 (s, 1H); 2.03 (s+m, 4H); 2.21 (s, 3H); 2.26 (s, 3H); 2.20–2.55 (m, 5H); 4.04 (d, 1H, J=8.5 Hz); 4.18 (d, 1H, J=7.5 Hz); 4.30 (d, 1H, J=8.5 Hz); 4.74 (d, 1H); 4.83 (m, 1H); 5.63 (d, 1H, J=7.5 Hz); 6.35 (s, 1H); 7.49 (m, 2H); 7.62 (m, 1H); 8.13 (m, 2H).

Carbon NMR (CDCl$_3$, TMS): 15.15, 15.28, 20.43, 20.82, 21.99, 25.90, 26.35, 31.63, 35.19, 38.57, 38.76, 42.20, 67.51, 75.30, 76.20, 76.49, 79.23, 79.91, 84.73, 128.50, 129.33, 129.99, 132.59, 133.54, 144.19, 167.20, 169.63, 170.00, 202.08.

EXAMPLE 40
Preparation of 7-α-azido-baccatin III (45)

A mixture of 7-trifluoromethanesulfonyl-baccatin III (102 mg, 0.14 mM), sodium azide (13 mg, 0.20 mM), and 18-crown-6 (32 mg, 0.12 mM) in 1,3-dimethyl-3,4,5,6-tetrahydro-2(1H)-pyrimidinone (1.0 mL) is stirred at room temperature overnight under an inert atmosphere. The reaction is partitioned between ethyl acetate and water. The organic layer is dried over anhydrous sodium sulfate and evaporated. The crude product is purified by column chromatography on silica gel 60 in 15% ethyl acetate—methylene chloride. The product is further purified by crystallization from methylene chloride-hexane giving 7-α-azido-baccatin III (45).

Proton NMR (CDCl$_3$, TMS): δ0.96 (s, 6H); 1.59 (s, 3H); 1.91(s, 3H); 2.13 (s, 3H); 2.25 (s, 3H); 2.10–2.35 (m, 4 H); 2.47 (m, 1H); 3.80 (m, 2H); 4.07 (d, 1H, J=8.0 Hz); 4.33 (d, 1H, J=8.0 Hz); 4.60 (s+m, 2H); 4.99 (dd, 1H); 5.35 (d, 1H); 5.48 (d, 1H, J=7.2 Hz); 6.79 (s, 1H); 7.59 (m, 2H); 7.69 (m, 1H); 8.05 (m, 2H).

Carbon NMR (CDCl$_3$, TMS): 15.40, 17.31, 20.67, 22.20, 25.93, 29.81, 39.22, 40.63, 41.73, 55.57, 64.28, 65.91, 75.33, 76.91, 77.33, 78.22, 80.44, 80.94, 128.77, 129.58, 129.98, 130.28, 133.33, 145.43, 165.30, 168.75, 169.09, 207.11.

EXAMPLE 41
Preparation of 13-(N-Boc-2'-TES-β-phenyl isoserinyl)-$\Delta^{12,13}$-iso-baccatin III (46)

13-(N-Boc-β-phenyl isoserinyl)-$\Delta^{12,13}$-iso-baccatin III (7, 60 mg, 0.071 mM) is stirred at room temperature under nitrogen in freshly distilled pyridine (0.7 mL). The solution is cooled in an ice bath and treated with triethylsilyl chloride (13 μl, 0.078 mM). The reaction is followed by TLC. No reaction is seen after 1 hr at 0° C. and 1 hr at room temperature. Thus, TES chloride is repeatedly added in the portions above until a total of 12 equivalents are added, at which point the reaction in seen to go to completion. This requires a total reaction time of 18 hours. The reaction is then partitioned between water-ethyl acetate. The layers are separated and the aqueous layer reextracted with ethyl acetate. The organic layers are combined, dried over sodium sulfate and evaporated under vacuum. Toluene is added and reevaporated. The crude product is chromatographed over silica gel (10 g), eluting with (30-70) acetone-hexane. Fractions of 3 mL are collected, analyzing them by TLC. Fractions 7–11 are combined and evaporated under vacuum to give 13-(N-Boc-2'-TES-β-phenyl isoserinyl)-$\Delta^{12,13}$-iso-baccatin III (46) as a solid.

TLC(silica gel 60): 30-70 acetone-hexane; Rf: 0.43

Proton NMR (CDCl$_3$; TMS): δ0.23–0.49 (m, 6H); 0.69–0.82 (t, 9H); 1.05 (s, 3H); 1.18 (s, 9H); 1.32 (s, 3H); 1.62 (s, 3H); 1.63 (s, 3H); 1.87–2.02 (m, 1H); 2.03–2.146(d, 1H); 2.22 (s, 3H); 2.46–2.60 (m, 1H); 2.64 (s, 3H); 2.79 (s, 1H); 2.84–2.99 (d, 1H); 3.50–3.57 (d, 1H); 3.70–3.77 (d, 1H); 4.32–4.46 (m, 3H); 4.62 (s, 1H); 4.92–5.00 (dd, 1H); 5.39–5.47 (bd, 1H); 5.49 (s, 1H); 5.53–5.63 (m, 2H); 7.24–7.43 (m, 5H); 7.44–7.53 (t, 2H); 7.53–7.62 (t, 1H); 8.07–8.16 (d, 2H).

EXAMPLE 42
Preparation of 7-(O-ethoxymethyl)-13-(N-Boc-2'-TES-β-phenyl isoserinyl)-$\Delta^{12,13}$-iso-baccatin III (47)

13-(N-Boc-2'-TES-β-phenyl isoserinyl)-$\Delta^{12,13}$-iso-baccatin III (46, 59 mg, 0.061 mM) is stirred at room temperature under nitrogen in methylene chloride (0.5 mL) and the solution treated with diisopropylethyl amine (55 μl, 0.31 mM) and chloromethyl ethyl ether (28 μl, 0.305 mM). The reaction is followed by TLC and is found to be complete in 3.5 days. The crude reaction mixture is purified by HPLC over an E. Merck size A prepacked silica gel column, eluting with (20-80) acetone-hexane. Fractions of 3 mL are collected, analyzing them by TLC. The product is found in fractions 10–16, which are combined and evaporated under vacuum to give 7-(O-ethoxymethyl)-13-(N-Boc-2'-TES-β-phenyl isoserinyl)-$\Delta^{12,13}$-iso-baccatin III (47) as a solid.

TLC (silica gel 60): (25-75) acetone-hexane; Rf: 0.50

Proton NMR (CDCl$_3$; TMS): δ0.22–0.49 (m, 6H); 0.70–0.80 (t, 9H); 1.08–1.16 (m, 3H); 1.20 (s, 9H); 1.27 (s, 3H); 1.30 (s, 3H); 1.66 (s, 3H); 1.69 (s, 3H); 1.90–2.04 (t, 1H); 2.04–2.14 (d, 1H); 2.17 (s, 3H); 2.64 (s, 3H); 2.80–2.98 (m, 2H); 3.30–3.42 (m, 1H); 3.61–3.75 (m, 1H); 3.86–3.94 (d, 1H); 4.03–4.13 (dd, 1H); 4.27–4.36 (d, 1H); 4.38–4.46 (d, 1H); 4.56–4.65 (d, 1H); 4.62 (s, 1H); 4.67–4.75 (md 1H); 4.90–4.98 (dd, 1H); 5.38–5.49 (bd, 1H); 5.51–5.60 (m, 2H); 5.80 (s, 1H); 7.25–7.53 (m, 7H); 7.53–7.61 (t, 1H); 8.08–8.16 (d, 2H).

EXAMPLE 43
Preparation of 7-(O-ethoxymethyl)-13-(N-Boc-β-phenyl isoserinyl)-$\Delta^{12,13}$-iso-baccatin III (41)

7-(O-ethoxymethyl)-13-(N-Boc-2'-TES-β-phenyl isoserinyl)-$\Delta^{12,13}$-iso-baccatin III (47, 62 mg, 0.061 mM) is stirred at room temperature under nitrogen in (80-20) acetic acid-water (4 mL). The reaction is followed by TLC and is found to be complete in 24 hours. The reaction is then freeze-dried. The crude product is purified by HPLC over an E. Merck size A prepacked silica gel column, eluting with (25-75) acetone-hexane. Fractions of 3 mL are collected, analyzing them by TLC. The product is found in fractions 17–24, which are combined and evaporated under vacuum to give 7-(O-ethoxymethyl)-13-(N-Boc-β-phenyl isoserinyl)-$\Delta^{12,13}$-iso-baccatin III (41) as a solid.

TLC (silica gel 60): (25-75) acetone-hexane; Rf: 0.33

Proton NMR (CDCl$_3$; TMS): δ1.10–1.18 (m, 6H); 1.24 (s, 9H); 1.62 (s, 3H); 1.68 (s, 3H); 1.88–2.04 (t, 1H); 2.04–2.15 (d, 1H); 2.18 (s, 3H); 2.60 (s, 3H); 2.83–2.97 (m, 2H); 3.28–3.42 (m, 1H); 3.60–3.73 (m, 1H); 3.84–3.90 (d, 1H); 4.00–4.10(dd, 1H); 4.25–4.34 (d, 1H); 4.36–4.45 (d, 1H); 4.57–4.65 (d, 1H); 4.66–4.74 (m, 2H); 4.87–4.96 (dd, 1H); 5.36–5.50 (m, 2H); 5.50–5.57 (d, 1H); 5.77 (s, 1H); 7.30–7.55 (m, 7H); 7.55–7.64 (t, 1H); 8.07–8.17 (d, 2H).

EXAMPLE 44
Preparation of 13-(N-(t-butylaminocarbonyl)-2'-TES-β-phenyl isoserinyl)-$\Delta^{12,13}$-iso-baccatin III (48)

Following the procedure of Example 41 but starting with 13-(N-(t-butylaminocarbonyl)-β-phenyl isoserinyl)-$\Delta^{12,13}$-iso-baccatin III (32b) is prepared 13-(N-(t-butylaminocarbonyl)-2'-TES-β-phenyl isoserinyl)-$\Delta^{12,13}$-iso-baccatin III (48).

EXAMPLE 45
Preparation of 7-(O-ethoxymethyl)-13-(N-(t-butylaminocarbonyl)-2'-TES-β-phenyl isoserinyl)-$\Delta^{12,13}$-iso-baccatin III (49)

Following the procedure of Example 42 but starting with 13-(N-(t-butylaminocarbonyl)-2'-TES-β-phenyl isoserinyl)-$\Delta^{12,13}$-iso-baccatin III (48) is prepared 7-(O-ethoxymethyl)-13-(N-(t-butylaminocarbonyl)-2'-TES-β-phenyl isoserinyl)-$\Delta^{12,13}$-iso-baccatin III (49)

EXAMPLE 46
Preparation of 7-(O-ethoxymethyl)-13-(N-(t-butylaminocarbonyl)-β-phenyl isoserinyl)-$\Delta^{12,13}$-iso-baccatin III (43)

Following the procedure of Example 43 but starting with 7-(O-ethoxymethyl)-13-(N-(t-butylaminocarbonyl)-2'-TES-β-phenyl isoserinyl)-$\Delta^{12,13}$-iso-baccatin III (49) is prepared 7-(O-ethoxymethyl)-13-(N-(t-butylaminocarbonyl)-β-phenyl isoserinyl)-$\Delta^{12,13}$-iso-baccatin III (43).

EXAMPLE 47
7-Triethylsilyl-12,13-isobaccatin III, 13-(4S,5R)-N-carbobenzyloxy-2-(2,4-dimethoxyphenyl)-4-phenyl-5-oxazolidinecarboxylic acid ester (51a,b)

A slurry of (4S,5R)-N-carbobenzyloxy-2-(2,4-dimethoxyphenyl)-4-phenyl-5-oxazolidine carboxylic acid potassium salt (9.63 g, 19.2 mmol) in EtOAc (1.2 L) is stirred vigorously during the addition of 5% $NaHSO_4$ solution until the pH is <2. The layers are separated and the EtOAc is washed with more 5% $NaHSO_4$ solution. The EtOAc layers are combined, washed with half-saturated brine, dried ($Na_2SO_4$, filtered and evaporated at a reduced pressure. The residue is redissolved in EtOAc (50 mL), toluene is added and the solvent re-evaporated. Toluene is added and evaporated two more times giving an oil (10.37 g). The oil is dissolved in $CH_2Cl_2$ (60 mL, purged with argon) plus toluene (75 mL, purged with argon) and then 4-dimethylaminopyridine (0.965 g, 7.91 mmol) added. The solution is purged with argon and added to a solution of 7-TES-12,13-isobaccatin III (3) (11.3 mmol, purged with argon) in $CH_2Cl_2$ (125 mL) plus toluene (65 mL). The acid is rinsed in with additional $CH_2Cl_2$ (2×15 mL) and then toluene (10 mL). Immediately after the solutions are combined at room temperature, 1,3-dicyclohexylcarbodiimide (4.66 g, 22.6 mmol) is added. Tlc indicates complete reaction after one hour. The reaction is worked up after an additional 0.75 hour by dilution with toluene and chilling with an ice-water bath. The precipitated solids (dicyclohexylurea, DCU) are removed by filtration. The filtrates are diluted with EtOAc and washed with 5% $NaHSO_4$ solution and 5% $NaHCO_3$ solution. More DCU precipitated during the $NaHCO_3$ wash which is removed by filtration through Celite. A half-saturated brine wash completes the workup. The organic layer is dried ($Na_2SO_4$), filtered, and evaporated at a reduced pressure to yield an oil. The oil is chromatographed on 790 g of 40–63 μm silica gel packed in two Michel-Miller (47×450 mm, Ace Glass) columns connected in series. The sample is applied in the minimum amount of acetone and eluted with 20% acetone/hexane (3 L), 25% acetone/hexane (4 L), and 30% acetone/hexane collecting fractions of 50 mL each. Fractions 100–104 (0.50 g) contain an impurity which is removed by a second chromatography. Fractions 105–127 (14.31 g) contain DCU as an impurity which is removed by a second chromatography on 40–63 μm silica gel (two Michel-Miller 47×450 mm columns) using the minimum amount of EtOAc for application to the column. The product is eluted with 10% EtOAc/toluene collecting fractions of 50 mL each. Eluted first in fractions 24–40 (1.30 g, 7%) is 7-Triethylsilyl-12,13-isobaccatin III, 13-(4S,5R)-N-carbobenzyloxy-2-(2,4-dimethoxyphenyl)-4-phenyl-5-oxazolidinecarboxylic acid ester, less polar isomer (51a)

$^1$H NMR ($CDCl_3$,TMS) δ8.05 (m, 2H), 7.63–7.37 (m, 8H), 7.22–6.99 (m, 6H), 6.48,6.39 (m, 2H), 5.97 (s, 1H), 5.54 (d, 1H, J=5.4 Hz), 5.45 (d, 1H, J=2.6 Hz), 5.01 (m, 3H, —$OCH_2Ph$), 4.88 (m, 1H), 4.43 (m, 1H), 4.38 (d, 1H, J=8.5 Hz), 4.27 (d, 1H, J=8.5) 3.85 (m, 1H), 3.82 (s, 6H), 2.77 (d, 1H, J=18.1 Hz), 2.52 (s, 1H), 2.47 (m, 1H), 2.27 (d, 1H, J=17.4 Hz) 2.19 (s, 3H), 2.15 (s, 3H), 1.88 (m, 1H), 1.78, 1.61, 1.28, 1.16 (4s, 12H), 0.89 (m, 9H), 0.53 (m, 6H);

mass spectrum: 1146.4927, $C_{63}H_{75}NO_{17}Si+H$ requires 1146.4882, 1146, 1116, 1038, 1010, 418, 374, 284, 254, 151, 105, 91, 43 m/z;

Fractions 41–62 (5.14 g, 28%) contain a mixture of isomers.

Fractions 63–130 (7.08 g, 38%) contain 7-Triethylsilyl-12,13-isobaccatin III, 13-(4S,5R)-N-carbobenzyloxy-2-(2, 4-dimethoxyphenyl)-4-phenyl-5-oxazolidinecarboxylic acid ester, more polar isomer (51b)

$^1$H NMR ($CDCl_3$, TMS) δ8.02 (m, 2H), 7.62 (m, 1H), 7.48,7.40 (m, 8H), 7.24–7.14 (m, 5H), 6.74 (m, 2H), 6.44 (m, 2H), 5.87 (s, 1H), 5.48 (d, 1H, J=4.7 Hz), 5.38 (d, 1H, J=5.9 Hz), 4.88 (d, 1H, 12.2 Hz), 4.81 (m, 1H), 4.73 (d, 1H, J=11.8 Hz), 4.61 (d, 1H, J=5.9 Hz), 4.34 (m, 1H), 4.33 (d,1H J=8.6 Hz), 4.22 (d, 1H, J=8.9 Hz), 3.82 (s, 3H), 3.72 (d, 1H J=5.5 Hz), 2.58 (d, 1H, J=17.5 Hz), 2.43 (m, 2H), 2.16 (s, 3H), 2.14 (m, 1H), 1.89(s, 3H), 1.82 (m, 1H), 1.56,1.42, 1.21,1.10 (4s, 12H), 0.88 (m, 9H), 0.51 (m, 6H);

mass spectrum: 1146.4904, $C_{63}H_{75}NO_{17}$ Si+H requires 1146.488, 1146, 1116, 1103, 1038, 1010, 446, 418, 374, 284, 254, 151, 105, 91, 43 m/z.

Tlc: Rf (15% Ethyl Acetate/Toluene)=0.22, 0.33 for the two product isomers.

EXAMPLE 48
N-Debenzoyl-N-benzyloxycarbonyl-12,13-isotaxol (52)

A solution of 7-triethylsilyl-12,13-isobaccatin III, 13-(4S, 5R)-N-carbobenzyloxy-2-(2,4-dimethoxyphenyl)-4-phenyl-5-oxazolidinecarboxylic acid ester (51a,b; 646.5 mg, 0.564 mmole) in MeOH (35 mL) is cooled to 0°–10° C. with an ice bath. Meanwhile, a 0.1 molar solution of HCl in MeOH is prepared by the slow addition of acetyl chloride (0.46 mL) to slightly cooled MeOH (30 mL). This solution is added to the solution of 51a,b in one portion. The resulting solution is allowed to warm to room temperature. The disappearance of the starting material and the appearance of the ortho-ester intermediate and the product is followed by TLC (50% acetone/hexane and 5% $CH_3CN/CH_2Cl_2$) and after 1.5 hours, water (6.2 mL) is added to the blue solution. The less polar ortho-ester intermediate is converted to the desired product within an additional hour. The reaction mixture is diluted with EtOAc (200 mL) and saturated aq. $Na_2CO_3$ (200 mL) solution is added. About one half of the organic layer is removed by rotoevaporation to maximize recovery. The layers are separated, the aqueous layer back-extracted with EtOAc and the combined organic layers are washed with saturated aq. NaCl solution. The organic layer is filtered through $Na_2SO_4$ and evaporated under vacuum. The crude solids (0.589 g) are flash-chromatographed using 6 inches of silica gel in a 30 mm column. The elution solvent is 42.5% EtOAc/hexane (250 mL), 45% EtOAc/hexane(250 mL) and 50% EtOAc/hexane (250 mL) and 20 mL fractions are collected. Fractions 13–16 are combined, the solvent is evaporated and replaced with acetone/hexane. Evaporation of the acetone-haxane under reduced pressure gives N-debenzoyl-N-benzyloxycarbonyl-12,13-isotaxol (0.434 g, 87%) as a white solid.

Tlc: Silica gel; 40% acetone/hexane; starting material Rf=0.53, 52 Rf=0.33, ortho-ester Rf=0.39.

1H NMR (CDCl3, TMS), δ8.18 (d, J=7.2 Hz, 2H), 7.33–7.60 (m, 9H), 7.19 (m, 3H), 6.96 (m, 2H), 5.75 (d, 1H, J=10.0 Hz), 5.56 (d, 1H, J=5.9 Hz), 5.51 (d, 1H, J=10.0 Hz), 5.44 (s, 1H), 4.91 (m, 1H), 4.84 (dd, 2H, J=12.6 Hz), 4.74 (s, 1H), 4.33–4.42 (m, 3H, H7), 3.67 (d, 1H, J=3.7 Hz), 3.47 (s, 1H), 3.26 (bs, 1H), 2.94 (d, 1H, J=19.0 Hz), 2.74 (s, 1H), 2.59 (s, 3H), 2.50 (m, 1H), 2.23 (s, 3H), 1.92 (m, 1H), 1.88 (d, 1H, J=1.90 Hz), 1.62 (s, 3H), 1.58 (s, 3H), 1.25 (s, 3H), 1.04 (s, 3H).

EXAMPLE 49
N-Debenzoyl-N-benzyloxycarbonyl-2'-triethylsilyl-12,13-isotaxol (53)

A solution of the N-debenzoyl-N-benzyloxycarbonyl-12,13-isotaxol (52; 6.61 g, 7.48 mmol) in freshly distilled pyridine (60 mL) under a nitrogen atmosphere is cooled to 0° C. with an ice-water bath. Chlorotriethylsilane (5.0 mL, 30.6 mmol) is added dropwise from a syringe over a three minute period. The temperature monitored internally does not rise above 1° C. The cooling bath is removed after the addition is complete. Tlc indicates complete reaction after one hour. Workup involves dilution with EtOAc (600 mL) and washing with half-saturated $CuSO_4$ (2×100 mL), saturated $CuSO_4$ (2×50 mL), water (2×100 mL), $NaHCO_3$ (1×100 mL), and brine (1×100 mL). All aqueous layers are back extracted. The organic layers are combined, dried ($Na_2SO_4$), filtered and evaporated at a reduced pressure to yield 8.23 g (theory=7.47 g) of a greasy white solid. The solid is chromatographed on 400 g of 40–63 μm silica gel in a Michel-Miller (47×450 mm) column. The sample is applied in the minimum amount of EtOAc and eluted with 30% EtOAc/hexane collecting fractions of 50 mL each. N-Debenzoyl-N-benzyloxycarbonyl-2'-triethylsilyl-12,13-isotaxol is obtained in fractions 25–45 (6.45 g, 86%).

tlc: silica gel; 1:1 EtOAc/hexane; starting material Rf=0.27, product Rf=0.62.

$^1$H NMR ($CDCl_3$,TMS) δ8.17 (d, 2H, J=7.1 Hz), 7.55–6.97 (m, 15H), 5.82 (d, 1H, J=9.8 Hz), 5.56 (d, 1H, J=5.9), 5.51 (d, 1H, J=9.9 Hz), 5.46(s, 1H), 4.94 (m, 1H), 4.80 (m, 2H), 4.64 (d, 1H), 4.38 (m, 1H), 3.69 (d, 1H, J=6.0 Hz), 3.49 (d, 1H, J=4.2), 2.92 (d, 1H, J=18.5 Hz), 2.76 (s, 1H), 2.64 (s, 3H), 2.50 (m, 1H), 2.22 (s, 3H), 1.96 (m, 1H), 1.88 (m, 1H), 1.63, 1.59, 1.26, 1.04 (4s, 12H), 0.74 (m, 9H), 0.35 (m, 6H).

EXAMPLE 50
N-Debenzoyl-N-benzyloxycarbonyl-12,13-isotaxol-7-O-triflate (54)

A solution of N-debenzoyl-N-benzyloxycarbonyl-2'-triethylsilyl-12,13-isotaxol (53; 2.0 g) in $CH_2Cl_2$ (12.2 mL) and pyridine (4.12 mL) is cooled to −30° C. in a 33% MeOH/water/dry ice bath. Triflic anhydride (2.02 mL) is slowly added via a syringe over 5 minutes keeping the temperature below −14° C. At the end of the addition, the reaction mixture is allowed to warm to room temperature. Aliquots of the yellow-orange solution are taken over 6 hours and quenched into EtOAc and saturated aq. $CuSO_4$ solution. The organic layer is checked by TLC (25% EtOAc/hexane) and just a trace of starting material is noted after 6 hours. The reaction mixture is quenched into EtOAc (100 mL) and saturated aq. $CuSO_4$ solution (100 mL). The layers are separated and the organic layer is washed separately with saturated aq. copper sulfate solution (100 mL) and water (100 mL). The water wash is back-extracted with EtOAc (25 mL) and combined with the main organic layer and then washed with saturated aq. $NaHCO_3$ and NaCl solutions respectively. The organic layer is dried through $Na_2SO_4$ and the solvent is removed by rotoevaporation. The residual oil is dissolved in a small amount of acetone and hexane is added until cloudiness develops. The solvent is removed and the residue is subjected to high vacuum to give N-Debenzoyl-N-benzyloxycarbonyl-12,13-isotaxol-7-O-triflate (54) as a yellow solid (2.20 g, 97%).

Tlc: Silica gel; 50% EtOAc/hexane; starting material Rf=0.35, triflate 54 Rf=0.57.

$^1$H NMR ($CDCl_3$, TMS), δ8.16 (d, J=7.1 Hz, 2H), 7.60–7.50 (m, 3H), 7.48–7.29 (m, 5H), 7.17 (m, 3H), 6.96 (m, 2H), 5.86 (s, 1H), 5.83 (d, J=10.0 Hz, 1H), 5.58 (d, J=6.7 Hz, 1H), 5.54 (m, 1H), 5.50 (d, J=8.1 Hz, 1H), 4.90 (m, 1H), 4.86 (d, J=12.8 Hz, 1H), 4.79 (d, J=12.5 Hz, 1H), 4.64 (d, J=1.8 Hz, 1H), 4.43 (d, J=8.7 Hz, 1H), 4.38 (d, J=8.7 Hz, 1H), 3.83 (d, J=5.7 Hz, 1H), 2.99 (m, 1H), 2.89 (d, J=20.6 Hz, 1H), 2.66 (s, 3H), 2.22 (m, 1H), 2.19 (s, 3H,), 1.87 (d, J=19.2 Hz, 1H), 1.77 (s, 3H), 1.66 (s, 3H), 1.25 (s, 3H), 1.07 (s, 3H), 0.74 (t, J=7.8 Hz, 9H), 0.33 (m, 6H).

EXAMPLE 51
2'-Triethylsilyl-N-debenzoyl-N-benzyloxycarbonyl-7-deoxy-7β,8β-methano-12,13-isotaxol (55) and 2'-triethylsilyl-N-debenzoyl-N-benzyloxycarbonyl-7-deoxy-Δ$^{6,7}$-12,13-isotaxol (56)

A solution of N-debenzoyl-N-benzyloxycarbonyl-12,13-isotaxol-7-O-triflate (54; 1.02 g) in ethylene dichloride (95 mL) is stirred with silica gel (35 g, EM, 40–63 μM) at 55°–65° C. in an oil bath for 1.5 hours. An aliquot is filtered and a TLC (5% $CH_3CN/CH_2Cl_2$) of the filtrate shows the reaction to be complete. The reaction mixture is filtered through a medium sintered-glass funnel and acetone (600 mL) is used as a rinse. The solvent is removed under vacuum. The crude solids (1.1 g) are flash-chromatographed using 6 inches of silica gel in a 55 mm column. The elution solvent is 6% $CH_3CN/CH_2Cl_2$ (750 mL), 8% (750 mL), 10% (750 mL and 12% (750 mL) and 40 mL fractions are collected. The combined fractions are concentrated, acetone/hexane added and concentrated again to give white solids. Fractions 29–37 contain 2'-triethylsilyl-N-debenzoyl-N-benzyloxycarbonyl-7-deoxy-Δ$^{6,7}$-12,13-isotaxol (56; 0.174 g, 18%).

$^1$H NMR spectrum is identical to the spectrum of 56 described in Example 57.

Fractions 41–64 contain 2'-Triethylsilyl-N-debenzoyl-N-benzyloxycarbonyl-7-deoxy-7β,8β-methano-12,13-isotaxol (55; 0.659 g, 67%).

Tlc: silica gel; 25% EtOAc/hexane; starting material Rf=0.63, cyclopropane 55 Rf=0.35, olefin 56 Rf=0.43.

$^1$H NMR ($CDCl_3$, TMS), δ8.21 (d, J=6.6 Hz, 2H), 7.54–7.18 (m, 11H), 6.93 (m, 2H), 5.82 (d, J=9.9 Hz, 1H), 5.60 (d, J=6.5, 1H), 5.51 (d, J=10.6 Hz, 1H), 5.23 (d, J=1.97 Hz, 1H), 4.79 (s, 1H), 4.67 (s, 2H), 4.63 (d, J=1.8 Hz, 1H), 4.39 (d, J=8.6 Hz, 1H), 4.13 (d, J=8.7 Hz, 1H), 2.96 (d, J=18.6 Hz, 1H), 2.75 (s, 1H), 2.62 (s, 3H), 2.47 (dt, J=16.0), 4.05 (Hz, 1H), 2.17 (m, 4H, H$_7$), 2.11 (d, 1H), 1.97 (d, J=18.9 Hz), 1.73 (m, 1H), 1.59 (s, 3H), 1.31 (s, 3H), 1.11 (s, 3H), 0.73 (t, J=7.9 Hz, 9H), 0.34 (m, 6H).

$^{13}$C NMR ($CDCl_3$, TMS), δ203.7, 170.1, 169.7, 168.8, 167.1, 155.6, 141.5, 138.7, 136.1, 133.6, 130.5, 129.2, 128.7, 128.6, 128.3, 127.9, 127.4, 126.4, 122.5, 85.1, 80.5, 78.9, 78.7, 78.3, 75.6, 75.2, 66.8, 57.4, 54.9, 39.7, 36.6, 33.1, 32.3, 30.3, 29.7, 29.4, 25.9, 22.4, 21.3, 20.9, 14.1, 13.0, 6.5, 4.1.

EXAMPLE 52
2'-Triethylsilyl-N-debenzoyl-7-deoxy-7β,8β-methano-12,13-isotaxol (57) 27548-PJD-152

Ammonium formate (0.96 g) and 10% Pd/C (0.44 g) are added to a solution of 2'-triethylsilyl-N-debenzoyl-N-benzyloxycarbonyl-7-deoxy-7β,8β-methano-12,13-isotaxol (55; 1.343 g) in MeOH (18 mL) and THF (12 mL). The mixture is stirred for 10 minutes at room temperature and then cooled to 0° C. The reaction mixture is monitored by TLC (50% EtOAc/hexane) and is complete after 2 hours of stirring. The mixture is filtered through Celite and rinsed with EtOAc (150 mL). The filtrate is washed with saturated aq. $NaHCO_3$ solution (100 mL). The aqueous layer is back-extracted with EtOAc and the combined organic layers are washed with saturated aq. NaCl solution. The organic layer is dried through Na$_2$SO$_4$, the solvent removed under vacuum and the solids subjected to high vacuum, giving 2'-triethylsilyl-N-debenzoyl-7-deoxy-7β,8β-methano-12,13-isotaxol (1.114 g).

Tlc: silica gel; 50% EtOAc/hexane; starting material Rf=0.64, amine 57 Rf=0.42.

$^1$H NMR (CDCl$_3$, TMS), δ8.09 (m, 2H), 7.65 (m, 1H), 7.53 (m, 2H), 7.34 (m, 4H), 7.17 (m, 1H), 5.59 (d, J=6.65 Hz, 1H), 5.19 (d, J=1.91 Hz, 1H), 4.76 (d, J=3.1 Hz, 1H), 4.4 (m, 2H), 4.30 (d, J=5.4, 1H), 4.08 (d, J=8.6 Hz, 1H), 3.81 (d, J=6.6 Hz, 1H), 2.72 (s, 1H), 2.53–2.39 (m, 2H), 2.30 (s, 3H), 2.16 (s, 3H), 1.92 (d, J=18.5 Hz, 1H), 1.69 (s, 3H), 1.28 (s, 3H), 1.10 (s, 3H), 0.90 (t, J=8.0 Hz, 9H), 0.56 (m, 6H).

EXAMPLE 53

2'-Triethylsilyl-N-debenzoyl-N-(t-butyl)oxycarbonyl-7-deoxy-7β,8β-methano-12,13-isotaxol (58)

A solution of 2'-triethylsilyl-N-debenzoyl-7-deoxy-7β,8β-methano-12,13-isotaxol (57; 0.438 g), triethylamine (88 μl) and di-t-butyldicarbonate (0.125 g) in THF (10 mL) is stirred at room temperature overnight. The reaction is determined to be complete by TLC (50% EtOAc/hexane). The mixture is diluted with EtOAc (100 mL) and the resulting organic layer is washed with saturated aq. NaHCO$_3$ and NaCl solutions. The organic layer is dried through Na$_2$SO$_4$, the solvent removed under vacuum and the crude solids subjected to high vacuum, giving 2'-triethylsilyl-N-debenzoyl-N-(t-butyl)oxycarbonyl-7-deoxy-7β,8β-methano-12,13-isotaxol (0.495 g).

Tlc, silica gel, 50% EtOAc/hexane; starting material Rf=0.45, 58 Rf=0.66

$^1$H NMR (CDCl$_3$, TMS): δ8.18 (d, J=7.2 Hz, 2H), 7.59–7.24 (m, 8H), 5.62 (d, J=6.8, 1H), 5.55 (d, J=10.0 Hz, 1H), 5.43 (d, J=10.0 Hz, 1H), 5.24 (d, J=2.0 Hz, 1H), 4.81 (s, 1H), 4.60 (s, 1H), 4.42 (d, J=8.6 Hz, 1H), 4.11 (d, J=8.6 Hz, 1H), 3.88 (d, J=6.7 Hz, 1H), 2.93 (d, J=18.5 Hz, 1H), 2.76 (s, 1H), 2.61 (s, 3H), 2.47 (dt, J=4.3 and 16.0 Hz, 1H), 2.17 (m, 4H), 2.00 (d, J=16.0 Hz, 1H), 1.71 (m, 1H), 1.52 (s, 3H), 1.26 (m, 1H), 1.12 (s, 3H), 1.10 (s, 3H), 0.74 (t, J=3.4, 9H), 0.34 (m, 6H).

EXAMPLE 54

N-Debenzoyl-N-(t-butyl)oxycarbonyl-7-deoxy-7β,8β-methano-12,13-isotaxol (17)

A solution of 2'-triethylsilyl-N-debenzoyl-N-(t-butyl)oxycarbonyl-7-deoxy-7β,8β-methano-12,13-isotaxol (58; 0.49 g) in CH$_3$CN (2.45 mL) is treated with Et$_3$N(HF)$_3$ (1.47 mL) and stirred at room temperature. The reaction is determined to be complete after 30 minutes by TLC (50% EtOAc/hexane). The reaction mixture is diluted with EtOAc (100 mL) and the organic layer washed with saturated aq. NaHCO$_3$ and NaCl solutions. The organic layer is dried through Na$_2$SO$_4$, the solvent removed under vacuum and the crude solids are subjected to high vacuum (0.422 g). The crude solids are flash-chromatographed using 6 inches of silica gel in a 30 mm column. The elution solvent is 42.5% EtOAc/hexane (300 mL), 45% (200 mL) and 50% (200 mL) and 20 mL fractions are collected. Fractions 9–14 contained 0.308 g (71%) of N-debenzoyl-N-(t-butyl)oxycarbonyl-7-deoxy-7β,8β-methano-12,13-isotaxol.

Tlc: silica gel; 50% EtOAc/hexane; starting material Rf=0.70, 17 Rf=0.47.

$^1$H NMR (CDCl$_3$, TMS): δ8.19 (d, J=7.3 Hz, 2H), 7.61–7.29 (m, 8H), 5.62 (d, J=6.7 Hz, 1H), 5.42 (m, 2H), 5.22 (d, J=2.0 Hz, 1H), 4.79 (d, J=3.2 Hz, 1H), 4.69 (d, J=3.4 Hz, 1H), 4.42 (d, J=8.6 Hz, 1H), 4.09 (d, J=8.6, 1H), 3.87 (d, J=6.7 Hz, 1H), 3.24 (d, J=4.4 Hz, 1H), 2.96 (d, J=19.1 Hz, 1H), 2.75 (s, 1H), 2.56 (s, 3H), 2.45 (dt, J=4.3 and 16.1 Hz, 1H), 2.17 (m, 5H), 2.10 (d, J=16.0 Hz, 1H), 1.69 (m, 4H), 1.58 (s, 3H), 1.33 (m, 4H), 1.13 (s, 9H).

$^{13}$C NMR (CDCl$_3$, TMS), δ203.5, 171.0, 170.1, 169.7, 167.3, 155.0, 141.8, 138.8, 133.6, 130.4, 129.1, 128.8, 128.7, 128.0, 126.5, 122.6, 85.2, 80.4, 80.0, 78.9, 78.6, 78.4, 75.7, 73.7, 55.6, 55.0, 39.8, 36.7, 32.9, 32.4, 30.1, 29.0, 28.0, 25.8, 22.4, 21.1, 20.9, 14.2, 12.9.

mass spectrum 832.3538 (C$_{45}$H$_{53}$NO$_{14}$+H requires 832.3544), 986, 832, 776, 758, 732, 551, 387, 180, 105, 77, 57, 43 m/z.

EXAMPLE 55

2'-Triethylsilyl-N-debenzoyl-N-(t-butyl)aminocarbonyl-7-deoxy-7β,8β-methano-12,13-isotaxol (59) (({2aR-[2aα,4β,4aβ,6β,7α,9, (αR*,βS*),11α,12α,12aα,12bα]}-β-[(t-butyl) aminocarbonylamino]-α-triethylsilyloxybenzenepropanoic acid, 6,12b-bis(acetyloxy)-12-(benzoyloxy)-2a,3,4,4a,5,6,7,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester))

A solution of crude 2'-triethylsilyl-N-debenzoyl-7-deoxy-7β,8β-methano-12,13-isotaxol (57; 1.11 g) and t-butylisocyanate (0.6 mL, 5.25 mmols) in THF (15 mL) and Et$_3$N (18 μL) is stirred overnight at rt. The solvent is removed under reduced pressure and the residue placed under high vacuum. 2'-Triethylsilyl-N-debenzoyl-N-(t-butyl)aminocarbonyl-7-deoxy-7β,8β-methano-12,13-isotaxol (59; 1.225 g) is obtained:

$^1$NMR (CDCl$_3$, TMS) δ8.18 (d, 2H, J=6.8 Hz), 7.57 (t, 1H), 7.49 (m, 2H), 7.35 (m, 2H), 7.27 (m, 3H), 5.64 (d, 1H, J=6.6 Hz), 5.56 (d, 1H, J=9.3 Hz), 5.23 (d, 1H, J=1.9 Hz), 5.18 (d, 1H, J=9.2 Hz), 4.82 (s, 1H), 4.60 (d, 1H, J=1.9 Hz), 4.42 (d, 1H, J=8.7 Hz), 4.12 (d, 1H, J=8.5 Hz), 3.90 (d, 1H, J=6.6 Hz), 2.95 (d, 1H, J=19.5 Hz), 2.76 (s, 1H), 2.64 (s, 3H), 2.44 (dt, 1H, J=16.2 Hz), 2.17 (s, 3H), 2.16 (m, 2H), 2.11(d, 1H, J=16.0 Hz), 1.34 (s, 3H), 1.13 (s, 3H), 1.00 (s, 9H), 0.74 (t, 9H), 0.30 (m, 6H).

EXAMPLE 56

N-Debenzoyl-N-(t-butyl)aminocarbonyl-7-deoxy-7β,8β-methano-12,13-isotaxol (36) (({2aR-[2aα,4β,4aβ,6β,7α,9,(αR*,βS*), 11α,12α,12aα,12bα]}-β-[(t-Butyl)aminocarbonylamino]-α-hydroxybenzenepropanoic acid, 6,12b-Bis(acetyloxy)-12-(benzoyloxy)-2a,3,4,4a,5,6,7,10,11,12,12a,12b-dodecahydro-11-hydroxy-8,13,13-trimethyl-5-oxo-4,4a;7,11-bismethano-1H-cyclodeca[3,4]benz[1,2-b]-oxet-9-yl Ester))

Using the procedure described for the preparation of 17, a solution of crude 2'-triethylsilyl-N-debenzoyl-N-(t-butyl)aminocarbonyl-7-deoxy-7β,8β-methano-12,13-isotaxol (59; 1.225 g) and triethylamine trihydrofluoride (3.66 mL) in CH$_3$CN (6 mL) is prepared at 0° C., then allowed to warm to rt while stirring for 1 hr. Following workup and flash chromatography over silica gel, N-debenzoyl-N-(t-butyl)aminocarbonyl-7-deoxy-7β,8β-methano-12,13-isotaxol (36; 0.919 g, 1.10 mmols; 81% from 55) is obtained:

1H NMR (CDCl$_3$, TMS) δ8.17 (d, 2H, J=7.0 Hz), 7.59 (t, 1H, J=7.3 Hz), 7.50 (t, 2H, J=7.6 Hz), 7.36 (m, 4H), 7.29 (m, 1H), 5.62 (d, 1H, J=6.5 Hz), 5.48 (dd, 1H, J=2.7, 9.2 Hz), 5.26 (d, 1H, J=9.2 Hz), 5.20 (d, 1H, J=1.9 Hz), 4.77 (m, 1H), 4.69 (m, 1H), 4.41 (d, 1H), 4.09 (d, 1H, J=8.6 Hz), 3.85 (d, 1H, J=6.6 Hz), 2.91 (d, 1H, J=19.0 Hz), 2.72 (s, 1H), 2.53 (s, 3H), 2.40 (dt, 1H, J=16.1 Hz), 2.16 (s, 3H), 2.11 (m, 2H), 2.07 (d, 1H, J=16.1 Hz), 1.71 (t, 1H, J=6.1 Hz), 1.54 (s, 3H), 1.30 (s, 3H), 1.30 (m, 1H), 1.11 (s, 3H), 1.04 (s, 9H).

$^{13}$C NMR (CDCl$_3$, TMS) δ203.6, 171.0, 170.4, 169.8, 167.3, 156.2, 141.8, 139.2, 133.6, 130.4, 129.0, 128.78, 128.76, 127.8, 126.6, 122.4, 85.2, 80.5, 78.9, 78.4, 78.3, 75.7, 74.4, 55.2, 55.0, 50.4, 39.7, 36.7, 32.8, 32.5, 30.1, 29.2, 28.8, 25.8, 22.4, 21.1, 20.9, 14.2, 12.8.

mass spectrum (FAB), found: 831.3701 ($C_{45}H_{54}N_2O_{13}$+H requires 831.37.04), 732, 263, 235, 205, 179, 136, 119, 106, 105, 57 m/z.

EXAMPLE 57
2'-Triethylsilyl-N-debenzoyl-N-benzyloxycarbonyl-7-deoxy-$\Delta^{6,7}$-12,13-isotaxol (56)

A solution of N-debenzoyl-N-benzyloxycarbonyl-12,13-isotaxol-7-O-triflate (54; 2.348 g) and DBU (3.11 mL) in toluene (180 mL) is heated with a 60° C. oil bath for 4 hours. A trace of starting material is noted by TLC (5% $CH_3CN$/$CH_2Cl_2$). The reaction mixture is diluted with EtOAc (100 mL) and the resulting organic layer is washed with saturated aq. $CuSO_4$ solution, water, saturated aq. $NaHCO_3$ and NaCl solutions. The organic layer is dried through $Na_2SO_4$ and the solvent removed under vacuum. The crude solids (2.07 g) are flash-chromatographed using 6 inches of silica gel in a 55 mm column. The elution solvent is 4% $CH_3CN$/$CH_2Cl_2$ (1000 mL), 5% (1000 mL), 6% (1000 mL), 8% (1000 mL) and 15% (1000 mL) and 40 mL fractions are collected. Fractions 27–74 contained 2'-triethylsilyl-N-debenzoyl-N-benzyloxycarbonyl-7-deoxy-$\Delta^{6,7}$-12,13-isotaxol (56; 1.43 g, 68%) as a white solid.

Tlc: silica gel; 5% $CH_3CN$/$CH_2Cl_2$; starting material Rf=0.64, olefin 56 Rf=0.47, cyclopropane 55 Rf=0.36.

$^1$H NMR (CDCl$_3$, TMS), $\delta$8.21 (d, J=7.1 Hz, 2H), 7.60–7.47 (m, 3H), 7.41–7.26 (m, 6H), 7.19–7.13 (2H), 6.97 (m, 2H), 6.09 (dd, J=5.3 and 9.9 Hz, 1H), 6.02 (d, J=9.8, 1H), 5.82 (d, J=9.8, 1H), 5.72 (d, J=5.8 Hz, 1H), 5.51 (d, J=10.3, 1H), 5.18 (s, 1H), 5.12 (d, J=5.3 Hz, 1H), 4.83 (d, J=12.5 Hz, 1H), 4.76 (d, J=12.4, 1H), 4.64 (d, J=1.8, 1H), 4.52 (d, J=8.4, 1H), 4.37 (d, J=8.3 Hz, 1H), 3.67 (d, J=5.6 Hz, 1H), 2.95 (d, J=18.6 Hz, 1H), 2.75 (s, 1H), 2.67 (s, 3H), 2.18 (s, 3H), 1.90 (d, J=18.5 Hz, 1H), 1.76 (s, 3H), 1.53 (s, 3H), 1.28 (s, 3H), 1.03 (s, 3H), 0.73 (t, J=8.0, 9H), 0.35 (m, 6H).

$^{13}$C NMR (CDCl$_3$, TMS), $\delta$207.7, 169.9, 169.6, 168.8, 166.7, 155.7, 142.2, 138.8, 138.6, 136.1, 133.7, 130.3, 129.2, 128.7, 128.6, 128.4, 127.9, 127.9, 127.4, 126.4, 125.6, 122.1, 81.2, 80.8, 79.1, 77, 75.0, 73.7, 66.8, 57.3, 56.0, 54.1, 39.6, 36.5, 32.6, 29.9, 23.3, 21.0, 20.8, 18.5, 14.1, 6.4, 4.1.

Fractions 82–90 contained 2'-triethylsilyl-N-debenzoyl-N-benzyloxycarbonyl-7-deoxy-7β,8β-methano-12,13-isotaxol (55; 0.14 g, 7%). $^1$H NMR spectrum is identical to the spectrum of 55 described in Example 51.

EXAMPLE 58
2'-Triethylsilyl-N-debenzoyl-7-deoxy-$\Delta^{6,7}$-12,13-isotaxol (60) (({2aR-[2aα, 4aβ,6β,7α9,(αR*,βS*), 11α,12α,12aα, 12bα]}-β-amino-α-triethylsilyloxybenzenepropanoic acid, 6,12b-bis(acetyloxy)-12-(benzoyloxy)-2a,4a,5,6,7,10,11,12, 12a,12b-decahydro-11-hydroxy-4a,8,13,13-tetramethyl-5-oxo-7,11-methano-1H-cyclodeca[3,4]benz[1,2-b]-oxet-9-yl Ester))

Using the procedure described for the preparation of 57, a solution of 2'-triethylsilyl-N-debenzoyl-N-benzyloxycarbonyl-7-deoxy-$\Delta^{6,7}$-12,13-isotaxol (56; 1.721 g, 1.75 mmols) and ammonium formate (1.07 g, 16.97 mmols) in MeOH (23 mL) and THF (12.6 mL) is stirred at rt with 10% palladium on carbon for 10 min and then at 0° C. for one hr. Following workup, 2'-triethylsilyl-N-debenzoyl-7-deoxy-$\Delta^{6,7}$-12,13-isotaxol (60; 1.47 g) is obtained.

$^1$H NMR (CDCl$_3$, TMS) $\delta$8.11 (d, 2H, J=8.0 Hz), 7.67 (t, 1H, J=7.4 Hz), 7.54 (t, 2H), 7.35 (m, 4H), 7.18 (m, 1H), 6.05 (m, 2H), 5.68 (d, 1H, J=5.1 Hz), 5.13 (s, 1H), 5.10 (d, 1H, J=4.5 Hz), 4.51 (d, 1H, J=8.2 Hz), 4.32 (m, 3H), 3.62 (d, 1H, J=5.3 Hz), 2.71 (s, 1H), 2.45 (d, 1H, J=17.9 Hz), 2.30 (s, 3H), 2.17 (s, 3H), 1.83 (d, 1H, J=17.9 Hz), 1.69 (s, 3H), 1.44 (s, 3H), 1.27 (s, 3H), 1.02 (s, 3H), 0.91 (t, 9H), 0.56 (m, 6H).

EXAMPLE 59
2'-Triethylsilyl-N-debenzoyl-N-(t-butyl)oxycarbonyl-7-deoxy-$\Delta^{6,7}$-12,13-isotaxol (61); (({2aR-[2aα,4aβ,6β,7α,9, (αR*,βS*), 11α,12α,12aα,12bα]}-β-[(t-Butyl)oxycarbonylamino]-α-hydroxybenzenepropanoic acid, 6,12b-bis(acetyloxy)-12-(benzoyloxy)-2a,4a,5,6,7,10,11,12, 12a,12b-decahydro-11-hydroxy-4a,8,13,13-tetramethyl-5-oxo-7,11-methano-1H-cyclodeca[3,4]benz[1,2-b]-oxet-9-yl Ester))

Using the procedure described for the preparation of 58, a solution of crude 2'-triethylsilyl-N-debenzoyl-7-deoxy-$\Delta^{6,7}$-12,13-isotaxol (60; 0.515 g) and di-t-butyl dicarbonate ("BOC anhydride," 0.147 g, 0.675 mmole) in THF (12 mL) and Et$_3$N (0.10 mL) is stirred overnight at RT. Additional di-t-butyl carbonate (0.013 g, 0.059 mmole) is added and the solution stirred another 2 hr. Following workup, 2'-triethylsilyl-N-debenzoyl-N-(t-butyl)oxycarbonyl-7-deoxy-$\Delta^{6,7}$-12,13-isotaxol (61; 0.546 g) is obtained.

$^1$H NMR (CDCl$_3$, TMS) $\delta$8.17 (d, 2H, J=7.3 Hz), 7.58 (t, 1H, J=7.4 Hz), 7.49 (t, 2H), 7.38 (m, 2H), 7.27 (m, 3H), 6.10 (dd, 1H, J=5.2, 9.9 Hz), 6.04 (d, 1H, J=9.8 Hz), 5.73 (d, 1H, J=4.3 Hz), 5.55 (d, 1H, J=10.0 Hz), 5.44 (d, 1H, J=10.5 Hz), 5.19 (s, 1H), 5.14 (d, 1H, J=5.1 Hz), 4.62 (s, 1H), 4.55 (d, 1H, J=8.1 Hz), 4.35 (d, 1H, J=8.3 Hz), 3.69 (d, 1H, J=5.4 Hz), 2.94 (d, 1H, J=18.8 Hz), 2.77 (q, 1H), 2.67 (s, 3H), 2.19 (s, 3H), 2.07 (d, 1H, J=10.9 Hz), 1.76 (s, 3H), 1.28 (s, 3H), 1.16 (s, 9H), 1.05 (s, 3H), 0.74 (t, 9H), 0.37 (m, 6H).

EXAMPLE 60
N-Debenzoyl-N-(t-butyl)oxycarbonyl-7-deoxy-$\Delta^{6,7}$-12,13-isotaxol. (18) (({2aR-[2aα,4aβ,6β,7α,9,(αR*,βS*),11α, 12α,12aα,12bα]}-β-[(t-Butyl)oxycarbonyl-amino]-α-hydroxybenzenepropanoic acid, 6,12b-bis(acetyloxy)-12-(benzoyloxy)-2a,4a,5,6,7,10,11,12,12a,12b-decahydro-11-hydroxy-4a,8,13,13-tetramethyl-5-oxo-7,11-methano-1H-cyclodeca[3,4]benz[1,2-b]-oxet-9-yl Ester))

Using the procedure described for the preparation of 17, a solution of 2'-triethylsilyl-N-debenzoyl-N-(t-butyl) oxycarbonyl- 7-deoxy-$\Delta^{6,7}$-12,13-isotaxol (61, 0.546 g) from the preceding experiment and triethylamine trihydrofluoride (1.64 mL) in CH$_3$CN (2.7 mL) is stirred at 0°–25° C. for 1 hr. Following workup and chromatographic purification over flash silica gel, N-debenzoyl-N-(t-butyl) oxycarbonyl-7-deoxy-$\Delta^{6,7}$-12,13-isotaxol (18; 0.445 g, 0.547 mmole, 87% from 56) is obtained.

$^1$H NMR (CDCl$_3$, TMS) $\delta$8.18 (d, 2H, J=7.2 Hz), 7.61 (t, 1H, J=7.3 Hz), 7.50 (t, 2H), 7.35 (m, 5H), 6.09 (dd, 1H, J=5.1, 9.9 Hz), 6.04 (d, 1H, J=9.8 Hz), 5.73 (d, 1H, J=5.5 Hz), 5.40 (s, 2H), 5.18 (s, 1H), 5.13 (d, 1H, J=5.1 Hz), 4.70 (s, 1H), 4.55(d, 1H, J=8.3 Hz), 4.34 (d, 1H, J=8.4 Hz), 3.68 (d, 1H, J=5.4 Hz), 2.97 (d, 1H, J=18.9 Hz), 2.74 (s, 1H), 2.61 (s, 3H), 2.20 (s, 3H), 2.09 (d, 1H, J=18.0 Hz), 1.75 (s, 3H), 1.53 (s, 3H), 1.32 (s, 3H), 1.20 (s, 9H), 1.05 (s, 3H).

mass spectrum (FAB), found 832.3538 ($C_{45}H_{53}NO_{14}$+H requires 832.3544), 776, 732, 180, 150, 105, 57 m/z.

EXAMPLE 61
2'-Triethylsilyl-N-debenzoyl-N-(t-butyl)aminocarbonyl-7-deoxy-$\Delta^{6,7}$-12,13-isotaxol (62) (({2aR-[2aα,4aβ,6β,7α,9, (αR*,βS*),11α,12α,12aα,12bα]}-β-[(t-Butyl) aminocarbonylamino]-α-triethylsilyloxybenzenepropanoic acid, 6,12b-bis(acetyloxy)-12-(benzoyloxy)-2a,4a,5,6,7,10,

73

11,12,12a,12b-decahydro-11-hydroxy-4a,8,13,13-tetramethyl-5-oxo-7,11-methano-1H-cyclodeca[3,4]benz[1,2-b]-oxet-9-yl Ester))

Using the procedure described for the preparation of 59, a solution of 2'-triethylsilyl-N-debenzoyl-7-deoxy-$\Delta^{6,7}$-12,13-isotaxol (60; 0.956 g) and t-butylisocyanate (0.52 mL, 4.52 mmols) in THF (19 mL) and Et$_3$N (16 µL) is prepared at ice bath temperature and then allowed to warm and stir at rt overnight. Following workup, 2'-triethylsilyl-N-debenzoyl-N-(t-butyl)aminocarbonyl-7-deoxy-$\Delta^{6,7}$-12,13-isotaxol (62; 1.027 g) is obtained.

$^1$H NMR (CDCl$_3$,TMS) δ8.17 (d, 2H, J=7.0 Hz), 7.59 (t, 1H, J=7.3 Hz), 7.50 (t, 2H), 7.35 (m, 2H), 7.26 (m, 3H), 6.08 (m, 2H), 5.73 (d, 1H, J=5.4 Hz), 5.51 (d, 1H, J=8.9 Hz), 5.18 (m, 3H), 4.60 (d, 1H, J=1.1 Hz), 4.55 (d, 1H), 4.37 (d, 1H, J=8.3 Hz), 3.70 (d, 1H, J=5.3 Hz), 2.95 (d, 1H, J=19.0 Hz), 2.76 (s, 1H), 2.70 (s, 3H), 2.19 (s, 3H), 2.11 (d, 1H, J=20.5 Hz), 1.76 (s, 3H), 1.55 (s, 3H), 1.32 (s, 3H), 1.07 (s, 9H), 1.06 (s, 3H), 0.73 (t, 9H), 0.30 (m, 6H).

EXAMPLE 62

N-Debenzoyl-N-(t-butyl)aminocarbonyl-7-deoxy-$\Delta^{6,7}$-12,13-isotaxol. (38) ((\{2aR-[2aα,4aβ,6β,7α,9,(αR*,βS*)],11α,12α,12aα,12bα]\}-β-[(t-Butyl)amino-carbonylamino]-α-hydroxybenzenepropanoic acid, 6,12b-bis(acetyloxy)-12-(benzoyloxy)-2a,4a,5,6,7,10,11,12,12a,12b-decahydro-11-hydroxy-4a,8,13,13-tetramethyl-5-oxo-7,11-methano-1H-cyclodeca[3,4]benz[1,2-b]-oxet-9-yl Ester))

Using the procedure described for the preparation of 17, a solution of crude 2'-triethylsilyl-N-debenzoyl-N-(t-butyl) aminocarbonyl-7-deoxy-$\Delta^{6,7}$-12,13-isotaxol (62; 1.02 g) and Et$_3$N.(HF)$_3$ in CH$_3$CN (5 mL) is prepared at 0° C. and then stirred while allowing to warm to rt for 1 hr. Following workup and flash chromatography over silica gel, N-debenzoyl-N-(t-butyl)aminocarbonyl-7-deoxy-$\Delta^{6,7}$-12,13-isotaxol (38; 0.842 g, 1.01 mmols, 91% yield from 56) is obtained.

$^1$H NMR (CDCl$_3$, TMS) δ8.16 (d, 2H, J=7.1 Hz), 7.60 (t, 1H, J=7.3 Hz), 7.50 (r, 2H), 7.35 (m, 4H), 7.30 (m, 1H), 6.05 (m, 2H), 5.71 (d, 1H, J=5.2 Hz), 5.46 (dd, 1H, J=2.5, 9.1 Hz), 5.39 (d, 1H, J=9.2 Hz), 5.12 (m, 2H), 4.69 (dd, 1H, J=2.5, 5.1 Hz), 4.53 (d, 1H), 4.33 (d, 1H, J=8.2 Hz), 3.77 (d, 1H, J=5.5 Hz), 3.65 (d, 1H, J=5.3 Hz), 2.92 (d, 1H, J=18.7 Hz), 2.71 (s, 1H), 2.58 (s, 3H), 2.19 (s, 3H), 2.10 (d, 1H, J=18.3 Hz), 1.74 (s, 3H), 1.47 (s, 3H), 1.30 (s, 3H), 1.10 (s, 9H), 1.04 (s, 3H);

$^{13}$C NMR (CDCl$_3$, TMS) δ206.7, 172.0, 171.3, 170.7, 166.6, 156.5, 143.3, 138.9, 133.7, 130.2, 128.9, 128.8, 127.9, 126.7, 121.7, 84.5, 81.1, 77.7, 77.6, 77.2, 74.7, 73.5, 71.7, 57.9, 55.7, 50.5, 39.5, 38.7, 35.3, 32.9, 29.8, 29.3, 23.2, 21.0, 19.8, 14.4, 9.1.

mass spectrum (FAB), found: 831.3701 (C$_{45}$H$_{54}$N$_2$O$_{13}$ requires 831.3704), 732, 263, 235, 205, 136, 106, 105, 57 m/z.

EXAMPLE 63

Preparation of (O-methoxymethyl)-13-(N-Cbz-2'-TES-β-phenyl isoserinyl)-$\Delta^{12,13}$-iso-baccatin III (63)

Following the procedure of Example 45 but using as starting material 13-(N-Cbz-2-TES-β-phenyl isoserinyl)-$\Delta^{12,13}$-iso-baccatin III (53) and chloromethyl methyl ether in place of chloromethyl ethyl ether is prepared (O-methoxymethyl)-13-(N-Cbz-2'-OTES-β-phenyl isoserinyl)-$\Delta^{12,13}$-iso-baccatin III (63)

74

EXAMPLE 64

Preparation of 7-(O-methoxymethyl)-13-(N-Cbz-β-phenyl isoserinyl)-$\Delta^{12,13}$-iso-baccatin III (64)

Following the procedure of Example 43 but using as starting material (O-methoxymethyl)-13-(N-Cbz-2-TES-β-phenyl isoserinyl)-$\Delta^{12,13}$-iso-baccatin III (63) in place of 7-(O-ethoxymethyl)-13-(N-Boc-2'-TES-β-phenyl isoserinyl)-$\Delta^{12,13}$-iso-baccatin III is prepared 7-(O-methoxymethyl)-13-(N-Cbz-β-phenyl isoserinyl)-$\Delta^{12,13}$-iso-baccatin III (64).

EXAMPLE 65

Preparation of 7-(O-methoxymethyl)-13-(β-phenyl isoserinyl)-$\Delta^{12,13}$-iso-baccatin III (65)

7-(O-Methoxymethyl)-13-(N-Cbz-β-phenyl isoserinyl)-$\Delta^{12,13}$-iso-baccatin III (64, 450 mg, 0.485 mM) is stirred at RT under nitrogen in methanol (7.5 mL) and dry THF (5 mL). To this solution is added ammonium formate (225 mg) and 10% Pd/C (125 mg). The reaction is allowed to react at RT for 10 min and then cooled in ice bath, following the reaction by HPLC while maintaining the temperature at 0° C. After a total of 55 minutes reaction time, the catalyst is filtered off and the filtrate diluted with ethyl acetate. The organic solution is washed with 5% sodium bicarbonate, dried over sodium sulfate and evaporated under vacuum, reevaporating the residue twice with ethyl acetate-toluene leaving 7-(O-methoxymethyl)-13-(β-phenyl isoserinyl)-$\Delta^{12,13}$-iso-baccatin III (65).

TLC: silica gel; 40–60 ethyl acetate-hexane; Rf: origin

Proton NMR (CDCl$_3$; TMS): δ1.09 (s, 3H); 1.25 (s, 3H); 1.61 (s, 3H); 1.66 (s, 3H); 2.16 (s, 3H); 2.18 (s, 3H); 3.25 (s, 3H); 3.76–3.83 (d, 1H); 3.93–4.05 (dd 1H); 4.20–4.40 (m, 4H); 4.45–4.54(d, 1H); 4.62–4.72 (d, 1H); 4.80–4.90 (dd, 1H); 5.44–5.53 (d, 1H); 5.73 (s, 1H); 7.26–7.40 (m, 5H); 7.45–7.55 (t, 2H); 7.57–7.67 (t, 1H); 7.99–8.09 (d, 2H).

EXAMPLE 66

Preparation of 7-(O-methoxymethyl)-13-(N-Boc-β-phenyl isoserinyl)-$\Delta^{12,13}$-iso-baccatin III (66)

7-(O-Methoxymethyl)-13-(β-phenyl isoserinyl)-$\Delta^{12,13}$-iso-baccatin III (65, 0.194 mM) is stirred at RT under nitrogen in dry THF (1 mL) and the solution treated with di-tert-butyl dicarbonate (43 mg, 0.197 mM) in dry THF (0.4 mL), followed by triethylamine (0.26 mL). The reaction is followed by HPLC and after 3.5 hours additional di-t-butyl dicarbonate (5 mg) is added. After 5.5 hours reaction the solvent is evaporated under vacuum. The crude product is purified by HPLC over a size B E. Merck prepacked silica gel column, eluting with (50-50) ethyl acetate-hexane. Fractions of 7 mL are collected, analyzing them by TLC. Fractions 39–46 are found to contained pure product and are combined and evaporated under vacuum to give 7-(O-methoxymethyl)-13-(N-Boc-β-phenyl isoserinyl)-$\Delta^{12,13}$-iso-baccatin III (66, 71% yield) as a white solid.

TLC: silica gel; 60–40 ethyl acetate-hexane; Rf: 0.69

Proton NMR (CDCl$_3$; TMS): δ1.11 (s, 3H); 1.24 (s, 9H); 1.27 (s, 3H); 1.62 (s, 3H); 1.69 (s, 3H); 1.87–2.15 (m, 3H); 2.17 (s, 3H); 2.56 (s, 3H); 2.62 (s, 1H); 2.76–2.94 (m, 2H); 3.26 (s, 3H); 3.42–3.50 (d, 1H); 3.82–3.89 (d, 1H); 3.98–4.10 (dd, 1H); 4.24–4.33 (d, 1H); 4.36–4.44 (d, 1H); 4.46–4.54 (d, 1H); 4.63–4.73 (d+s, 2H); 4.85–4.93 (dd, 1H); 5.34–5.45 (d, 1H); 5.50–5.59 (m, 2H); 5.77 (s, 1H); 7.27–7.43 (m, 5H); 7.43–7.53 (t, 2H); 7.54–7.63 (t, 1H); 8.04–8.16 (d, 2H).

EXAMPLE 67
Preparation of 7-(O-methoxymethyl)-13-(N-t-butylaminocarbonyl-β-phenyl isoserinyl)-$\Delta^{12,13}$-iso-baccatin III (67)

7-(O-Methoxymethyl)-13-(β-phenyl isoserinyl)-$\Delta^{12,13}$-iso-baccatin III (65, 0.485 mM) is stirred at 0° C. under nitrogen in dry THF (5 mL) and the solution treated with t-butylisocyanate (75 mL). After 5 minutes the reaction is allowed to warm to RT. The reaction is followed by HPLC and allowed to stand overnight. After 18 hr the solvent is evaporated under vacuum. The crude product is purified by silica gel chromatography, eluting with a gradient of (50-50) to (60-40) ethyl acetate-hexane. Fractions of 15 mL are collected, analyzing them by TLC. Fractions 44–66 are found to contained pure product and are combined and evaporated under vacuum to give 7-(O-methoxymethyl)-13-(N-t-butylaminocarbonyl-β-phenyl isoserinyl)-$\Delta^{12,13}$-iso-baccatin III (67, 85% yield) as a white solid.

TLC: silica gel; (50-50) ethyl acetate-hexane; Rf: 0.33
Proton NMR (CDCl$_3$; TMS): δ1.11 (s, 3H); 1.14 (s, 9H); 1.25 (s, 3H); 1.59 (s, 3H); 1.69 (s, 3H); 1.88–2.15 (m, 3H); 2.17 (s, 3H); 2.56 (s, 3H); 2.60 (s, 1H); 2.77–2.93 (m, 2H); 3.26 (s, 3H); 3.70–3.76 (d, 1H); 3.83–3.90 (d, 1H); 3.97–4.06 (dd, 1H); 4.24–4.32 (d, 1H); 4.36–4.44 (d, 1H); 4.44–4.54 (d+s, 2H); 4.65–4.73 (d+s, 2H); 4.86–4.94 (dd, 1H); 5.19–5.26 (d, 1H); 5.44–5.51 (dd, 1H); 5.51–5.56 (d, 1H); 5.76 (s, 1H); 7.27–7.43 (m, 5H); 7.44–7.55 (t, 2H); 7.55–7.63 (t, 1H); 8.07–8.14 (d, 2H).

EXAMPLE 68
Preparation of 7-(O-ethoxymethyl)-13-(N-Cbz-2'-TES-β-phenyl isoserinyl)-$\Delta^{12,13}$-iso-baccatin III (68)

Following the procedure of Example 42 but using as starting material 13-(N-Cbz-2'-TES-β-phenyl isoserinyl)-$\Delta^{12,13}$-iso-baccatin III (53) in place of 13-(N-Boc-2'-TES-β-phenyl isoserinyl)-$\Delta^{12,13}$-iso-baccatin III (46) is prepared 7-(O-ethoxymethyl)-13-(N-Cbz-2'-TES-β-phenyl isoserinyl)-$\Delta^{12,13}$-iso-baccatin III (68)

EXAMPLE 69
Preparation of 7-(O-ethoxymethyl)-13-(N-Cbz-β-phenyl isoserinyl)-$\Delta^{12,13}$-iso-baccatin III (69)

Following the procedure of Example 43 but using as starting material 7-(O-ethoxymethyl)-13-(N-Cbz-2'-TES-β-phenyl isoserinyl)-$\Delta^{12,13}$-iso-baccatin III (68) in place of 7-(O-ethoxymethyl)-13-(N-Boc-2'-TES-β-phenyl isoserinyl)-$\Delta^{12,13}$-iso-baccatin III (47) is prepared 7-(O-ethoxymethyl)-13-(N-Cbz-β-phenyl isoserinyl)-$\Delta^{12,13}$-iso-baccatin III (69).

EXAMPLE 70
Preparation of 7-(O-ethoxymethyl)-13-(β-phenyl isoserinyl)-$\Delta^{12,13}$-iso-baccatin III (70)

7-(O-Ethoxymethyl)-13-(N-Cbz-β-phenyl isoserinyl)-$\Delta^{12,13}$-iso-baccatin III (69, 99 mg, 0.105 mM) is stirred at RT under nitrogen in methanol (2 mL) and dry THF (1 mL). To this solution is added ammonium formate (50 mg) and 10% Pd/C (30 mg). The mixture is allowed to react at RT for 10 minutes and then cooled in ice bath, following the reaction by HPLC. After a total of 35 minutes reaction time, the catalyst is filtered off. The reaction mixture is diluted with ethyl acetate, washed with 5% sodium bicarbonate, dried over sodium sulfate and evaporated under vacuum. The residue is reevaporated twice with ethyl acetate-toluene leaving 7-(O-ethoxymethyl)-13-(β-phenyl isoserinyl)-$\Delta^{12,13}$-iso-baccatin III (70).

HPLC: Versapack C$_{18}$; 229 nm; 1 ml/min.; (25-75-0.2) water-acetonitrile-TFA; retention time: 3.80 minutes.

Proton NMR (CDCl$_3$; TMS): δ1.07–1.18 (t+s, 6H); 1.26 (s, 3H); 1.63 (s, 3H); 1.66 (s, 3H); 1.34–2.00 (m, 1H); 2.00–2.15 (d, 1H); 2.17 (s, 3H); 2.22 (s, 3H); 2.80–2.94 (m, 1H); 3.26–3.40 (m, 1H); 3.59–3.70 (m, 1H); 3.79–3.86 (d, 1H); 3.94–4.07 (dd 1H); 4.22–4.44 (m, 3H); 4.56–4.64 (d, 1H); 4.64–4.74 (d, 1H); 4.83–4.94 (d, 1H); 5.44–5.54 (d, 1H); 5.74 (s, 1H); 7.23–7.47 (m, 5H); 7.47–7.59 (t, 2H); 7.59–7.70 (t, 1H); 8.00–8.10 (d, 2H).

EXAMPLE 71
Preparation of 7-(O-ethoxymethyl)-13-(N-Boc-β-phenyl isoserinyl)-$\Delta^{12,13}$-iso-baccatin III (41)

7-(O-Ethoxymethyl)-13-(β-phenyl isoserinyl)-$\Delta^{12,13}$-iso-baccatin III (70, 0.531 mM) is stirred at RT under nitrogen in dry THF (3 mL) and the solution treated with di-tert-butyl dicarbonate (116 mg) in dry THF (1 mL), followed by triethylamine (0.076 mL). The reaction is followed by HPLC and after 2 hours additional di-t-butyl dicarbonate (15 mg) is added. After 4.5 hours reaction time, methanol (0.05 mL) is added. The solvent is evaporated under vacuum and the residue twice reevaporated with methylene chloride-hexane. The crude product is purified by HPLC over a size B E. Merck prepacked silica gel column, eluting with (30-70) acetone-hexane. Fractions of 15 mL are collected, analyzing them by TLC. Fractions 18–22 are found to contained pure product and were combined and evaporated under vacuum to give 7-(O-ethoxymethyl)-13-(N-Boc-β-phenyl isoserinyl)-$\Delta^{12,13}$-iso-baccatin III (41, 82%) as a white solid.

TLC: silica gel; 30-70 acetone-hexane; Rf: 0.33
Proton NMR (CDCl$_3$; TMS): δ1.09–1.17 (t, 3H); 1.24 (s, 9H); 1.27 (s, 3H); 1.62 (s, 3H); 1.68 (s, 3H); 1.90–2.02 (t, 1H); 2.02–2.14 (d, 1H); 2.17 (s, 3H); 2.18 (s, 3H); 2.57 (s, 3H); 2.62 (s, 1H); 2.80–2.98 (m, 2H); 3.30–3.40 (m, 1H); 3.62–3.73 (m, 1H); 3.84–3.90 (d, 1H); 4.00–4.10 (dd, 1H); 4.26–4.34 (d, 1H); 4.38–4.45 (d, 1H); 4.57–4.64 (d, 1H); 4.65–4.74 (m 2H); 4.87–4.95 (d, 1H); 5.35–5.49 (m, 2H); 5.50–5.57 (d, 1H); 5.77 (s, 1H); 7.30–7.44 (m, 5H); 7.44–7.53 (t, 2H); 7.55–7.64 (t, 1H); 8.07–8.18 (d, 2H).

EXAMPLE 72
Preparation of 7-(O-ethoxymethyl)-13-(N-t-butylaminocarbonyl-β-phenyl isoserinyl)-$\Delta^{12,13}$-iso-baccatin III (43)

7-(O-Ethoxymethyl)-13-(β-phenyl isoserinyl)-$\Delta^{12,13}$-iso-baccatin III (70, 0.105 mM) is stirred at 0° C. under nitrogen in dry THF (1 mL) and the solution treated with t-butylisocyanate (20 μL). After 5 minutes the reaction is left to warm to RT. The reaction is followed by HPLC and allowed to proceed for 50 min. The solvent is then evaporated under vacuum and the residue purified by silica gel chromatography, eluting with (30-70) acetone-hexane. Fractions of 7 mL are collected, analyzing them by TLC. Fractions 50–67 are found to contain pure product and are combined and evaporated under vacuum to give 7-(O-ethoxymethyl)-13-(N-t-butylaminocarbonyl-β-phenyl isoserinyl)-$\Delta^{12,13}$-iso-baccatin III (43, 74%) as a white solid.

TLC: silica gel; (30-70) acetone-hexane; Rf: 0.22
Proton NMR (CDCl$_3$; TMS): δ1.04–1.18 (m, 15H); 1.23 (s, 3H); 1.57 (s, 3H); 1.67 (s, 3H); 1.86–2.00 (t, 1H); 2.00–2.13 (d, 1H); 2.15 (s, 3H); 2.53 (s, 3H); 2.58 (s, 1H); 2.73–2.93 (m, 2H); 3.26–3.39 (m, 1H); 3.58–3.70 (m, 1H); 3.82–3.89 (d, 1H); 3.96–4.05 (dd, 1H); 4.21–4.30 (d, 1H); 4.34–4.43 (d, 1H); 4.55–4.64 (d, 1H); 4.64–4.73 (m, 2H); 4.84–4.94 (d, 1H); 5.37–5.53 (m, 3H); 5.74 (s, 1H); 7.25–7.40 (m, 5H); 7.43–7.53 (t, 2H); 7.54–7.63 (t, 1H); 8.04–8.12 (d, 2H).

EXAMPLE 73
Preparation of 7-(O-methylthiomethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b)

$\Delta^{12,13}$-Iso-baccatin III-13-(4S,5R)-N-(t-butylaminocarbonyl)-2-(2,4-dimethoxyphenyl)-4-phenyl-5-oxazolidinecarboxylic acid ester (33a,b, 100 mg, 0.10 mM) is stirred at 0° C. under nitrogen in acetonitrile (1 mL). To this solution is added dimethyl sulfide (0.060 mL) by syringe and then four times benzoyl peroxide (25 mg each) 5 min apart. By 30 min everything dissolves and after 2 hours the reaction is complete by TLC.

The reaction is partitioned between ethyl acetate-5% sodium bicarbonate. After separation of the aqueous phase the organic layer is dried over sodium sulfate and evaporated under vacuum. The residue is chromatographed over silica gel (10 g), eluting with (40-60) and (50-50) ethyl acetate-hexane. Fractions of 4 mL are collected, analyzing them by TLC. Fractions 19–40 are found to contained pure product and are combined and evaporated under vacuum to give 7-(O-methylthiomethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b, 72 mg, 68% yield) product as a white solid.

TLC: silica gel; (50-50) ethyl acetate-hexane; $R_f$: 0.47.

Proton NMR (CDCL$_3$; TMS): δ1.06 (s, 3H); 1.10 (s, 9H); 1.22 (s. 3H); 1.61 (s, 3H); 1.69 (s, 3H); 2.03 (s, 3H); 2.08 (s, 3H); 2.12 (s, 3H); 3.74 (s, 3H); 3.78–3.85 (s, 3H+m, 1H); 4.00–4.13 (dd, 1H); 4.13–4.24 (d, 1H); 4.26–4.36 (d, 1H); (d, 1H); 4.42–4.52 (d, 1H); 4.52–4.61 (d, 1H); 4.62 (s, 1H); 4.78–4.86 (d, 1H); 4.99 (s, 1H); 5.42–5.50 (d, 1H); 5.56–5.63 (d, 1H); 5.81 (s, 1H); 6.33–6.42 (d, 1H); 6.44 (s, 1H); 6.68 (s, 1H); 7.03–7.13 (d, 1H); 7.23–7.49 (m, 6H); 7.49–7.58 (t, 1H); 7.93–8.03 (d, 2H).

EXAMPLE 74

Preparation of 7-(O-methylthiomethyl)-13-(N-t-butylaminocarbonyl-β-phenyl isoserinyl)-$\Delta^{12,13}$-iso-baccatin III (72)

7-(O-Methylthiomethyl)-$\Delta^{12,13}$-iso-baccatin III-13-(4S, 5R)-N-(t-butylaminocarbonyl)-2-(2,4-dimethoxyphenyl)-4-phenyl-5-oxazolidinecarboxylic acid ester (71a,b, 72 mg, 0.068 mM) is stirred at RT under nitrogen in (80-20) acetic acid-water (5 mL). TLC after 5 hours shows the reaction to be complete. The reaction is then freeze-dried. The residue is chromatographed over silica gel (13 g), eluting with (50-50) ethyl acetate-hexane. Fractions of 4 mL are collected, analyzing them by TLC. Fractions 11–24 are found to contained 7-(O-methylthiomethyl)-13-(N-t-butylaminocarbonyl-β-phenyl isoserinyl)-$\Delta^{12,13}$-iso-baccatin III (72, 57 mg, 92%) as a white solid.

TLC: silica gel; 50-50 ethyl acetate-hexane; $R_f$: 0.39.

Proton NMR (CDCL$_3$; TMS): δ1.03 (s, 3H); 1.06 (s, 9H); 1.17 (s, 3H); 1.56 (s, 3H); 1.60 (s, 3H); 1.73–1.87 (t, 1H); 2.02 (s, 3H); 2.09 (s, 3H); 2.48 (s, 3H); 3.77–3.85 (d, 1H); 4.00–4.10 (dd, 1H); 4.16–4.24 (d, 1H); 4.29–4.36 (d, 1H); 4.41–4.49 (d, 1H); 4.49–4.56 (d, 1H); 4.57 (s, 1H); 4.61 (s, 1H); 4.80–4.88 (d, 1H); 5.31–5.41 (s+t, 2H); 5.41–5.48 (d, 1H); 5.80 (s, 1H); 7.20–7.34 (m, 5H); 7.37–7.47 (t, 2H); 7.47–7.56 (t, 1H); 7.99–8.06 (d, 2H).

Mass Spec (FAB, m/z) (M+H)$^+$ measured at 909.3840; theory for C$_{47}$H$_{61}$O$_{14}$N$_2$S$_1$ is 909.3843; 861, 847, 831, 263, 235, 205, 136, 119, 105, 61, 57.

EXAMPLE 75

Preparation of 7-(O-methyl)-13-(N-t-butylaminocarbonyl-β-phenyl isoserinyl)-$\Delta^{12,13}$-iso-baccatin III (73)

Raney Nickel (8 mL), prewashed with 5% sodium bicarbonate, water, and ethanol is stirred at 0° C. under nitrogen. To this is added by syringe 7-(O-methylthiomethyl)-13-(N-t-butylaminocarbonyl-β-phenyl isoserinyl)-$\Delta^{12,13}$-iso-baccatin III (72, 100 mg, 0.11 mM) in absolute ethanol (10 mL). The temperature is kept at 0° C. throughout the reaction and the subsequent washing process described below. The reaction is followed by TLC and allowed to proceed for 4 hr, when it judged to be complete. The Raney Nickel is then allowed to settle and the upper layer of liquid removed by suction. The residual Raney nickel is treated with THF (40 mL) and the mixture stirred for 2 minutes. After the nickel has settled the liquid is removed as above. This washing process is repeated 9 times. All the washings are combined and evaporated under vacuum, leaving 65 mg solid. The residue is chromatographed over silica gel (10 g), eluting with ethyl acetate-hexane (50-50, 100 mL) and (60-40, 200 mL). Fractions of 3 mL are collected, analyzing them by TLC. Fractions 13–18 are found to contain recovered starting material, fractions 19–28 contain 7-(O-methyl)-13-(N-t-butylaminocarbonyl-β-phenyl isoserinyl)-$\Delta^{12,13}$-iso-baccatin III (73, 43 mg, 43%) as a white solid.

TLC: silica gel; (50-50) ethyl acetate-hexane; $R_f$: 0.33.

Proton NMR (CDCL$_3$; TMS): δ1.03 (s, 3H); 1.06 (s, 9H); 1.17 (s, 3H); 1.52 (s, 3H); 1.56 (s, 3H); 1.90–2.05 (d, 2H); 2.10 (s, 3H); 2.48 (s, 3H); 2.56–2.68 (m, 1H);2.68–2.83 (d, 2H); 3.13 (s, 3H); 3.69–3.82 (m, 2H); 4.14–4.24 (d, 1H); 4.27–4.36 (d, 1H); 4.55 (s, 1H); 4.61 (s, 1H); 4.80–4.91 (d, 1H); 5.25–5.43 (t, 2H); 5.43–5.49 (d, 1H); 5.76 (s, 1H); 7.16–7.35 (m, 5H); 7.35–7.46 (t, 2H); 7.46–7.57 (t, 1H); 7.96–8.07 (d, 2H).

Mass Spec (FAB, m/z) (M+H)$^+$ measured at 863.3981; theory for C$_{46}$H$_{59}$O$_{14}$N$_2$ is 863.3966; 563, 263, 235, 205, 179, 136, 119, 106, 105, 58, 57, 43.

EXAMPLE 76

Preparation of $\Delta^{12,13}$-iso-baccatin III-13-(4S,5R)-N-Cbz-2-(2,4-dimethoxyphenyl)-4-phenyl-5-oxazolidinecarboxylic acid ester (74a,b)

7-TES-$\Delta^{12,13}$-iso-baccatin III-13-(4S,5R)-N-Cbz-2-(2,4-dimethoxyphenyl)-4-phenyl-5-oxazolidinecarboxylic acid ester (51a,b, 215 mg, 0.188 mM) is stirred at RT under nitrogen in acetonitrile (0.75 mL) and 98% triethylamine trihydrofluoride (0.25 mL). The reaction is followed by TLC and is found to be complete after 7.5 hours. The reaction mixture is then diluted with ethyl acetate and washed with 5% sodium bicarbonate, 5% sodium bisulfate and brine. The organic layer is dried over sodium sulfate and evaporated under vacuum. The crude product is chromatographed over silica gel (20 g), eluting with (40-60) acetone-hexane. Fractions of 7 mL are collected, analyzing them by TLC. Fractions 13–22 are combined and evaporated under vacuum to give $\Delta^{12,13}$-iso-baccatin III-13-(4S,5R)-N-Cbz-2-(2,4-dimethoxyphenyl)-4-phenyl-5-oxazolidinecarboxylic acid ester (74a,b, 182 mg, 94% yield) as a white solid.

TLC: silica gel; (40-60) ethyl acetate-hexane; Rf: 0.23

Proton NMR (CDCl$_3$; TMS): δ1.16 (s, 12H); 1.28 (s, 3H); 1.66 (s, 3H); 1.90 (s, 3H); 1.98 (s, 3H); 2.26 (s, 3H); 2.43–2.55 (m, 2H); 3.73–3.81 (d, 1H); 3.84 (s, 3H); 3.91 (s, 3H); 4.11–4.16 (d, 1H); 4.21–4.27 (d, 1H); 4.36–4.47 (m, 1H); 4.50 (s 1H); 4.82–4.92 (bd, 1H); 4.92–4.96 (d, 1H); 5.50–5.55 (d, 1H); 5.61–5.68 (d, 1H); 6.25–6.37 (m, 2H); 6.47–6.55 (m, 2H); 6.71 (s, 1H); 7.23–7.57 (m, 8H); 7.57–7.64 (t, 1H); 8.00–8.07 (d, 2H).

EXAMPLE 77

Preparation of 7-(O-methoxymethyl)-$\Delta^{12,13}$-iso-baccatin III-13-(4S,5R)-N-Cbz-2-(2,4-dimethoxyphenyl)-4-phenyl-5-oxazolidinecarboxylic acid ester (75a,b)

$\Delta^{12,13}$-Iso-baccatin III-13-(4S,5R)-N-Cbz-2-(2,4-dimethoxyphenyl)-4-phenyl-5-oxazolidinecarboxylic acid ester (74a,b, 215 mg, 0.208 mM) is stirred at RT under nitrogen in methylene chloride (1 mL) and the solution treated with chloromethyl methyl ether (97 μL, 1.25 mM) and diisopropyl ethyl amine (225 μL,1.25 mM). The reaction is followed by TLC. After 21 hours the reaction is found to be incomplete. Thus, additional chloromethyl methyl ether (48 μL, 0.62 mM) and diisopropyl ethyl amine (112 μL,0.62 mM) are added and the reaction continued for 24 hours, when it is found to be complete. The reaction is then diluted with methylene chloride and washed with 5% sodium bisulfate and 5% sodium bicarbonate, dried over sodium sulfate and evaporated under vacuum. The residue is chromatographed over silica gel (20 g), eluting with (40-60) acetone-hexane. Fractions of 5 mL are collected, analyzing them by TLC. Fractions 17–26 are combined and evaporated under vacuum to give 7-(O-methoxymethyl)-$\Delta^{12,13}$-iso-baccatin III-13-(4S,5R)-N-Cbz-2-(2,4-dimethoxyphenyl)-4-phenyl-5-oxazolidinecarboxylic acid ester (75a,b, 224 mg, 100% yield) as a white solid.

TLC: silica gel; (40-60) acetone-hexane; Rf: 0.44

Proton NMR (CDCl$_3$; TMS): δ1.06 (s, 3H); 1.21 (s, 3H); 1.26 (s, 3H); 1.64 (s, 3H); 2.11 (s, 3H); 2.16 (s, 3H); 2.44–2.69 (s+d, 2H); 2.70–2.88 (m, 1H); 3.23 (s, 3H); 3.57–4.04 (m, 2H); 3.80 (s, 6H); 4.14–4.28 (d, 1H); 4.28–4.38 (d, 1H); 4.43–4.54 (d, 1H); 4.55–4.84 (m, 4H); 4.84–4.96 (d, 1H); 5.34–5.44 (d, 1H); 5.44–5.53 (d, 1H); 5.67 (s, 1H); 6.30–6.58 (bd, 1H); 6.74 (bs, 3H); 7.04–7.29 (m, 4H); 7.29–7.54 (m, 7H); 7.54–7.65 (t, 1H); 7.93–8.06 (d, 2H).

EXAMPLE 78

Preparation of 7-(O-methoxymethyl)-13-(N-Cbz-β-phenyl isoserinyl)-$\Delta^{12,13}$-iso-baccatin III (64)

7-(O-Methoxymethyl)-$\Delta^{12,13}$-iso-baccatin III-13-(4S,5R)-N-Cbz-2-(2,4-dimethoxyphenyl)-4-phenyl-5-oxazolidinecarboxylic acid ester (75a,b, 224 mg, 0.208 mM) is stirred at RT under nitrogen in (80-20) acetic acid-water (9 mL). The reaction is followed by TLC and is found to be complete in 4.5 hours. The reaction is then freeze-dried. The residue is purified by chromatography over a silica gel column (25 g), eluting with a gradient of (40-60) to (60-40) ethyl acetate-hexane. Fractions of 7 mL are collected, analyzing them by TLC. The product is found in fractions 38–60 which are combined and evaporated under vacuum to give 7-(O-methoxymethyl)-13-(N-Cbz-β-phenyl isoserinyl)-$\Delta^{12,13}$-iso-baccatin III (64,180 mg, 93% yield) as a white solid.

TLC: silica gel; (40-60) ethyl acetate-hexane; Rf: 0.19

Proton NMR (CDCl$_3$; TMS): δ1.08 (s, 3H); 1.21 (s, 3H); 1.59 (s, 3H); 1.68 (s, 3H); 1.82–2.03 (m, 2H); 2.12 (s, 3H); 2.16 (s, 3H); 2.74–2.94 (m, 2H); 3.23 (s, 3H); 3.66 (bs, 1H); 3.77–3.86 (d, 1H); 3.96–4.10 (dd 1H); 4.23–4.35 (d, 1H); 4.35–4.42(d, 1H); 4.44–4.52 (d, 1H); 4.60–4.94 (m, 5H); 5.40–5.56 (m, 2H); 5.75 (s, 1H); 5.94–6.05 (d, 1H); 6.94–7.04 (m, 2H); 7.10–7.23 (m, 3H); 7.25–7.42 (m, 9H); 7.42–7.53 (t, 2H); 7.53–7.62 (t, 1H); 8.08–8.20 (d, 2H).

Mass Spec (FAB, m/z) (M+H)$^+$ measured at 928.3743; theory for C$_{51}$H$_{57}$N$_1$O$_{16}$ is 928.3755; 928, 896, 866, 105, 91, 43.

EXAMPLE 79

Preparation of 7-(O-ethoxymethyl)-13-(N-Cbz-β-phenyl isoserinyl)-$\Delta^{12,13}$-iso-baccatin III (69)

$\Delta^{12,13}$-Iso-baccatin III-13-(4S,5R)-N-Cbz-2-(2,4-dimethoxyphenyl)-4-phenyl-5-oxazolidinecarboxylic acid ester (74a,b, 1.9 g, 1.84 mM) is dissolved in CH$_2$Cl$_2$ (15 mL) and the solution treated with chloromethylethyl ether (850 μL, 9.2 mM) and diisopropylethyl amine (2 mL, 11 mM). After stirring overnight TLC indicates reaction about 40% complete. Additional chloromethylethyl ether (850 mL, 9.2 mM) and diisopropylethyl amine (2 mL, 11 mM) are 2 times at 24 hour intervals after which the reaction is allowed to stir for two additional days. At this time TLC indicates no starting material left so the reaction is partitioned between EtOAc and 1N HCl. The organic layer is reextracted with 5% NaHCO$_3$ and then brine. The organic layer is filtered through Na$_2$SO$_4$ and concentrated in vacuo. To the residue is added (80-20) acetic acid water (100 mL). After 4 hr TLC shows that no starting material remains and the reaction mixture is lyophilized. The residue is chromatographed over silica gel (200 g) packed in (1-2) ethyl acetate hexane and the product added using CH$_2$Cl$_2$. The column was eluted with 1.5 L (2-3) ethyl acetate hexane (2-3,1.5 L; 1-1, 1 L; and 2-1, 500 mL), collecting 50 mL fractions. 7-(O-ethoxymethyl)-13-(N-Cbz-β-phenyl isoserinyl)-$\Delta^{12,13}$-iso-baccatin III (69, 1.45 g, 82% yield) was found in fractions 34–51.

MS: Theory 942.3912 Found 942.3901

Proton NMR (CDCl$_3$; TMS): δ1.13 (m); 1.27 (m); 1.60 (s); 1.68 (s, 3H); 1.94 (m, 2H); 2.17 (s); 2.91 (m, 2H); 3.19 (d, 1H); 3.35 (m, 1H); 3.68 (m, 1H); 3.83 (d, 1H); 4.06 (m, 1H); 4.32 (d, 1H); 4.41 (d, 1H); 4.59 (d, 1H); 4.69 (d, 1H); 4.75 (m, 1H); 4.89 (m, 3H); 5.52 (m, 2H); 5.69 (d, 1H); 5.76 (s, 1H); 7.02 (m, 2H); 7.20 (m, 3H); 7.41–7.61 (m, 9H); 8.15 (d, 1H).

EXAMPLE 80

Preparation of 13-(2'-TES-β-phenyl isoserinyl)-$\Delta^{12,13}$-iso-baccatin III (76)

13-(N-Cbz-2'-TES-β-phenyl isoserinyl)-$\Delta^{12,13}$-iso-baccatin III (53, 100 mg, 0.1 mM) is stirred at RT under nitrogen in dry THF (1 mL) and methanol (1 mL) and the solution treated with ammonium formate (45 mg) and 10% Pd/C (25 mg). After 10 minutes the reaction is cooled in an ice bath and allowed to proceed for 60 min when TLC shows it to be complete. The reaction is then filtered through Celite, washing with ethyl acetate. The combined filtrate and wash are washed with 5% sodium bicarbonate, dried over sodium sulfate and evaporated under vacuum. The residue is reevaporated twice with toluene and once with ethyl acetate-hexane to give 13-(2'-TES-β-phenyl isoserinyl)-$\Delta^{12,13}$-iso-baccatin III (76, 88 mg, 100%) as a white solid.

TLC: silica gel; (50-50) ethyl acetate-hexane; R$_f$: 0.67.

Proton NMR (CDCL$_3$; TMS): δ0.40–0.58 (m, 6H); 0.76–0.90 (t, 9H); 0.94 (s, 3H); 1.17 (s, 3H); 1.45 (s, 3H); 1.51 (s, 3H); 2.13 (s, 3H); 2.70 (s, 3H); 3.53–3.63 (d, 1H); 4.13–4.35 (m, 4H); 4.76–4.87 (dd, 1H); 5.37 (s, 1H); 5.40–5.48 (d, 1H); 7.06–7.37 (m, 5H); 7.38–7.50 (t, 2H); 7.50–7.63 (t, 1H); 7.90–8.02 (d, 2H).

EXAMPLE 81

Preparation of 13-(N-t-butylaminocarbonyl-2'-TES-β-phenyl isoserinyl)-$\Delta^{12,13}$ -iso-baccatin III (77)

13-(2'-TES-β-phenyl isoserinyl)-$\Delta^{12,13}$-iso-baccatin III (76, 88 mg, 0.1 mM) is stirred at 0° C. under nitrogen in dry THF (1 mL). To this solution is added by syringe t-butyl isocyanate (0.02 mL). After 5 minutes, the reaction is warmed to RT, following it by TLC. After 1 hour the reaction is again cooled in ice bath and treated with t-butyl isocyanate (0.02 mL). The reaction is then warmed to RT and allowed to proceed overnight after which it is complete. The reaction is then evaporated under vacuum and the residue chromatographed over silica gel (10 g). The column is eluted with ethyl acetate-hexane (30-70, 200 mL) and (40-60, 100 mL). Fractions of 3 mL are collected, analyzing them by TLC. Fractions 22–72 are found to contained pure product and are combined and evaporated under vacuum to give 13-(N-t-butylaminocarbonyl-2'-TES-β-phenyl isoserinyl)-$\Delta^{12,13}$-iso-baccatin III (77, 87 mg, 92%) as a white solid.

TLC: silica gel; (40-60) ethyl acetate-hexane; $R_f$: 0.81.

Proton NMR (CDCL$_3$; TMS): δ0.17–0.44 (m, 6H); 0.64–0.80 (t, 9H); 1.03 (s, 3H); 1.06 (s. 9H); 1.28 (s, 3H); 1.60 (s, 3H); 1.61 (s, 3H); 1.77 (s, 1H); 1.84–1.99 (t, 1H); 2.00–2.15 (d, 1H); 2.19 (s, 3H); 2.40–2.57 (m, 1H); 2.65 (s, 3H); 2.76 (s, 1H); 2.82–2.96 (d, 1H); 3.52–3.59 (d, 1H); 3.67–3.76 (d, 1H); 4.26–4.43 (m, 3H); 4.46 (s, 1H); 4.59 (s, 1H); 4.89–4.99 (d, 1H); 5.15–5.25 (d, 1H); 5.47 (s, 1H); 5.47–5.60 (m, 2H); 7.18–7.38 (m, 5H); 7.40–7.50 (t, 2H); 7.50–7.58 (t, 1H); 8.04–8.14 (d, 2H).

EXAMPLE 82

Preparation of 7-(O-methylthiomethyl)-13-(N-t-butylaminocarbonyl-2'-TES-β-phenyl isoserinyl)-$\Delta^{12,13}$-iso-baccatin III (78)

13-(N-t-Butylaminocarbonyl-2'-TES-β-phenyl isoserinyl)-$\Delta^{12,13}$-iso-baccatin III (77, 87 mg, 0.091 mM) is stirred at 0° C. under nitrogen in acetonitrile (1 mL). To this solution is added dimethyl sulfide (0.055 mL) by syringe followed by four additions of benzoyl peroxide (25 mg each portion) at 5 min intervals. After 4 hours the reaction is found to be complete by TLC. The reaction is then partitioned between ethyl acetate-5% sodium bicarbonate. The organic layer is dried over sodium sulfate and evaporated under vacuum. The residue is chromatographed over silica gel (10 g), eluting with ethyl acetate-hexane (30-70). Fractions of 4 mL are collected, analyzing them by TLC. Fractions 9–21 contain pure product and are combined and evaporated under vacuum to give 7-(O-methylthiomethyl)-13-(N-t-butylaminocarbonyl-2'-TES-β-phenyl isoserinyl)-$\Delta^{12,13}$-iso-baccatin III (78, 73 mg, 78%) as a white solid.

TLC: silica gel; (30-70) ethyl acetate-hexane; $R_f$: 0.47.

Proton NMR (CDCL$_3$; TMS): δ0.12–0.37 (m, 6H); 0.61–0.74 (t, 9H); 1.04 (s, 9H); 1.05 (s. 3H); 1.21 (s, 3H); 1.63 (s, 3H); 1.64 (s, 3H); 1.78–1.92 (t, 1H); 2.03 (s, 3H); 2.11 (s, 3H); 2.57 (s, 3H); 2.61 (s, 3H); 2.75–2.92 (m, 2H); 3.83–3.90 (d, 1H); 4.04–4.14 (dd, 1H); 4.21–4.29 (d, 1H); 4.31–4.39 (d, 1H); 4.42–4.60 (m, 4H); 4.85–4.93 (d, 1H); 5.14–5.22 (d, 1H); 5.44–5.52 (m, 2H); 5.84 (s, 1H); 7.15–7.35 (m, 5H); 7.35–7.45 (t, 2H); 7.45–7.55 (t, 1H); 8.00–8.08 (d, 2H).

EXAMPLE 83

Preparation of 7-(O-methylthiomethyl)-13-(N-t-butylaminocarbonyl-β-phenyl isoserinyl)-$\Delta^{12,13}$-iso-baccatin III (72)

7-(O-Methylthiomethyl)-13-(N-t-butylaminocarbonyl-2'-TES-β-phenyl isoserinyl)-$\Delta^{12,13}$-iso-baccatin III (78, 73 mg, 0.071 mM) is stirred at RT under nitrogen in (80-20) acetic acid-water (7 mL). TLC after 1 hour shows the reaction to be complete after which the reaction is freeze-dried. The residue is chromatographed over silica gel (10 g), eluting with (50-50) ethyl acetate-hexane. Fractions of 4 mL are collected, analyzing them by TLC. Fractions 12–30 are found to contain the pure product which upon evaporating leave 7-(O-methylthiomethyl)-13-(N-t-butylaminocarbonyl-β-phenyl isoserinyl)-$\Delta^{12,13}$-iso-baccatin III (72, 50 mg, 77%) as a white solid.

TLC: silica gel; (50-50) ethyl acetate-hexane; $R_f$: 0.24.

Proton NMR (CDCL$_3$; TMS): δ1.03 (s, 3H); 1.06 (s, 9H); 1.17 (s, 3H); 1.56 (s, 3H); 1.60 (s, 3H); 1.73–1.87 (t, 1H); 2.02 (s, 3H); 2.09 (s, 3H); 2.48 (s, 3H); 2.52 (s, 1H); 2.69–2.86 (m, 2H); 3.76–3.84 (d, 1H); 4.00–4.10 (dd, 1H); 4.14–4.24 (d, 1H); 4.28–4.36 (d, 1H); 4.40–4.65 (m, 4H); 4.80–4.90 (d, 1H); 5.24–5.33 (d, 1H); 5.33–5.42 (m, 1H); 5.42–5.47 (d, 1H); 5.80 (s, 1H); 7.16–7.35 (m, 5H); 7.37–7.47 (t, 2H); 7.47–7.56 (t, 1H); 7.99–8.06 (d, 2H).

EXAMPLE 84

PART A: Preparation of 2-(3-methylbutyl)dimethylsilyl-10-desacetylbaccatin III (80a)

A solution of 1.04 g of 10-DAB in 3 mL of pyridine at room temperature is treated with 1.03 g of 2-(3-methylbutyl) dimethylsilylchloride (PDMSCl). The reaction mixture is stirred at room temperature for 7 hours at which point HPLC showed the reaction to be 99% complete. The mixture is poured into water and the product isolated with ethyl acetate. The ethyl acetate solution is dried over MgSO$_4$ and concentrated to afford 1.34 g of a foam after vacuum drying.

PART B: Preparation of 2-(3-methylbutyl)dimethylsilyl-Baccatin III (81a)

The crude material from Part A is dissolved in 8 mL of pyridine and cooled to 0° C. Acetyl chloride (0.735 mL) is then slowly added. The solution becomes a thick slurry and is stirred at 0° C. for 6.5 hours and then placed in a −20° C. freezer overnight. The next morning the reaction is quenched with methanol and the product isolated with ethyl acetate. The ethyl acetate solution is concentrated to an oil and the excess pyridine removed by azeotropic distillation with toluene. The crude product is chromatographed on silica gel with 40% ethyl acetate/cyclohexane to afford 1.14 g (84%) of 2-(3-methylbutyl)dimethylsilyl-Baccatin III.

EXAMPLE 85

Preparation of cyclohexyldimethylsilyl-10-DAB (80b)

A solution of 182 mg of 10-DAB in 2 mL of pyridine is treated with 0.3 mL of cyclohexyldimethylsilyl chloride (CDMSCl) at room temperature. The solution is stirred at room temperature for 16 hours, quenched with ethanol, then poured into water and the product isolated with ethyl acetate. The crude product is chromatographed on silica gel with 40% ethyl acetate/cyclohexane to afford 131 mg of pure silyl derivative. (Note: extended stir time results in considerable over silylation and results in reduced yield of cyclohexyldimethylsilyl-10-DAB (80b).

EXAMPLE 86

As illustrated in Examples 84 and 85, silyl protective groups can be added by means well known to persons skilled in the art. See, for example, "Protective Groups in Organic Synthesis, 2ed.", Peter G. M. Wuts, pp 74–83, Wiley, New york, 1991 which is incorporated herein by reference.

It has been reported that tributyldimethylsilyl (TBDMS) could not be introduced cleanly onto baccatin III, see footnote 13 in the Journal of the American Chemical Society (JACS), 110, 5917 (1988). Under reaction conditions tried to date, the introduction of TBDMS to baccatin III has not been successful. However, it is contemplated that TBDMS and triisopropylsilyl (TIPS) can be introduced onto baccatin III as well as iso-baccatin III under reaction conditions known in the art.

EXAMPLE 87

Preparation of 10-Deacetylbaccatin-7-O-triflate (82)

A stirred solution of 10-deacetylbaccatin (10-DAB, 10.0 g, 0.0184 mole) in CH$_2$Cl$_2$ (50 mL) and pyridine (50 mL) is cooled to −30° C. and triflic anhydride (3.85 mL, 6.42 g, 0.0229 mole) is added over a period of 20 minutes. The temperature of the solution is held below −15° C. during the addition and is kept at −20° to −25° C. for 30 min following the addition. A TLC (20% AcCN-CH$_2$Cl$_2$) at this time shows a ratio of about 1:3 product to starting material. The reaction is then stirred at 0° C. for two hours. A TLC at this time shows three spots of which the most polar and the least polar are smaller and the middle spot is major. At this point the reaction mixture may be acetylated as described in Example 88 or may be worked up as described below.

The reaction mixture is first diluted with $CH_2Cl_2$ (2.5 L) and this solution is washed successively with 1M $NaHSO_4$ (3×1 L), sat'd $NaHCO_3$ (2×1 L), and 50% sat'd NaCl (1 L). Each aqueous wash is back-extracted with $CH_2Cl_2$ (100 mL each) and the combined organic layers are dried ($Na_2SO_4$) and filtered. Since the reaction components do not move on silica gel when $CH_2Cl_2$ is used as a solvent and because the 7-O-triflate is relatively insoluble, the entire extract (3 L) is applied directly to a flash silica gel column (28 cm in 72 mm diameter column packed in $CH_2Cl_2$). The column is eluted with the following solvents: $CH_2Cl_2$ (1.5 L), 7.5% AcCN in $CH_2Cl_2$ (2 L), 10% AcCN in $CH_2Cl_2$ (2 L), 20% AcCN in $CH_2Cl_2$ (3 L), and with AcCN (2 L). Fractions (200 mL each) 20–22 contained 1.89 g (0.00233 mole, 12%) of bis-triflate. Fractions 31–37 contained 7.57 g (0.0112 mole, 61%) of 82 and fractions 42–47 contained 1.18 (12%) of recovered 10-DAB.

Spectral data for 10-deacetylbaccatin-7-O-triflate (82)
$^1$H NMR ($CDCl_3$, TMS) δ8.09 (d), 7.64, 7.49 (t), 5.65 (d), 5.46 (dd), 5.43 (s), 4.94 (m), 4.37 (d), 4.18 (d), 4.00 (s), 2.31 (s), 2.10 (s), 1.91 (s), 1.10 (s).

EXAMPLE 88
Preparation of Baccatin-III-7-O-triflate. (83=20)

To the reaction mixture at 0° C. from Example 87, acetic anhydride (43.5 mL, 47.1 g, 0.461 mole) is added. Following the addition, the reaction solution is warmed in an oil bath at 50° C. for 15 minutes after which TLC indicates about 90% conversion of the major triflation product to a new material. The reaction is cooled in an ice bath and quenched by the addition of water (50 mL) from an addition funnel over a period of 30 min while maintaining the temperature below 10° C. EtOAc (50 mL) is stirred into the mixture with no additional release of heat. This mixture is added to EtOAc (500 mL) and the resulting mixture washed with 5% $NaHSO_4$ (2×500 mL), with sat'd $NaHCO_3$ (3×500 mL), and with sat'd NaCl (500 mL). Each aqueous layer is back-extracted with the same 50 mL of EtOAc. The combined organic extracts were dried ($Na_2SO_4$), filtered, and concentrated. The crude product (14.5 g) is dissolved in $CH_2Cl_2$ (150 mL plus two 50 mL rinses) and applied to a flash silica gel column (7 inches dry packed in an 80 mm diameter column). The column is eluted with $CH_2Cl_2$ (500 mL), 5% AcCN in $CH_2Cl_2$ (1 L), 7.5% AcCN in $CH_2Cl_2$ (2 L), 10% AcCN in $CH_2Cl_2$ (2 L), and AcCN (2L). Baccatin III-7-O-triflate (83) is eluted in fractions 11–19 (7.36 g, 0.0102 mole, 55% from 10-DAB); $^1$H NMR spectrum in $CDCl_3$ is identical to the spectrum described for 20 derived in Example 15 from baccatin III.

EXAMPLE 89
Preparation of 13-ketobaccatin III 7-triflate (84)

Baccatin III 7-triflate (83, 100 mg, 0.17 mM) is dissolved in methylene chloride (2 mL) and the solution treated with manganese dioxide (300 mg, 3.45 mM) and the solution stirred for 18 hr at which point TLC indicates the reaction is not yet completed. Additional manganese dioxide (100 mg, 1.15 mM) is add and the reaction stirred an additional 3 hr. The reaction is then filtered through celite and concentrated under vacuum leaving 13-ketobaccatin III 7-triflate (84, 90 mg).

Proton NMR ($CDCl_3$; TMS): δ1.21 (s, 3H); 1.28 (s, 3H); 1.86(s, 3H); 2.22 (s, 3H); 2.23 (s, 3H); 2.26 (s, 3H); 2.82 (d, J=20 Hz, 1H); 2.80–2.89 (m, 1H); 2.95 (d, J=20 Hz, 1H); 4.02 (d, J=8.6 Hz 1H); 4.11 (d, J=8.4, 1H); 4.38 (d, J=8.4 Hz, 1H); 4.91 (d, J=7.8 Hz, 1H); 5.50 (dd, 1H); 5.74 (d, J=6.6 Hz, 1H); 6.75 (s, 1H); 7.51 (t, 2H); 7.65 (t, 1H); 8.06 (d, 2H).

EXAMPLE 91
Preparation of $\Delta^{12,13}$-iso-baccatin III 7-triflate (85)

As described for the preparation of 7-TES-$\Delta^{12,13}$-isobaccatin III (3) in Example 2 but starting with 13-ketobaccatin III 7-triflate (84) is prepared $\Delta^{12,13}$-iso-baccatin III 7-triflate (85).

EXAMPLE 92
Preparation of 7-(O-trifluoromethanesulfonyl)-$\Delta^{12,13}$-isobaccatin III, 13-(4S,5R)-N-Carbobenzyloxy-2-(2,4-dimethoxyphenyl)-4-phenyl-5-oxazolidinecarboxylic Acid Ester (86a,b)

As described for the preparation of 7-TES-$\Delta^{12,13}$-isobaccatin III, 13-(4S,5R)-N-Cbz-2-(2,4-dimethoxyphenyl)-4-phenyl-5-oxazolidinecarboxylic acid ester (51a,b) in Example 47 but starting with $\Delta^{12,13}$-iso-baccatin III 7-triflate (85) is prepared 7-(O-trifluoromethanesulfonyl)-$\Delta^{12,13}$-isobaccatin III, 13-(4S, 5R)-N-Cbz-2-(2,4-dimethoxyphenyl)-4-phenyl-5-oxazolidinecarboxylic Acid Ester (86a,b).

EXAMPLE 93
Preparation of 7-(O-trifluoromethanesulfonyl)-13-(N-Cbz-β-phenyl isoserinyl)-$\Delta^{12,13}$-iso-baccatin III (87)

As described for the preparation of 13-(N-Cbz-β-phenyl isoserinyl)-$^{12,13}$-iso-baccatin III (52) in Example 48 but starting with 7-(O-trifluoromethanesulfonyl)-$\Delta^{12,13}$-isobaccatin III, 13-(4S,5R)-N-Cbz-2-(2,4-dimethoxyphenyl)-4-phenyl-5-oxazolidinecarboxylic Acid Ester (86a,b) is prepared 7-(O-trifluoromethanesulfonyl)-13-(N-Cbz-β-phenyl isoserinyl)-$\Delta^{12,13}$-iso-baccatin III (87).

EXAMPLE 94
Preparation of 7-(O-trifluoromethanesulfonyl)-13-(N-Cbz-2'-TES-β-phenyl isoserinyl)-$\Delta^{12,13}$-iso-baccatin III (54)

As described for the preparation of 13-(N-Cbz-2'-TES-β-phenyl isoserinyl)-$\Delta^{12,13}$-iso-baccatin III (53) in Example 49 is prepared 7-(O-trifluoromethanesulfonyl)-13-(N-Cbz-2'-TES-β-phenyl isoserinyl)-$\Delta^{12,13}$-iso-baccatin III (54). This material gives the same physical data on TLC and in the NMR as compound 54 prepared in example 50.

EXAMPLE 95
Preparation of 13-(N-Cbz-β-phenyl isoserinyl)-7-deoxy-7β, 8β-methano-$\Delta^{12,13}$-iso-baccatin III (88)

As described for the preparation of 13-(N-Cbz-2'-TES-β-phenyl isoserinyl)-7-deoxy-7β,8β-methano-$\Delta^{12,13}$-iso-baccatin III (55) in Example 51 but starting with 7-(O-trifluoromethanesulfonyl)-13-(N-Cbz-β-phenyl isoserinyl)-$\Delta^{12,13}$-iso-baccatin III (87) in place of 7-(O-trifluoromethanesulfonyl)-13-(N-Cbz-2'-TES-β-phenyl isoserinyl)-$\Delta^{12,13}$-iso-baccatin III (54) is prepared 13-(N-Cbz-β-phenyl isoserinyl)-7-deoxy-7β,8β-methano-$\Delta^{12,13}$-iso-baccatin III (88).

EXAMPLE 96
Preparation of 13-(β-phenyl isoserinyl)-7-deoxy-7β,8β-methano-$\Delta^{12,13}$-iso-baccatin III (89)

As described for the preparation of 13-(2'-TES-β-phenyl isoserinyl)-7-deoxy-7β,8β-methano-$\Delta^{12,13}$-iso-baccatin III (57) in Example 52 but starting with starting with 13-(N-Cbz-β-phenyl isoserinyl)-7-deoxy-7β,8β-methano-$\Delta^{12,13}$-iso-baccatin III (88) in place of 13-(N-Cbz-2'-TES-β-phenyl isoserinyl)-7-deoxy-7β,8β-methano-$\Delta^{12,13}$-iso-baccatin III (55) is prepared 13-(β-phenyl isoserinyl)-7-deoxy-7β,8β-methano-$\Delta^{12,13}$-iso-baccatin III (89).

EXAMPLE 97
Preparation of 13-(N-Boc-β-phenyl isoserinyl)-7-deoxy-7β,8β-methano-$\Delta^{12,13}$-iso-baccatin III (17)

As described for the preparation of 13-(N-Boc-2'-TES-β-phenyl isoserinyl)-7-deoxy-7β,8β-methano-$\Delta^{12,13}$-iso-baccatin III (58) in Example 53 but starting with 13-(β-phenyl isoserinyl)-7-deoxy-7β,8β-methano-$\Delta^{12,13}$-iso-baccatin III (89) in place of 13-(2'-TES-β-phenyl isoserinyl)-7-deoxy-7β,8β-methano-$\Delta^{12,13}$-iso-baccatin III (57) is prepared 13-(N-Boc-β-phenyl isoserinyl)-7-deoxy-7β,8β-methano-$\Delta^{12,13}$-iso-baccatin III (17).

EXAMPLE 98
Preparation of 13-(N-(t-butylaminocarbonyl)-β-phenyl isoserinyl)-7-deoxy-7β,8β-methano-$\Delta^{12,13}$-iso-baccatin III (36)

As described for the preparation of 13-(N-(t-butylaminocarbonyl)-2'-TES-β-phenyl isoserinyl)-7-deoxy-7β,8β-methano-$\Delta^{12,13}$-iso-baccatin III (59) in Example 55 but starting with 13-(β-phenyl isoserinyl)-7-deoxy-7β,8β-methano-$\Delta^{12,13}$-iso-baccatin III (89) in place of 13-(2'-TES-β-phenyl isoserinyl)-7-deoxy-7β,8β-methano-$\Delta^{12,13}$-iso-baccatin III (57) is prepared 13-(N-(t-butylaminocarbonyl)-β-phenyl isoserinyl)-7-deoxy-7β,8β-methano-$\Delta^{12,13}$-iso-baccatin III (36).

EXAMPLE 99
Preparation of 13-(N-Cbz-β-phenyl isoserinyl)-7-deoxy-$\Delta^{6,7},\Delta^{12,13}$-iso-baccatin III (90)

As described for the preparation of 13-(N-Cbz-2'-TES-β-phenyl isoserinyl)-7-deoxy-$^{6,7},\Delta^{12,13}$-iso-baccatin III (56) in Example 57 but starting with 7-(O-trifluoromethanesulfonyl)-13-(N-Cbz-β-phenyl isoserinyl)-$\Delta^{12,13}$-iso-baccatin III (87) in place of 7-(O-trifluoromethanesulfonyl)-13-(N-Cbz-2'-TES-β-phenyl isoserinyl)-$\Delta^{12,13}$-iso-baccatin III (54) is prepared 13-(N-Cbz-β-phenyl isoserinyl)-7-deoxy-$\Delta^{6,7},\Delta^{12,13}$-iso-baccatin III (90).

EXAMPLE 100
Preparation of 13-(β-phenyl isoserinyl)-7-deoxy-$\Delta^{6,7},\Delta^{12,13}$-iso-baccatin III (91)

As described for the preparation of 13-(2'-TES-β-phenyl isoserinyl)-7-deoxy-$\Delta^{6,7},\Delta^{12,13}$-iso-baccatin III (60) in Example 58 but starting with starting with 13-(N-Cbz-β-phenyl isoserinyl)-7-deoxy-$\Delta^{6,7},\Delta^{12,13}$-iso-baccatin III (90) in place of 13-(N-Cbz-2'-TES-β-phenyl isoserinyl)-7-deoxy-$\Delta^{6,7},\Delta^{12,13}$-iso-baccatin III (56) is prepared 13-(β-phenyl isoserinyl)-7-deoxy-$\Delta^{6,7},\Delta^{12,13}$-iso-baccatin III (91).

EXAMPLE 101
Preparation of 13-(N-Boc-β-phenyl isoserinyl)-7-deoxy-$\Delta^{6,7},\Delta^{12,13}$-iso-baccatin III (18)

As described for the preparation of 13-(N-Boc-2'-TES-β-phenyl isoserinyl)-7-deoxy-$\Delta^{6,7},\Delta^{12,13}$-iso-baccatin III (61) in Example 59 but starting with 13-(β-phenyl isoserinyl)-7-deoxy-$\Delta^{6,7},\Delta^{12,13}$-iso-baccatin III (91) in place of 13-(2'-TES-β-phenyl isoserinyl)-7-deoxy-$\Delta^{6,7},\Delta^{12,13}$-iso-baccatin III (56) is prepared 13-(N-Boc-β-phenyl isoserinyl)-7-deoxy-$\Delta^{6,7},\Delta^{12,13}$-iso-baccatin III (18).

EXAMPLE 102
Preparation of 13-(N-(t-butylaminocarbonyl)-β-phenyl isoserinyl)-7-deoxy-$\Delta^{6,7},\Delta^{12,13}$-iso-baccatin III (38)

As described for the preparation of 13-(N-(t-butylaminocarbonyl)-2'-TES-β-phenyl isoserinyl)-7-deoxy-$\Delta^{6,7},\Delta^{12,13}$-iso-baccatin III (62) in Example 61 but starting with 13-(β-phenyl isoserinyl)-7-deoxy-$\Delta^{6,7},\Delta^{12,13}$-iso-baccatin III (91) in place of 13-(2'-TES-β-phenyl isoserinyl)-7-deoxy-$\Delta^{6,7},\Delta^{12,13}$-iso-baccatin III (60) is prepared 13-(N-(t-butylaminocarbonyl)-β-phenyl isoserinyl)-7-deoxy-$\Delta^{6,7},\Delta^{12,13}$-iso-baccatin III (38).

EXAMPLE 103
Preparation of 10-deacetyl-13-keto-baccatin III (93)

Jones reagent is prepared by dissolving chromium trioxide (10.3 g, 0.103 mM) in a mixture of concentrated sulfuric acid (8.7 mL) and water (30 mL). A solution of 10-deacetylbaccatin III (92, 23 mg, 0.043 mM) in acetone (1.6 mL) is cooled to −50° C. To this is added the Jones reagent (11 μL, 0.028 mM). The reaction is stirred 20 minutes, then quenched with 2-propanol. The mixture is partitioned between ethyl acetate and 5% sodium bicarbonate solution. The organic layer is dried over anhydrous sodium sulfate and evaporated to give 25 mg of crude product. The product is purified by column chromatography on silica gel in acetone-hexane mixtures, giving 10-deacetyl-13-keto-baccatin III (93, 5.3 mg-23% yield). Starting material (12 mg, 52%) is also recovered.

TLC (Silica Gel GF): $R_f$ of product in (50-50) acetone-hexane=0.44; $R_f$ of starting material=0.31.)

Proton NMR (CDCl$_3$; TMS): δ1.19 (s, 3H); 1.24 (s, 3H); 1.47 (d, 1H); 1.75 (s, 3H); 1.85 (m, 1H); 2.10 (s, 3H); 2.20 (s, 3H); 2.60 (m, 1H); 2.68 (d, 1H); 2.97 (d, 1H); 4.02 (d, 1H); 4.15 (d, 1H); 4.26 (d, 1H); 4.30 (m, 1H); 4.35 (d, 1H); 4.95 (dd, 1H); 5.42 (d, 1H); 5.70 (d, 1H); 7.51 (m, 2H); 7.64 (m, 1H); 8.07 (d, 2H).

EXAMPLE 104
Preparation of 10-deacetyl-$\Delta^{12,13}$-iso-baccatin III (94)

As described for the preparation of 7-TES-$\Delta^{12,13}$-iso-baccatin III (3) in example 2 but starting with 10-deacetyl-13-keto-baccatin III (93) in place of 13-keto-7-TES-baccatin III (2) is prepared 10-deacetyl-$\Delta^{12,13}$-iso-baccatin III (94).

EXAMPLE 105
Preparation of 10-deacetyl-7-(O-trifluoromethanesulfonyl)-$\Delta^{12,13}$-iso-baccatin III (95)

As described for the preparation of 10-deacetyl-7-(O-trifluoromethanesulfonyl-baccatin III (82) in example 87 but starting with 10-deacetyl-$\Delta^{12,13}$-iso-baccatin III (94) in place of 10-deacetyl-baccatin III (79) is prepared 10-deacetyl-7-(O-trifluoromethanesulfonyl)-$\Delta^{12,13}$-iso-baccatin III (95).

EXAMPLE 106
Preparation of 7-(O-trifluoromethanesulfonyl)-$\Delta^{12,13}$-iso-baccatin III (85)

As described for the preparation of 7-(O-trifluoromethanesulfonyl)-baccatin III (83) in example 88 but starting with 10-deacetyl-(O-trifluoromethanesulfonyl)-$\Delta^{12,13}$-iso-baccatin III (95) in place of 10-deacetyl-7-(O-trifluoromethanesulfonyl)-baccatin III (82) is prepared 7-(O-trifluoromethanesulfonyl)-$\Delta^{12,13}$-iso-baccatin III (85)

EXAMPLE 107
Preparation of 10-deacetyl-7-(O-methoxymethyl)-baccatin III (96)

As described for the preparation of 7-(O-methoxymethyl)-$\Delta^{12,13}$-iso-baccatin III-13-(4S,5R)-N-Cbz-2-(2,4-dimethoxyphenyl)-4-phenyl-5-oxazolidinecarboxylic acid ester (75a,b,) in example 77 but starting with 10-deacetylbaccatin III (92) in place of $\Delta^{12,13}$-iso-baccatin III-13-(4S,5R)-N-Cbz-2-(2,4-dimethoxyphenyl)-4-phenyl-5-oxazolidinecarboxylic acid ester (74a,b) is prepared 10-deacetyl-7-(O-methoxymethyl)-baccatin III (96).

EXAMPLE 108
Preparation of 7-(O-methoxymethyl)-baccatin III (97)

As described for the preparation of 7-(O-trifluoromethanesulfonyl)-baccatin III (83) in example 88 but starting with 10-deacetyl-7-(O-methoxymethyl)-baccatin III (96) in place of 10-deacetyl-7-trifluoromethanesulfonyl-baccatin III (82) is prepared 7-(O-methoxymethyl)-baccatin III (97).

EXAMPLE 109
Preparation of 13-keto-7-(O-methoxymethyl)-baccatin III (98)

As described for the preparation of 13-keto-7-TES-baccatin III (2) in example 1 but starting with 7-(O-methoxymethyl)-baccatin III (97) in place of 7-TES-baccatin III (1) is prepared 13-keto-7-(O-methoxymethyl)-baccatin III (98).

EXAMPLE 110
Preparation of 7-(O-methoxymethyl)-$\Delta^{12,13}$-iso-baccatin III (99)

As described for the preparation of 7-TES-$\Delta^{12,13}$-iso-baccatin III (3) in example 2 but starting with 13-keto-7-(O-methoxymethyl)-baccatin III (98) in place of 13-keto-7-TES-baccatin III (2) is prepared 7-(O-methoxymethyl)-$\Delta^{12,13}$-iso-baccatin III (99).

EXAMPLE 111
Preparation of 7-(O-methoxymethyl)-$\Delta^{12,13}$-iso-baccatin III-13-(4S,5R)-N-Boc-2-(2,4-dimethoxyphenyl)-4-phenyl-5-oxazolidinecarboxylic acid ester (75a,b)

As described for the preparation of 7-TES-$\Delta^{12,13}$-iso-baccatin III-13-(4S,5R)-N-Boc-2-(2,4-dimethoxyphenyl)-4-phenyl-5-oxazolidinecarboxylic acid ester (5a,b) in example 3 but starting with 7-(O-methoxymethyl)-$\Delta^{12,13}$-iso-baccatin III (99) in place of 7-TES-$\Delta^{12,13}$-iso-baccatin III (3) is prepared 7-(O-methoxymethyl)-$\Delta^{12,13}$-iso-baccatin III-13-(4S,5R)-N-Boc-2-(2,4-dimethoxyphenyl)-4-phenyl-5-oxazolidinecarboxylic acid ester (75a,b).

EXAMPLE 112
Preparation of 10-deacetyl-7-(O-methylthiomethyl)-baccatin III (100)

As described for the preparation of 7-(O-methylthiomethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b) in example 73 but starting with 10-deacetyl-baccatin III (92) in place of $\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (33a,b) is prepared 10-deacetyl-7-(O-methylthiomethyl)-baccatin III (100).

EXAMPLE 113
Preparation of 7-(O-methylthiomethyl)-baccatin III (101)

As described for the preparation of 7-(O-trifluoromethanesulfonyl)-baccatin III (83) in example 88 but starting with 10-deacetyl-7-(O-methylthiomethyl)-baccatin III (100) in place of 10-deacetyl-7-trifluoromethanesulfonyl-baccatin III (82) is prepared 7-(O-methylthiomethyl)-baccatin III (101).

EXAMPLE 114
Preparation of 13-keto-7-(O-methylthiomethyl)-baccatin III (102)

As described for the preparation of 13-keto-7-TES-baccatin III (2) in example 1 but starting with 7-(O-methylthiomethyl)-baccatin III (101) in place of 7-TES-baccatin III (1) is prepared 13-keto-7-(O-methylthiomethyl)-baccatin III (102).

EXAMPLE 115
Preparation of 7-(O-methylthiomethyl)-$\Delta^{12,13}$-iso-baccatin III (103)

As described for the preparation of 7-TES-$\Delta^{12,13}$-iso-baccatin III (3) in example 2 but starting with 13-keto-7-(O-methylthiomethyl)-baccatin III (102) in place of 13-keto-7-TES-baccatin III (2) is prepared 7-(O-methylthiomethyl)-$\Delta^{12,13}$-iso-baccatin III (103).

EXAMPLE 116
Preparation of 7-(O-methylthiomethyl)-$\Delta^{12,13}$-iso-baccatin III-13-(4S,5R)-N-Cbz-2-(2,4-dimethoxyphenyl)-4-phenyl-5-oxazolidinecarboxylic acid ester (104a,b)

As described for the preparation of 7-TES-$\Delta^{12,13}$-iso-baccatin III-13-(4S,5R)-N-Cbz-2-(2,4-dimethoxyphenyl)-4-phenyl-5-oxazolidinecarboxylic acid ester (51a,b) in example 47 but starting with 7-(O-methylthiomethyl)-$\Delta^{12,13}$-iso-baccatin III (103) in place of 7-TES-$\Delta^{12,13}$-iso-baccatin III (3) is prepared 7-(O-methylthiomethyl)-$\Delta^{12,13}$-iso-baccatin III-13-(4S,5R)-N-Cbz-2-(2,4-dimethoxyphenyl)-4-phenyl-5-oxazolidinecarboxylic acid ester (104a,b).

EXAMPLE 117
Preparation of 7-(O-methylthiomethyl)-13-(N-Cbz-$\beta$-phenyl isoserinyl)-$\Delta^{12,13}$-iso-baccatin III (105)

As described for the preparation of 7-(O-methylthiomethyl)-13-(N-t-butylaminocarbonyl-$\beta$-phenyl isoserinyl)-$\Delta^{12,13}$-iso-baccatin III (72) in example 74 but starting with 7-(O-methylthiomethyl)-$\Delta^{12,13}$-iso-baccatin III-13-(4S,5R)-N-Cbz-2-(2,4-dimethoxyphenyl)-4-phenyl-5-oxazolidinecarboxylic acid ester (104a,b) in place of 7-(O-methylthiomethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b) is prepared 7-(O-methylthiomethyl)-13-(N-Cbz-$\beta$-phenyl isoserinyl)-$\Delta^{12,13}$-iso-baccatin III (105)

EXAMPLE 118
Preparation of 7-(O-methylthiomethyl)-13-($\beta$-phenyl isoserinyl)-$\Delta^{12,13}$-iso-baccatin III (106)

As described for the preparation of 7-(O-methoxymethyl)-13-($\beta$-phenyl isoserinyl)-$\Delta^{12,13}$-iso-baccatin III (65) in example 65 but starting with 7-(O-methylthiomethyl)-13-(N-Cbz-$\beta$-phenyl isoserinyl)-$\Delta^{12,13}$-iso-baccatin III (105) in place of 7-(O-methoxymethyl)-13-(N-Cbz-$\beta$-phenyl isoserinyl)-$\Delta^{12,13}$-iso-baccatin III (64) is prepared 7-(O-methylthiomethyl)-13-($\beta$-phenyl isoserinyl)-$\Delta^{12,13}$-iso-baccatin III (106)

EXAMPLE 119
Preparation of 7-(O-methylthiomethyl)-13-(N-Boc-$\beta$-phenyl isoserinyl)-$\Delta^{12,13}$-iso-baccatin III (107)

As described for the preparation of 7-(O-methoxymethyl)-13-(N-Boc-$\beta$-phenyl isoserinyl)-$\Delta^{12,13}$-iso-baccatin III (66) in example 66 but starting with 7-(O-methylthiomethyl)-13-($\beta$-phenyl isoserinyl)-$\Delta^{12,13}$-iso-baccatin III (106) in place of 7-(O-methoxymethyl)-13-($\beta$-phenyl isoserinyl)-$\Delta^{12,13}$-iso-baccatin III (65) is prepared 7-(O-methylthiomethyl)-13-(N-Boc-$\beta$-phenyl isoserinyl)-$\Delta^{12,13}$-iso-baccatin III (107)

EXAMPLE 120
Preparation of 7-(O-methylthiomethyl)-13-(N-(t-butylaminocarbonyl)-$\beta$-phenyl isoserinyl)-$\Delta^{12,13}$-iso-baccatin III (72)

As described for the preparation of 7-(O-methoxymethyl)-13-(N-(t-butylaminocarbonyl)-β-phenyl isoserinyl)-Δ$^{12,13}$-iso-baccatin III (67) in example 67 but starting with 7-(O-methylthiomethyl)-13-(β-phenyl isoserinyl)-Δ$^{12,13}$-iso-baccatin III (106) in place of 7-(O-methoxymethyl)-13-(β-phenyl isoserinyl)-Δ$^{12,13}$-iso-baccatin III (65) is prepared 7-(O-methylthiomethyl)-13-(N-(t-butylaminocarbonyl)-Boc-β-phenyl isoserinyl)-Δ$^{12,13}$-iso-baccatin III (72.)

EXAMPLE 121
Preparation of 10-deacetyl-7-(O-methyl)-baccatin III (108)

As described for the preparation of 7-(O-methyl)-13-(N-t-butylaminocarbonyl-β-phenyl isoserinyl)-Δ$^{12,13}$-iso-baccatin III (73) in example 75 but starting with 10-deacetyl-7-(O-methylthiomethyl)-baccatin III (100) in place of 7-(O-methylthiomethyl)-13-(N-t-butylaminocarbonyl-β-phenyl isoserinyl)-Δ$^{12,13}$-iso-baccatin III (72) is prepared 10-deacetyl-7-(O-methyl)-baccatin III (108).

EXAMPLE 122
Preparation of 7-(O-methyl)-baccatin III (109)

As described for the preparation of 7-(O-trifluoromethanesulfonyl)-baccatin III (83) in example 88 but starting with 10-deacetyl-(O-methyl)-baccatin III (108) in place of 10-deacetyl-7-(O-trifluoromethanesulfonyl)-baccatin III (82) is prepared 7-(O-methyl)-baccatin III (109)

EXAMPLE 123
Preparation of 7-(O-methyl)-baccatin III (109)

As described for the preparation of 7-(O-methyl)-13-(N-t-butylaminocarbonyl-β-phenyl isoserinyl)-Δ$^{12,13}$-iso-baccatin III (73) in example 75 but starting with 7-(O-methylthiomethyl)-baccatin III (101) in place of 7-(O-methylthiomethyl)-13-(N-t-butylaminocarbonyl-β-phenyl isoserinyl)-Δ$^{12,13}$-iso-baccatin III (72) is prepared 7-(O-methyl)-baccatin III (109).

EXAMPLE 124
Preparation of 13-keto-7-(O-methyl)-baccatin III (110)

As described for the preparation of 13-keto-7-TES-baccatin III (2) in example 1 but starting with 7-(O-methyl)-baccatin III (109) in place of 7-TES-baccatin III (1) is prepared 13-keto-7-(O-methyl)-baccatin III (110).

EXAMPLE 125
Preparation of 7-(O-methyl)-Δ$^{12,13}$-iso-baccatin III (111)

As described for the preparation of 7-TES-Δ$^{12,13}$-iso-baccatin III (3) in example 2 but starting with 13-keto-7-(O-methyl)-baccatin III (110) in place of 13-keto-7-TES-baccatin III (2) is prepared 7-(O-methyl)-Δ$^{12,13}$-iso-baccatin III (111).

EXAMPLE 126
Preparation of 7-(O-methyl)-Δ$^{12,13}$-iso-baccatin III-13-(4S,5R)-N-Cbz-2-(2,4-dimethoxyphenyl)-4-phenyl-5-oxazolidinecarboxylic acid ester (112a,b)

As described for the preparation of 7-TES-Δ$^{12,13}$-iso-baccatin III-13-(4S,5R)-N-Cbz- 2-(2,4-dimethoxyphenyl)-4-phenyl-5-oxazolidinecarboxylic acid ester (51a,b) in example 47 but starting with 7-(O-methyl)-Δ$^{12,13}$-iso-baccatin III (111) in place of 7-TES-Δ$^{12,13}$-iso-baccatin III (3) is prepared 7-(O-methyl)-Δ$^{12,13}$-iso-baccatin III-13-(4S,5R)-N-Cbz-2-(2,4-dimethoxyphenyl)-4-phenyl-5-oxazolidinecarboxylic acid ester (112a,b).

EXAMPLE 127
Preparation of 7-(O-methyl)-13-(N-Cbz-β-phenyl isoserinyl)-Δ$^{12,13}$-iso-baccatin III (113)

As described for the preparation of 7-(O-methylthiomethyl)-13-(N-t-butylaminocarbonyl-β-phenyl isoserinyl)-Δ$^{12,13}$-iso-baccatin III (72) in example 74 but starting with 7-(O-methyl)-Δ$^{12,13}$-iso-baccatin III-13-(4S,5R)-N-Cbz-2-(2,4-dimethoxyphenyl)-4-phenyl-5-oxazolidinecarboxylic acid ester (112a,b) in place of 7-(O-methylthiomethyl)-Δ$^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b) is prepared 7-(O-methyl)-13-(N-Cbz-β-phenyl isoserinyl)-Δ$^{12,13}$-iso-baccatin III (113).

EXAMPLE 128
Preparation of 7-(O-methyl)-13-(β-phenyl isoserinyl)-Δ$^{12,13}$-iso-baccatin III (114)

As described for the preparation of 7-(O-methoxymethyl)-13-(β-phenyl isoserinyl)-Δ$^{12,13}$-iso-baccatin III (65) in example 65 but starting with 7-(O-methyl)-13-(N-Cbz-β-phenyl isoserinyl)-Δ$^{12,13}$-iso-baccatin III (113) in place of 7-(O-methoxymethyl)-13-(N-Cbz-β-phenyl isoserinyl)-Δ$^{12,13}$-iso-baccatin III (64) is prepared 7-(O-methyl)-13-(β-phenyl isoserinyl)-Δ$^{12,13}$-iso-baccatin III (114).

EXAMPLE 129
Preparation of 7-(O-methyl)-13-(N-Boc-β-phenyl isoserinyl)-Δ$^{12,13}$-iso-baccatin III (115)

As described for the preparation of 7-(O-methoxymethyl)-13-(N-Boc-β-phenyl isoserinyl)-Δ$^{12,13}$-iso-baccatin III (66) in example 66 but starting with 7-(O-methyl)-13-(β-phenyl isoserinyl)-Δ$^{12,13}$-iso-baccatin III (114) in place of 7-(O-methoxymethyl)-13-(β-phenyl isoserinyl)-Δ$^{12,13}$-iso-baccatin III (65) is prepared 7-(O-methyl)-13-(N-Boc-β-phenyl isoserinyl)-Δ$^{12,13}$-iso-baccatin III (115).

EXAMPLE 130
Preparation of 7-(O-methyl)-13-(N-(t-butylaminocarbonyl)-β-phenyl isoserinyl)-Δ$^{12,13}$-iso-baccatin III (73)

As described for the preparation of 7-(O-methoxymethyl) -13-(N-(t-butylaminocarbonyl)-β-phenyl isoserinyl)-Δ$^{12,13}$-iso-baccatin III (67) in example 67 but starting with 7-(O-methyl)-13-(β-phenyl isoserinyl)-Δ$^{12,13}$-iso-baccatin III (114) in place of 7-(O-methoxymethyl)-13-(β-phenyl isoserinyl)-Δ$^{12,13}$-iso-baccatin III (65) is prepared 7-(O-methyl)-13-(N-(t-butylaminocarbonyl)-Boc-β-phenyl isoserinyl)-Δ$^{12,13}$-iso-baccatin III (73.)

EXAMPLE 131
Preparation of 10-deacetyl-7-(O-methoxymethyl)-Δ$^{12,13}$-iso-baccatin III 116)

As described for the preparation of 7-(O-methoxymethyl)-Δ$^{12,13}$-iso-baccatin III-13-(4S,5R)-N-Cbz-2-(2,4-dimethoxyphenyl)-4-phenyl-5-oxazolidinecarboxylic acid ester (75a,b,) in example 77 but starting with 10-deacetyl-baccatin III (94) in place of Δ$^{12,13}$-iso-baccatin III-13-(4S,5R)-N-Cbz-2-(2,4-dimethoxyphenyl)-4-phenyl-5-oxazolidinecarboxylic acid ester (74a,b) is prepared 10-deacetyl-7-(O-methoxymethyl)-Δ$^{12,13}$-iso-baccatin III (116).

EXAMPLE 132
Preparation of 7-(O-methoxymethyl)-Δ$^{12,13}$-iso-baccatin III (99)

As described for the preparation of 7-(O-trifluoromethanesulfonyl)-baccatin III (83) in example 88 but starting with 10-deacetyl-7-(O-methoxymethyl)-Δ$^{12,13}$-iso-baccatin III (116) in place of 10-deacetyl-7-trifluoromethanesulfonyl-baccatin III (82) is prepared 7-(O-methoxymethyl)-Δ$^{12,13}$-iso-baccatin III (99).

EXAMPLE 133
Preparation of 10-deacetyl-7-(O-methylthiomethyl)-$\Delta^{12,13}$-iso-baccatin III (117)

As described for the preparation of 7-(O-methylthiomethyl)-$\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (71a,b) in example 73 but starting with 10-deacetyl-$\Delta^{12,13}$-baccatin III (94) in place of $\Delta^{12,13}$-iso-baccatin III-13-(4S,5R)-N-(t-butylaminocarbonyl)-2-(2,4-dimethoxyphenyl)-4-phenyl-5-oxazolidinecarboxylic acid ester (33a,b) is prepared 10-deacetyl-7-(O-methylthiomethyl)-$\Delta^{12,13}$-iso-baccatin III (117).

EXAMPLE 134
Preparation of 7-(O-methylthiomethyl)-$\Delta^{12,13}$-iso-baccatin III (103)

As described for the preparation of 7-(O-trifluoromethanesulfonyl)-baccatin III (83) in example 88 but starting with 10-deacetyl-7-(O-methylthiomethyl)-$\Delta^{12,13}$-iso-baccatin III (117) in place of 10-deacetyl-7-trifluoromethanesulfonyl-baccatin III (82) is prepared 7-(O-methylthiomethyl)-$\Delta^{12,13}$-iso-baccatin III (103).

EXAMPLE 135
Preparation of 7-(O-methyl)-$\Delta^{12,13}$-iso-baccatin III (111)

As described for the preparation of 7-(O-methyl)-13-(N-t-butylaminocarbonyl-β-phenyl isoserinyl)-$\Delta^{12,13}$-iso-baccatin III (73) in example 75 but starting with 7-(O-methylthiomethyl)-$\Delta^{12,13}$-iso-baccatin III (103) in place of 7-(O-methylthiomethyl)-13-(N-t-butylaminocarbonyl-β-phenyl isoserinyl)-$\Delta^{12,13}$-iso-baccatin III (72) is prepared 7-(O-methyl)-$\Delta^{12,13}$-iso-baccatin III (111).

EXAMPLE 136
Part A

Charge oxazoline acid (2.60 g, 9.73 mmol) into a round bottom flask and slurry in toluene (20 ml). At room temperature add 1,3-dicyclohexylcarbodiimide (960 mg, 4.65 mmol) and stir for 20 minutes. Add 7-2-(3-methylbutyl) dimethylsilyloxy baccatin III (1.0 g, 1.40 mmol) in toluene (15 ml) followed by catalytic 4-pyrrolidinopyridine. Stir the mixture at room temperature. After 1 hour, reaction is complete by TLC. Quench with 20% NaHCO$_3$ (50 ml) and stir at room temperature for 2 hours. Filter on a coarse frit to remove the DCU and separate the phases. Back extract the aqueous with methyl t-butylether (35 ml). Wash the combined organics with 50% NaHCO$_3$ (50 ml), brine (50 ml) and dry over Na$_2$SO$_4$. Concentrate to solids. Purify by column chromatography with 3:1 cyclohexanes/Ethyl acetate to afford coupled ester 118 as a white solid.

Part B

Charge the coupled ester (1.16 g, 1.2 mmol) into a round bottom flask and dissolve in MeOH (11 ml). Add 1N HCl (1.25 ml, 1.25 mmol) at room temperature. Heat the resultant mixture to reflux. After 2 hours at reflux, the reaction is done by TLC. Cool to room temperature. Add aq NaHCO$_3$ (535 mg/10 ml H$_2$O). Stir at room temperature for 2 hours. Remove the MeOH under vacuum, then extract mixture with EtOAc (2×25 ml). Dry the organics over Na$_2$SO$_4$ and concentrate to solids. By TLC the solids are a mixture of the O-benzoyl salt and taxol. Dissolve the solids in a small amount of EtOAc and add 2 drops of triethylamine. Leave overnight. After 16 hours, the migration is complete and the crude solids are purified by column chromatography using 1.5:1 Ethyl acetate/cyclohexanes to afford taxol.

EXAMPLE 137

Following the general procedure of Example 136 but substituting 7-2-(3-ethylbutyl)dimethylsilyloxy $\Delta^{12,13}$-iso-baccatin III for 7-2-(3-methylbutyl)dimethylsilyloxy baccatin III, $\Delta^{12,13}$-iso-taxol is prepared.

EXAMPLE 138
Formation of 7-[0-2-(3-methylbutyl)dimethylsilyl]-taxol (119)

A solution of 1.02 g of the product of Example 136, Part A (Compound 118) in 12 mL of AcOH and 1.5 mL water is heated at 80 C. for one hour. The solution is cooled and the product isolated by chromatography after isolation with ethyl acetate to afford 680 mg of Compound 119.

Preparation A 2'-{[(2,2,2-trichloroethyl)oxy]carbonyl}-$\Delta^{12,13}$-iso-taxol is prepared as described for the preparation of 2'-{[(2,2,2-trichloroethyl)oxy]carbonyl}taxol [Magri, N. F.; Kingston, D. G. I. *J. Org. Chem.*, 1986, 51, 797]

Preparation B 2'-[{(2,2,2-Trichloroethyl)oxy}carbonyl]-$\Delta^{12,13}$-iso-taxol, 7-Methanesulfonate Methanesulfonyl chloride (1.2 equivalents) is added dropwise to a solution of 2'-[{(2,2,2-Trichloroethyl)oxy}carbonyl]-$\Delta^{12,13}$-iso-taxol (1 equivalent) and pyridine (5 equivalents) in CH$_2$Cl$_2$ which is stirred at ice-bath temperature. The reaction mixture is allowed to warm and stirring is continued until tlc evidence indicates that reaction is complete. The reaction mixture is quenched with ice water and is extracted with CH$_2$Cl$_2$ and these extracts are washed successively with dilute aqueous acid, dilute aqueous NaHCO$_3$, and water and then are dried, filtered, and concentrated to give the crude reaction product. Chromatography of the crude product over silica gel gives pure title compound.

Preparation C 2'-[{(2,2,2-Trichloroethyl)oxy}carbonyl]-7-deoxy-7α-chloro-$\Delta^{12,13}$-iso-taxol A solution of 2'-[{(2,2,2-trichloroethyl)oxy}carbonyl]-$\Delta^{12,13}$-iso-taxol, 7-methanesulfonate (1 equiv.) in N,N-dimethylformamide (DMF) is stirred with potassium chloride (10 equiv.). A phase transfer catalyst is added and the reaction mixture is warmed to increase the rate of reaction. The course of the reaction is followed by tlc. The reaction mixture is worked up by the addition of water and extraction with CH$_2$Cl$_2$. The organic extracts are dried, filtered, and concentrated and the crude reaction product residue is chromatographed over silica gel, yielding the pure title compound.

Preparation D Preparation of 7-deoxy-7α-chloro-$\Delta^{12,13}$-iso-taxol

A solution of 2'-[{(2,2,2-Trichloroethyl)oxy}carbonyl]-7-deoxy-7α-chloro-$\Delta^{12,13}$-iso-taxol in 9:1 methanol/acetic acid is stirred with activated zinc metal at room temperature. After 90 min, the reaction is worked up by removal of the zinc by filtration and concentration of the filtrate under reduced pressure. The residue is dissolved in CH$_2$Cl$_2$ and this solution washed with 0.1N aq. HCl, with 5% aq. NaHCO$_3$, and with water. The aqueous layer is back extracted with CH$_2$Cl$_2$ and the combined organic extracts are dried (Na$_2$SO$_4$), filtered, and concentrated to give a residue. The residue is purified by chromatography over silica gel and is obtained as a solid.

Preparation E 7-Deoxy-7β-chloro-$\Delta^{12,13}$-iso-taxol

Following the procedures of Examples A,B,C,D and E, but starting with 2'-[{(2,2,2-trichloroethyl)oxy}carbonyl]-7-epi-$\Delta^{12,13}$-iso-taxol, the title compound is prepared.

Following the general procedures of Examples 15 and 11 but using appropriate metal salts, such as sodium or potassium bromide and sodium or potassium iodide or sodium or potassium azide, in the procedure of Example 15, the following compounds are prepared:

7-Deoxy-7α-bromo-$\Delta^{12,13}$-iso-taxol;

7-Deoxy-7β-bromo-$\Delta^{12,13}$-iso-taxol;

7-Deoxy-7α-iodo-$\Delta^{12,13}$-iso-taxol;

7-Deoxy-7β-iodo-$\Delta^{12,13}$-iso-taxol;

7-Deoxy-7α-azido-$\Delta^{12,13}$-iso-taxol; and

7-Deoxy-7β-azido-$\Delta^{12,13}$-iso-taxol.

Compounds of Formula xii wherein $R^6$ is H, $R^8$ is methyl and $R^7$ is a chlorine, bromine or iodine atom can also prepared by reaction of an appropriately protected precursor (e.g., I wherein $R_1$=—$C_6H_5$; $R_2$=—NHC(O)$C_6H_5$; $R_3$=H; $R_4$=—OTROC;

$R_5$=H; $R_{30}$=—OCOCH$_3$; and $X_7$=OH) with $(C_6H_5)_3P/X_2$; $(C_6H_5)_3P/CX_4$; or $(C_6H_5O)_3P/X_2$) following, for example, the numerous examples and experimental conditions described in Castro, B. R., *Organic Reactions*, 1983, 29, pp 1–162.

Derivatives of the 7-deoxy-7-halo-$\Delta^{12,13}$-iso-taxols in which the 2'-hydroxyl group is esterified are prepared directly from the desired 7-deoxy-7-halo-$\Delta^{12,13}$-iso-taxol by methods which are given in: Mathew, A. E., et. al., *J. Med. Chem.*, 1992, 35, 145; U.S. Pat. No. 4,960,790; U.S. Pat. No. 4,942,184; U.S. Pat. No. 5,059,699.

Following the general procedures of Mathew et al. (see, e.g., U.S. Pat. Nos. 4,960,790, 4,924,184 and 5,059,699) but substituting the appropriate 7-deoxy-7-halo-$\Delta^{12,13}$-iso-taxol analog, the following compounds are prepared:

2'-succinyl-7-deoxy-7-fluoro-$\Delta^{12,13}$-iso-taxol;
2'-(β-alanyl)-7-deoxy-7-fluoro-$\Delta^{12,13}$-iso-taxol formate;
2'-glutaryl-7-deoxy-7-fluoro-$\Delta^{12,13}$-iso-taxol;
2'-[-C(O)(CH$_2$)$_3$C(O)NH(CH$_2$)$_3$N(CH$_3$)$_2$]-7-deoxy-7-fluoro-$\Delta^{12,13}$-iso-taxol;
2'-(β-sulfopropionyl)-7-deoxy-7-fluoro-$\Delta^{12,13}$-iso-taxol;
2'-(2-sulfoethylamido)succinyl-7-deoxy-7-fluoro-$\Delta^{12,13}$-iso-taxol;
2'-(3-sulfopropylamido)succinyl-7-deoxy-7-fluoro-$\Delta^{12,13}$-iso-taxol;
2'-(triethylsilyl)-7-deoxy-7-fluoro-$\Delta^{12,13}$-iso-taxol;
2'-(t-butyldimethylsilyl)-7-deoxy-7-fluoro-$\Delta^{12,13}$-iso-taxol;
2'-(N,N-diethylaminopropionyl)-7-deoxy-7-fluoro-$\Delta^{12,13}$-iso-taxol;
2'-(N,N-dimethylglycyl)-7-deoxy-7-fluoro-$\Delta^{12,13}$-iso-taxol;
2'-(glycyl)-7-deoxy-7-fluoro-$\Delta^{12,13}$-iso-taxol;
2'-(L-alanyl)-7-deoxy-7-fluoro-$\Delta^{12,13}$-iso-taxol;
2'-(L-leucyl)-7-deoxy-7-fluoro-$\Delta^{12,13}$-iso-taxol;
2'-(L-isoleucyl)-7-deoxy-7-fluoro-$\Delta^{12,13}$-iso-taxol;
2'-(L-valyl)-7-deoxy-7-fluoro-$\Delta^{12,13}$-iso-taxol;
2'-(L-phenylalanyl)-7-deoxy-7-fluoro-$\Delta^{12,13}$-iso-taxol;
2'-(L-prolyl)-7-deoxy-7-fluoro-$\Delta^{12,13}$-iso-taxol;
2'-(L-lysyl)-7-deoxy-7-fluoro-$\Delta^{12,13}$-iso-taxol;
2'-(L-glutamyl)-7-deoxy-7-fluoro-$\Delta^{12,13}$-iso-taxol;
2'-(L-arginyl)-7-deoxy-7-fluoro-$\Delta^{12,13}$-iso-taxol;
7-deoxy-7-fluoro-$\Delta^{12,13}$-iso-taxotere;
2'-succinyl-7-deoxy-7-chloro-$\Delta^{12,13}$-iso-taxol;
2'-(β-alanyl)-7-deoxy-7-chloro-$\Delta^{12,13}$-iso-taxol formate;
2'-glutaryl-7-deoxy-7-chloro-$\Delta^{12,13}$-iso-taxol;
2'-[-C(O)(CH$_2$)$_3$C(O)NH(CH$_2$)$_3$N(CH$_3$)$_2$]-7-deoxy-7-chloro-$\Delta^{12,13}$-iso-taxol;
2'-(β-sulfopropionyl)-7-deoxy-7-chloro-$\Delta^{12,13}$-iso-taxol;
2'-(2-sulfoethylamido)succinyl-7-deoxy-7-chloro-$\Delta^{12,13}$-iso-taxol;
2'-(3-sulfopropylamido)succinyl-7-deoxy-7-chloro-$\Delta^{12,13}$-iso-taxol;
2'-(triethylsilyl)-7-deoxy-7-chloro-$\Delta^{12,13}$-iso-taxol;
2'-(t-butyldimethylsilyl)-7-deoxy-7-chloro-$\Delta^{12,13}$-iso-taxol;
2'-(N,N-diethylaminopropionyl)-7-deoxy-7-chloro-$\Delta^{12,13}$-iso-taxol;
2'-(N,N-dimethylglycyl)-7-deoxy-7-chloro-$\Delta^{12,13}$-iso-taxol;
2'-(glycyl)-7-deoxy-7-chloro-$\Delta^{12,13}$-iso-taxol;
2'-(L-alanyl)-7-deoxy-7-chloro-$\Delta^{12,13}$-iso-taxol;
2'-(L-leucyl)-7-deoxy-7-chloro-$\Delta^{12,13}$-iso-taxol;
2'-(L-isoleucyl)-7-deoxy-7-chloro-$\Delta^{12,13}$-iso-taxol;
2'-(L-valyl)-7-deoxy-7-chloro-$\Delta^{12,13}$-iso-taxol;
2'-(L-phenylalanyl)-7-deoxy-7-chloro-$\Delta^{12,13}$-iso-taxol;
2'-(L-prolyl)-7-deoxy-7-chloro-$\Delta^{12,13}$-iso-taxol;
2'-(L-lysyl)-7-deoxy-7-chloro-$\Delta^{12,13}$-iso-taxol;
2'-(L-glutamyl)-7-deoxy-7-chloro-$\Delta^{12,13}$-iso-taxol;
2'-(L-arginyl)-7-deoxy-7-chloro-$\Delta^{12,13}$-iso-taxol;
7-deoxy-7-chloro-$\Delta^{12,13}$-iso-taxotere;
2'-succinyl-7-deoxy-7-bromo-$\Delta^{12,13}$-iso-taxol;
2'-(β-alanyl)-7-deoxy-7-bromo-$\Delta^{12,13}$-iso-taxol formate:
2'-glutaryl-7-deoxy-7-bromo-$\Delta^{12,13}$-iso-taxol;
2'-[-C(O)(CH$_2$)$_3$C(O)NH(CH$_2$)$_3$N(CH$_3$)$_2$]-7-deoxy-7-bromo-$\Delta^{12,13}$-iso-taxol;
2'-(β-sulfopropionyl)-7-deoxy-7-bromo-$\Delta^{12,13}$-iso-taxol;
2'-(2-sulfoethylamido)succinyl-7-deoxy-7-bromo-$\Delta^{12,13}$-iso-taxol;
2'-(3-sulfopropylamido)succinyl-7-deoxy-7-bromo-$\Delta^{12,13}$-iso-taxol;
2'-(triethylsilyl)-7-deoxy-7-bromo-$\Delta^{12,13}$-iso-taxol;
2'-(t-butyldimethylsilyl)-7-deoxy-7-bromo-$\Delta^{12,13}$-iso-taxol;
2'-(N,N-diethylaminopropionyl)-7-deoxy-7-bromo-$\Delta^{12,13}$-iso-taxol;
2'-(N,N-dimethylglycyl)-7-deoxy-7-bromo-$\Delta^{12,13}$-iso-taxol;
2'-(glycyl)-7-deoxy-7-bromo-$\Delta^{12,13}$-iso-taxol;
2'-(L-alanyl)-7-deoxy-7-bromo-$\Delta^{12,13}$-iso-taxol;
2'-(L-leucyl)-7-deoxy-7-bromo-$\Delta^{12,13}$-iso-taxol;
2'-(L-isoleucyl)-7-deoxy-7-bromo-$\Delta^{12,13}$-iso-taxol;
2'-(L-valyl)-7-deoxy-7-bromo-$\Delta^{12,13}$-iso-taxol;
2'-(L-phenylalanyl)-7-deoxy-7-bromo-$\Delta^{12,13}$-iso-taxol;
2'-(L-prolyl)-7-deoxy-7-bromo-$\Delta^{12,13}$-iso-taxol;
2'-(L-lysyl)-7-deoxy-7-bromo-$\Delta^{12,13}$-iso-taxol;
2'-(L-glutamyl)-7-deoxy-7-bromo-$\Delta^{12,13}$-iso-taxol;
2'-(L-arginyl)-7-deoxy-7-bromo-$\Delta^{12,13}$-iso-taxol;
7-deoxy-7-bromo-$\Delta^{12,13}$-iso-taxotere;
2'-succinyl-7-deoxy-7-iodo-$\Delta^{12,13}$-iso-taxol;
2'-(β-alanyl)-7-deoxy-7-iodo-$\Delta^{12,13}$-iso-taxol formate;
2'-glutaryl-7-deoxy-7-iodo-$\Delta^{12,13}$-iso-taxol;
2'-[-C(O)(CH$_2$)$_3$C(O)NH(CH$_2$)$_3$N(CH$_3$)$_2$]-7-deoxy-7-iodo-$\Delta^{12,13}$-iso-taxol;
2'-(β-sulfopropionyl)-7-deoxy-7-iodo-$\Delta^{12,13}$-iso-taxol;
2'-(2-sulfoethylamido)succinyl-7-deoxy-7-iodo-$\Delta^{12,13}$-iso-taxol;
2'-(3-sulfopropylamido)succinyl-7-deoxy-7-iodo-$\Delta^{12,13}$-iso-taxol;
2'-(triethylsilyl)-7-deoxy-7-iodo-$\Delta^{12,13}$-iso-taxol;
2'-(t-butyldimethylsilyl)-7-deoxy-7-iodo-$\Delta^{12,13}$-iso-taxol;
2'-(N,N-diethylaminopropionyl)-7-deoxy-7-iodo-$\Delta^{12,13}$-iso-taxol;
2'-(N,N-dimethylglycyl)-7-deoxy-7-iodo-$\Delta^{12,13}$iso-taxol;
2'-(glycyl)-7-deoxy-7-iodo-$\Delta^{12,13}$-iso-taxol;
2'-(L-alanyl)-7-deoxy-7-iodo-$\Delta^{12,13}$-iso-taxol;
2'-(L-leucyl)-7-deoxy-7-iodo-$\Delta^{12,13}$-iso-taxol;
2'-(L-isoleucyl)-7-deoxy-7-iodo-$\Delta^{12,13}$-iso-taxol;
2'-(L-valyl)-7-deoxy-7-iodo-$\Delta^{12,13}$-iso-taxol;
2'-(L-phenylalanyl)-7-deoxy-7-iodo-$\Delta^{12,13}$-iso-taxol;
2'-(L-prolyl)-7-deoxy-7-iodo-$\Delta^{12,13}$-iso-taxol;
2'-(L-lysyl)-7-deoxy-7-iodo-$\Delta^{12,13}$-iso-taxol;
2'-(L-glutamyl)-7-deoxy-7-iodo-$\Delta^{12,13}$-iso-taxol;
2'-(L-arginyl)-7-deoxy-7-iodo-$\Delta^{12,13}$-iso-taxol;
7-deoxy-7-iodo-$\Delta^{12,13}$-iso-taxotere; and
pharmaceutically acceptable salts thereof when the compound contains either an acidic or basic functional group.

EXAMPLE 138

Emulsion Formulation of N-Debenzoyl-N-(t-butyl) aminocarbonyl-7-deoxy-7β,8β-methano-12,13-isotaxol (Cpd 36)

A 14.5 mg sample of N-Debenzoyl-N-(t-butyl) aminocarbonyl-7-deoxy-7β,8β-methano-12,13-isotaxol (Cpd 36) is weighed and added to 0.5 gm of water with probe sonication. An aliquot of 0.5 gm oil (Miglyol 810) is added with mixing for four hours. An aliquot of an aqueous phase containing phospholipid (egg lecithin) and glycerine is then added to the oil-drug mixture to yield a 20% oil emulsion containing 12.5 mg/gm phospholipid, 22.5 mg/gm glycerine, and 6 mg/gm drug. The mixture is prehomogenized by sonication prior to final emulsification with an EmulsiFlex B3. A physically stable emulsion with mean particle size of 240 nm (measured by light scattering) results.

EXAMPLE 139

Emulsion Formulation of N-Debenzoyl-N-(t-butyl) aminocarbonyl-7-deoxy-$\Delta^{6,7}$-12,13-isotaxol (Cpd 38)

A 70 mg sample of N-Debenzoyl-N-(t-butyl) aminocarbonyl-7-deoxy-$\Delta^{6,7}$-12,13-isotaxol (Cpd 38) is weighed and added to 1 gm water with probe sonication. An aliquot of 4.0 gm of oil (Miglyol 810) is added with mixing for 36 hours. The oil/water/drug mixture is centrifuged and oil phase removed, assayed and split into three different aliquots, which are then diluted with oil to 3.4, 6.9 and 13.8 mg drug/gm oil. Aliquots of an aqueous phase containing phospholipid (egg lecithin) and glycerine are then added to the oil-drug mixtures to yield a 20% oil emulsion containing 12.5 mg/gm phospholipid, 22.5 mg/gm glycerine, and either 0.7, 1.4, or 2.8 mg/gm drug. The mixture is prehomogenized by sonication prior to final emulsification with an EmulsiFlex B3. Physically stable emulsions with mean particle sizes of 200–215 nm (measured by light scattering) is obtained.

Procedures for the preparation of $\Delta^{12,13}$-iso-taxol 7-ethers.

Preparation 1: Preparation of 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester Sodium hydride (55% dispersion in mineral oil, 43 mg, 1 mmol) is washed three times, by decantation, with anhydrous n-hexane. A solution of $\Delta^{12,13}$-iso-baccatin III-13 (4S,5R)-N-Boc-2-(2,4-dimethoxyphenyl)-4-phenyl-5-oxazolidinecarboxylic acid ester (10a, 1 mmol) in anhydrous DMF (6 mL) is add at 0° C. and the resulting mixture stirred at rt for 30 min. The resulting mixture is then treated with methyl iodide (82 μL, 1.3 mmol) and stirred for an additional 60 min. The reaction is then quenched with 5% aqueous ammonium chloride solution and extracted with ether. The organic layer is dried ($MgSO_4$) and the solvent evaporated under vacuum. The residue is purified by chromatography over silica gel, leaving 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester.

See: Banfi, L.; Bernardi, A.; Columbo, L.; Gennari, C.; Scolastico, C. *J. Org. Chem.* 1984, 49, 3784.

Preparation 2: Preparation of 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester $\Delta^{12,13}$-Iso-baccatin III-13 (4S,5R)-N-Boc-2-(2,4-dimethoxyphenyl)-4-phenyl-5-oxazolidinecarboxylic acid ester (10a, 1 mmol), methyl iodide (1.2 mmol), silver tetrafluoroborate (1.2 mmol) and silver carbonate (2 mmol) are added to acetonitrile (5 mL) and the mixture stirred at rt for 48 hr. The reaction is then diluted with ethyl acetate (20 mL) and filtered. The filtrate is extracted with water, 5% aqueous bicarbonate and dried ($MgSO_4$) and the solvent evaporated under vacuum. The residue is purified by chromatography over silica gel, leaving 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester.

See: Bhatia, S. K.; Hajdu, J. *Tetrahedron Lett.* 1987, 28, 271.

Preparation 3 Preparation of 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester $\Delta^{12,13}$-Iso-baccatin III-13 (4S,5R)-N-Boc-2-(2,4-dimethoxyphenyl)-4-phenyl-5-oxazolidinecarboxylic acid ester (10a, 1 mmol), 2,6-di-t-butyl pyridine (2.3 mmol) and mercuric cyanide (5.8 mg, 0.023 mmol) is dissolved in methylene chloride (4.5 mL) and the solution treated with methyl trifluoromethane sulfonate (0.24 mL, 2.2 mmol). The solution is heated under reflux for 50 hr, then treated with methanol (0.2 mL). The reaction is then evaporated under vacuum and the residue purified by chromatography over silica gel, leaving 7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester.

See: *J. Carbohyd. Chem.* 1986, 5, 115.

Deprotection of Methyl ethers

Preparation 4 Preparation of 7-(O-methyl)-13-(N-Boc-β-phenyl isoserinyl)-$\Delta^{12,13}$-iso-baccatin III (41)

7-(O-methyl)-$\Delta^{12,13}$-iso-baccatin III-13-(4S,5R)-N-Boc-2-(2,4-dimethoxyphenyl)-4-phenyl-5-oxazolidinecarboxylic acid ester (1 mmol) is stirred at RT under nitrogen in (80-20) acetic acid-water (4 mL). The reaction is followed by TLC and is found to be complete in 24 hours. The reaction is then freeze-dried. The crude product is purified by chromatography over silica gel to give 7-(O-methyl)-13-(N-Boc-β-phenyl isoserinyl)-$\Delta^{12,13}$-iso-baccatin III.

Allyl ether Syntheses

Preparation 5 Preparation of 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester A solution of $\Delta^{12,13}$-iso-baccatin III-13 (4S,5R)-N-Boc-2-(2,4-dimethoxyphenyl)-4-phenyl-5-oxazolidinecarboxylic acid ester (10a, 1 mmol) in methylene chloride is treated with allyl trichloroacetimidate (2 mmol) and trifluoromethane sulfonic acid (25 μL) and the reaction stirred 48 hours at room temperature. The reaction is filtered and the filtrate washed with 5% aqueous sodium bicarbonate solution. The organic layer is then dried ($MgSO_4$) and the solvent evaporated under vacuum. The residue is purified by chromatography over silica gel, leaving 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester.

See: Wessel H.-P.; Iverson, T.; Bundle, D. R. *J. Chem. Soc. Perkin Trans. I.* 1985, 2247.

Preparation 6 Preparation of 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester Sodium hydride (55% dispersion in mineral oil, 43 mg, 1 mmol) is washed three times, by decantation, with anhydrous n-hexane. A solution of $\Delta^{12,13}$-iso-baccatin III-13 (4S,5R)-N-Boc-2-(2,4-dimethoxyphenyl)-4-phenyl-5-oxazolidinecarboxylic acid ester (10a, 1 mmol) in anhydrous DMF (6 mL) is add at 0° C. and the resulting mixture stirred at rt for 30 mm. The resulting mixture is then treated with allyl bromide (1.3 mmol) and stirred for an additional 60 min. The reaction is then quenched with 5% aqueous ammonium chloride solution and extracted with ether. The organic layer is dried ($MgSO_4$) and the solvent evaporated under vacuum. The residue is purified by chromatography over silica gel, leaving 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester.

See: Kloosterman, M.; de Nijs, M. P.; van Boom, J. H. *J. Carbohyd. Chem.* 1986, 5, 2247.

Preparation 7 Preparation of 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester Under an argon atmosphere, tris(dibenzylideneacetone) dipalladium (0.025 mmol), and 1,4-bis(biphenylphosphino) butane (0.1 mmol) are added to tetrahydrofuran (2 mL). This solution is treated with $\Delta^{12,13}$-iso-baccatin III-13(4S,5R)-N-Boc-2-(2,4-dimethoxyphenyl)-4-phenyl-5-oxazolidinecarboxylic acid ester (10a, 1 mmol) and allyl ethyl carbonate in tetrahydrofuran (2 mL). After stirring at 65° C. for 4 h, the solvent is evaporated under vacuum. The residue is purified by chromatography over silica gel, leaving 7-(O-allyl)-$\Delta^{12,13}$iso-baccatin III-13-(4S,5R)-N-Boc-2-(2,4-dimethoxyphenyl)-4-phenyl-5-oxazolidinecarboxylic acid ester.

See: Lakhmiri, R.; Lhoste, P.; Sinou, D. *Tetrahedron Let.* 1989, 30, 4669.

Deprotection of 7-(O-allyl)-$\Delta^{12,13}$-iso-baccatin III-13-(4S,5R)-N-Boc-2-(2,4-dimethoxyphenyl)-4-phenyl-5-oxazolidinecarboxylic acid ester The protected allyl ethers may be deprotected to 7-(O-allyl)-13-(N-Boc-β-phenyl isoserinyl)-$\Delta^{12,13}$-iso-baccatin III in the same manner as 7-(O-methyl)-13-(N-Boc-β-phenyl isoserinyl)-$\Delta^{12,13}$-iso-baccatin III is deprotected in preparation 4.

Following the procedure described in Carboni, J. M.; Farina, V.; Srinivasa, R.; Hauck, S. I.; Horowitz, S. B.; Ringel, I. *J. Med. Chem.* 1993, 36, 513 but using the appropriate starting material of examples 5, 7, 26 and $\Delta^{12,13}$-iso-taxol the following 7-ester $\Delta^{12,13}$-iso-taxol analogs are prepared:

7-acetyl-$\Delta^{12,13}$-iso-taxol;
7-acetyl-$\Delta^{12,13}$-iso-taxotere;
7,10-diacetyl-$\Delta^{12,13}$-iso-taxotere;
N-debenzoyl-N-t-butylaminocarbonyl-7-acetyl-$\Delta^{12,13}$-iso-taxol;
7-propionyl-$\Delta^{12,13}$-iso-taxol;
7-propionyl-$\Delta^{12,13}$-iso-taxotere;
7-propionyl-10-acetyl-$\Delta^{12,13}$-iso-taxotere;
N-debenzoyl-N-t-butylaminocarbonyl-7-propionyl-$\Delta^{12,13}$-iso-taxol;
7-butyryl-$\Delta^{12,13}$-iso-taxol;
7-butyryl-$\Delta^{12,13}$-iso-taxotere;
7-butyryl-10-acetyl-$\Delta^{12,13}$-iso-taxotere;
N-debenzoyl-N-t-butylaminocarbonyl-7-butyryl-$\Delta^{12,13}$-iso-taxol;
7-benzoyl-$\Delta^{12,13}$-iso-taxol;
7-benzoyl-$\Delta^{12,13}$-iso-taxotere;
7-benzoyl-10-acetyl-$\Delta^{12,13}$-iso-taxotere;
N-debenzoyl-N-t-butylaminocarbonyl-7-benzoyl-$\Delta^{12,13}$-iso-taxol;
7-(4-methylbenzoyl)-$\Delta^{12,13}$-iso-taxol;
7-(4-methylbenzoyl)-$\Delta^{12,13}$-iso-taxotere;
7-(4-methylbenzoyl)-10-acetyl-$\Delta^{12,13}$-iso-taxotere; and
N-debenzoyl-N-t-butylaminocarbonyl-7-(4-methylbenzoyl)-$\Delta^{12,13}$-iso-taxol.

Following the procedure described in Denis, J.-N.; Greene, A. E.; Guenard, D.; Gueritte-Vogelein, F.; Mangatal, L.; Potier, P. *J. Am. Chem. Soc.* 1988, 110, 5917 but using the appropriate starting material of examples 5, 7, 26 and $\Delta^{12,13}$-iso-taxol the following 7-silyl ether $\Delta^{12,13}$-iso-taxol analogs are prepared:

7-(O-trimethylsilyl)-$\Delta^{12,13}$-iso-taxol;
7-(O-trimethylsilyl)-$\Delta^{12,13}$-iso-taxotere;
7-(O-trimethylsilyl)-10-diacetyl-$\Delta^{12,13}$-iso-taxotere;
N-debenzoyl-N-t-butylaminocarbonyl-7-(O-trimethylsilyl)-$\Delta^{12,13}$-iso-taxol;
7-(O-triethylsilyl)-$\Delta^{12,13}$-iso-taxol;
7-(O-triethylsilyl)-$\Delta^{12,13}$-iso-taxotere;
7-(O-triethylsilyl)-10-diacetyl-$\Delta^{12,13}$-iso-taxotere;
N-debenzoyl-N-t-butylaminocarbonyl-7-(O-triethylsilyl)-$\Delta^{12,13}$-iso-taxol;
7-(O-triisopropylsilyl)-$\Delta^{12,13}$-iso-taxol;
7-(O-triisopropylsilyl)-$\Delta^{12,13}$-iso-taxotere;
7-(O-triisopropylsilyl)-10-diacetyl-$\Delta^{12,13}$-iso-taxotere;
N-debenzoyl-N-t-butylaminocarbonyl-7-(O-triisopropylsilyl)-$\Delta^{12,13}$-iso-taxol;
7-(O-t-butyldimethylsilyl)-$\Delta^{12,13}$-iso-taxol;
7-(O-t-butyldimethylsilyl)-$\Delta^{12,13}$-iso-taxotere;
7-(O-t-butyldimethylsilyl)-10-diacetyl-$\Delta^{12,13}$-iso-taxotere;
N-debenzoyl-N-t-butylaminocarbonyl-7-(O-t-butyldimethylsilyl)-$\Delta^{12,13}$-iso-taxol;
7-(O-ethoxymethyl)-13-(N-Boc-β-phenyl isoserinyl)-$\Delta^{12,13}$-iso-baccatin III; and
7-(O-ethoxymethyl)-13-(N-(t-butylaminocarbonyl)-β-phenyl isoserinyl)-$\Delta^{12,13}$-iso-baccatin III.

Following the procedure described in Denis, J.-N.; Greene, A. E.; Guenard, D.; Gueritte-Vogelein, F.; Mangatal, L.; Potier, P. *J. Am. Chem. Soc.* 1988, 110, 5917 but using the appropriate starting material of examples 84 and 85 and $\Delta^{12,13}$-10-DAD-iso-taxol 94 the following 7-silyl ether $\Delta^{12,13}$-iso-taxol analogs are prepared:

7-[O-2-(3-methylbutyl)dimethylsilyl]-$\Delta^{12,13}$-iso-taxol;
7-[O-2-(3-methylbutyl)dimethylsilyl]-$\Delta^{12,13}$-iso-taxotere;
7-[O-2-(3-methylbutyl)dimethylsilyl]-10-diacetyl-$\Delta^{12,13}$-iso-taxotere;
N-debenzoyl-N-t-butylaminocarbonyl-7-[O-2-(3-methylbutyl)dimethyl-silyl]-$\Delta^{12,13}$-iso-taxol;
7-(O-tri-n-butylsilyl)-$\Delta^{12,13}$-iso-taxol;
7-(O-tri-n-butylsilyl)-$\Delta^{12,13}$-iso-taxotere;
7-(O-tri-n-butylsilyl)-10-diacetyl-$\Delta^{12,13}$-iso-taxotere;
N-debenzoyl-N-t-butylaminocarbonyl-7-(O-tri-n-butylsilyl)-$\Delta^{12,13}$-iso-taxol;
7-(O-cyclohexyldimethylsilyl)-$\Delta^{12,13}$-iso-taxol;
7-(O-cyclohexyldimethylsilyl)-$\Delta^{12,13}$-iso-taxotere;
7-(O-cyclohexyldimethylsilyl)-10-diacetyl-$\Delta^{12,13}$-iso-taxotere;
N-debenzoyl-N-t-butylaminocarbonyl-7-(O-cyclohexyldimethylsilyl)-$\Delta^{12,13}$-iso-taxol;
7-(O-i-propyldiethylsilyl)-$\Delta^{12,13}$-iso-taxol;
7-(O-i-propyldiethylsilyl)-$\Delta^{12,13}$-iso-taxotere;
7-(O-i-propyldiethylsilyl)-10-diacetyl-$\Delta^{12,13}$-iso-taxotere;
N-debenzoyl-N-t-butylaminocarbonyl-7-(O-i-propyldiethylsilyl)-$\Delta^{12,13}$-iso-taxol;
7-(O-cycloheptyldimethylsilyl)-$\Delta^{12,13}$-iso-taxol;
7-(O-cycloheptyldimethylsilyl)-$\Delta^{12,13}$-iso-taxotere;
7-(O-cycloheptyldimethylsilyl)-10-diacetyl-$\Delta^{12,13}$-iso-taxotere;
N-debenzoyl-N-t-butylaminocarbonyl-7-(O-cycloheptyldimethylsilyl)-$\Delta^{12,13}$-iso-taxol.

Following the procedure described in Denis, J.-N.; Greene, A. E.; Guenard, D.; Gueritte-Vogelein, F.; Mangatal, L.; Potier, P. *J. Am. Chem. Soc.* 1988, 110, 5917 but using the appropriate starting material of examples 84 and 85 and 10-DAB-iso-taxol 94 the following 7-silyl ether taxol analogs are prepared:

7-[O-2-(3-methylbutyl)dimethylsilyl]-taxol;
7-[O-2-(3-methylbutyl)dimethylsilyl]-taxotere;
7-[O-2-(3-methylbutyl)dimethylsilyl]-10-diacetyl-taxotere;
N-debenzoyl-N-t-butylaminocarbonyl-7-[O-2-(3-methylbutyl)dimethyl-silyl]-taxol;
7-(O-tri-n-butylsilyl)-taxol;

7-(O-tri-n-butylsilyl)-taxotere;
7-(O-tri-n-butylsilyl)-10-diacetyl-taxotere;
N-debenzoyl-N-t-butylaminocarbonyl-7-(O-tri-n-butylsilyl)taxol;
7-(O-cyclohexyldimethylsilyl)-taxol;
7-(O-cyclohexyldimethylsilyl)-taxotere;
7-(O-cyclohexyldimethylsilyl)-10-diacetyl-taxotere;
N-debenzoyl-N-t-butylaminocarbonyl-7-(O-cyclohexyldimethyl-silyl)taxol
7-(O-i-propyldiethylsilyl)taxol;
7-(O-i-propyldiethylsilyl)taxotere;
7-(O-i-propyldiethylsilyl)-10-diacetyl-taxotere;
N-debenzoyl-N-t-butylaminocarbonyl-7-(O-i-propyldiethylsilyl)taxol;
7-(O-cycloheptyldimethylsilyl)taxol;
7-(O-cycloheptyldimethylsilyl)taxotere;
7-(O-cycloheptyldimethylsilyl)-10-diacetyl-taxotere;
N-debenzoyl-N-t-butylaminocarbonyl-7-(O-cycloheptyldimethylsilyl)-taxol.

Following the procedure described in Magri, N. F.; Kingston, D. G. I.; Jitrangsri, C.; Piccariello, T. *J. Org. Chem.* 1986, 51, 3239 but using the appropriate starting material of examples 5, 7, 26 and $\Delta^{12,13}$-iso-taxol the following 7-carbonate $\Delta^{12,13}$-iso-taxol analogs are prepared:
7-(O-methylcarbonate)-$\Delta^{12,13}$-iso-taxol;
7-(O-methylcarbonate)-$\Delta^{12,13}$-iso-taxotere;
7-(O-methylcarbonate)-10-acetyl-$\Delta^{12,13}$-iso-taxotere;
N-debenzoyl-N-t-butylaminocarbonyl-7-(O-methylcarbonate)-$\Delta^{12,13}$-iso-taxol;
7-(O-ethylcarbonate)-$\Delta^{12,13}$-iso-taxol;
7-(O-ethylcarbonate)-$\Delta^{12,13}$-iso-taxotere;
7-(O-ethylcarbonate)-10-acetyl-$\Delta^{12,13}$-iso-taxotere;
N-debenzoyl-N-t-butylaminocarbonyl-7-(O-ethylcarbonate)-$\Delta^{12,13}$-iso-taxol;
7-(O-propylcarbonate)-$\Delta^{12,13}$-iso-taxol;
7-(O-propylcarbonate)-$\Delta^{12,13}$-iso-taxotere;
7-(O-propylcarbonate)-10-acetyl-$\Delta^{12,13}$-iso-taxotere;
N-debenzoyl-N-t-butylaminocarbonyl-7-(O-propylcarbonate)-$\Delta^{12,13}$-iso-taxol;
7-[O-(2,2,2-trichloroethyl)carbonate]-$\Delta^{12,13}$-iso-taxol;
7-[O-(2,2,2-trichloroethyl)carbonate]-$\Delta^{12,13}$-iso-taxotere;
7-[O-(2,2,2-trichloroethyl)carbonate]-10-acetyl-$\Delta^{12,13}$-iso-taxotere;
N-debenzoyl-N-t-butylaminocarbonyl-7-[O-(2,2,2-trichloroethyl)carbonate]-$\Delta^{12,13}$-iso-taxol;
7-[O-(2,2-dichloroethyl)carbonate]-$\Delta^{12,13}$-iso-taxol;
7-[O-(2,2-dichloroethyl)carbonate]-$\Delta^{12,13}$-iso-taxotere;
7-[O-(2,2-dichloroethyl)carbonate]-10-acetyl-$\Delta^{12,13}$-iso-taxotere;
N-debenzoyl-N-t-butylaminocarbonyl-7-[O-(2,2-dichloroethyl)carbonate]-$\Delta^{12,13}$-iso-taxol;
7-[O-(2-chloroethyl)carbonate]-$\Delta^{12,13}$-iso-taxol;
7-[O-(2-chloroethyl)carbonate]-$\Delta^{12,13}$-iso-taxotere;
7-[O-(2-chloroethyl)carbonate]-10-acetyl-$\Delta^{12,13}$-iso-taxotere; and
N-debenzoyl-N-t-butylaminocarbonyl-7-[O-(2-chloroethyl)carbonate]-$^{12,13}$-iso-taxol.

Following the procedure described in EP 524 093 A1 but using the appropriate starting material of examples 5, 7, 26 and $\Delta^{12,13}$-iso-taxol the following 7-carbamate $\Delta^{12,13}$-iso-taxol analogs are prepared:
7-[O-(N-methyl)carbamate]-$\Delta^{12,13}$-iso-taxol;
7-[O-(N-methyl)carbamate]-$\Delta^{12,13}$-iso-taxotere;
7-[O-(N-methyl)carbamate]-10-acetyl-$\Delta^{12,13}$-iso-taxotere;
N-debenzoyl-N-t-butylaminocarbonyl-7-[O-(N-methyl)carbamate]-$\Delta^{12,13}$-iso-taxol;
7-[O-(N,N-dimethyl)carbamate]-$\Delta^{12,13}$-iso-taxol;
7-[O-(N,N-dimethyl)carbamate]-$\Delta^{12,13}$-iso-taxotere;
7-[O-(N,N-dimethyl)carbamate]-10-acetyl-$\Delta^{12,13}$-iso-taxotere;
N-debenzoyl-N-t-butylaminocarbonyl-7-[O-(N,N-dimethyl)carbamate]-$\Delta^{12,13}$-iso-taxol;
7-[O-(N-ethyl)carbamate]-$\Delta^{12,13}$-iso-taxol;
7-[O-(N-ethyl)carbamate]-$\Delta^{12,13}$-iso-taxotere;
7-[O-(N-ethyl)carbamate]-10-acetyl-$\Delta^{12,13}$-iso-taxotere;
N-debenzoyl-N-t-butylaminocarbonyl-7-[O-(N-ethyl)carbamate]-$\Delta^{12,13}$-iso-taxol;
7-(O-morpholinocarbonyl)-$\Delta^{12,13}$-iso-taxol;
7-(O-morpholinocarbonyl)-$\Delta^{12,13}$-iso-taxotere;
7-(O-morpholinocarbonyl)-10-acetyl-$\Delta^{12,13}$-iso-taxotere; and
N-debenzoyl-N-t-butylaminocarbonyl-7-(O-morpholinocarbonyl)-$\Delta^{12,13}$-iso-taxol.

Following the procedure described in examples 36 and 38 but using the appropriate starting material of examples 5, 7, 26 and $\Delta^{12,13}$-iso-taxol the following 7-carbamate $\Delta^{12,13}$-iso-taxol analogs are prepared:
7-(O-methyl)-13-(N-Boc-β-phenyl isoserinyl)-$\Delta^{12,13}$-iso-baccatin III;
7-(O-methyl)-13-(N-(t-butylaminocarbonyl)-β-phenyl isoserinyl)-$\Delta^{12,13}$-iso-baccatin III;
7-(O-ethyl)-13-(N-Boc-β-phenyl isoserinyl)-$\Delta^{12,13}$-iso-baccatin III;
7-(O-ethyl)-13-(N-(t-butylaminocarbonyl)-β-phenyl isoserinyl)-$\Delta^{12,13}$-iso-baccatin III;
7-(O-propyl)-13-(N-Boc-β-phenyl isoserinyl)-$\Delta^{12,13}$-iso-baccatin III;
7-(O-propyl)-13-(N-(t-butylaminocarbonyl)-β-phenyl isoserinyl)-$\Delta^{12,13}$-iso-baccatin III;
7-(O-allyl)-13-(N-Boc-β-phenyl isoserinyl)-$\Delta^{12,13}$-iso-baccatin III;
7-(O-allyl)-13-(N-(t-butylaminocarbonyl)-β-phenyl isoserinyl)-$\Delta^{12,13}$-iso-baccatin III;
7-(O-benzyl)-13-(N-Boc-β-phenyl isoserinyl)-$\Delta^{12,13}$-iso-baccatin III;
7-(O-benzyl)-13-(N-(t-butylaminocarbonyl)-β-phenyl isoserinyl)-$\Delta^{12,13}$-iso-baccatin III;
7-(O-methoxymethyl)-13-(N-Boc-β-phenyl isoserinyl)-$\Delta^{12,13}$-iso-baccatin III;
7-(O-methoxymethyl)-13-(N-(t-butylaminocarbonyl)-β-phenyl isoserinyl)-$\Delta^{12,13}$-iso-baccatin III;
7-(O-methoxyethoxymethyl)-13-(N-Boc-β-phenyl isoserinyl)-$\Delta^{12,13}$-iso-baccatin III;
7-(O-methoxyethoxymethyl)-13-(N-(t-butylaminocarbonyl)-β-phenyl isoserinyl)-$\Delta^{12,13}$-iso-baccatin III;
7-(O-benzyloxymethyl)-13-(N-Boc-β-phenyl isoserinyl)-$\Delta^{12,13}$-iso-baccatin III;
7-(O-benzyloxymethyl)-13-(N-(t-butylaminocarbonyl)-β-phenylisoserinyl)-$\Delta^{12,13}$-iso-baccatin III;
7-[O-(2,2,2-trichloroethoxy)methyl]-13-(N-Boc-β-phenyl isoserinyl)-$\Delta^{12,13}$-iso-baccatin III;
7-[O-(2,2,2-trichloroethoxy)methyl]-13-(N-(t-butylaminocarbonyl)-β-phenylisoserinyl)-$\Delta^{12,13}$-iso-baccatin III;
7-[O-(2,2,2-trichloroethoxy)methoxymethyl]-13-(N-Boc-β-phenyl isoserinyl)-$\Delta^{12,13}$-iso-baccatin III; and
7-[O-(2,2,2-trichloroethoxy)methoxymethyl]-13-(N-(t-butylaminocarbonyl)-β-phenyl isoserinyl)-$\Delta^{12,13}$-iso-baccatin III.

Taxol and the other starting taxol analogs are known or can be readily prepared by known methods. See The Chemistry of Taxol, Pharmac. Ther., Vol 52, pp 1–34, 1991 as well as:

U.S. Pat. Nos. 4,814,470; 4,857,653; 4,942,184; 4,924,011; 4,924,012; 4,960,790; 5,015,744; 5,059,699; 5,136,

060; 5,157,049; 4,876,399; 5,227,400, 5,254,580 as well as PCT Publication No. WO 92/09589, European Patent Application 90305845.1 (Publication No. A2 0 400 971), 89400935.6 (Publication No. A1 0 366 841) and 90402333.0 (Publication No. 0 414 610 A1), 87401669.4 (A1 0 253 739), 92308608.6 (A1 0 534 708), 92308609.4 (A1 534 709), and PCT Publication Nos. WO 91/17977, WO 91/17976, WO 91/13066, WO 91/13053 all of which are incorporated herein by reference.

The compounds of the invention can be formulated per se in pharmaceutical preparations or formulated in the form of pharmaceutically acceptable salts thereof, particularly as nontoxic pharmaceutically acceptable addition salts or acceptable basic salts. These salts can be prepared from those compounds of the invention which contain acidic or basic groups according to conventional chemical methods.

Normally, the salts are prepared by reacting the free base or acid with stoichiometric amounts or with an excess thereof of the desired salt forming inorganic or organic acid in a suitable solvent or various combination of solvents. As an example, the free base can be dissolved in an aqueous solution of the appropriate acid and the salt recovered by standard techniques, for example, by evaporation of the solution. Alternatively, the free base can be dissolved in an organic solvent such as a lower alkanoyl, an ether, an alkyl ester, or mixtures thereof, for example, methanol, ethanol, ether, ethylacetate, an ethylacetate-ether solution, and the like, whereafter it is treated with the appropriate acid to form the corresponding salt. The salt is recovered by standard recovery techniques, for example, by filtration of the desired salt on spontaneous separation from the solution or it can be precipitated by the addition of a solvent in which the salt is insoluble and recovered therefrom.

The taxol derivatives of the invention can be utilized in the treatment of cancers, due to their cytotoxic, antitumor activity. In addition the taxol derivatives of the present invention can be utilized in the treatment of arthritis, in particular rheumatoid arthritis, see Arthritis & Rheumatism, 32, 839, 1994 and Nature, 368, 757 (1994) which are incorporated herein by reference. In addition the taxol derivatives of the present invention can be utilized in preventing the restenosis of arteries following angioplasty.

The new compounds are administrable in the form of tablets, pills, powder mixtures, capsules, injectables, solutions, suppositories, emulsions, dispersions, food premix, and in other suitable form. The pharmaceutical preparation which contains the compound is conveniently admixed with a nontoxic pharmaceutical organic carrier or a nontoxic pharmaceutical inorganic carrier, usually about 0.01 mg up to 2500 mg, or higher per dosage unit, preferably 50–500 mg. Typical of pharmaceutically acceptable carriers are, for example, mannitol, urea, dextrans, lactose, potato and maize starches, magnesium stearate, talc, vegetable oils, polyalkylene glycols, ethyl cellulose, poly (vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

Exemplary of a typical method for preparing a tablet containing the active agents is to first mix the agent with a nontoxic binder such as gelatin, acacia mucilage, ethyl cellulose, or the like. The mixing is suitably carried out in a standard V-blender and usually under anhydrous conditions. Next, the just prepared mixture can be slugged through conventional tablet machines and the slugs fabricated into tablets. The freshly prepared tablets can be coated, or they can be left uncoated. Representative of suitable coatings are the nontoxic coatings including shellac, methylcellulose, carnauba wax, styrene-maleic acid copolymers, and the like. For oral administration, compressed tablets containing 0.01 milligram, 5 milligrams, 25 milligrams, 50 milligrams, 500 milligrams, etc., up to 2500 milligrams are manufactured in the light of the above disclosure and by art known fabrication techniques well known to the art and set forth in Remington's Pharmaceutical Science, Chapter 39, Mack Publishing Co., 1965.

To formulate the tablet, the active compound, cornstarch, lactose, dicalcium phosphate and calcium carbonate are uniformly blended under dry conditions in a conventional V-blender until all the ingredients are uniformly mixed together. Next, the cornstarch paste is prepared as a 10% paste and it is blended with the just prepared mixture until a uniform mixture is obtained. The mixture is then passed through a standard light mesh screen, dried in an anhydrous atmosphere and then blended with calcium stearate, and compressed into tablets, and coated if desired. Other tablets containing 10, 50, 100, 150 mgs, etc., are prepared in a like fashion.

The following Formulation I is an example of a tablet formulation comprising a compound of the invention.

| FORMULATION I | |
|---|---|
| Ingredients: | Per tablet, mg. |
| Active compound | 50.0 |
| Cornstarch | 15.0 |
| Cornstarch paste | 4.5 |
| Calcium carbonate | 15.0 |
| Lactose | 67.0 |
| Calcium stearate | 2.0 |
| Dicalcium phosphate | 50.0 |

The manufacture of capsules containing 10 milligrams to 2500 milligrams for oral use consists essentially of mixing the active compound with a nontoxic carrier and enclosing the mixture in a polymeric sheath, usually gelatin or the like. The capsules can be in the art known soft form of a capsule made by enclosing the compound in intimate dispersion within an edible, compatible carrier, or the capsule can be a hard capsule consisting essentially of the novel compound mixed with a nontoxic solid such as talc, calcium stearate, calcium carbonate, or the like. Capsules containing 25 mg, 75 mg, 125 mg, and the like, of the novel compound, singularly or mixtures of two or more of the novel compounds are prepared, for example, as follows:

| FORMULATION II | |
|---|---|
| Ingredients | Per Capsule, mg. |
| Active compound | 50.0 |
| Calcium carbonate | 100.0 |
| Lactose, U.S.P. | 200.0 |
| Starch | 130.0 |
| Magnesium stearate | 4.5 |

The above ingredients are blended together in a standard blender and then discharged into commercially available capsules. When higher concentrations of the active agent is used, a corresponding reduction is made in the amount of lactose. The compounds of the invention can also be freeze dried and, if desired, combined with other pharmaceutically acceptable excipients to prepare formulations suitable for parenteral, injectable administration. For such administration, the formulation can be reconstituted in water (normal, saline), or a mixture of water and an organic solvent, such as propylene glycol, ethanol, and the like.

The dose administered, whether a single dose, multiple dose, or a daily dose, will of course, vary with the particular compound of the invention employed because of the varying potency of the compound, the chosen route of administration, the size of the recipient and the nature of the patient's condition. The dosage administered is not subject to definite bounds, but it will usually be an effective amount, or the equivalent on a molar basis of the pharmacologically active free form produced from a dosage formulation upon the metabolic release of the active drug to achieve its desired pharmacological and physiological effects.

Typically the compounds of the invention can be administered by intravenous injection at doses of 1–500 mg per patient per course of cancer treatment, preferable with doses of 20–200 mg, the exact dosage being dependent on the age, weight, and condition of the patient. An example of a suitable formulation for injection is using a solution of the compound of the invention in a mixture of polysorbate alcohol and dehydrated alcohol (e.g., 1:1) followed by dilution with 5% dextrose in water prior to infusion or injection.

Typically the compounds of the invention can be administered by oral administration at doses of 1–500 mg per patient per course of cancer treatment, preferable with doses of 20–600 mg, the exact dosage being dependent on the age, weight, and condition of the patient.

The compounds of Formula I (including II, IIa, III, IIIa, IV, IVa, V, Va, and VI) are useful for the same cancers for which taxol has been shown active, including human ovarian tumors, mammary tumors, and malignant melanoma, lung tumors, gastric tumors, colon tumors, head and neck tumors, and leukemia. See, e.g., the clinical pharmacology of taxol is reviewed by Eric K. Rowinsky and Ross C. Donehower, The Clinical Pharmacology and Use of Anti-microtubule Agents in Cancer Chemotherapeutics, Pharmac. Ther., Vol 52, pp 35–84, 1991. Clinical and preclinical studies with taxol are reviewed by William J. Slichenmyer and Daniel D. Von Hoff, Taxol: A New and Effective Anti-cancer Drug, Anti-Cancer Drugs, Vol. 2, pp 519–530, 1991.

The biological activity of the 7-deoxy-7β,8β-methano-iso-taxol compounds (Formula II) of the invention has been confirmed using well known procedures. For example, comparison of the cytotoxicity of Cpd 17 with taxol itself in L1210 mouse leukemia carcinoma cells in culture indicated that the $IC_{90}$ (90% growth inhibitory concentration) for 7-deoxy-7β,8β-methano-iso-taxol was 0.017 micrograms/ml and for taxol was 0.018 micrograms/ml. In an in vitro tubulin polymerization assay, conducted after the manner of F. Gaskin, et al., *J. Mol. Biol.*, 89:737, 1974, 7-deoxy-7β,8β-methano-taxol was able to induce tubulin polymerization in vitro at 20° C. in a manner very similar to taxol.

The biological activity of 7-deoxy-7-halo-iso-taxol compounds (Formula III) of the invention has been confirmed using well known procedures. For example, comparison of the cytotoxicity of Cpd 16 with taxol itself in A2780 (human ovarian carcinoma) cells in culture indicated that the $IC_{90}$ (90% growth inhibitory concentration) for 7-deoxy-7-fluoro-$\Delta^{12,13}$-iso-taxol was 0.0029 micrograms/ml and for taxol was 0.017 micrograms/ml.

The biological activity of the compounds of this invention has been further confirmed using well known procedures against A2780 human ovarian carcinoma and the results set forth in Table II. The results were obtained using standard well known procedure (Perez, R. P.; O'Dwyer, P. J.; Handel, L. M.; Ozols, R. F.; Hamilton, T. C. Int. J. Cancer 1991, 48, 265, Alley, M. C.; Scudiero, D. A.; Monks, A.; Hursey, M. L.; Czerwinski, M. J.; Fine, D. L. et al.; Cancer Res. 1988, 48:589).

The biological activity of the compounds of this invention has been further confirmed using well known procedures against L1210 leukemia and the results set forth in Table I. The results were obtained using standard well known procedure (Li, L. H.; Kuentzel, S. L.; Murch, L. L.; Pschigoga, L. M.; and W. C. Krueger, "Comparative biological and biochemical effects of nogalamycin and its analogs on L1210 leukemia," Cancer Res. 39:4816–4822 (1979)). The results are expressed as an $IC_{50}$ which is the drug concentration required to inhibit cell proliferation to 50% of that of untreated control cells. Lower numbers indicated greater activity.

It is well known that many human tumors are resistant to chemotherapeutic agents due to a phenomenon called multidrug resistance (MDR). Cells that are multidrug resistant are resistant to a wide variety of drugs including taxol, taxotere and other chemotherapeutic agents such as doxorubicin, vinblastine and etoposide. This multidrug resistance undoubtedly contributes to the limited success of some therapeutic agents including taxol and taxotere. Therefore, development of a taxol or taxotere analog that could circumvent this multidrug resistance, and could kill multidrug resistant (MDR) cells more efficiently than taxol or taxotere would be expected to provide a better efficacy against multidrug resistant tumors in the clinic. Several of the compounds described in this patent have been tested for their ability to circumvent multidrug resistance and kill multidrug resistant cells.

An in vitro assay to compare the killing ability of taxol analogs on the non-multidrug resistant (non-MDR) cell line, KB-3-1 as compared to the MDR cell line, KB-V1, by taxol analogs (Shen et al., 1986, J. Biol. Chem. 261:7762; Mossman, T. J., 1983, Immunol. Methods 65:55–63; Abraham et al., 1994, Cancer Res. 54:5889). KB-V1 expresses high levels of the drug efflux pump, P-glycoprotein (p170) (Shen et al., 1986, ibid.) has been used. This overexpression of the P-glycoprotein pump is thought to be the major source of the drug resistance in these cells (Endicott and Ling, 1989, Ann. Rev. Biochem. 58:137). The assays were performed in order to assess whether any of the analogs can bypass the P-glycoprotein drug efflux pump and can kill cells that are multidrug resistant. The IC50 (inhibiting dose) for KB-3-1 and KB-V1 was determined and the ratio of the IC50 for KB-V1 to that of KB-3-1 was also presented. IC50 measures the amount of drug required to kill 50% of the cells. A large ratio (IC50 KB-V1/IC50 KB-3-1) shows that a high concentration of the test compound is required to kill resistant cells as compared to the amount required to kill the drug sensitive cells. Compounds with large ratios do not efficiently circumvent the drug resistance mechanism in the resistant cells. On the other hand, compounds with small ratios are effective at killing both the resistant and sensitive cells and require much smaller increases in drug to kill the resistant cells, as compared to the sensitive cells.

A compound with a lower ratio, therefore, would present an advantage in cancer treatment by allowing the more effective killing of multidrug resistant cells.

The ratios obtained are indicated in the table below and ranged from 20 to $5 \times 10^5$. The compounds with lower ratios that more effectively kill drug resistant cells include Compound 7, Compound 17, Compound 18, Compound 38, and Compound 6; ratios ranged from 34 to 300. As a comparison, taxol and taxotere are very ineffective at overcoming resistance, with an average ratio of 7,570. Several of the tested compounds were also more effective than taxol or taxotere in retarding growth of a multidrug resistant tumor implanted in mice. These results suggest that these new taxol analogs may be more effective in killing resistant tumor cells in cancer patients than taxotere and could establish a new therapeutic niche for these analogs.

In using compounds of Formula I for use in angioplasty, an oral route of administration is one method of their systemic administration. Alternatively, however, these compounds may be administered by other convenient routes of administration whereby systemic activity is obtained.

The patient or animal being treated must be given periodic doses of the drug in amounts effective in preventing arterial occlusion in vascular trauma associated with coronary by-pass grafts, vascular surgery, restenosis following successful percutaneous transluminal coronary angioplasty (PTCA) or organ transplantation.

Such effective dosages are readily determined by methods known in the art. Dosages may be administered orally, parenterally, or by local administration to the site of vascular injury by a catheter. Daily dosing of drug (0.01–200 mg/kg) may be administered initially with higher succeeding doses as tolerated. While the preferred dosage regimen is with single daily dosing in patients either by the oral or parenteral route, smaller locally acting doses either by the oral or parenteral route, smaller locally acting doses (1 ng/kg–1 mg/kg) may be administered at the time of the vascular intervention via local catheter installation or infusion in proper formulation.

While the preferred dosage regimen is with single daily dosing of patients, also preferred for obtaining more uniform serum levels of drug are multiple dosages per day (e.g., up to 4–6 times daily). Accordingly, when 4 daily doses of drug are to be administered, each such dose may be about 50 mg/kg per patient per dose, or higher depending on tolerance.

Similar doses are employed in hon-human mammals, e.g. 0.01–200 mg/kg/day.

TABLE I

| Compound | L1210 (IC$_{50}$ µg/ml) |
|---|---|
| taxol | 0.017 |
| taxotere | 0.004 |
| 6 | >0.1 |
| 7 | 0.0046 |
| 8 | 0.0059 |
| 12 | 0.011 |
| 14 | 0.012 |
| 15 | 0.0066 |
| 16 | 0.0029 |
| 17 | 0.0018 |
| 18 | 0.0022 |
| 32a | 0.070 |
| 32b | 0.0053 |
| 41 | 0.0007 |
| 43 | 0.0014 |

TABLE II

| COMPOUND | A2780 (IC$_{50}$ µg/ml) |
|---|---|
| taxol | 0.002–0.003 |
| taxotere | 0.001–0.0016 |
| 64 | 0.0029 |
| 66 | 0.00026 |
| 67 | 0.00042 |

TABLE II-continued

| COMPOUND | A2780 (IC$_{50}$ µg/ml) |
|---|---|
| 72 | 0.0004 |
| 73 | 0.00039 |

TABLE III

Ability of compounds to kill KB-V-1 multidrug resistant cells and KB-3-1 drug sensitive cells

| cpd no. | KB-3-1 (IC50; nM) | KB-V1 (IC50; nM) | Ratio: KBV-1/ KB-3-1 |
|---|---|---|---|
| taxol | 1.3 | 15000 | 11,538 |
| Taxotere | 0.25 | 1700 | 7,570 |
| Cpd 36 | 0.050 | 360 | 11,400 |
| Cpd 67 | 0.00075 | 140 | 5.7 × 10$^5$ |
| Cpd 7 | 0.20 | 40 | 228 |
| Cpd 18 | 0.20 | 6.2 | 34 |
| Cpd 17 | 0.22 | 13 | 61 |
| Cpd 66 | 0.00014 | 0.046 | 300 |
| Cpd 41 | 0.011 | 0.77 | 170 |
| Cpd 32b | 0.081 | 1100 | 17,650 |
| Cpd 38 | 0.078 | 360 | 4,800 |
| Cpd 43 | 0.00057 | 120 | 2.5 × 10$^5$ |

CHART 1

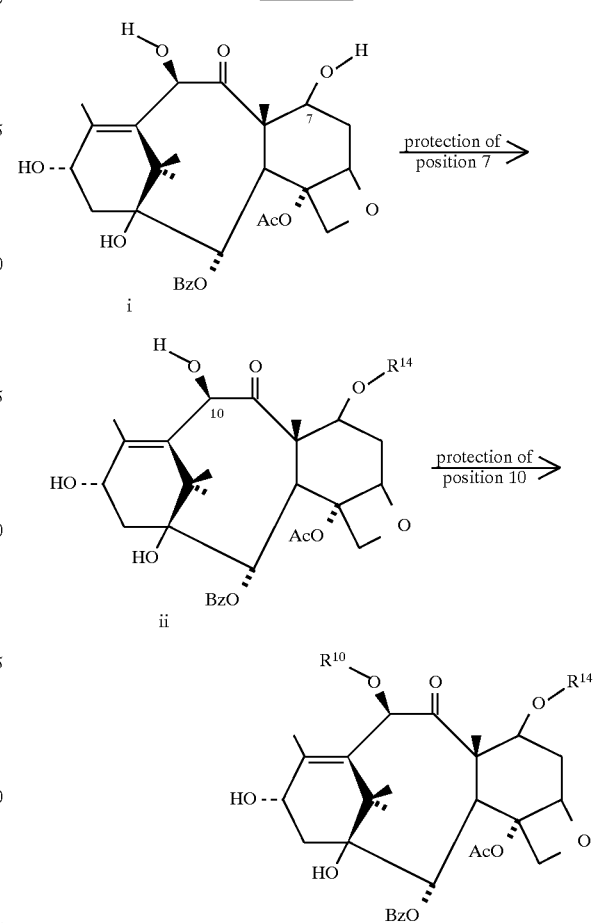

107

Where $R^{10}$ is —C(O)CH$_3$ and $R^{14}$ is —C(O)C$_1$–C$_6$alkyl, —C(O)OC$_1$–C$_6$alkyl (preferably t-butyl), —C(O)OCH$_2$CX$_3$ where X is Halo, —OC(O)OCH$_2$CH$_2$Si(R$_{20}$)$_3$ (where R$_{20}$ is C$_1$–C$_6$alkyl), or —Si(R$_{16}$)$_3$.

CHART 2

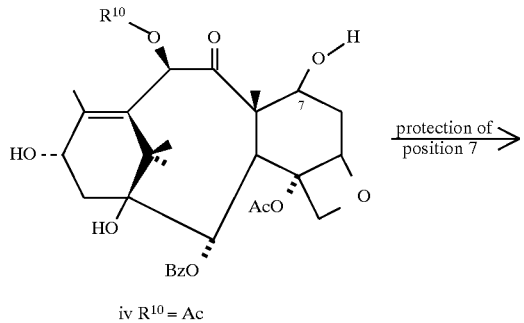

iv R$^{10}$ = Ac protection of position 7

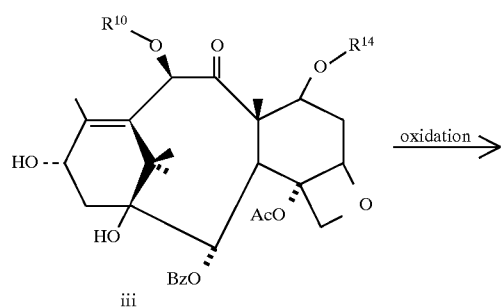

iii oxidation

108

-continued

CHART 2

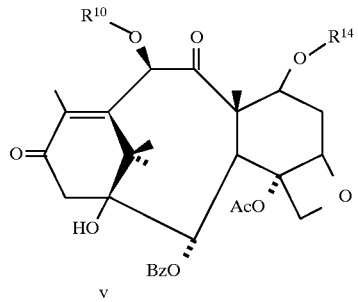

v

Where $R^{10}$ is —C(O)CH$_3$ and $R^{14}$ is —C(O)C$_1$–C$_6$alkyl, —C(O)OC$_1$–C$_6$alkyl (preferably t-butyl), —C(O)OCH$_2$CX$_3$ where X is Halo, —OC(O)OCH$_2$CH$_2$Si(R$_{20}$)$_3$ (where R$_{20}$ is C$_1$–C$_6$alkyl), or —Si(R$_{16}$)$_3$.

CHART 3

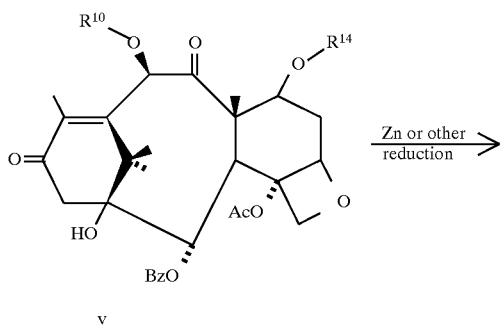

v

Zn or other reduction

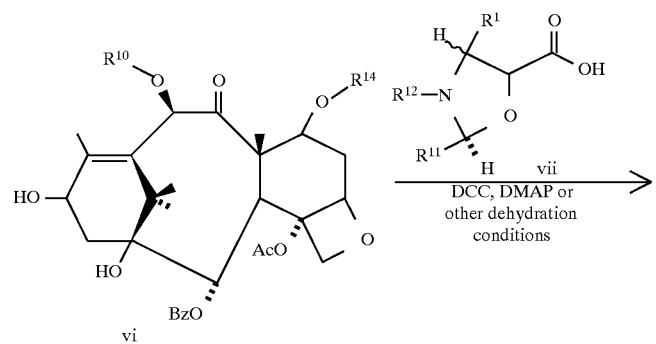

vi

DCC, DMAP or other dehydration conditions

-continued
CHART 3
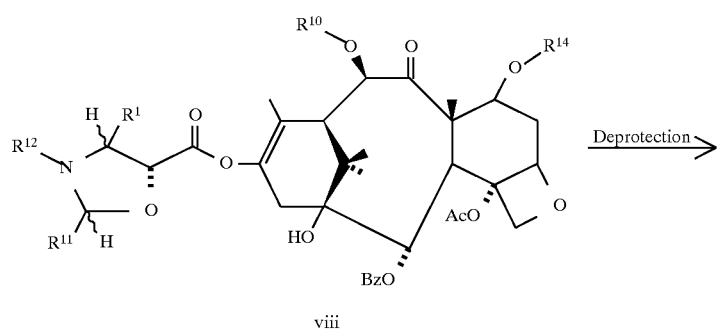
viii
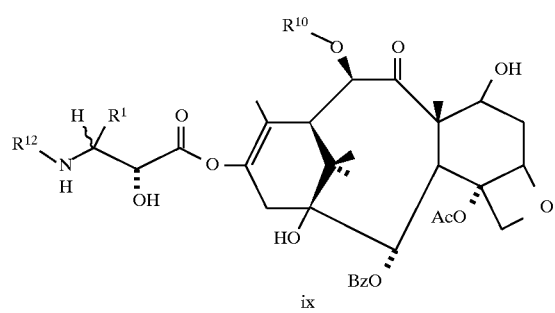
ix
CHART 4
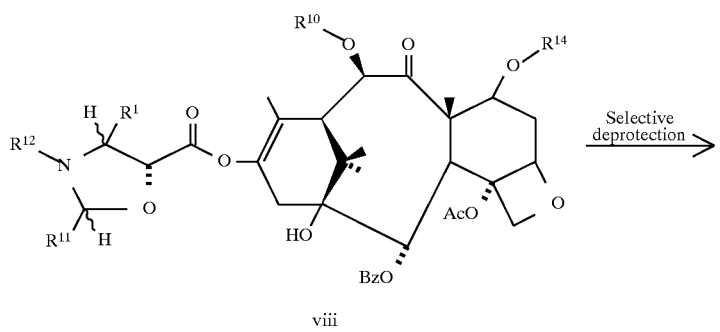
viii
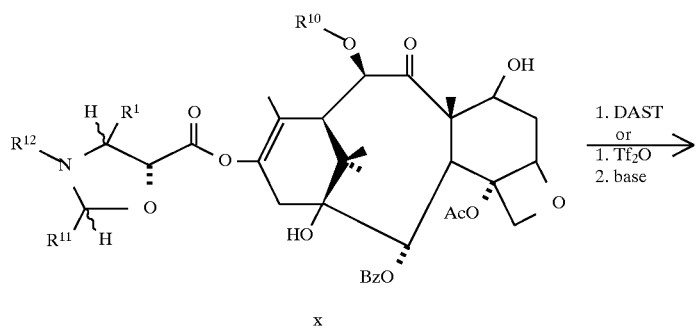
x -continued
CHART 4
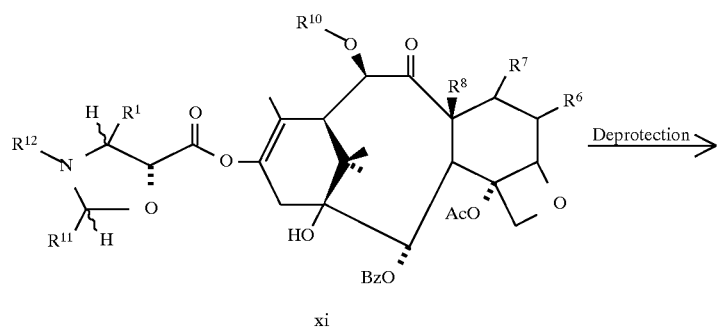
xi
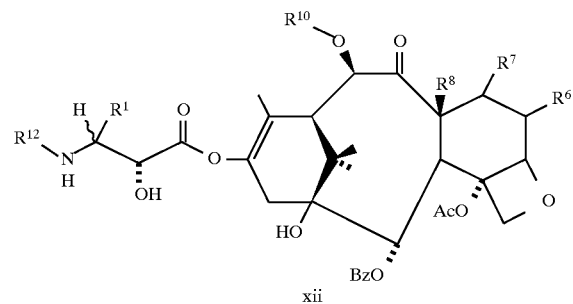
xii
CHART 5
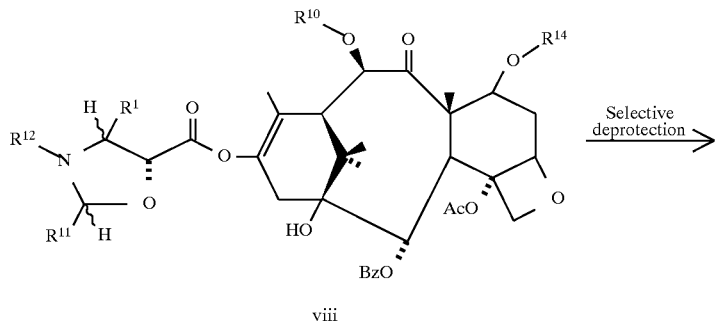
viii
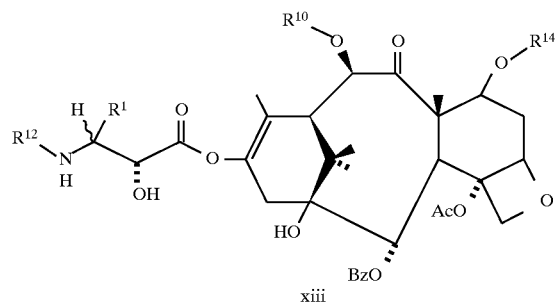
xiii

CHART 6

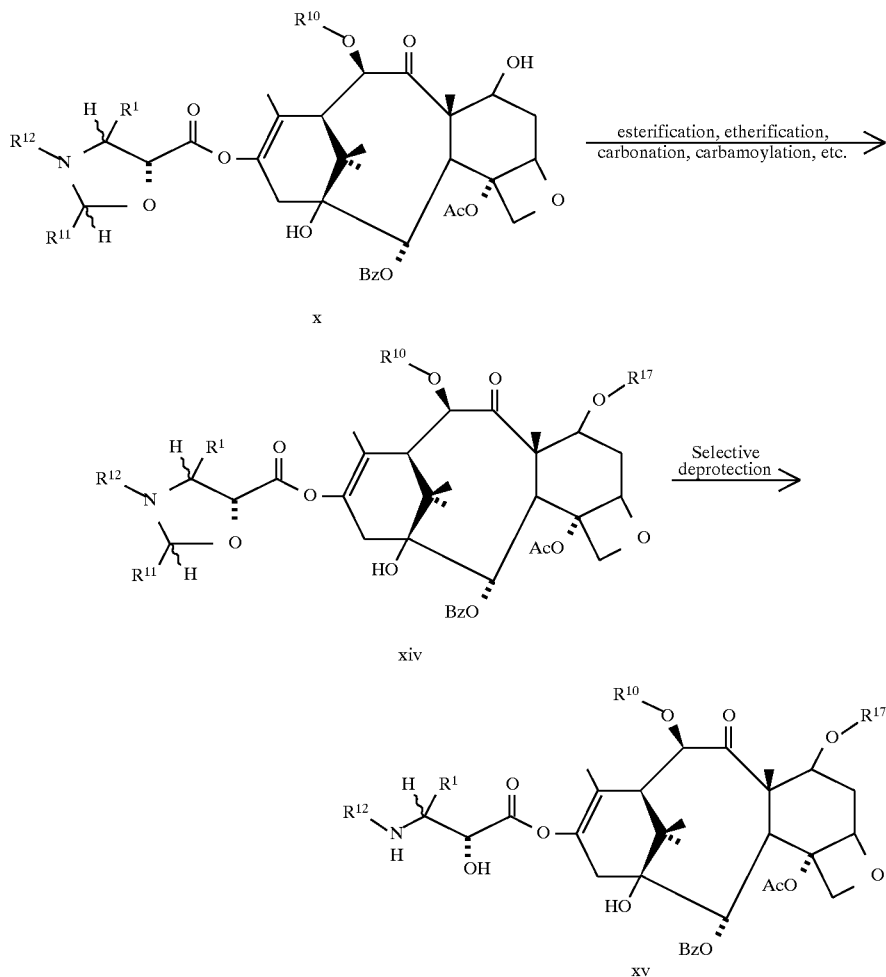

Where $R^{17}$ is —$C_1$–$C_6$alkyl, —$C_3$–$C_6$ycloalkyl, —$(CH_2)_n$phenyl where n is 1–6, —C(O)$C_1$–$C_{10}$alkyl, —C(O)phenyl, —C(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —C(O)naphthyl, —C(O)naphthyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —C(O)Ophenyl, —C(O)Ophenyl substituted with one, 2 or 3 $C_1$–$C_4$ alkyl, $C_1$–$C_3$ alkoxy, halo,

CHART 6 (cont.)

$C_1$–$C_3$ alkylthio, trifluoromethyl, $C_2$–$C_6$ dialkylamino, or nitro, —C(O)Onaphthyl, —C(O)Onaphthyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —C(O)O$C_1$–$C_{10}$alkyl, —C(O)NH$C_1$–$C_{10}$alkyl, —C(O)NHphenyl, —C(O)NHphenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —C(O)NHnaphthyl, —O—C(O)NHnaphthyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —C(O))$CH_2$CHCH$Cl_2$, —C(O)O$CH_2$C$Cl_3$, —Si$R^{16}$ (where $R^{16}$ is $C_1$–$C_6$alkyl or cyclo ($C_5$–$C_8$) alkyl, with the proviso that at least two $R_{16}$ moieties are $C_1$–$C_6$alkyl], —$CH_2$—O—$C_1$–$C_6$alkyl, —$CH_2$—O—$(CH_2)_n$phenyl where $_n$ is 1–3, —$CH_2$—O—$(CH_2)_n$phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro and where $_n$ is 1–3, —$CH_2$—O—$CH_2$—$CX_qH_{3-q}$ where q=0–3 and X is halogen.

CHART 7

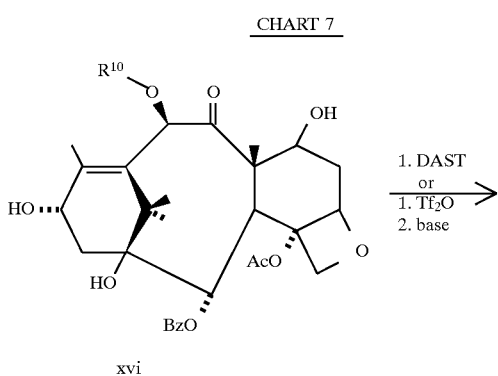

CHART 7 -continued
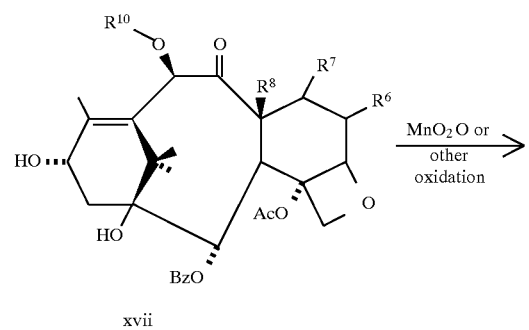
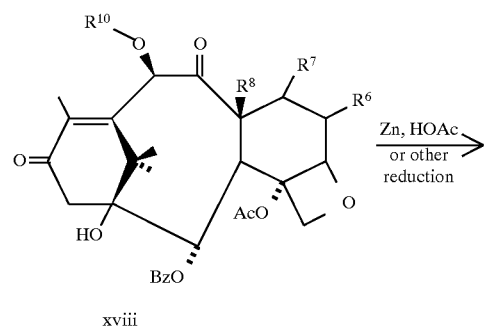
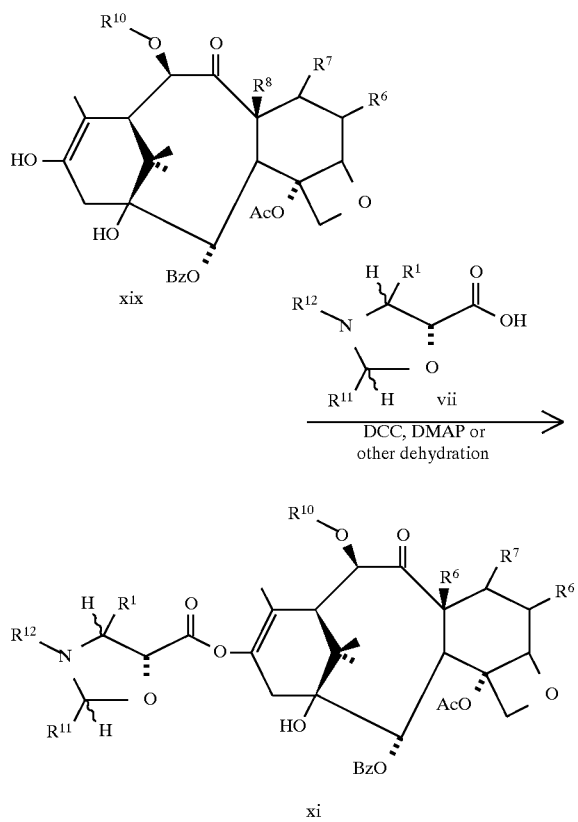
CHART 8
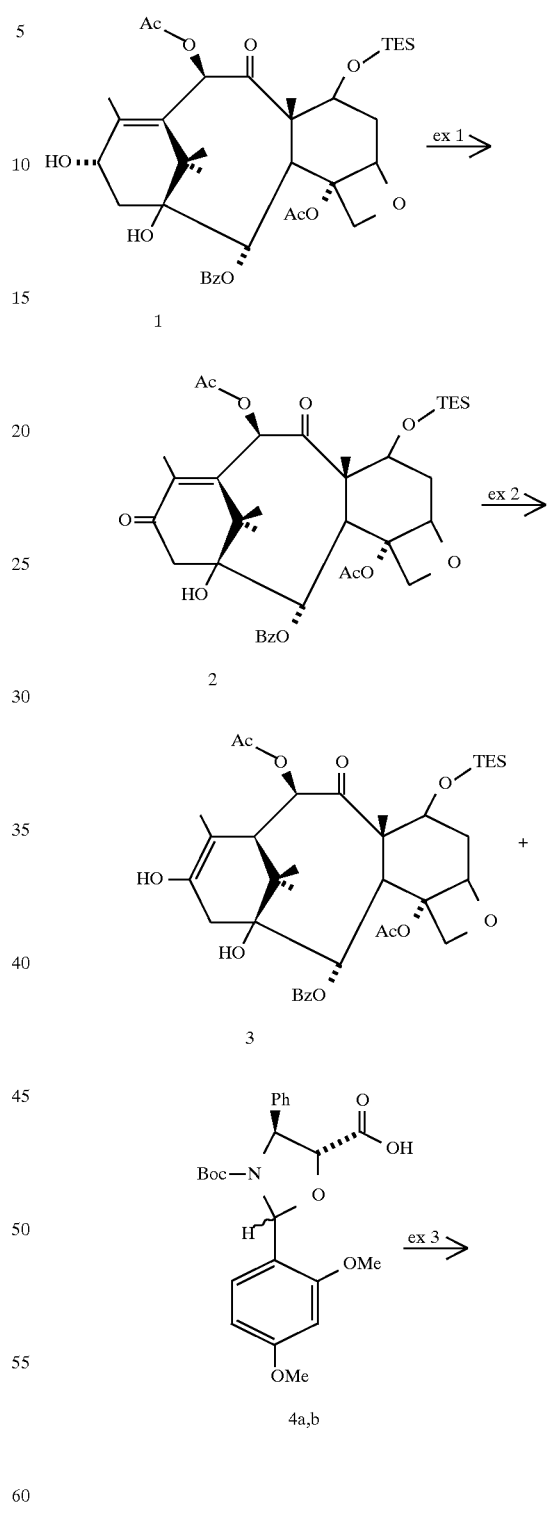

CHART 8
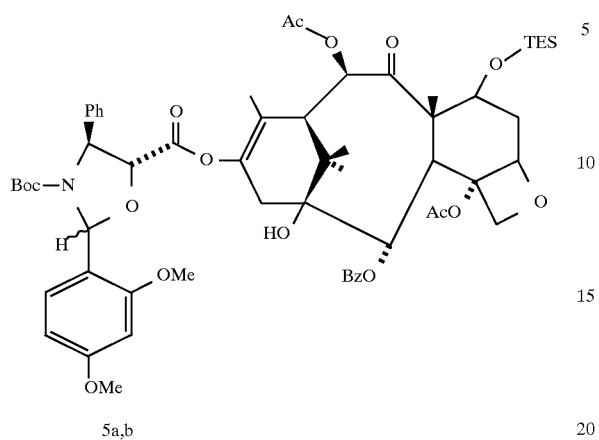
5a,b
CHART 9
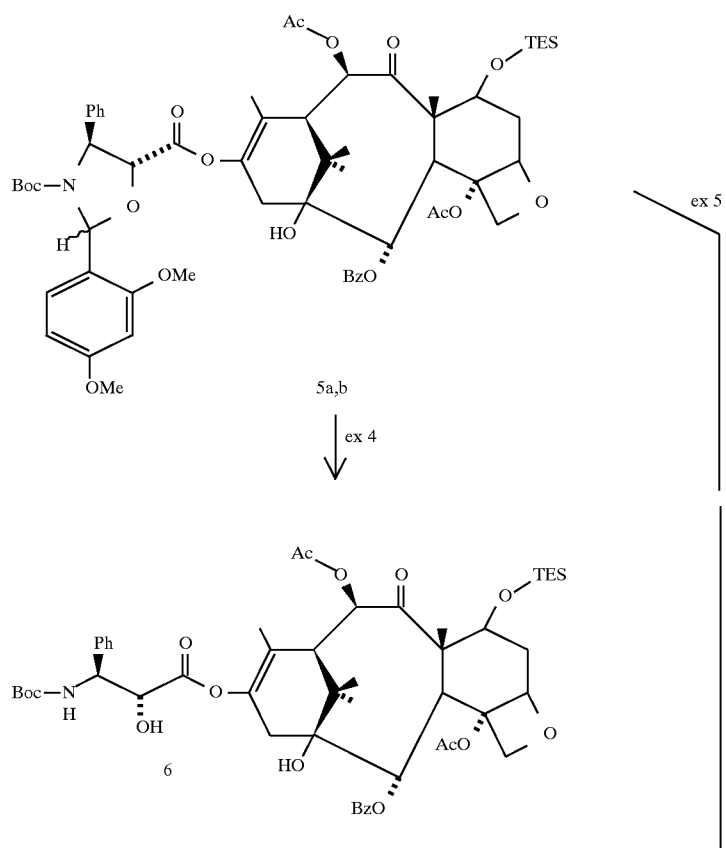

-continued
CHART 9
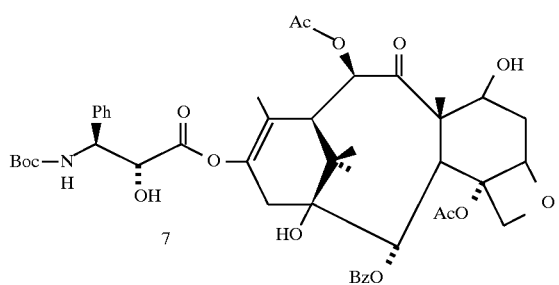
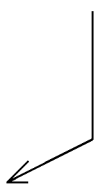
CHART 10
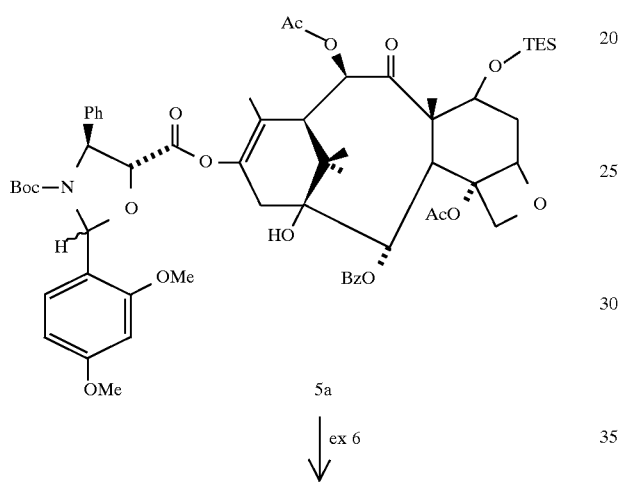
-continued
CHART 10
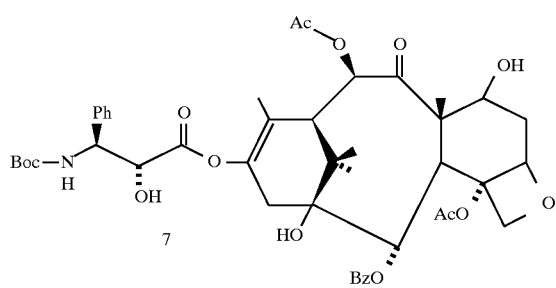
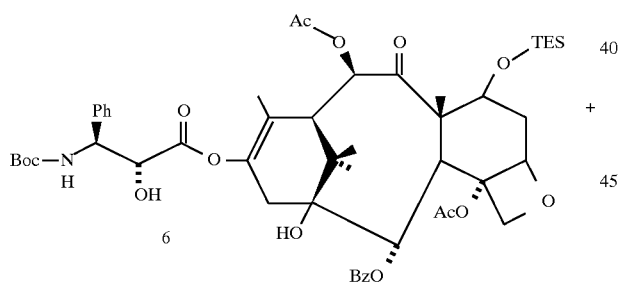

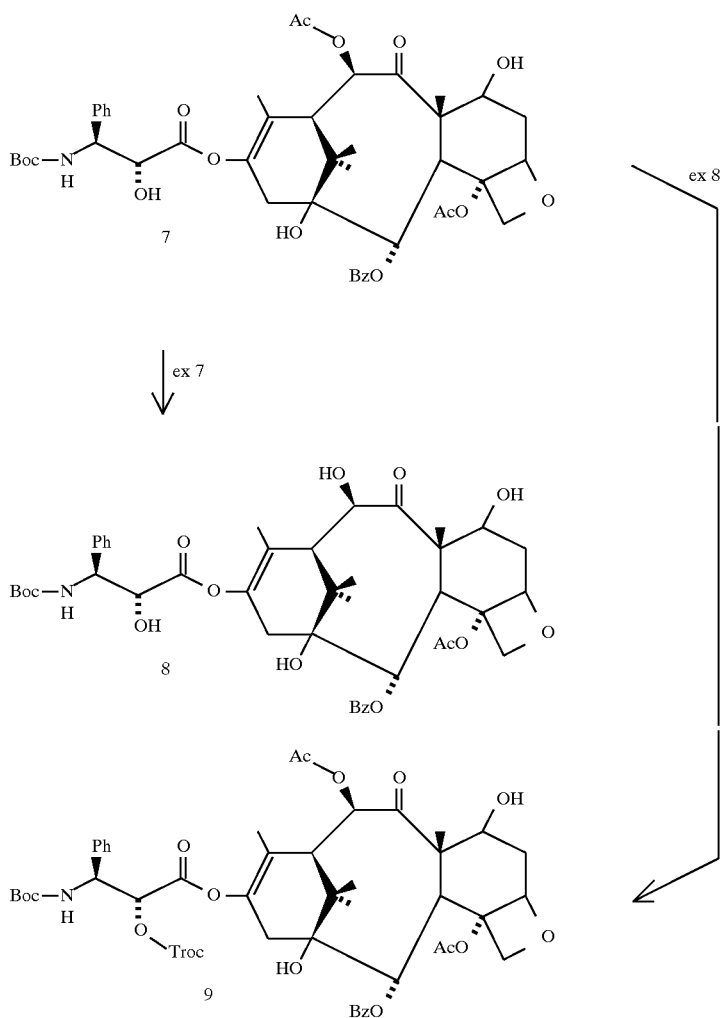
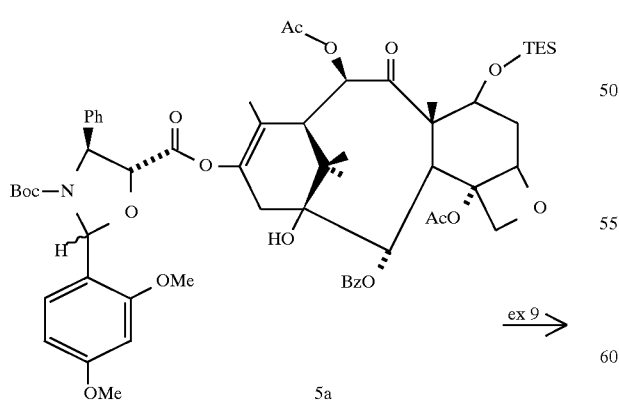
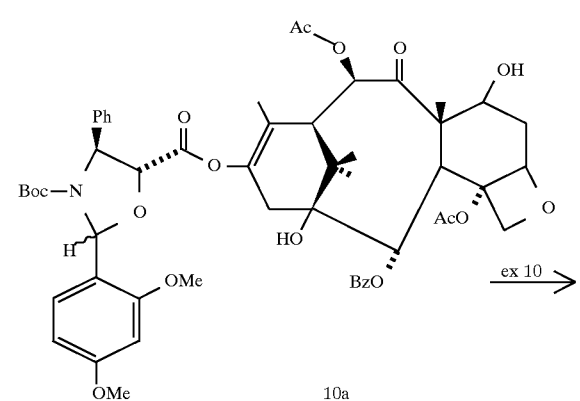

123
-continued
CHART 12
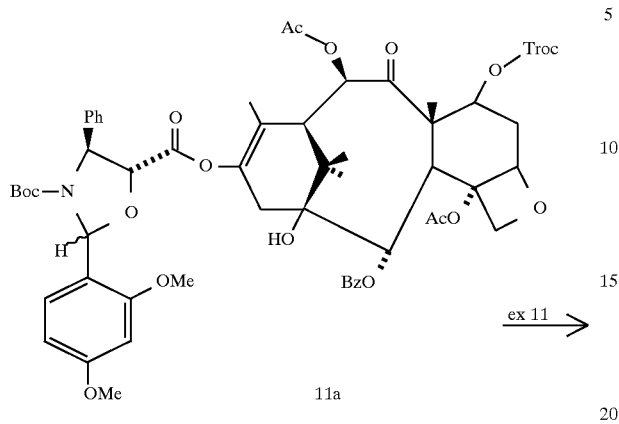
11a
ex 11 →
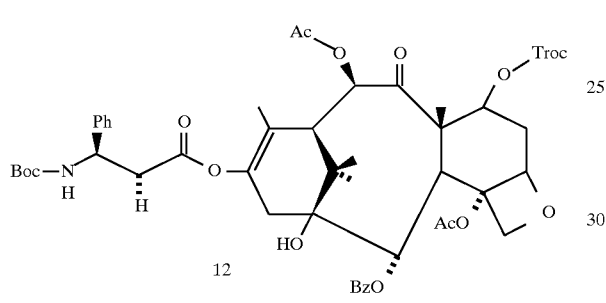
12
CHART 13
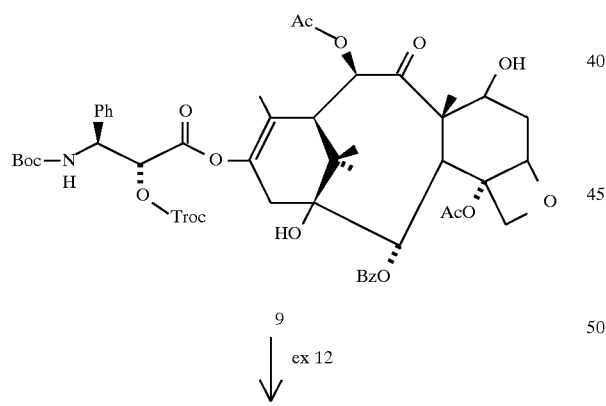
9
ex 12 ↓
124
-continued
CHART 13
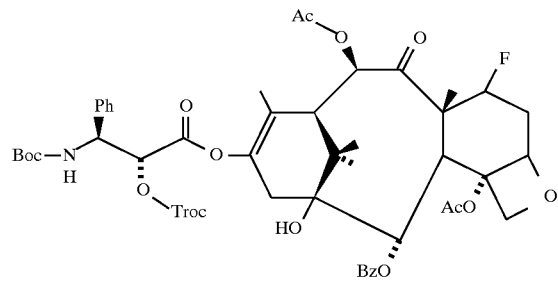
13
+
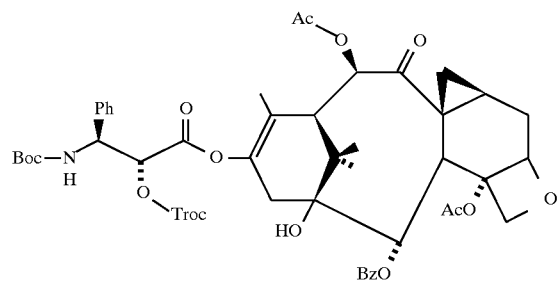
14
+
15

125              126
CHART 14
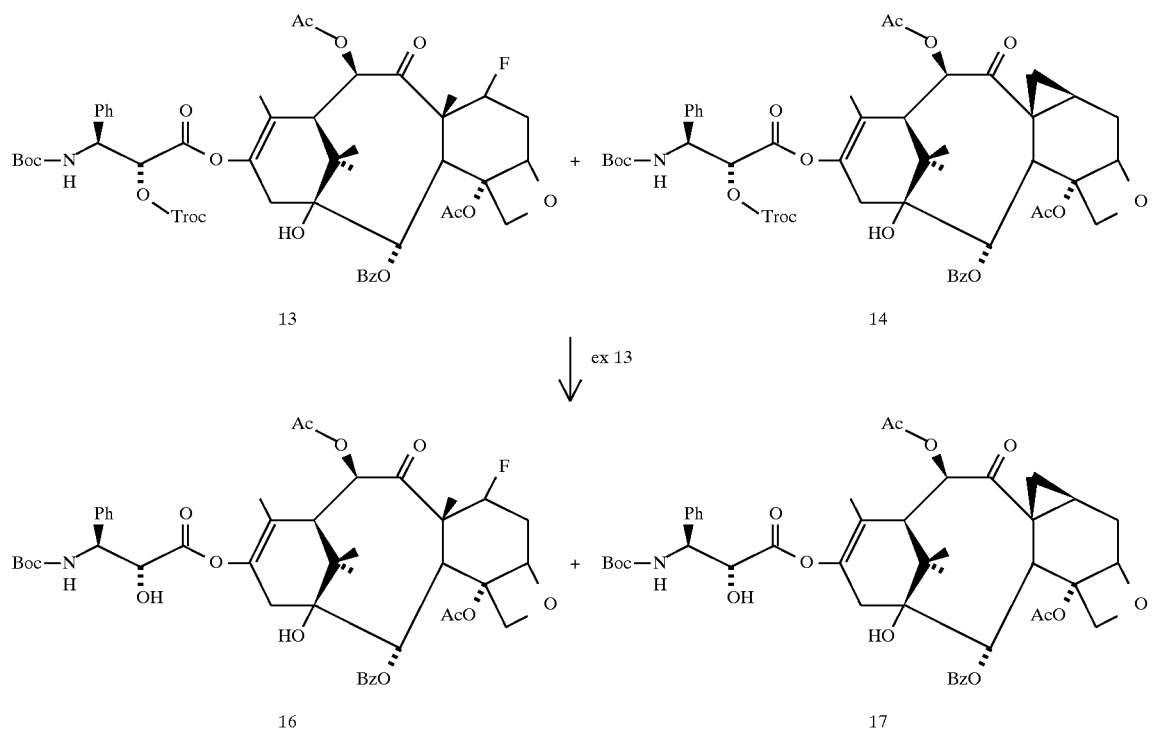
CHART 15
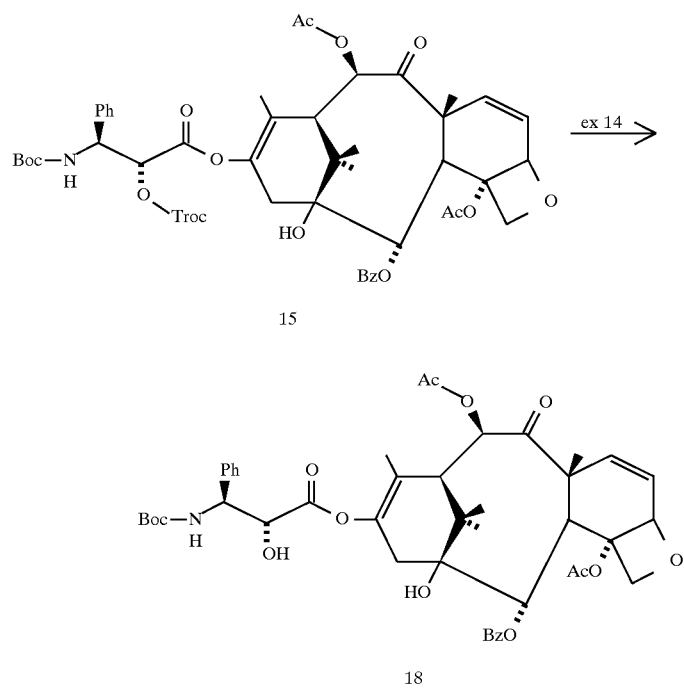

CHART 16
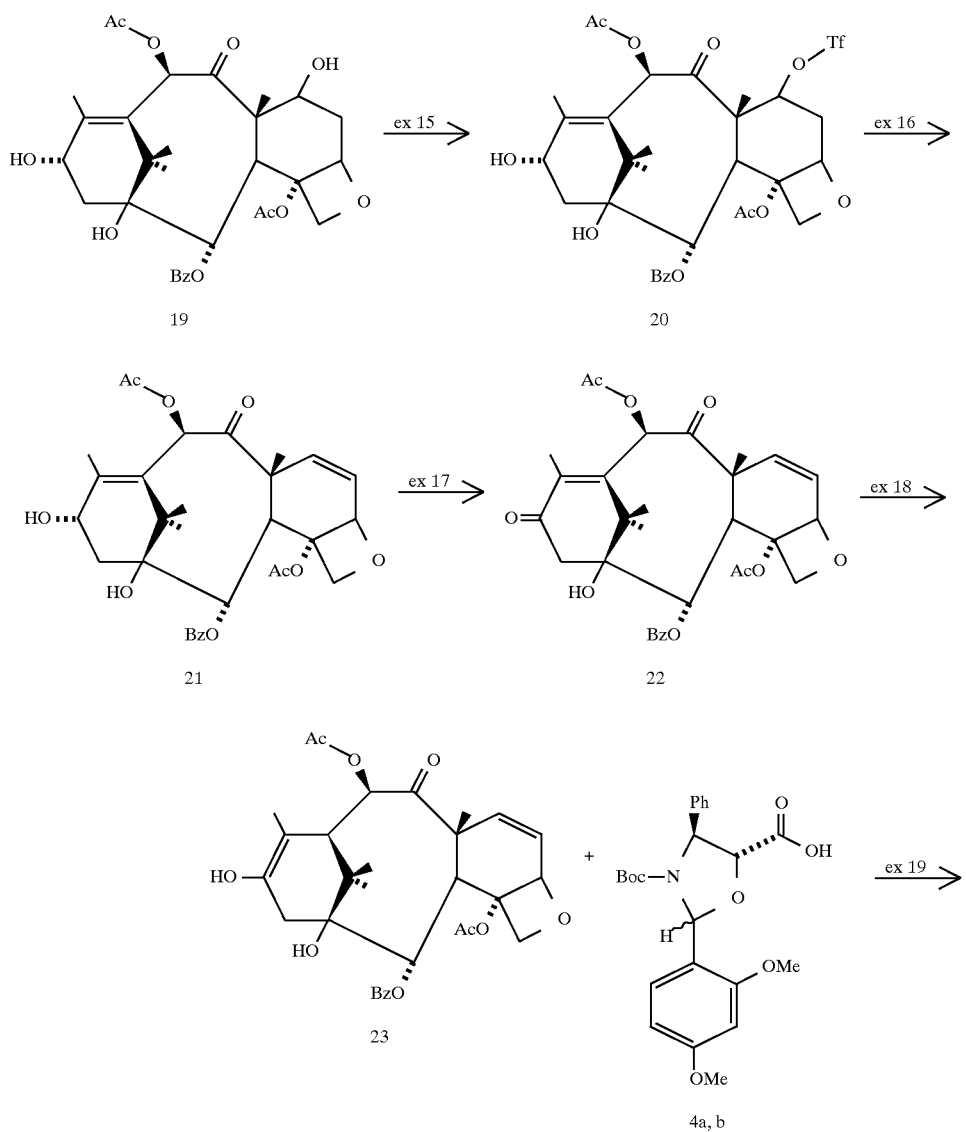
CHART 17
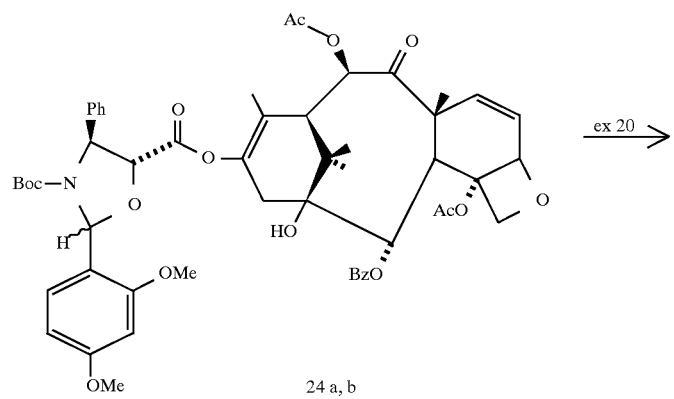

-continued
CHART 17
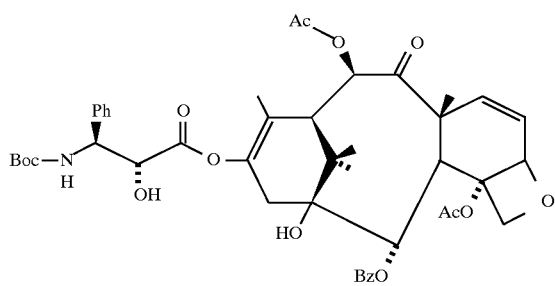
18
CHART 18
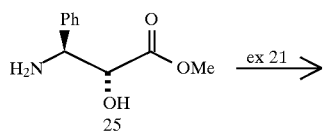
25
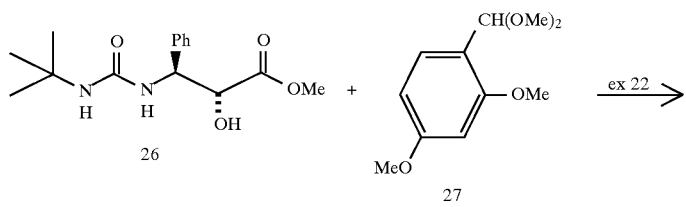
26 + 27
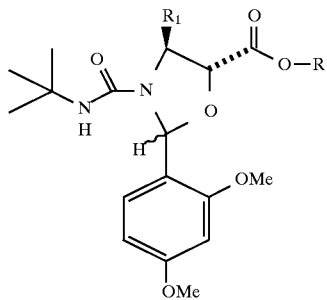
28 a, b R = Me
29 a, b R = K
30 a, b R = H
ex 23, 23a
ex 24

CHART 19
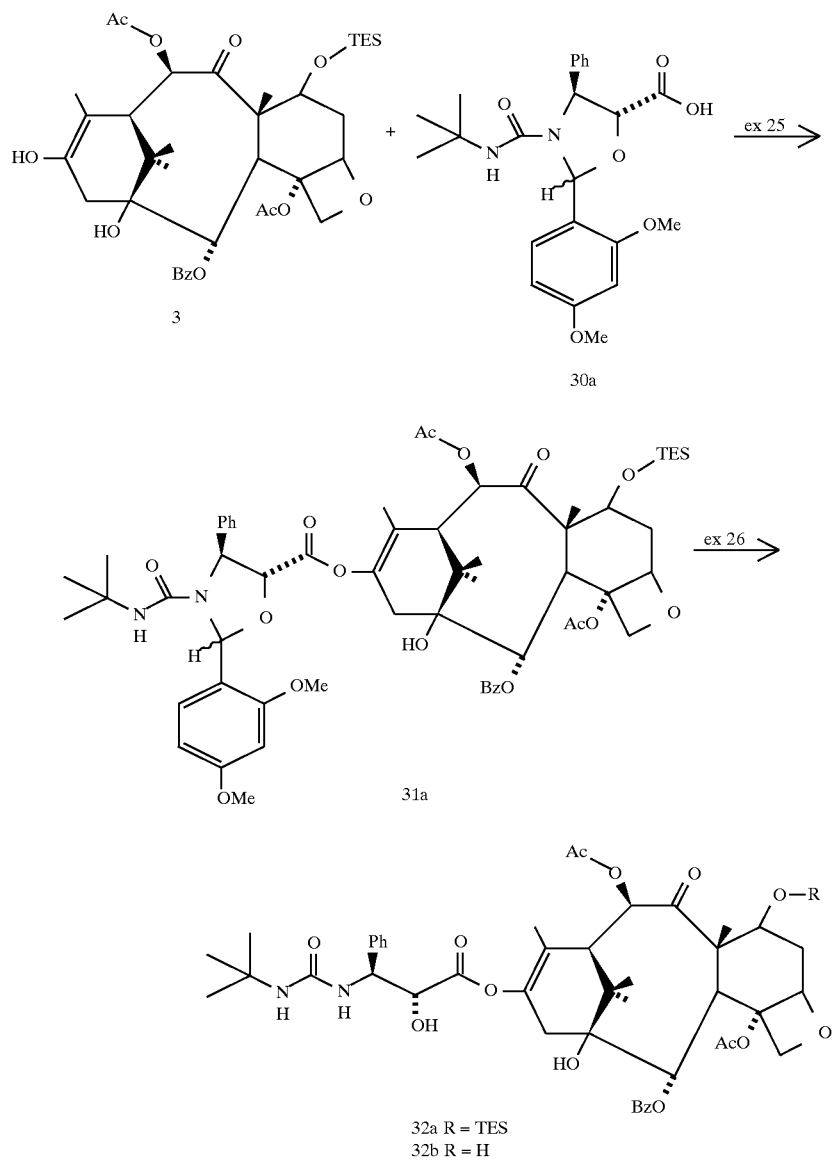
CHART 20
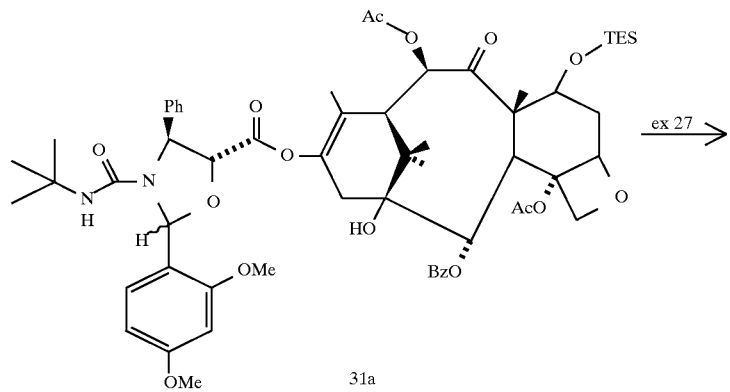

-continued
CHART 20
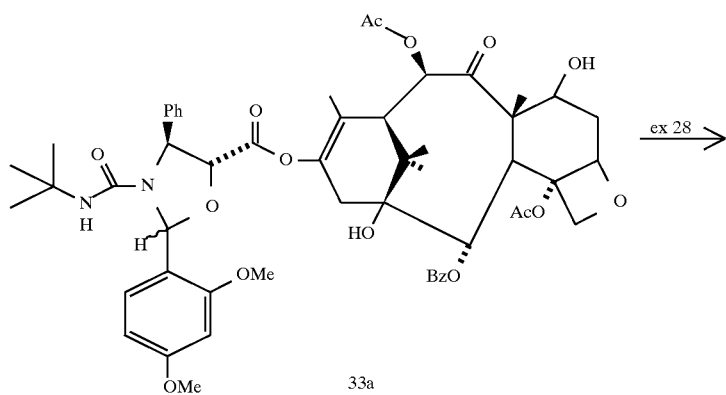
33a
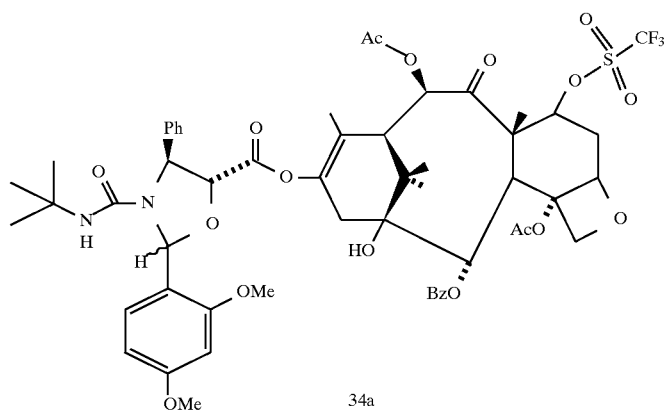
34a
CHART 21
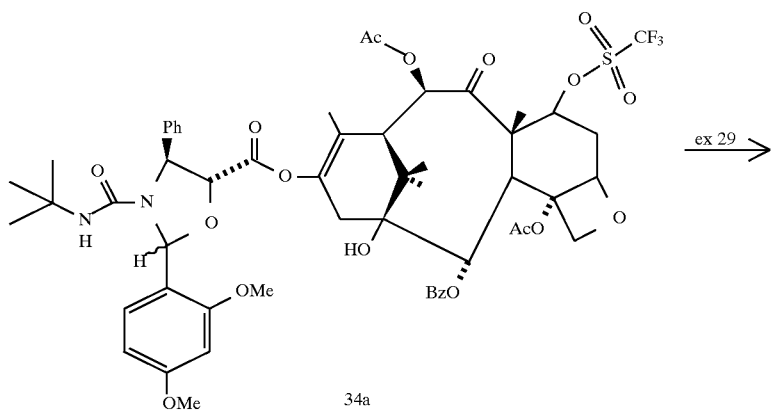
34a

-continued
CHART 21
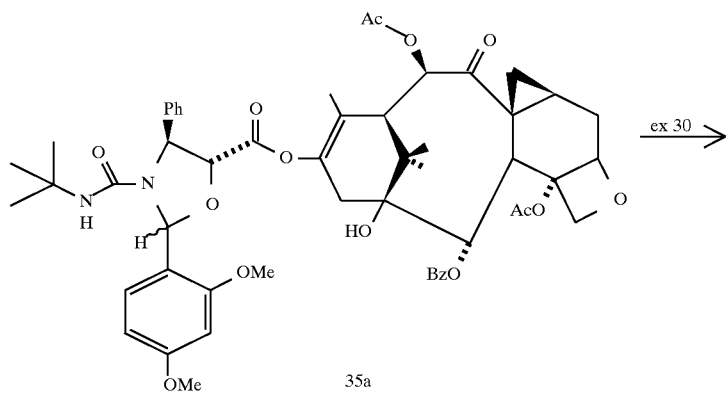
CHART 22
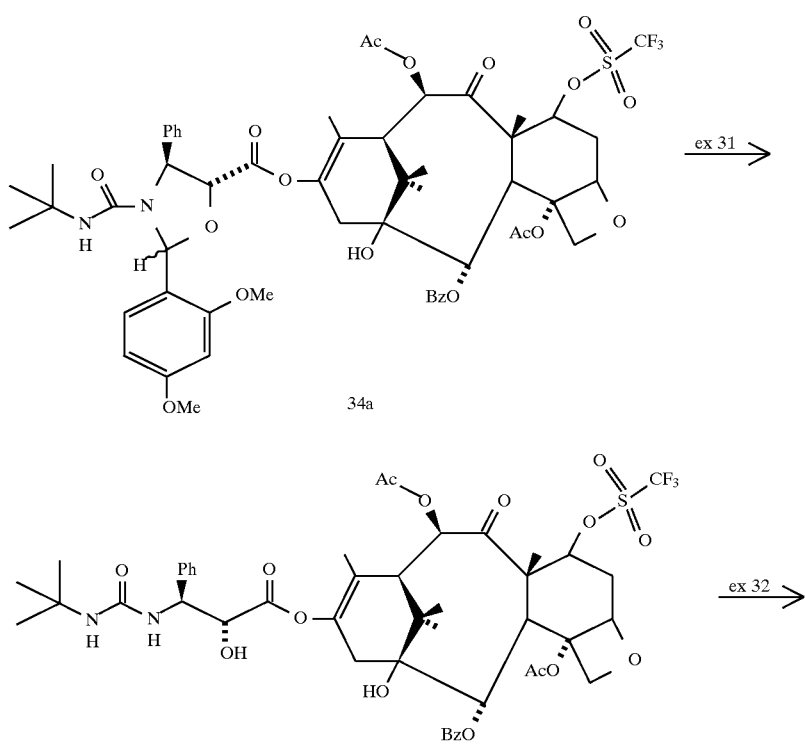

-continued
CHART 22
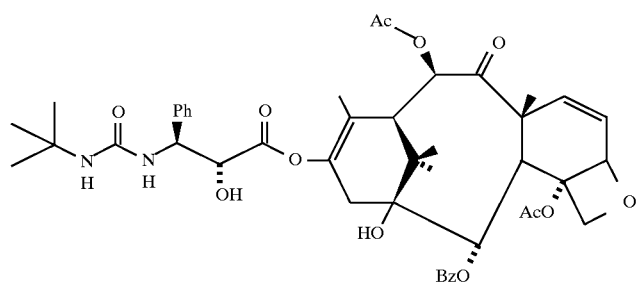
38
CHART 23
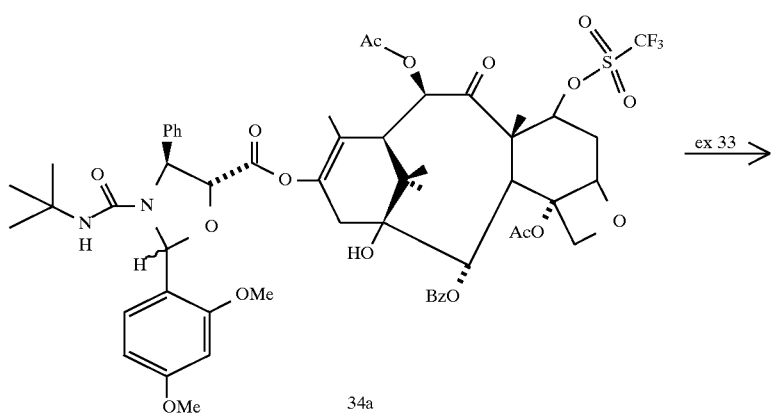
34a → ex 33
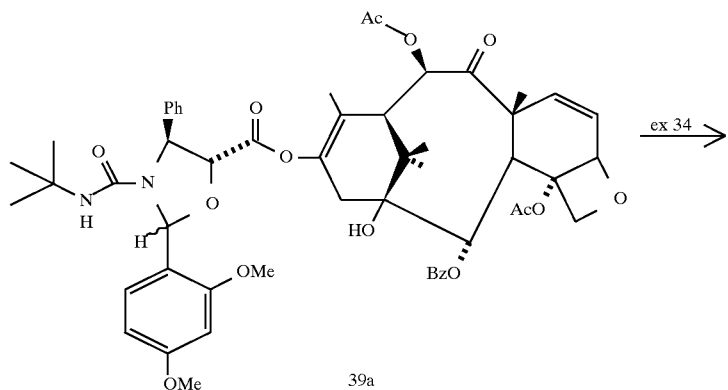
39a → ex 34
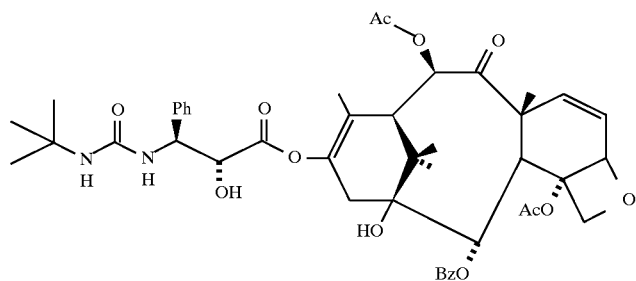
38

CHART 24
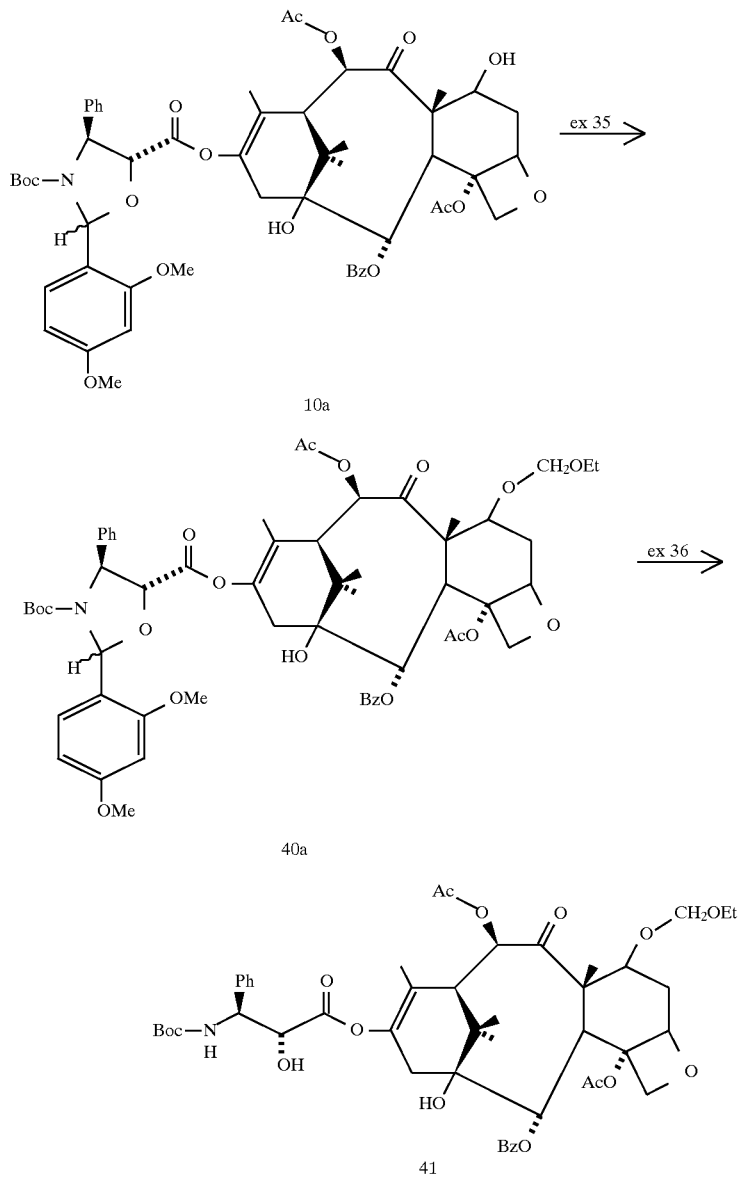
CHART 25
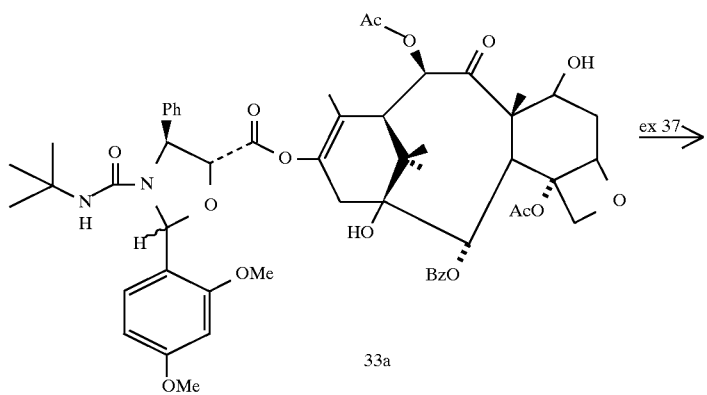

-continued
CHART 25
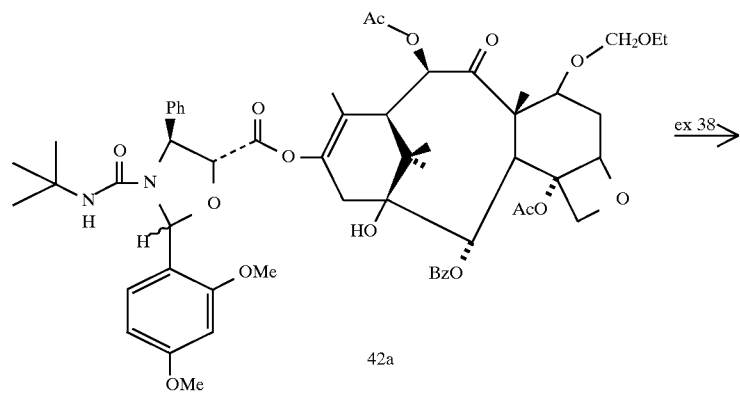
42a
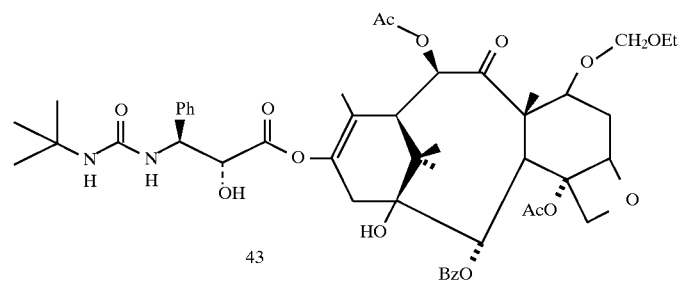
43
CHART 26
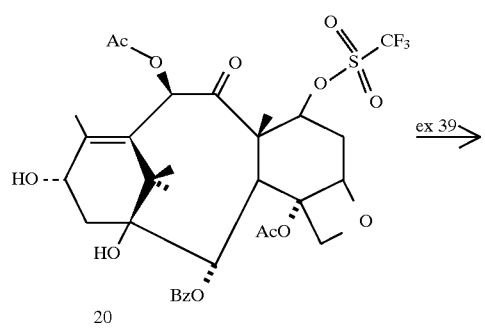
20
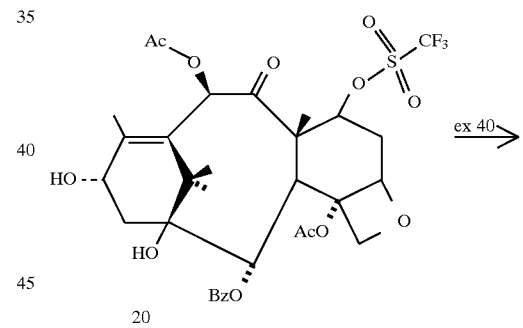
20
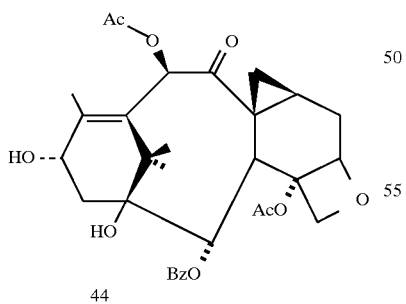
44
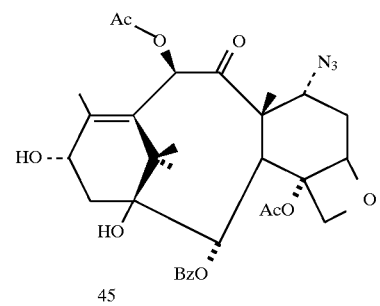
45

CHART 27
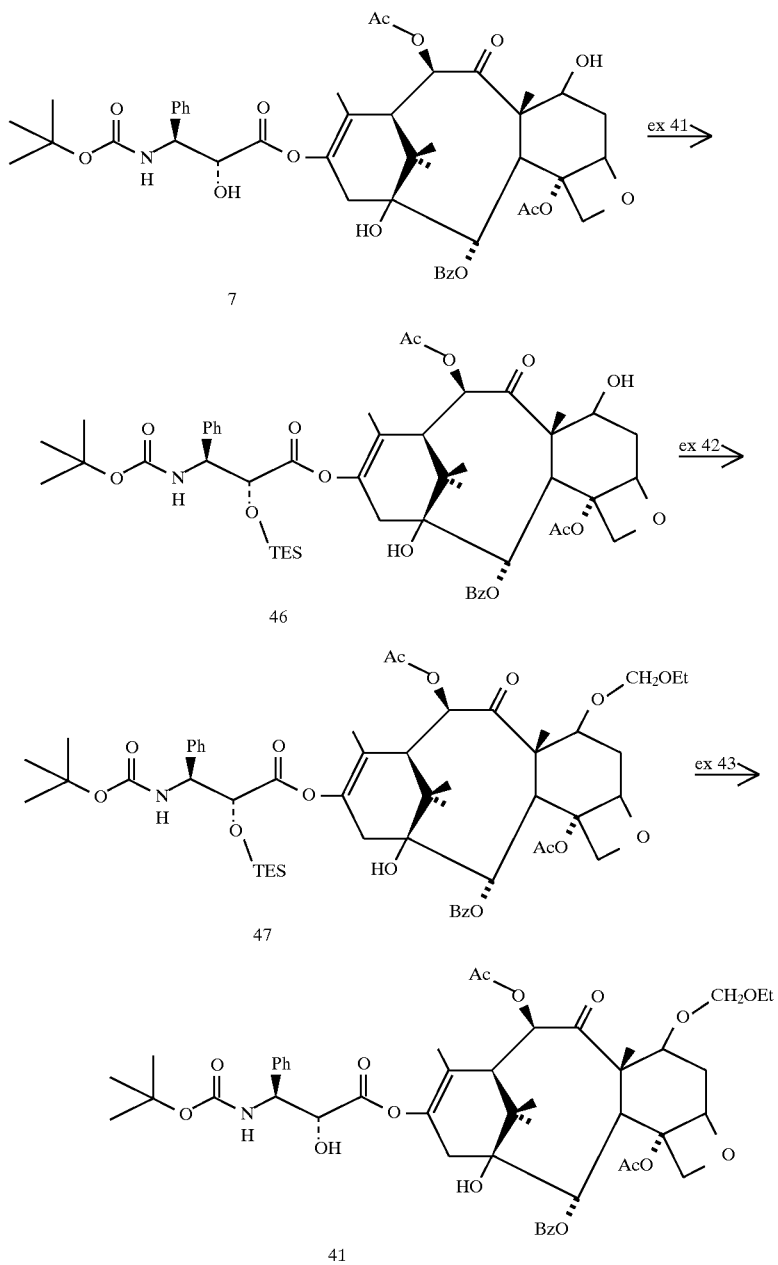
CHART 28
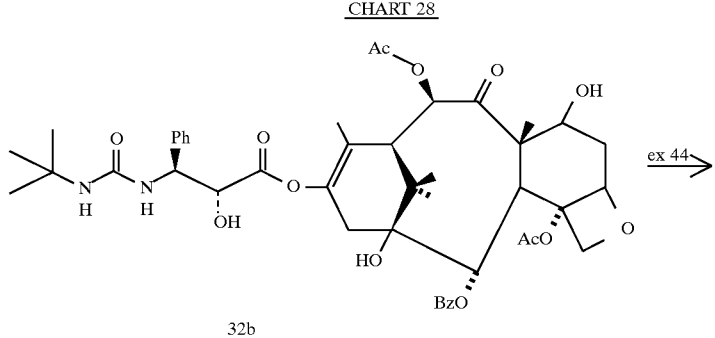

-continued
CHART 28
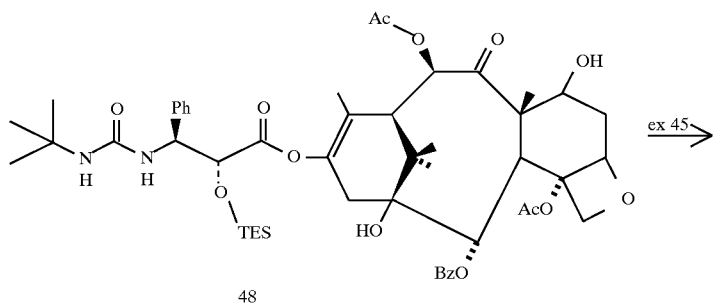
48
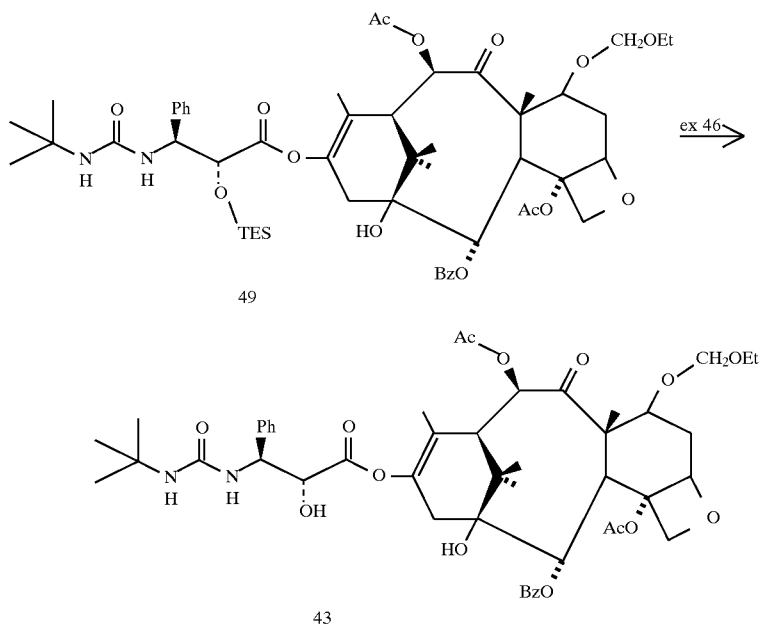
49
43
CHART 29
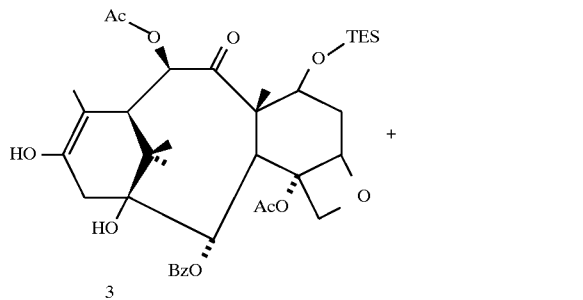
3
-continued
CHART 29
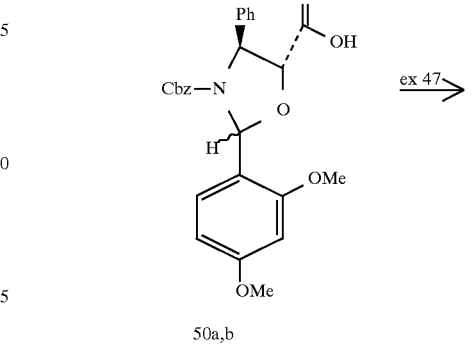
50a,b

147
-continued
CHART 29
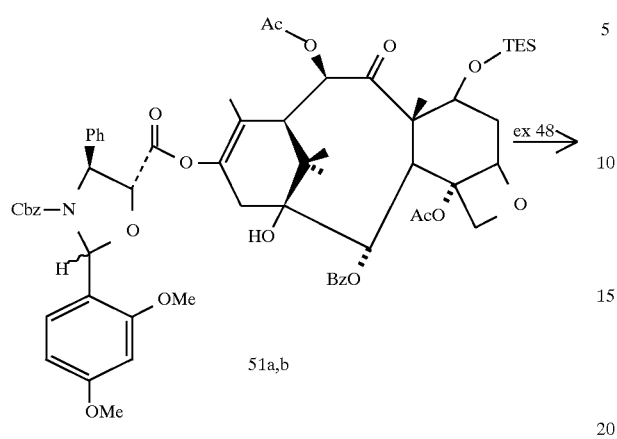
51a,b
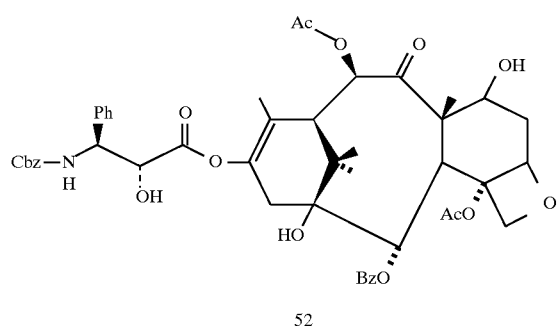
52
CHART 30
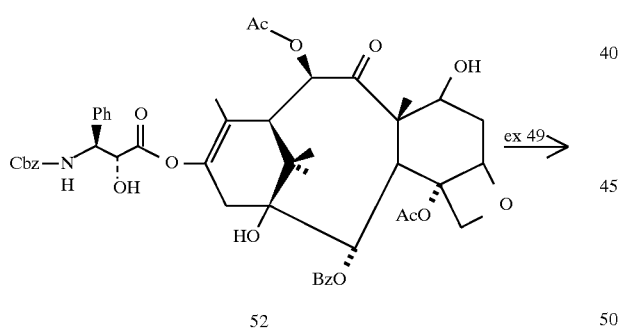
52
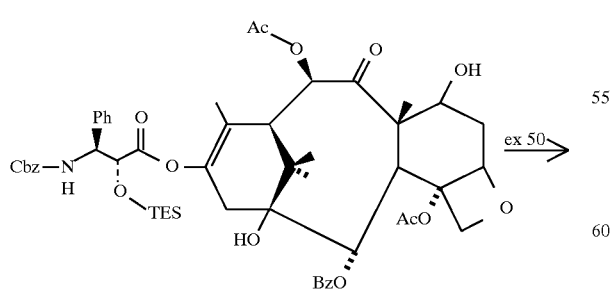
53
148
-continued
CHART 30
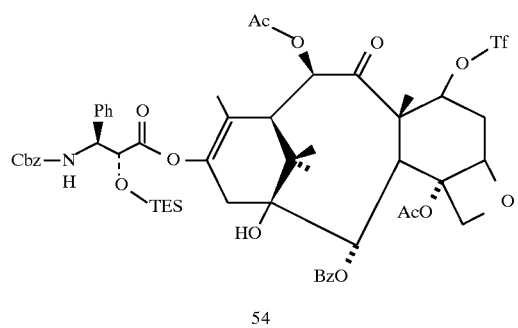
54
CHART 31
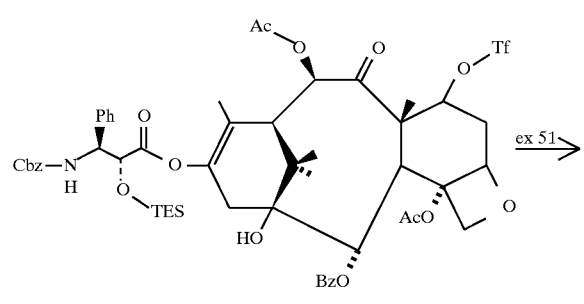
54
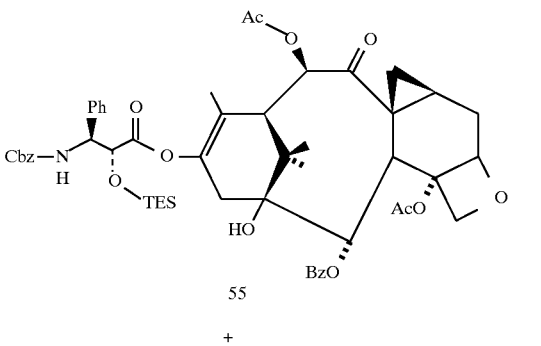
55
+
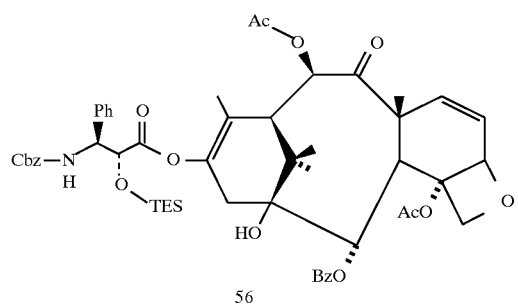
56

CHART 32
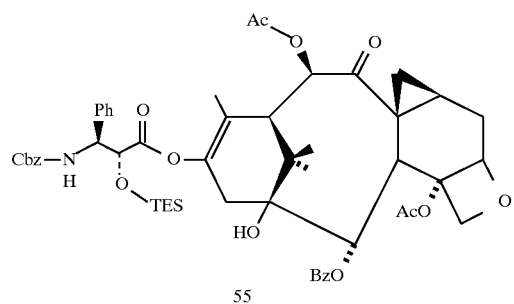
55
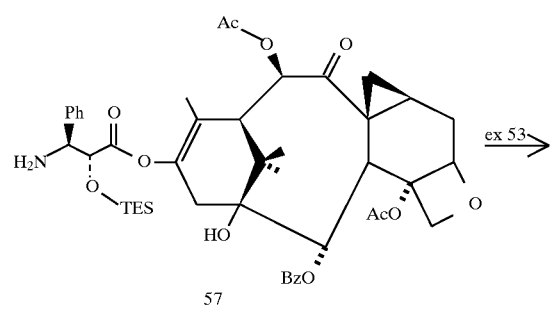
57
CHART 32 -continued
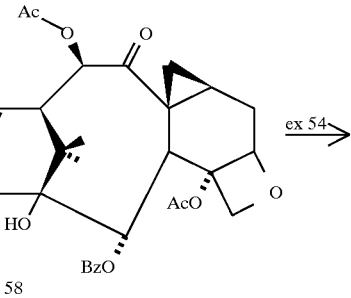
58
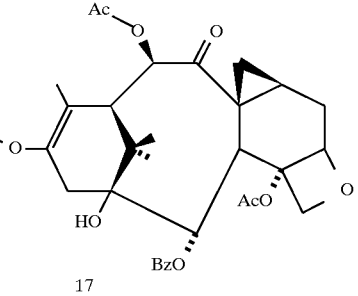
17
CHART 33
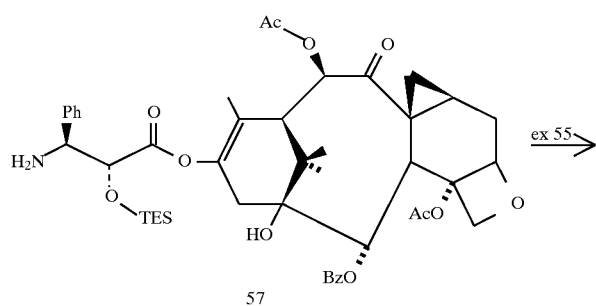
57
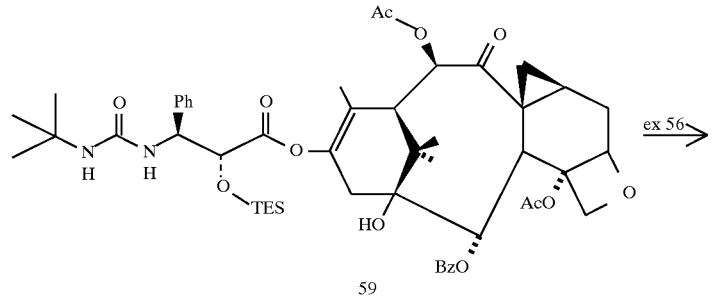
59

-continued
CHART 33
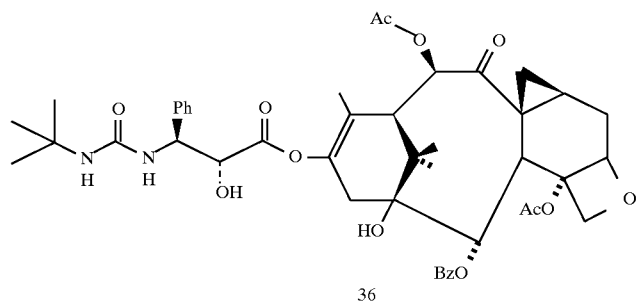
36
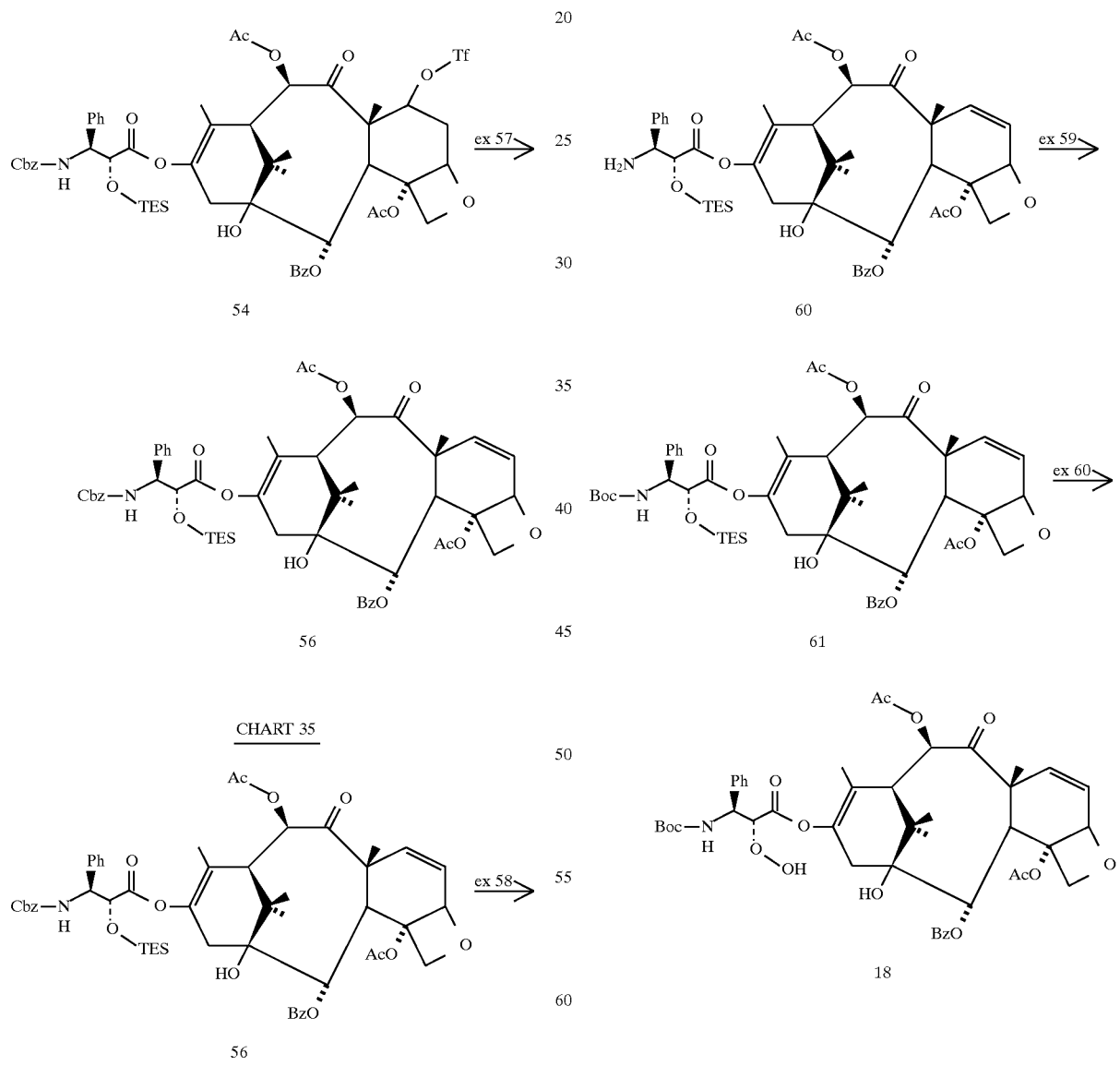

CHART 36
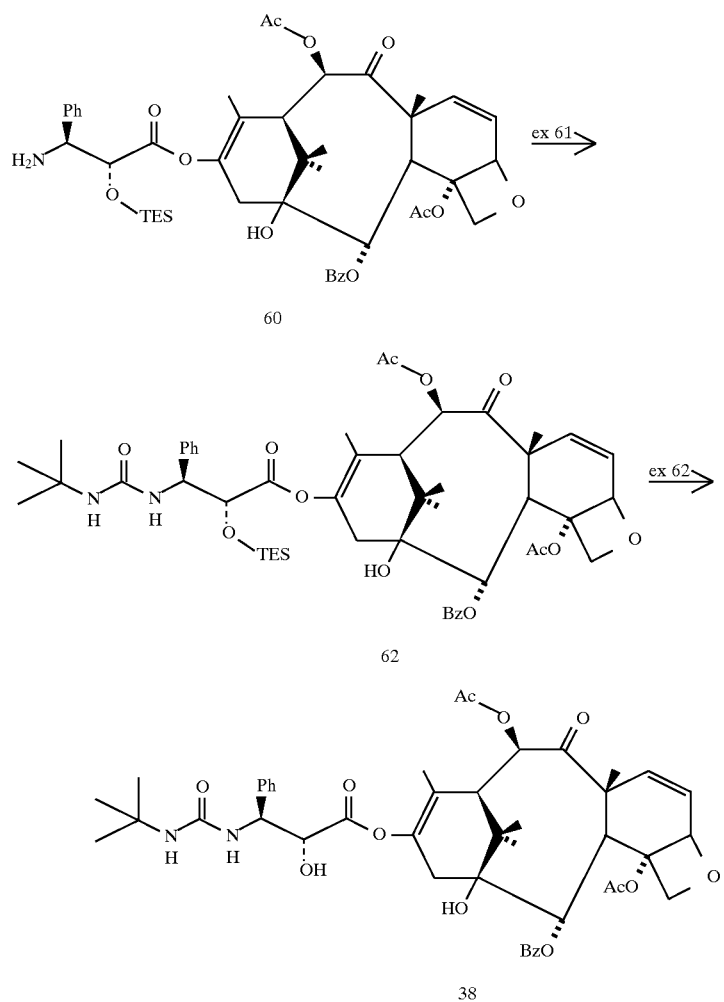
CHART 37
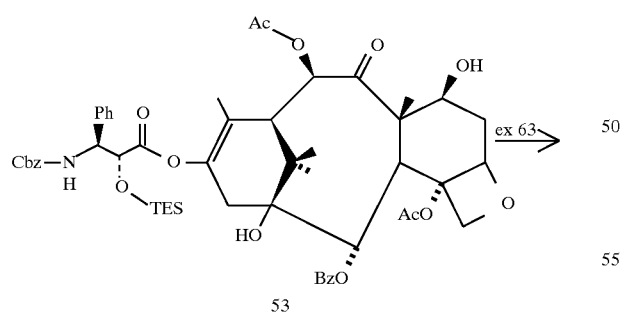
-continued
CHART 37
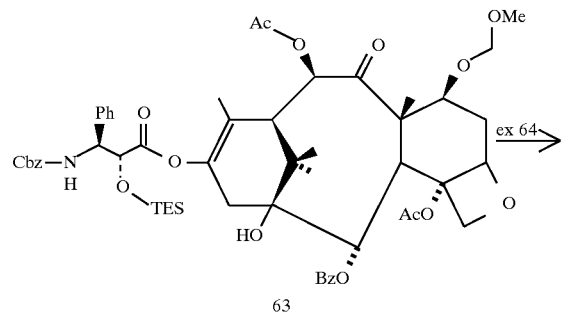

155
-continued
CHART 37
156
-continued
CHART 37
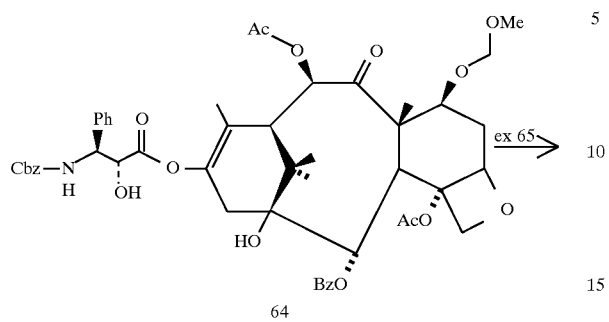
CHART 38
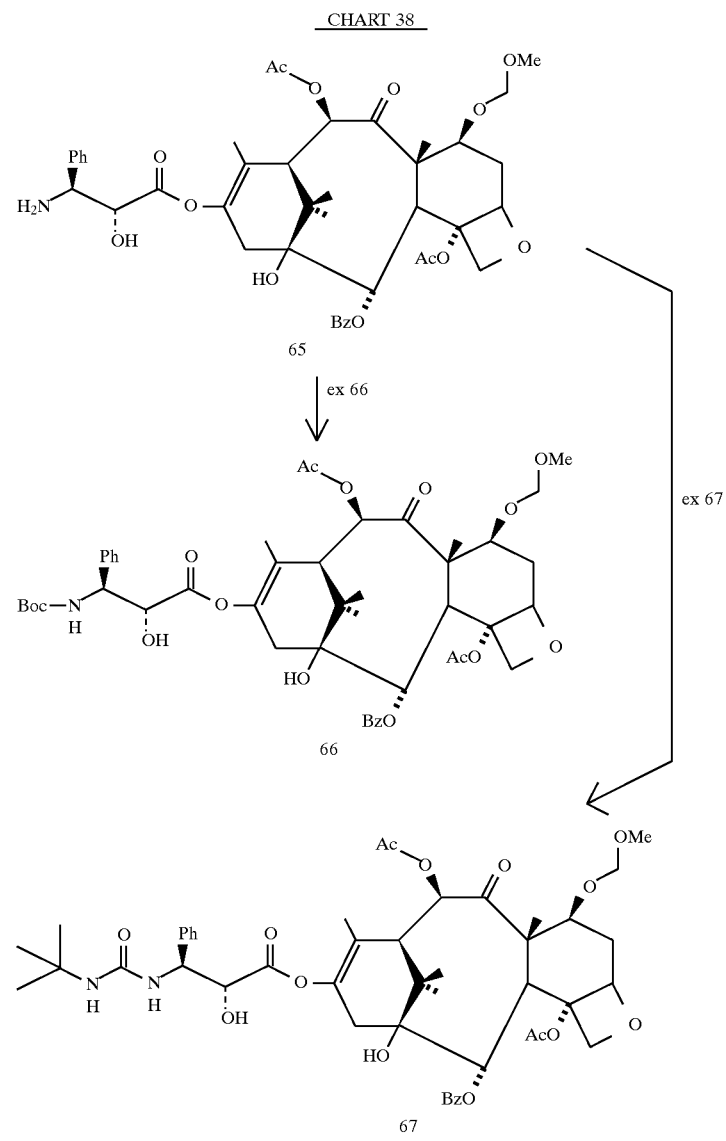

CHART 39
157
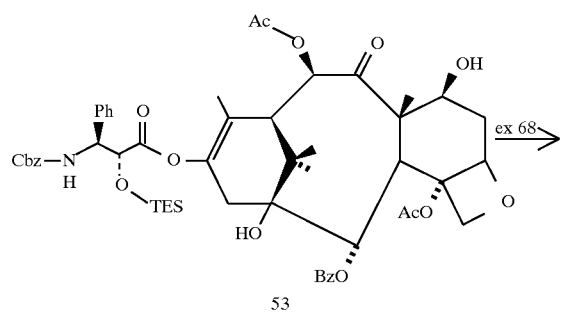
53
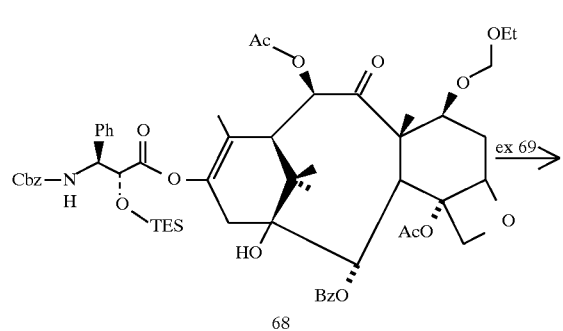
68
158
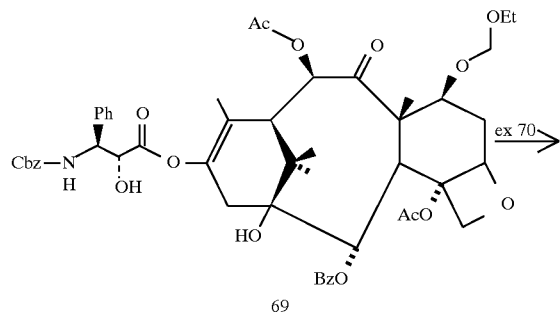
69
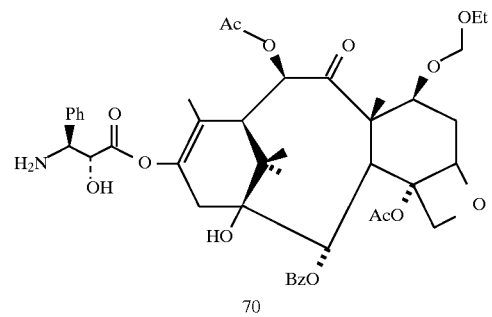
70
CHART 40
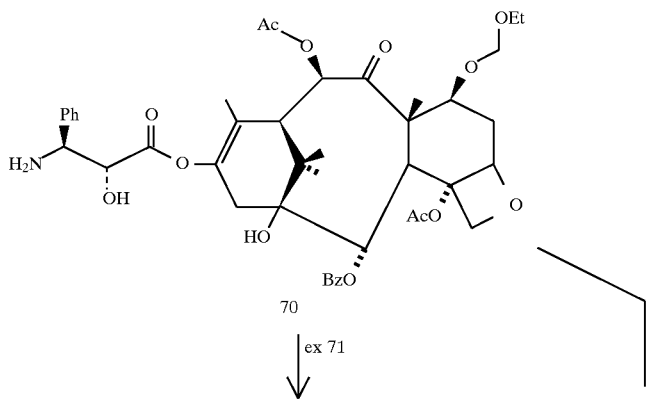
70
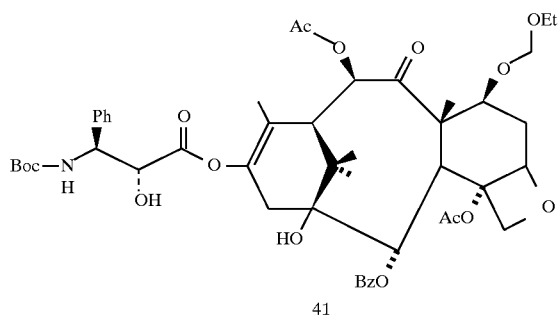
41

-continued
CHART 40
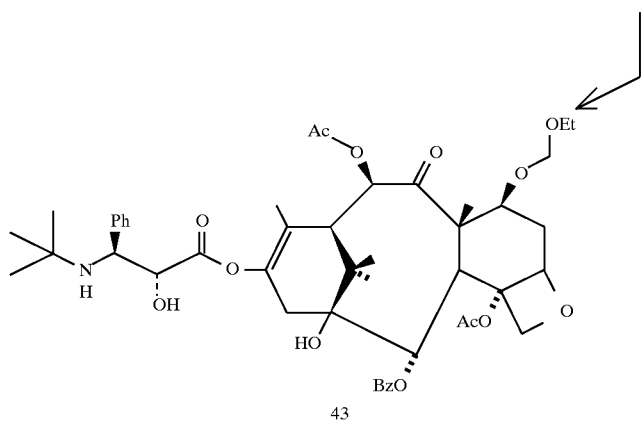
CHART 41
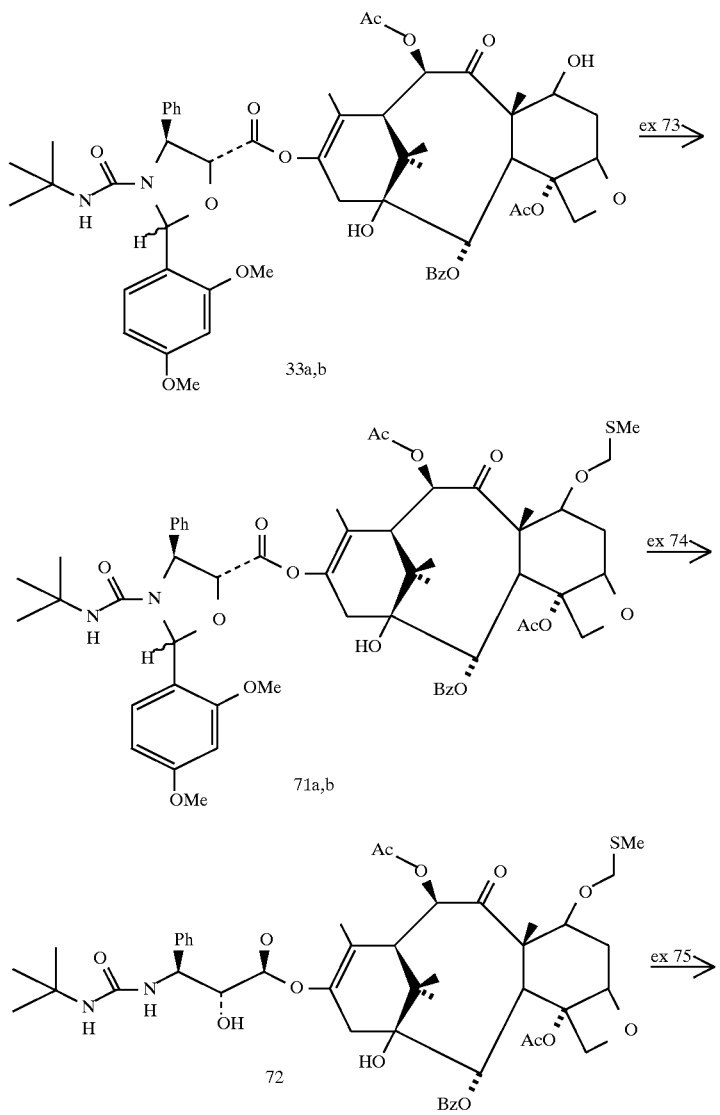

-continued
CHART 41
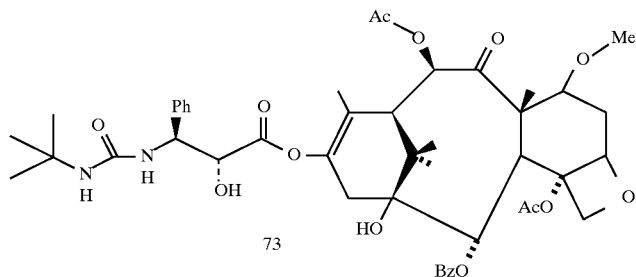
73
CHART 42
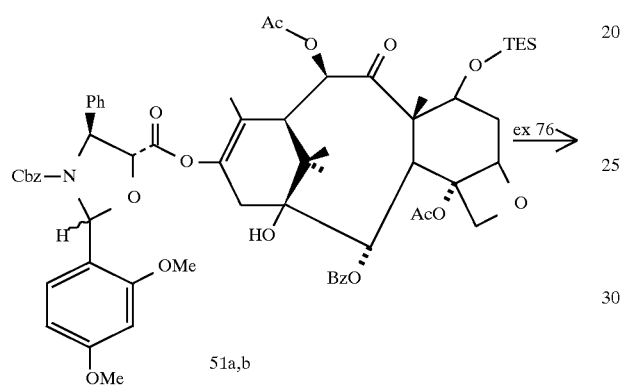
51a,b
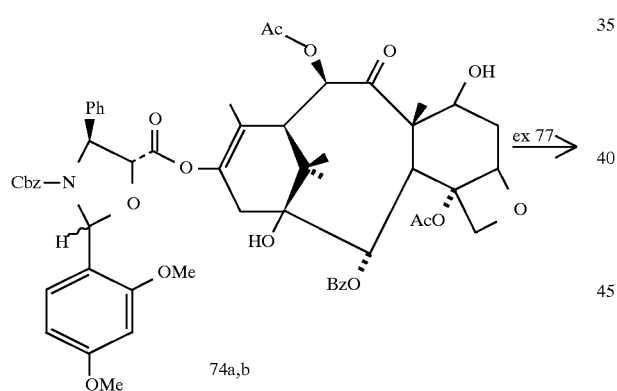
74a,b
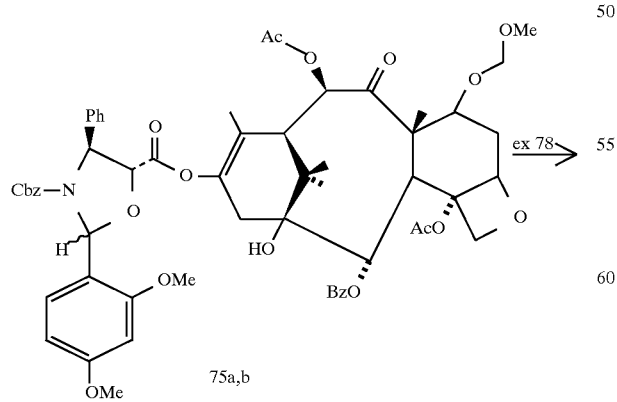
75a,b
-continued
CHART 42
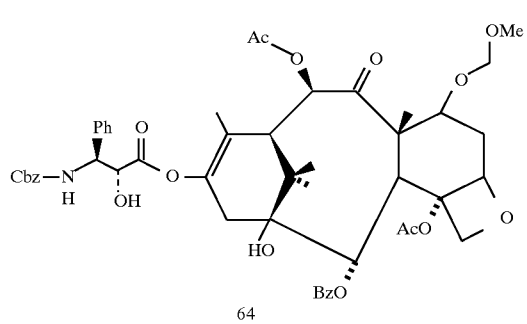
64
CHART 43
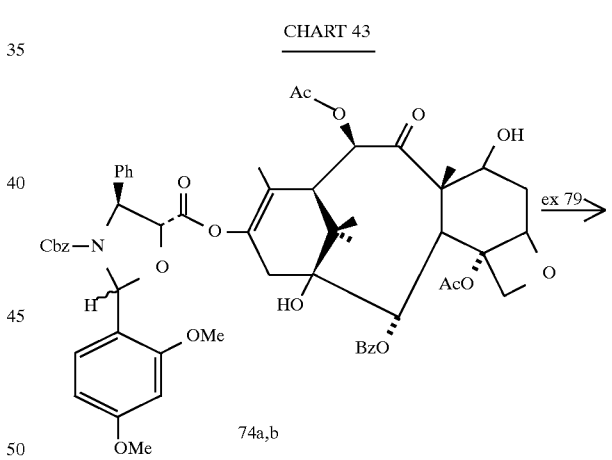
74a,b
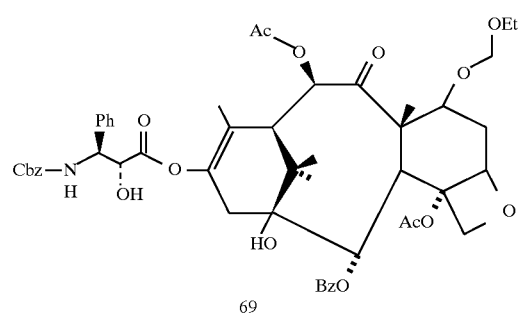
69

163
CHART 44
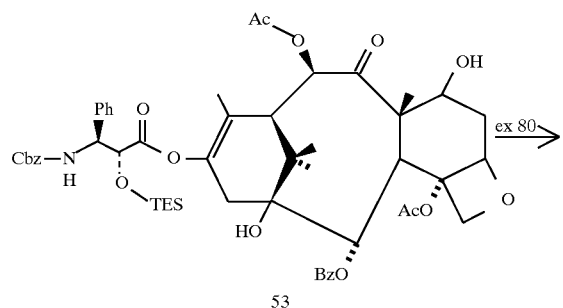
53
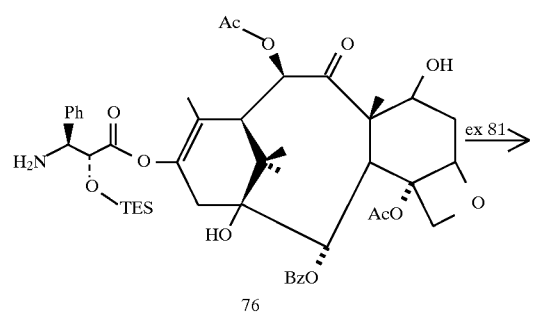
76
164
-continued
CHART 44
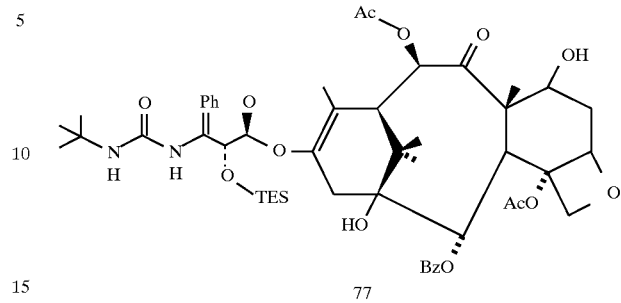
77
CHART 45
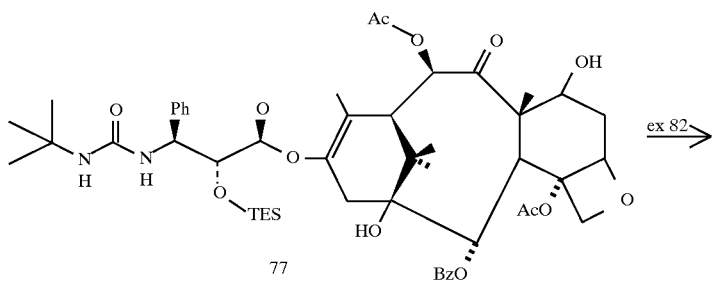
77
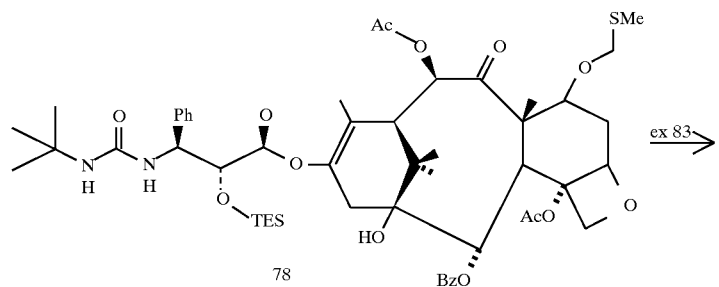
78

-continued
CHART 45
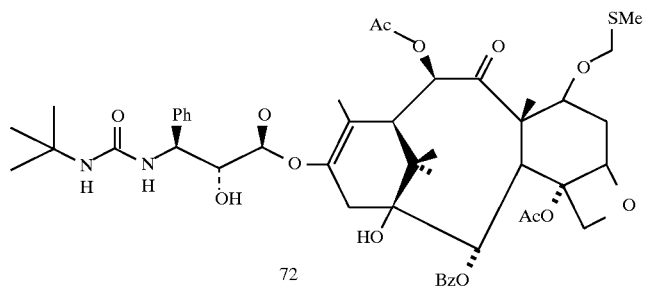
72
CHART 46
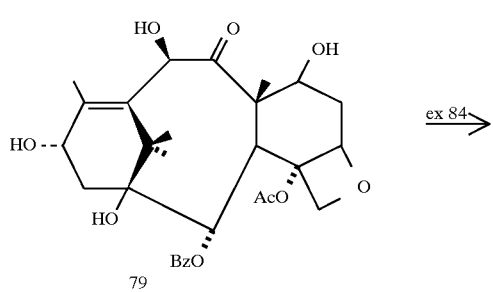
79
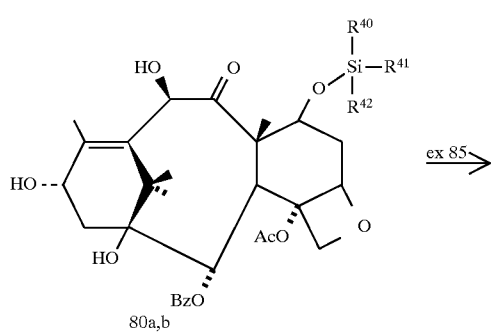
80a,b
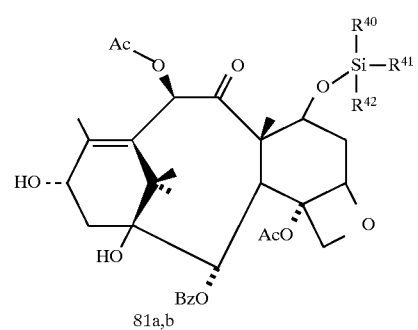
81a,b
80a: TLC Silica gel; 50% ethyl acetate:heptane, rf = .44
80b: TLC Silica gel; 50% ethyl acetate:heptane, rf = .44
81a: TLC Silica gel; 50% ethyl acetate:heptane, rf = .55
a = $R^{40}$ = $R^{41}$ = Me, $R^{42}$ = 2-(3-methylbutyl)
b = $R^{40}$ = $R^{41}$ = Me, $R^{42}$ = cyclohexyl
CHART 47
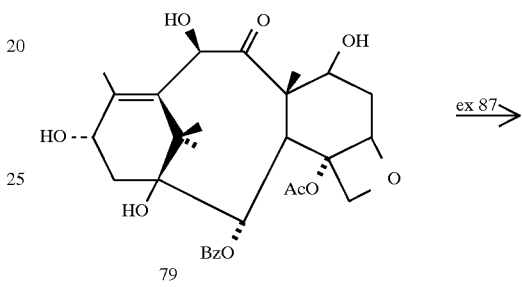
79
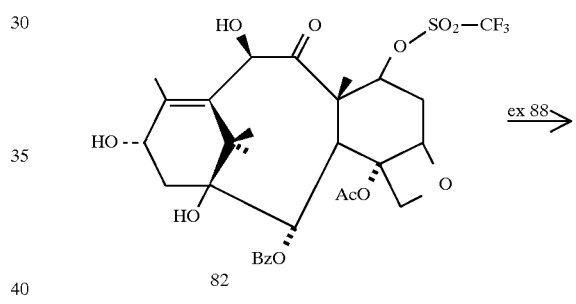
82
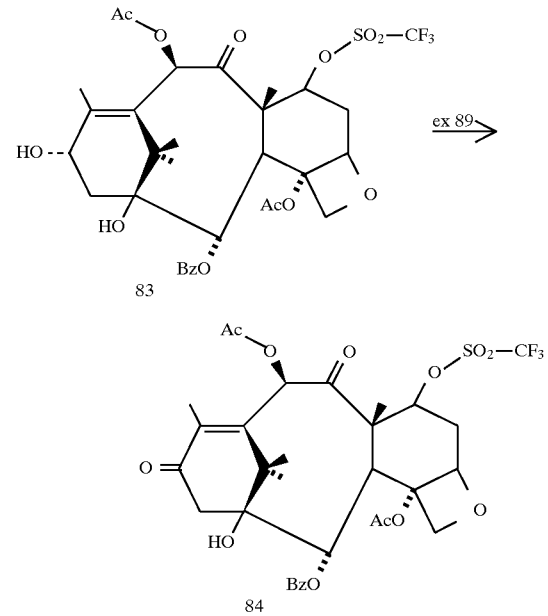
83
84

CHART 48
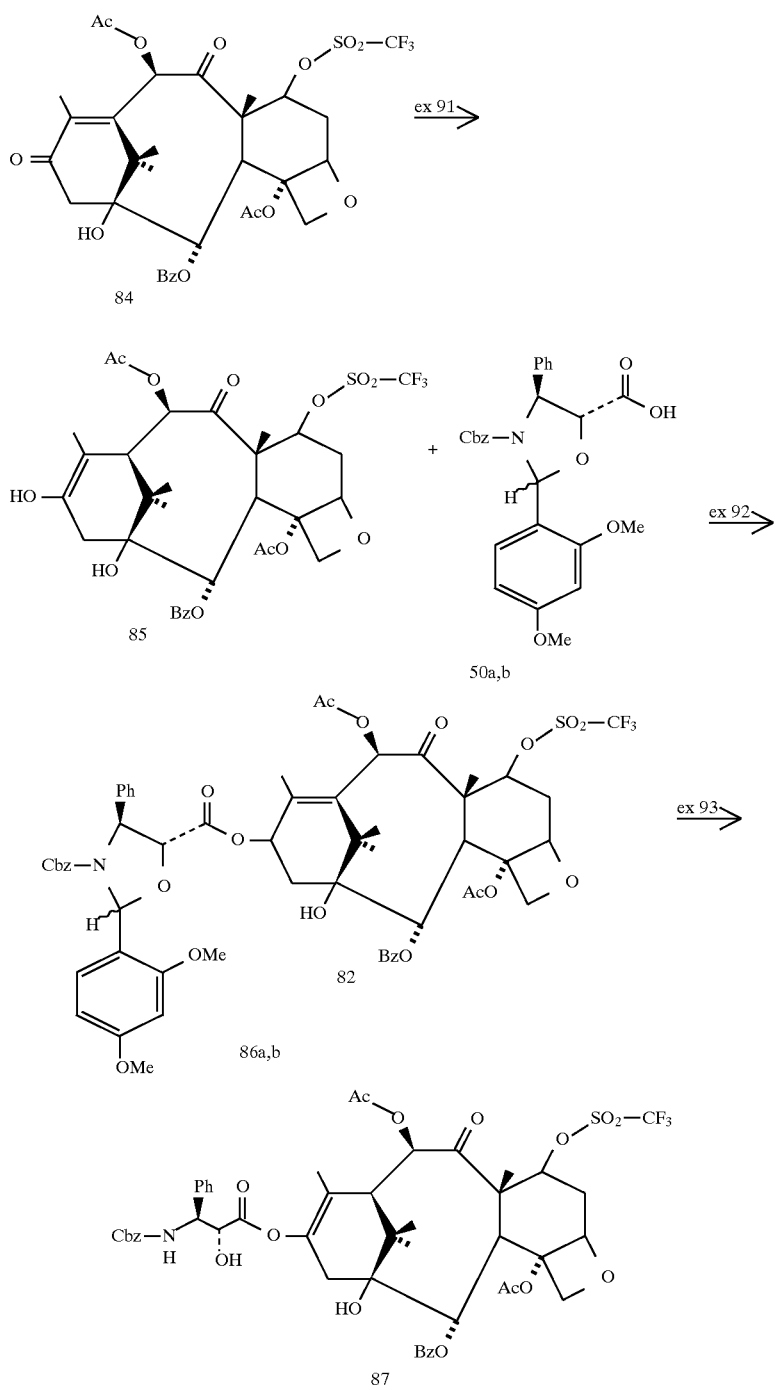

CHART 49
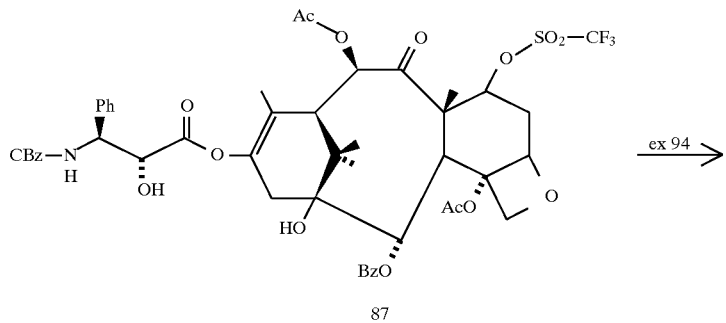
CHART 50
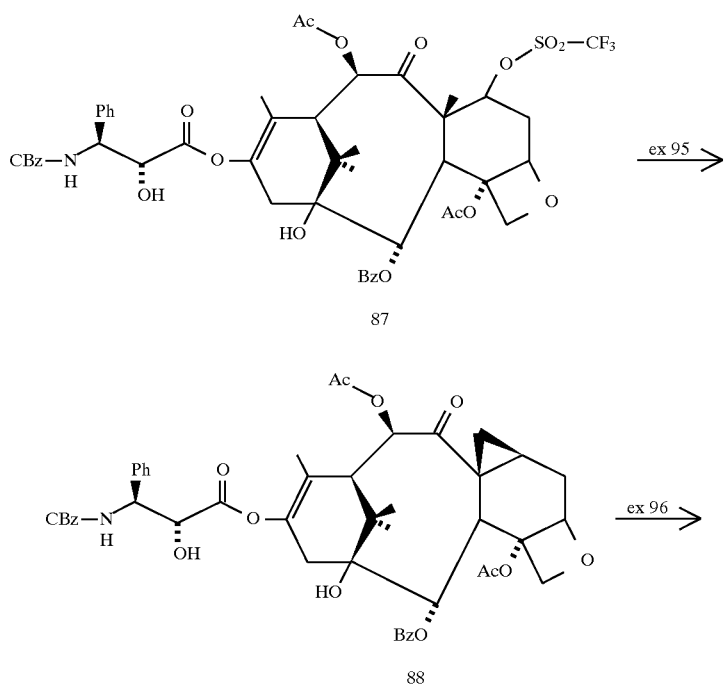

-continued
CHART 50
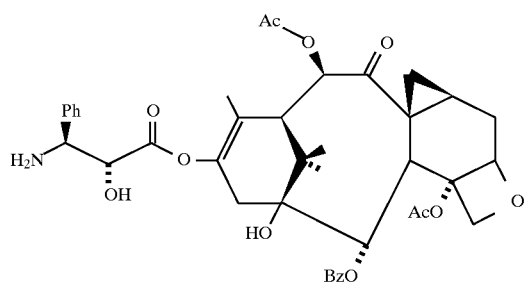
89
CHART 51
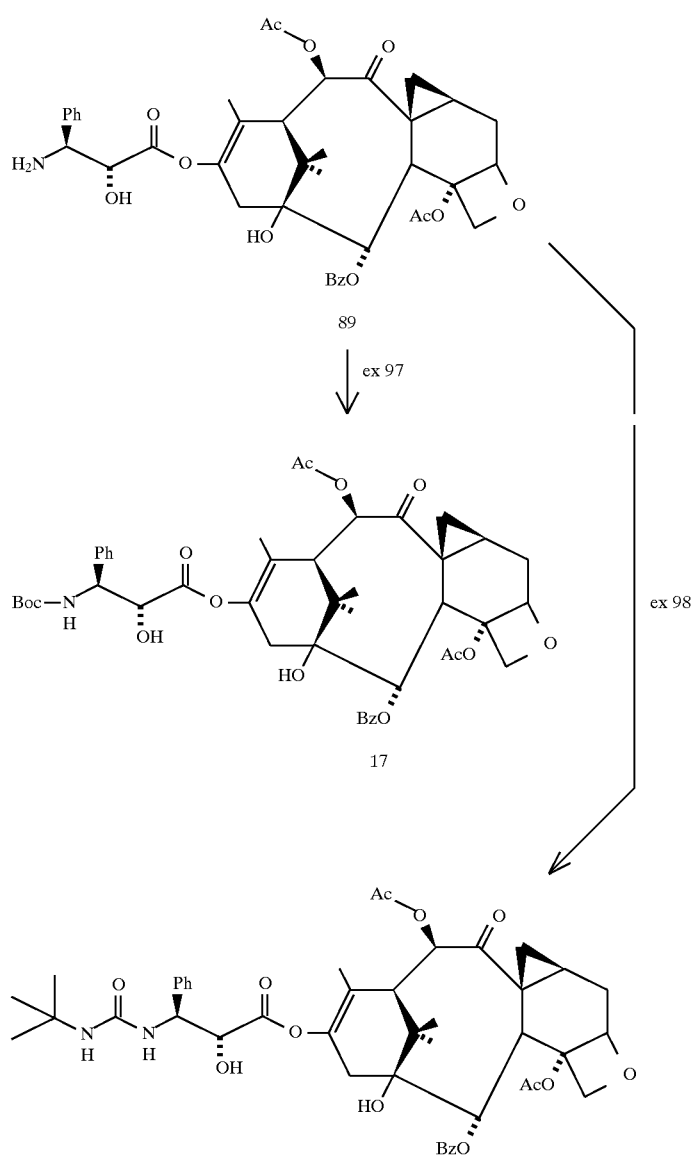

CHART 52
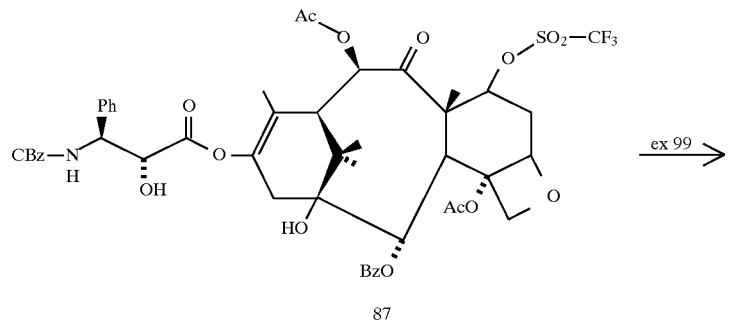
87
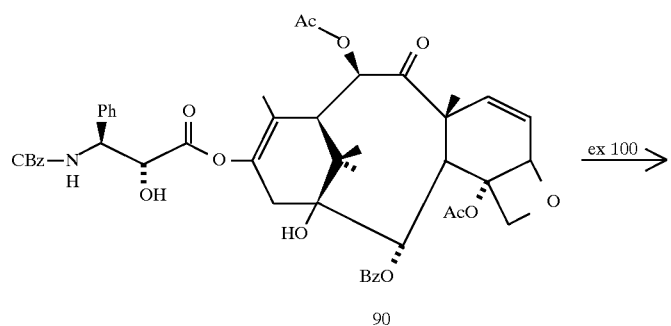
90
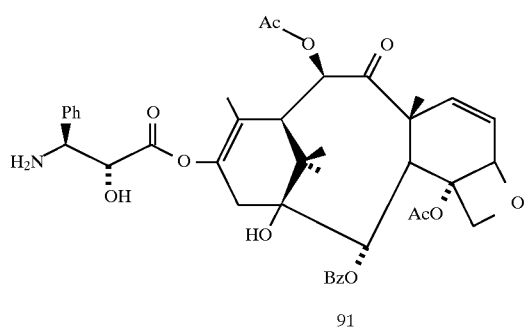
91
CHART 53
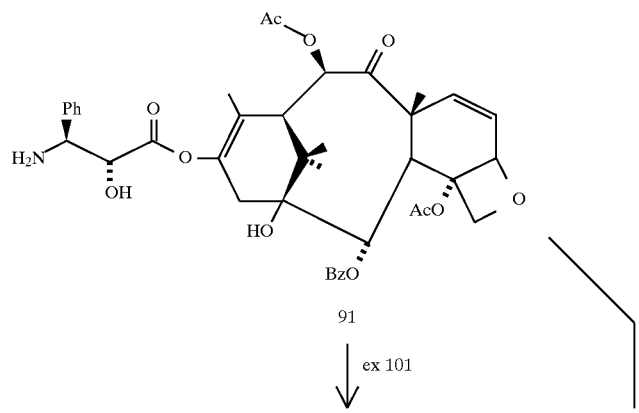
91

-continued
CHART 53
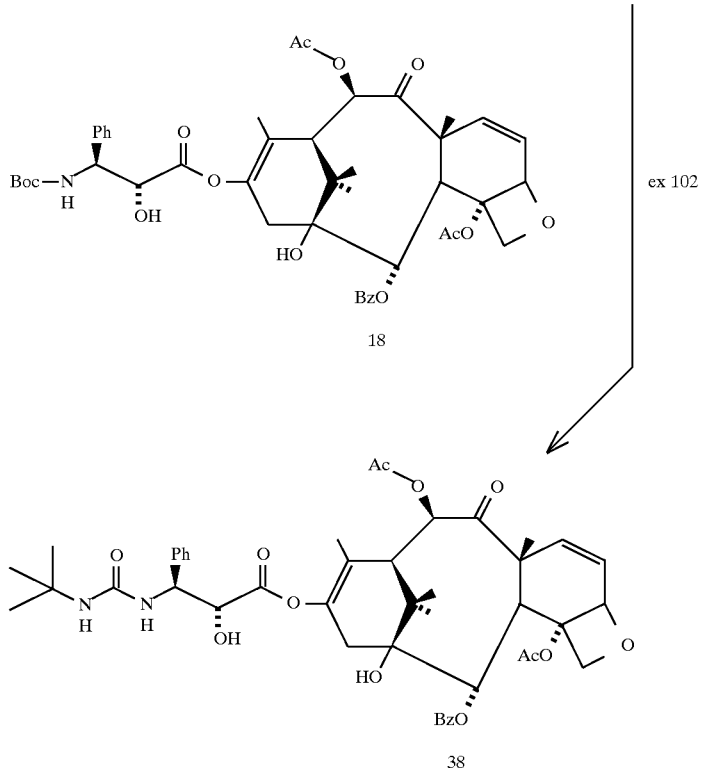
CHART 54
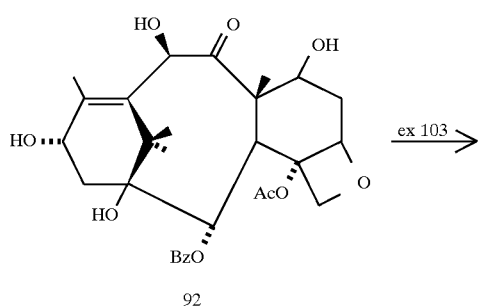
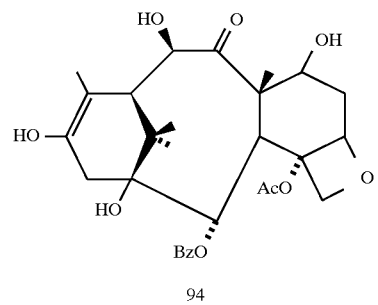
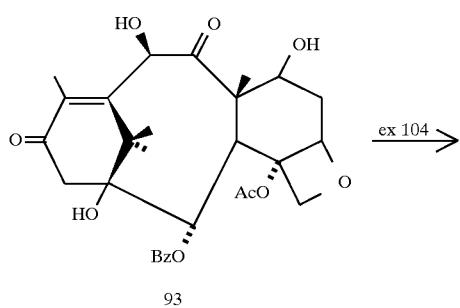
CHART 55
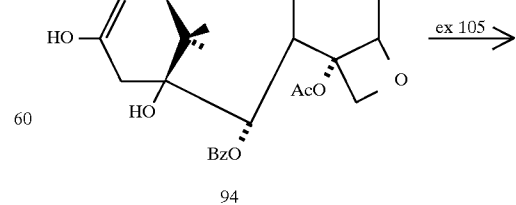

CHART 55

CHART 56

CHART 57 -continued
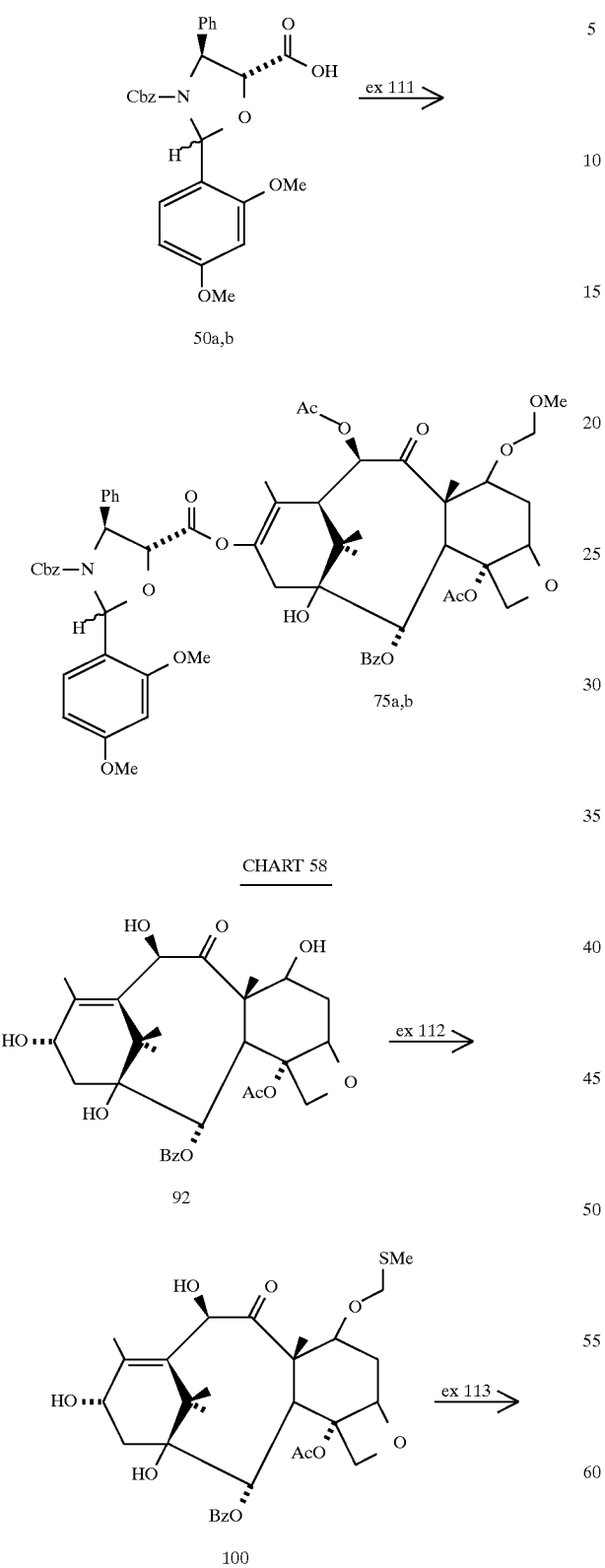
CHART 58
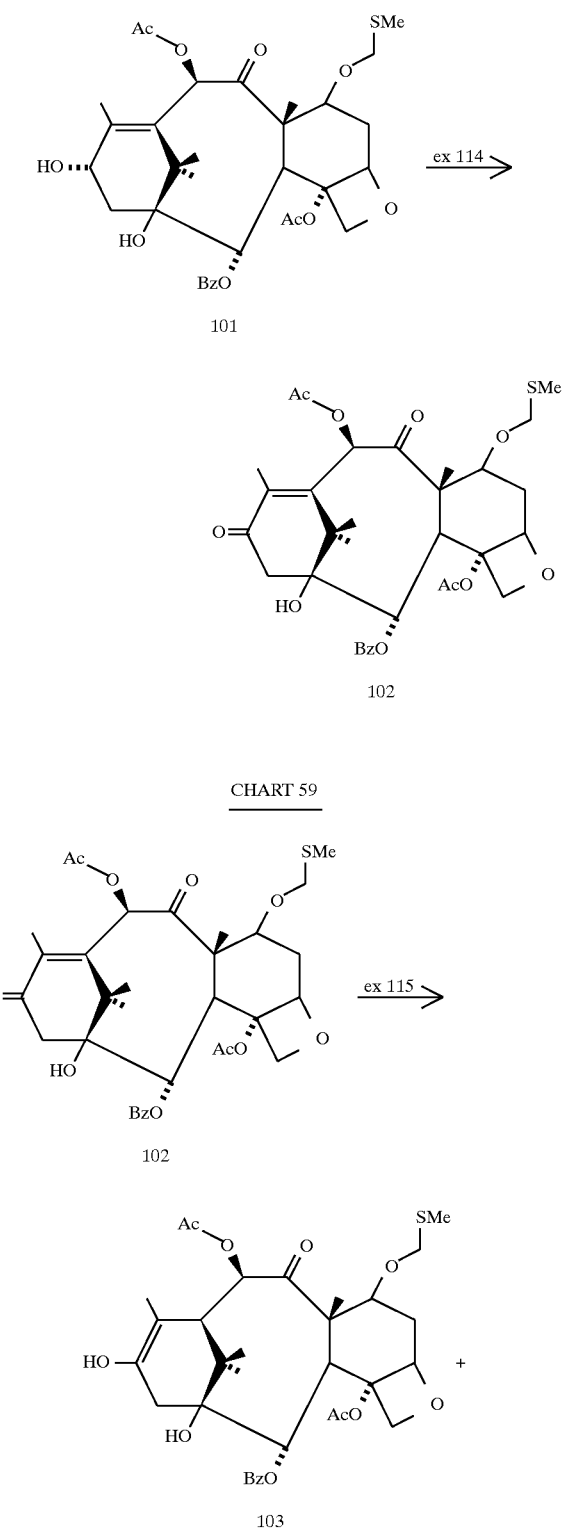

-continued
CHART 59
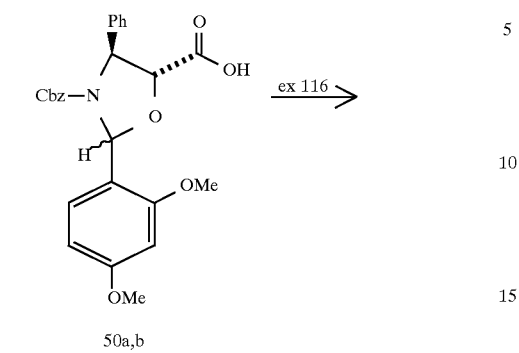
50a,b
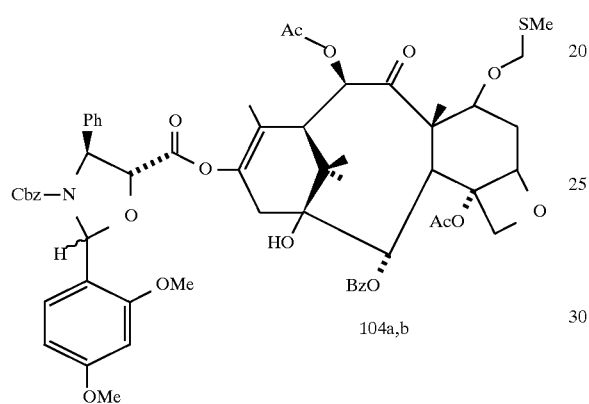
104a,b
CHART 60
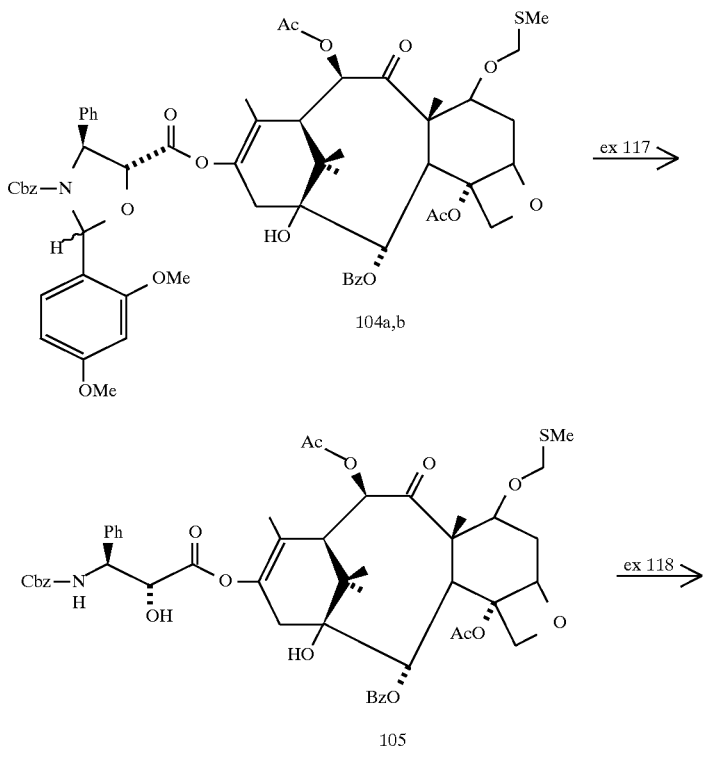
104a,b
105

-continued
CHART 60
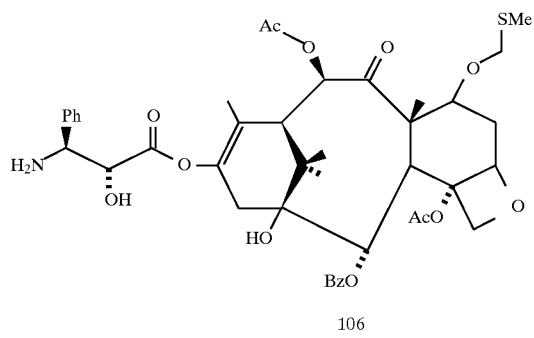
106
CHART 61
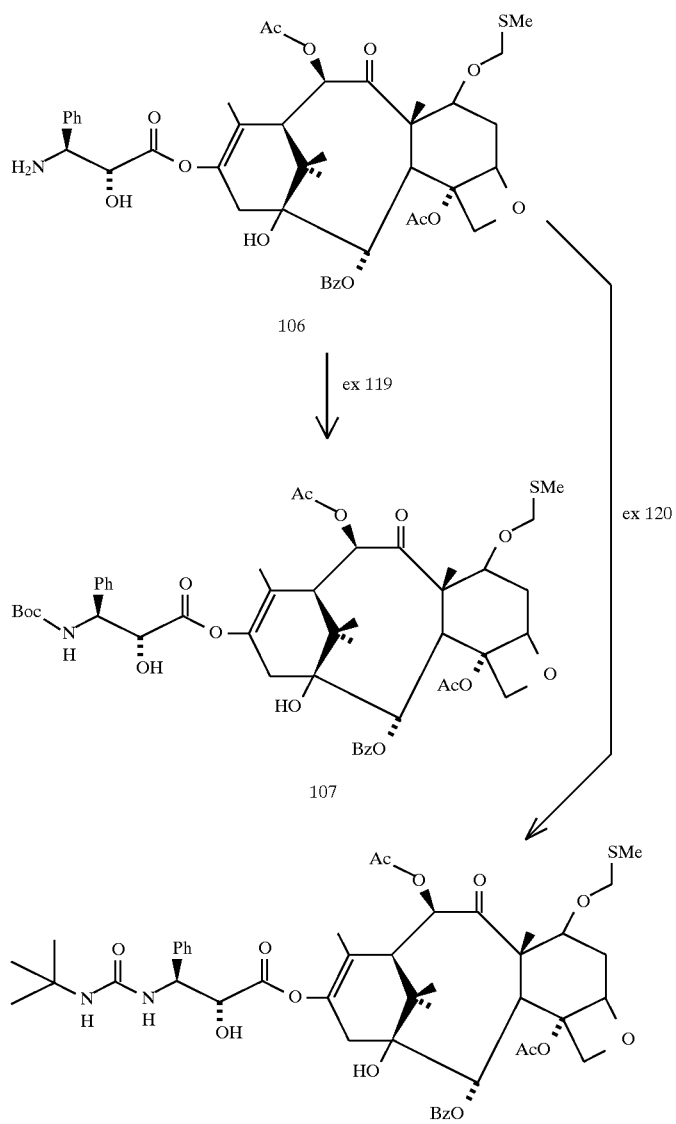

CHART 62
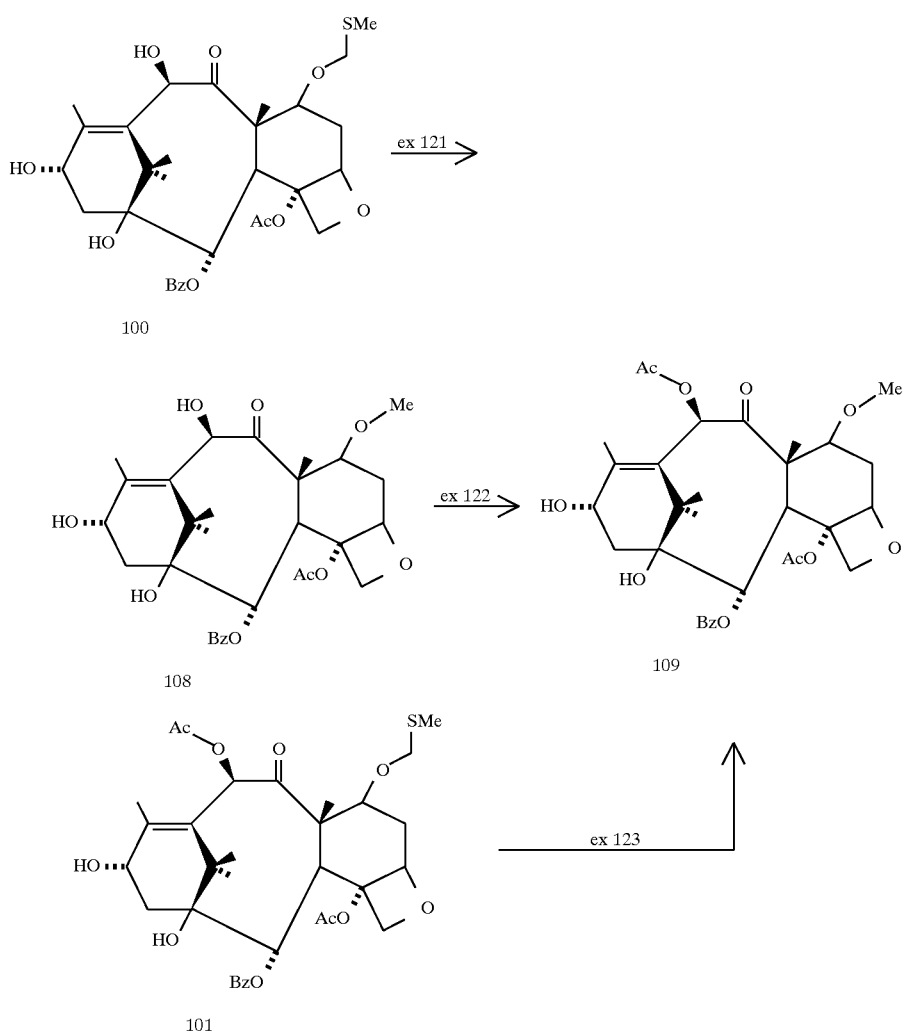
CHART 63
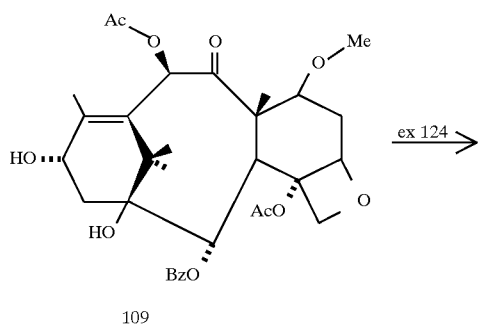
-continued
CHART 63
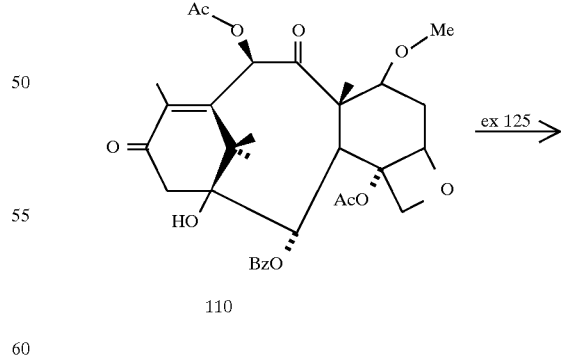

187
-continued
CHART 63
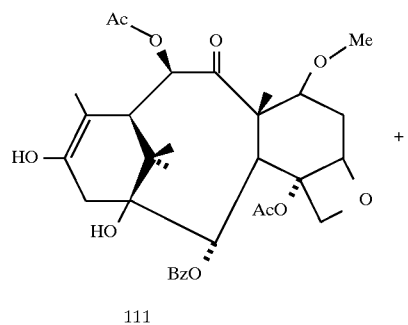
111
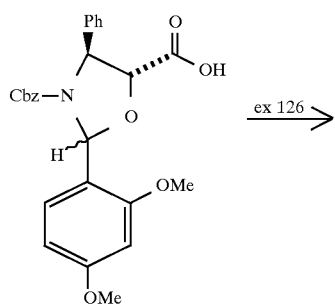 ex 126 →
50a,b
188
-continued
CHART 63
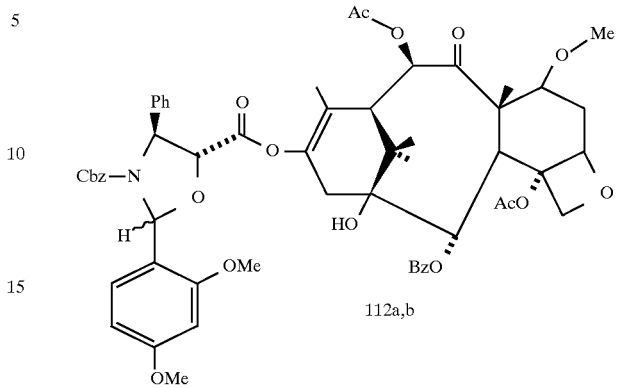
112a,b
CHART 64
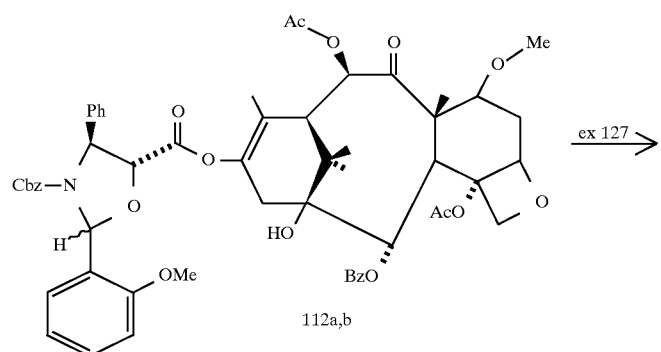
112a,b ex 127 →
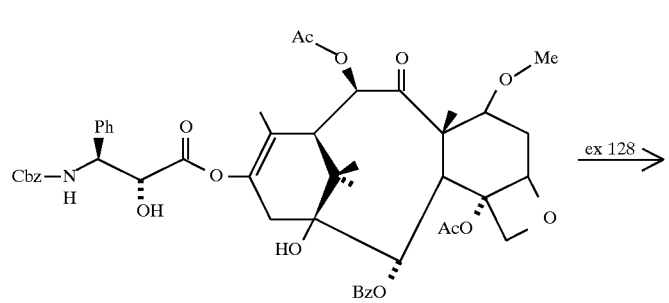
113 ex 128 →

-continued
CHART 64
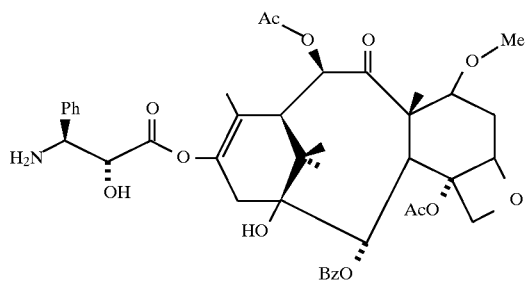
114
CHART 65
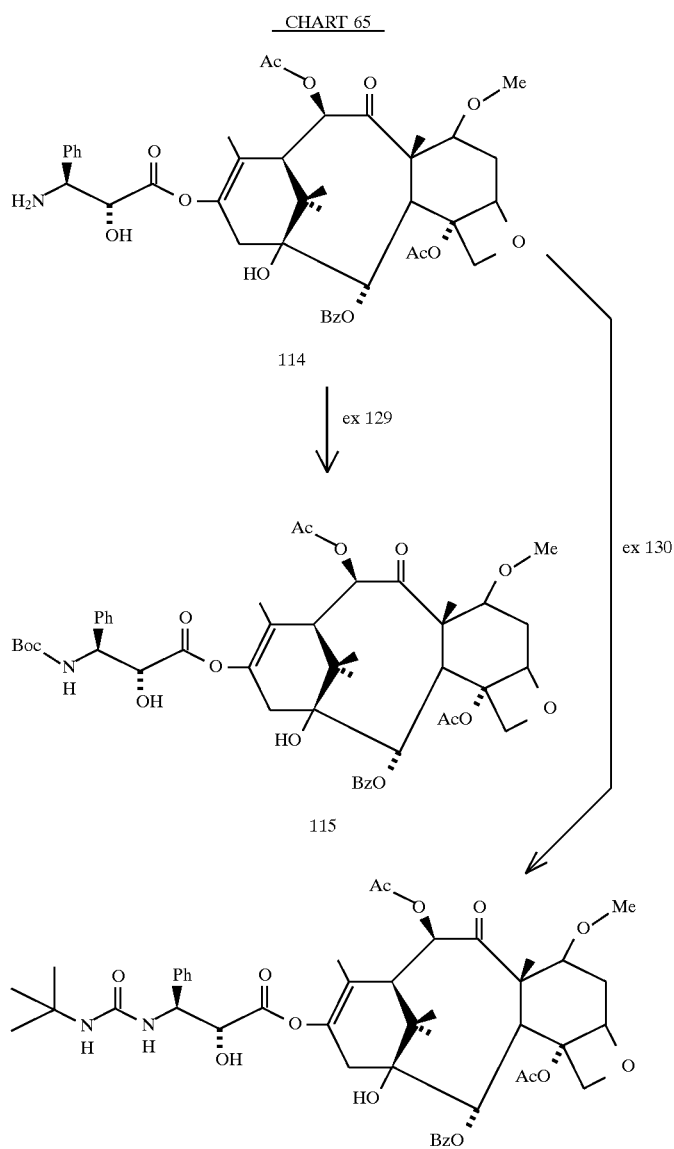

CHART 66
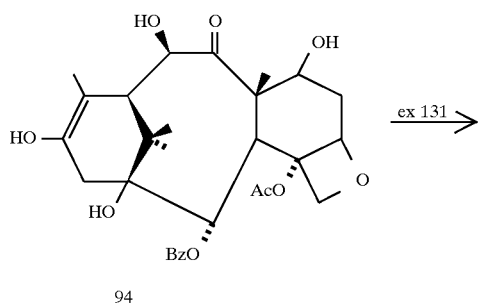
94
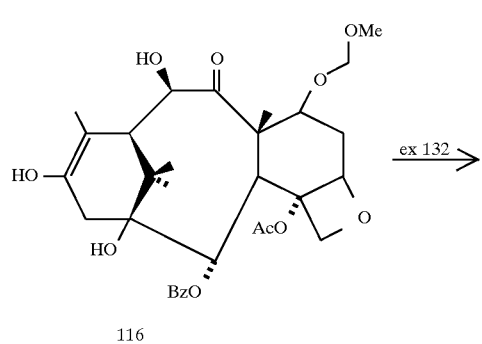
116
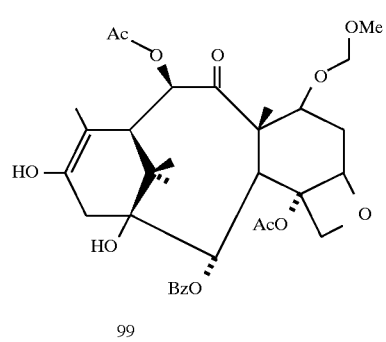
99
CHART 67
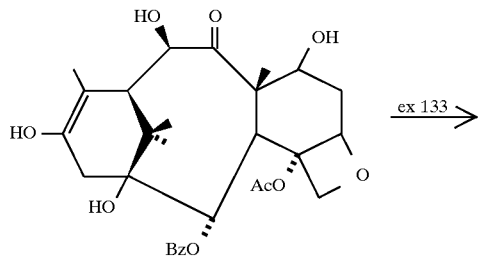
94
CHART 67
-continued
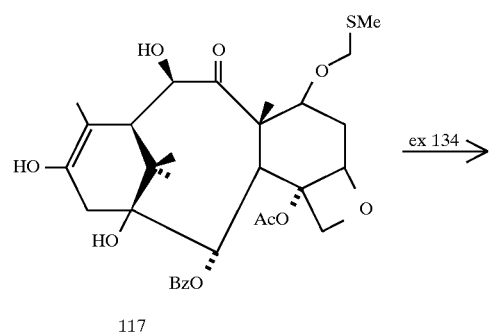
117
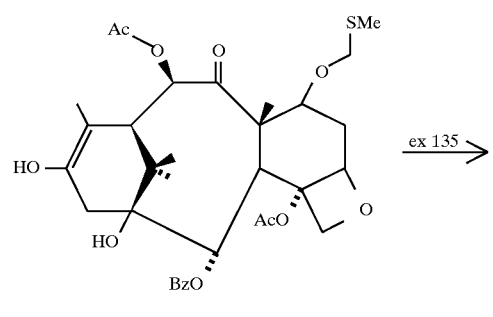
103
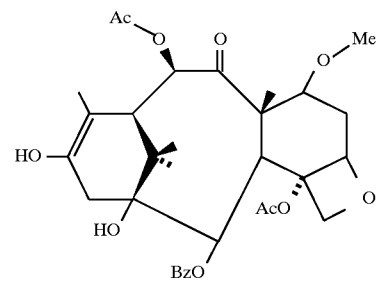
111

CHART 68

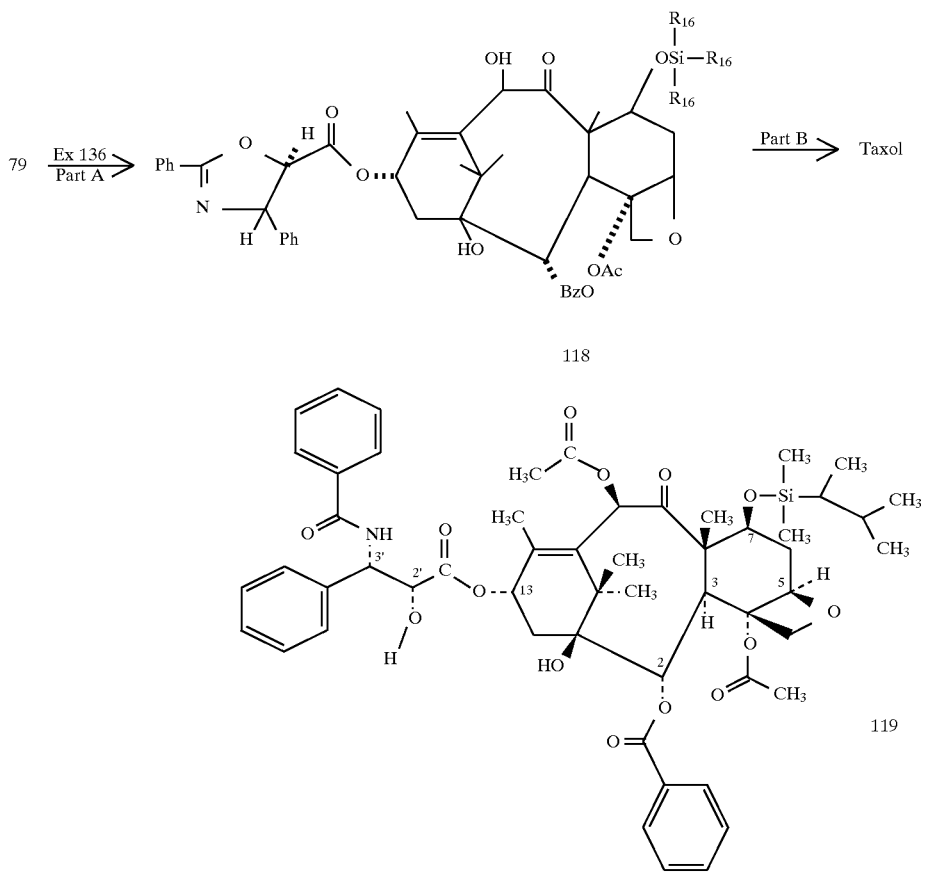

What is claimed is:
1. A compound of the Formula I:

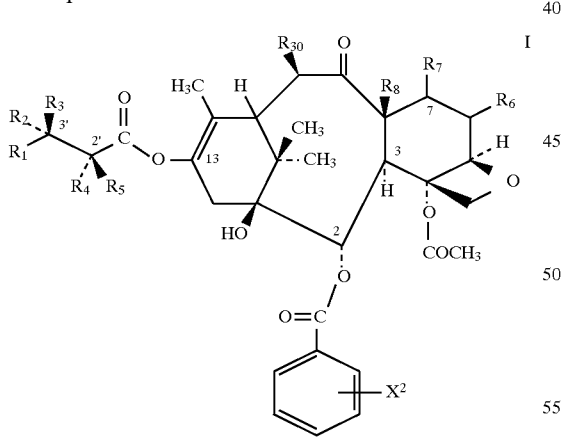

wherein:
X² is selected from the group consisting of
—H,
—$C_1$–$C_4$ alkyl,
—$C_1$–$C_3$ alkoxy,
halo,
—$C_1$–$C_3$ alkylthio,
-trifluoromethyl,
—$C_2$–$C_6$ dialkylamino,
benzyloxymethyl,
cyano,
azide ($N_3$),
or nitro;
$R_1$ is selected from the group consisting of
—$CH_3$,
—$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, -2-furyl, 2-thienyl, 1-naphthyl, 2-naphthyl or 3,4-methylenedioxyphenyl;
$R_2$ is selected from the group consisting of —H, —NHC(O)H, —NHC(O)$C_1$–$C_{10}$alkyl, —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C($CH_3$)=CH$CH_3$, —NHC(O)OC($CH_3$)$_3$, —NHC(O)OC$H_2$phenyl, —$NH_2$, —NH$SO_2$-4-methylphenyl, —NHC(O)($CH_2$)$_3$COOH, —NHC(O)-4-($SO_3$H)phenyl, —OH, —NHC(O)-1-adamantyl, —NHC(O)O-3-tetrahydrofuranyl, —NHC(O)O-4-tetrahydropyranyl, —NHC(O)$CH_2$C($CH_3$)$_3$, —NHC(O)C($CH_3$)$_3$, —NHC(O)O$C_1$–$C_{10}$alkyl, —NHC(O)NH$C_1$–$C_{10}$alkyl, —NHC(O)NHPh, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl, —NHC(O)OC(CH$_2$CH$_3$)$_2$CH$_3$, —NHC(O)OC(CH$_3$)$_2$CH$_2$Cl, —NHC(O)OC($CH_3$)$_2$$CH_2$$CH_3$, phthalimido, —NHC(O)-1-phenyl-1-cyclopentyl, —NHC(O)-1-methyl-1-cyclohexyl, —NHC(S)NHC($CH_3$)$_3$ or —NHC(O)NHC($CH_3$)$_3$;

$R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3$$^+$HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R' (where Z is ethylene (—CH$_2$CH$_2$—), propylene (—CH$_2$CH$_2$CH$_2$—), —CH=CH—, 1,2-cyclohexane or 1,2-phenylene, R' is —OH, —OH base, —NR'$_2$R'$_3$, —OR'$_3$, —SR'$_3$, —OCH$_2$C(O)NR'$_4$R'$_5$ where R'$_2$ is —H or —CH$_3$, R'$_3$ is —(CH$_2$)$_n$NR'$_6$R'$_7$ or (CH$_2$)$_n$N$^+$R'$_6$R'$_7$R'$_8$ X$^-$ where n is 1–3, R'$_4$ is —H or —C$_1$–C$_4$alkyl, R'$_5$ is —H, —C$_1$–C$_4$alkyl, benzyl, hydroxyethyl, —CH$_2$CO$_2$H or dimethylaminoethyl, R'$_6$ and R'$_7$ are —CH$_3$, —CH$_2$CH$_3$, benzyl or R'$_6$ and R'$_7$ together with the nitrogen of NR'$_6$R'$_7$ form a pyrrolidino, piperidino, morpholino, or N-methylpiperizino group; R'$_8$ is —CH$_3$, —CH$_2$CH$_3$ or benzyl, X$^-$ is halide, and base is NH$_3$, (HOC$_2$H$_4$)$_3$N, N(CH$_3$)$_3$, CH$_3$N(C$_2$H$_4$)$_2$NH, NH$_2$(CH$_2$)$_6$NH$_2$, N-methylglucamine, NaOH or KOH), —OC(O)(CH$_2$)$_n$NR$^2$R$^3$ (where n is 1–3, R$^2$ is —H or —C$_1$–C$_3$alkyl and R$^3$ —H or —C$_1$–C$_3$alkyl), —OC(O)CH(R")NH$_2$ (where R" is selected from the group consisting of —H, —CH$_3$, —CH$_2$CH(CH$_3$)$_2$, —CH(CH$_3$)CH$_2$CH$_3$, —CH(CH$_3$)$_2$, —CH$_2$phenyl, —(CH$_2$)$_4$NH$_2$, —CH$_2$CH$_2$COOH, —(CH$_2$)$_3$NHC(=NH)NH$_2$), the residue of the amino acid proline, —OC(O)CH=CH$_2$, —C(O)CH$_2$CH$_2$C(O)NHCH$_2$CH$_2$SO$_3$$^-$Y$^+$, —OC(O)CH$_2$CH$_2$C(O)NHCH$_2$CH$_2$CH$_2$SO$_3$$^-$Y$^+$ wherein Y$^+$ is Na$^+$ or N$^+$(Bu)$_4$, —OC(O)CH$_2$CH$_2$C(O)OCH$_2$CH$_2$OH;

$R_5$ is —H or —OH, with the overall proviso that when $R_5$ is —OH, $R_4$ is —H and with the further proviso that when $R_5$ is —H, $R_4$ is other than —H;

$R_6$ is —H:—H when $R_7$ is α-$R_{71}$:β-$R_{72}$ where one of $R_{71}$ and $R_{72}$ is —H and the other of $R_{71}$ and $R_{72}$ is —X$_7$ where X$_7$ is halo or azido (—N$_3$) and $R_8$ is —CH$_3$;

$R_6$ is —H:—H when $R_7$ is α-H:β-$R_{74}$ where $R_{74}$ and $R_8$ are taken together to form a cyclopropyl ring;

$R_6$ is $R_{65}$:$R_{66}$ when $R_7$ is $R_{75}$:$R_{76}$ where one of $R_{65}$ and $R_{66}$ is taken together with one of $R_{75}$ and $R_{76}$ to form a second bond between the carbon atoms to which they are attached and the other of $R_{65}$ and $R_{66}$ is —H, and the other of $R_{75}$ and $R_{76}$ is —H and where $R_8$ is —CH$_3$;

$R_6$ is —H:—H when $R_7$ is α-$R_{81}$:β-$R_{82}$ where one of $R_{81}$ and $R_{82}$ is —H and the other of $R_{81}$ and $R_{82}$ is —OH or —H and $R_8$ is —CH$_3$;

$R_6$ is —H:—H when $R_7$ is α-$R_{91}$:β-$R_{92}$ where one of $R_{91}$ and $R_{92}$ is —H and the other of $R_{91}$ and $R_{92}$ is —W where W is selected from the group consisting of —O—C$_1$–C$_6$alkyl, —O—C$_3$–C$_6$cycloalkyl, —O—(CH$_2$)$_n$phenyl where n is 1–6, —O—C(O)C$_1$–C$_{10}$alkyl, —O—C(O)phenyl, —O—C(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)naphthyl, —O—C(O)naphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Ophenyl, —O—C(O)Ophenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Onaphthyl, —O—C(O)Onaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OC$_1$–C$_{10}$alkyl, —O—C(O)NHC$_1$–C$_{10}$alkyl, —O—C(O)NHphenyl, —O—C(O)NHphenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)NHnaphthyl, —O—C(O)NHnaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OCH$_2$CHCl$_2$, —O—C(O)OCH$_2$CCl$_3$, —Si(R$^{16}$)$_3$, —O—CH$_2$—O—C$_1$–C$_6$alkyl, —O—CH$_2$—O—(CH$_2$)$_n$phenyl where n is 1–3, —O—CH$_2$—O—(CH$_2$)$_n$phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro and where $_n$ is 1–3, —O—CH$_2$—O—CH$_2$—CX$_q$H$_{3-q}$ where $_q$=0–3 and X is halogen, and $R_8$ is —CH$_3$;

$R_{30}$ is —H, —OH, or —OC(O)CH$_3$; and pharmaceutically acceptable salts thereof when the compound contains either an acidic or basic functional group.

2. A compound according to claim 1 wherein $R_2$ is —NHC(O)C$_6$H$_5$, $R_4$ is hydroxy, $R_3$ and $R_5$ are —H, and $R_1$ is phenyl or substituted phenyl.

3. A compound according to claim 1 wherein $R_2$ is —NHC(O)OC(CH$_3$)$_3$, $R_1$ is phenyl or substituted phenyl, $R_4$ is hydroxy, and $R_3$ and $R_5$ are —H.

4. A compound according to claim 1 wherein $R_6$ is $R_{65}$:$R_{66}$ when $R_7$ is $R_{75}$:$R_{76}$ where one of $R_{65}$ and $R_{66}$ is taken together with one of $R_{75}$ and $R_{76}$ to form a second bond between the carbon atoms to which they are attached and the other of $R_{65}$ and $R_{66}$ is —H, and the other of $R_{75}$ and $R_{76}$ is —H and where $R_8$ is —CH$_3$.

5. A compound according to claim 4 namely, 7-deoxy-$\Delta^{6,7}$-$\Delta^{12,13}$-iso-taxol and 10-acetyl-7-deoxy-$\Delta^{6,7}$-$\Delta^{12,13}$-iso-taxotere.

6. A compound according to claim 1 wherein $R_6$ is —H:—H when $R_7$ is α-$R_{71}$:β-$R_{72}$ where one of $R_{71}$ and $R_{72}$ is —H and the other of $R_{71}$ and $R_{72}$ is —X$_7$ where X$_7$ is halo or azido (—N$_3$) and $R_8$ is —CH$_3$.

7. A compound according to claim 6 selected from the group consisting of 7-deoxy-7α-fluoro-$\Delta^{12,13}$-iso-taxol and 7-deoxy-7β-fluoro-$\Delta^{12,13}$-iso-taxol and 10-acetyl-7-deoxy-7α-fluoro-$\Delta^{12,13}$-iso-taxotere, and 10-acetyl-7-deoxy-7β-fluoro-$\Delta^{12,13}$-iso-taxotere.

8. A compound according to claim 1 wherein $R_6$ is —H:—H when $R_7$ is α-H:β-$R_{74}$ where $R_{74}$ and $R_8$ are taken together to form a cyclopropyl group.

9. A compound according to claim 8 namely, 7-deoxy-7β,8β-methano-$\Delta^{12,13}$-iso-taxol and 10-acetyl-7-deoxy-7β,8β-methano-$\Delta^{12,13}$-iso-taxotere.

10. A compound according to claim 1 wherein $R_6$ is —H:—H when $R_7$ is α-$R_{81}$:β-$R_{82}$ where one of $R_{81}$ and $R_{82}$ is —H or and the other of $R_{81}$ and $R_{82}$ is —OH and $R_8$ is —CH$_3$.

11. A compound according to claim 1 wherein $R_6$ is —H:—H when $R_7$ is α-$R_{91}$:β-$R_{92}$ where one of $R_{91}$ and $R_{92}$ is —H and the other of $R_{91}$ and $R_{92}$ is —W where W is selected from the group consisting of —O—C$_1$–C$_6$alkyl, —O—C$_3$–C$_6$cycloalkyl, —O—(CH$_2$)$_n$phenyl where n is 1–6, —O—C(O)C$_1$–C$_{10}$alkyl, —O—C(O)phenyl, —O—C(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)naphthyl, —O—C(O)naphthyl substituted with one, 2 or 3 C$_1$–C$_4$ alkyl, C$_1$–C$_3$ alkoxy, halo, $C_1$–$C_3$ alkylthio, trifluoromethyl, $C_2$–$C_6$ dialkylamino, or nitro, —O—C(O)Ophenyl, —O—C(O) Ophenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —O—C(O)Onaphthyl, —O—C(O) Onaphthyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —O—C(O)OC$_1$–C$_{10}$alkyl, —O—C(O)NHC$_1$–C$_{10}$alkyl, —O—C(O)NHphenyl, —O—C(O)NHphenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —O—C(O)NHnaphthyl, —O—C(O)NHnaphthyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —O—C(O)OCH$_2$CHCl$_2$, —O—C(O)OCH$_2$CCl$_3$, —Si(R$^{16}$)$_3$, —O—CH$_2$—O—C$_1$–C$_6$alkyl, —O—CH$_2$—O—(CH$_2$)$_n$phenyl where $_n$ 1–3, —O—CH$_2$—O—(CH$_2$)$_n$phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro and where $_n$ is 1–3, —O—CH$_2$—O—CH$_2$—CX$_q$H$_{3-q}$ where $_q$=0–3 and X is halogen and R$_8$ is —CH$_3$.

12. A compound according to claim 11 where W is selected from the group consisting of propionyl;

O-(2,2-dichloroethyl)carbonate;

O-(2-chloroethyl)carbonate;

O-methyl;

O-propyl;

O-allyl;

O-methoxymethyl;

O-ethoxymethyl;

O-methoxyethoxymethyl;

O-benzyloxymethyl;

O-(2,2,2-trichloroethoxy)methyl; and

O-(2,2,2-trichloroethoxy)methoxymethyl.

13. A compound according to claim 1 selected from the group consisting of
7-deoxy-$\Delta^{6,7}$-$\Delta^{12,13}$-iso-taxol;
10-acetyl-7-deoxy-$\Delta^{6,7}$-$\Delta^{12,13}$-iso-taxotere;
2'-succinyl-7-deoxy-$\Delta^{6,7}$-$\Delta^{12,13}$-iso-taxol;
2'-(β-alanyl)-7-deoxy-$\Delta^{6,7}$-$\Delta^{12,13}$-iso-taxol formate;
2'-glutaryl-7-deoxy-$\Delta^{6,7}$-$\Delta^{12,13}$-iso-taxol;
2'-[-C(O)(CH$_2$)$_3$C(O)NH(CH$_2$)$_3$N(CH$_3$)$_2$]-7-deoxy-$\Delta^{6,7}$-$\Delta^{12,13}$-iso-taxol;
2'-(β-sulfopropionyl)-7-deoxy-$\Delta^{6,7}$-$\Delta^{12,13}$-iso-taxol;
2'-(2-sulfoethylamido)succinyl-7-deoxy-$\Delta^{6,7}$-$\Delta^{12,13}$-iso-taxol;
2'-(3-sulfopropylamido)succinyl-7-deoxy-$\Delta^{6,7}$-$\Delta^{12,13}$-iso-taxol;
2'-(triethylsilyl)-7-deoxy-$\Delta^{6,7}$-$\Delta^{12,13}$-iso-taxol;
2'-(t-butyldimethylsilyl)-7-deoxy-$\Delta^{6,7}$-$\Delta^{12,13}$-iso-taxol;
2'-(N,N-diethylaminopropionyl)-7-deoxy-$\Delta^{6,7}$-$\Delta^{12,13}$-iso-taxol;
2'-(N,N-dimethylglycyl)-7-deoxy-$\Delta^{6,7}$-$\Delta^{12,13}$-iso-taxol;
2'-(glycyl)-7-deoxy-$\Delta$6,7-$\Delta^{12,13}$-iso-taxol;
2'-(L-alanyl)-7-deoxy-$\Delta^{6,7}$-$\Delta^{12,13}$-iso-taxol;
2'-(L-leucyl)-7-deoxy-$\Delta^{6,7}$-$\Delta^{12,13}$-iso-taxol;
2'-(L-isoleucyl)-7-deoxy-$\Delta^{6,7}$-$\Delta^{12,13}$-iso-taxol;
2'-(L-valyl)-7-deoxy-$\Delta^{6,7}$-$\Delta^{12,13}$-iso-taxol;
2'-(L-phenylalanyl)-7-deoxy-$\Delta^{6,7}$-$\Delta^{12,13}$-iso-taxol;
2'-(L-prolyl)-7-deoxy-$\Delta^{6,7}$-$\Delta^{12,13}$-iso-taxol;
2'-(L-lysyl)-7-deoxy-$\Delta^{6,7}$-$\Delta^{12,13}$-iso-taxol;
2'-(L-glutamyl)-7-deoxy-$\Delta^{6,7}$-$\Delta^{12,13}$-iso-taxol;
2'-(L-arginyl)-7-deoxy-$\Delta^{6,7}$-$\Delta^{12,13}$-iso-taxol;
7-deoxy-$\Delta^{6,7}$-$\Delta^{12,13}$-iso-taxotere;
7-deoxy-7-fluoro-$\Delta^{12,13}$-iso-taxol;
2'-[{(2,2,2-trichloroethyl)oxy}carbonyl]-7-deoxy-7-fluoro-66 $^{12,13}$-iso-taxol;
2'-succinyl-7-deoxy-7-fluoro-$\Delta^{12,13}$-iso-taxol;
2'-(β-alanyl)-7-deoxy-7-fluoro-$\Delta^{12,13}$-iso-taxol formate;
2'-glutaryl-7-deoxy-7-fluoro-$\Delta^{12,13}$-iso-taxol;
2'-[-C(O)(CH$_2$)$_3$C(O)NH(CH$_2$)$_3$N(CH$_3$)$_2$]-7-deoxy-7-fluoro-$\Delta^{12,13}$-iso-taxol;
2'-(β-sulfopropionyl)-7-deoxy-7-fluoro-$\Delta^{12,13}$-iso-taxol;
2'-(2-sulfoethylamido)succinyl-7-deoxy-7-fluoro-$\Delta^{12,13}$-iso-taxol;
2'-(3-sulfopropylamido)succinyl-7-deoxy-7-fluoro-$\Delta^{12,13}$-iso-taxol;
2'-(triethylsilyl)-7-deoxy-7-fluoro-$\Delta^{12,13}$-iso-taxol;
2'-(t-butyldimethylsilyl)-7-deoxy-7-fluoro-$\Delta^{12,13}$-iso-taxol;
2'-(N,N-diethylaminopropionyl)-7-deoxy-7-fluoro-$\Delta^{12,13}$-iso-taxol;
2'-(N,N-dimethylglycyl)-7-deoxy-7-fluoro-$\Delta^{12,13}$-iso-taxol;
2'-(glycyl)-7-deoxy-7-fluoro-$\Delta^{12,13}$-iso-taxol;
2'-(L-alanyl)-7-deoxy-7-fluoro-$\Delta^{12,13}$-iso-taxol;
2'-(L-leucyl)-7-deoxy-7-fluoro-$\Delta^{12,13}$-iso-taxol;
2'-(L-isoleucyl)-7-deoxy-7-fluoro-$\Delta^{12,13}$-iso-taxol;
2'-(L-valyl)-7-deoxy-7-fluoro-$\Delta^{12,13}$-iso-taxol;
2'-(L-phenylalanyl)-7-deoxy-7-fluoro-$\Delta^{12,13}$-iso-taxol;
2'-(L-prolyl)-7-deoxy-7-fluoro-$\Delta^{12,13}$-iso-taxol;
2'-(L-lysyl)-7-deoxy-7-fluoro-$\Delta^{12,13}$-iso-taxol;
2'-(L-glutamyl)-7-deoxy-7-fluoro-$\Delta^{12,13}$-iso-taxol;
2'-(L-arginyl)-7-deoxy-7-fluoro-$\Delta^{12,13}$-iso-taxol;
N-debenzoyl-N-tetrahydropyran-4-yloxycarbonyl-7-deoxy-7-fluoro-$\Delta^{12,13}$-iso-taxol;
N-debenzoyl-N-pivaloyl-7-deoxy-7-fluoro-$\Delta^{12,13}$-iso-taxol;
N-debenzoyl-N-n-hexylaminocarbonyl-7-deoxy-7-fluoro-$\Delta^{12,13}$-iso-taxol;
7-deoxy-7α-fluoro-$\Delta^{12,13}$-iso-taxol;
7-deoxy-7β-fluoro-$\Delta^{12,13}$-iso-taxol;
2'-[{(2,2,2-trichloroethyl)oxy}carbonyl]-7-deoxy-7α-fluoro-$\Delta^{12,13}$-iso-taxol;
2'-[{(2,2,2-trichloroethyl)oxy}carbonyl]-7-deoxy-7β-fluoro-$\Delta^{12,13}$-iso-taxol;
2'-succinyl-7-deoxy-7α-fluoro-$\Delta^{12,13}$-iso-taxol;
2'-(β-alanyl)-7-deoxy-7α-fluoro-$\Delta^{12,13}$-iso-taxol formate;
2'-glutaryl-7-deoxy-7α-fluoro-$\Delta^{12,13}$-iso-taxol;
2'-[-C(O)(CH$_2$)$_3$C(O)NH(CH$_2$)$_3$N(CH$_3$)$_2$]-7-deoxy-7α-fluoro-$\Delta^{12,13}$-iso-taxol;
2'-(β-sulfopropionyl)-7-deoxy-7α-fluoro-$\Delta^{12,13}$-iso-taxol;
2'-(2-sulfoethylamido)succinyl-7-deoxy-7α-fluoro-$\Delta^{12,13}$-iso-taxol;
2'-(3-sulfopropylamido)succinyl-7-deoxy-7α-fluoro-$\Delta^{12,13}$-iso-taxol;
2'-(triethylsilyl)-7-deoxy-7α-fluoro-$\Delta^{12,13}$-iso-taxol;
2'-(t-butyldimethylsilyl)-7-deoxy-7α-fluoro-$\Delta^{12,13}$-iso-taxol;
2'-(N,N-diethylaminopropionyl)-7-deoxy-7α-fluoro-$\Delta^{12,13}$-iso-taxol;
2'-(N,N-dimethylglycyl)-7-deoxy-7α-fluoro-$\Delta^{12,13}$-iso-taxol;
2'-(glycyl)-7-deoxy-7α-fluoro-$\Delta^{12,13}$-iso-taxol;
2'-(L-alanyl)-7-deoxy-7α-fluoro-$\Delta^{12,13}$-iso-taxol;
2'-(L-leucyl)-7-deoxy-7α-fluoro-$\Delta^{12,13}$-iso-taxol;
2'-(L-isoleucyl)-7-deoxy-7α-fluoro-$\Delta^{12,13}$-iso-taxol;
2'-(L-valyl)-7-deoxy-7α-fluoro-$\Delta^{12,13}$-iso-taxol;
2'-(L-phenylalanyl)-7-deoxy-7α-fluoro-$\Delta^{12,13}$-iso-taxol;
2'-(L-prolyl)-7-deoxy-7α-fluoro-$\Delta^{12,13}$-iso-taxol;
2'-(L-lysyl)-7-deoxy-7α-fluoro-$\Delta^{12,13}$-iso-taxol;
2'-(L-glutamyl)-7-deoxy-7α-fluoro-$\Delta^{12,13}$-iso-taxol;
2'-(L-arginyl)-7-deoxy-7α-fluoro-$\Delta^{12,13}$-iso-taxol;

2'-succinyl-7-deoxy-7β-fluoro-$\Delta^{12,13}$-iso-taxol;
2'-(β-alanyl)-7-deoxy-7β-fluoro-$\Delta^{12,13}$-iso-taxol formate;
2'-glutaryl-7-deoxy-7β-fluoro-$\Delta^{12,13}$-iso-taxol;
2'-[-C(O)(CH$_2$)$_3$C(O)NH(CH$_2$)$_3$N(CH$_3$)$_2$]-7-deoxy-7β-fluoro-$\Delta^{12,13}$-iso-taxol;
2'-(β-sulfopropionyl)-7-deoxy-7β-fluoro-$\Delta^{12,13}$-iso-taxol;
2'-(2-sulfoethylamido)succinyl-7-deoxy-7β-fluoro-$\Delta^{12,13}$-iso-taxol;
2'-(3-sulfopropylamido)succinyl-7-deoxy-7β-fluoro-$\Delta^{12,13}$-iso-taxol;
2'-(triethylsilyl)-7-deoxy-7β-fluoro-$\Delta^{12,13}$-iso-taxol;
2'-(t-butyldimethylsilyl)-7-deoxy-7β-fluoro-$\Delta^{12,13}$-iso-taxol;
2'-(N,N-diethylaminopropionyl)-7-deoxy-7β-fluoro-$\Delta^{12,13}$-iso-taxol;
2'-(N,N-dimethylglycyl)-7-deoxy-7β-fluoro-$\Delta^{12,13}$-iso-taxol;
2'-(glycyl)-7-deoxy-7β-fluoro-$\Delta^{12,13}$-iso-taxol;
2'-(L-alanyl)-7-deoxy-7β-fluoro-$\Delta^{12,13}$-iso-taxol;
2'-(L-leucyl)-7-deoxy-7β-fluoro-$\Delta^{12,13}$-iso-taxol;
2'-(L-isoleucyl)-7-deoxy-7β-fluoro-$\Delta^{12,13}$-iso-taxol;
2'-(L-valyl)-7-deoxy-7β-fluoro-$\Delta^{12,13}$-iso-taxol;
2'-(L-phenylalanyl)-7-deoxy-7β-fluoro-$\Delta^{12,13}$-iso-taxol;
2'-(L-prolyl)-7-deoxy-7β-fluoro-$\Delta^{12,13}$-iso-taxol;
2'-(L-lysyl)-7-deoxy-7β-fluoro-$\Delta^{12,13}$-iso-taxol;
2'-(L-glutamyl)-7-deoxy-7β-fluoro-$\Delta^{12,13}$-iso-taxol;
2'-(L-arginyl)-7-deoxy-7β-methano-$\Delta^{12,13}$-iso-taxol;
7-deoxy-7β,8β-methano-$\Delta^{12,13}$-iso-taxol;
2'-[{(2,2,2-trichloroethyl)oxy}carbonyl]-7-deoxy-7β,8β-methano-$\Delta^{12,13}$-iso-taxol;
2'-succinyl-7-deoxy-7β,8β-methano-$\Delta^{12,13}$-iso-taxol;
2'-(β-alanyl)-7-deoxy-7β,8β-methano-$\Delta^{12,13}$-iso-taxol formate;
2'-glutaryl-7-deoxy-7β,8β-methano-$\Delta^{12,13}$-iso-taxol;
2'-[-C(O)(CH$_2$)$_3$C(O)NH(CH$_2$)$_3$N(CH$_3$)$_2$]-7-deoxy-7β,8β-methano-$\Delta$12,13-iso-taxol;
2'-(β-sulfopropionyl)-7-deoxy-7β,8β-methano-$\Delta^{12,13}$-iso-taxol;
2'-(2-sulfoethylamido)succinyl-7-deoxy-7β,8β-methano-$\Delta^{12,13}$-iso-taxol;
2'-(3-sulfopropylamido)succinyl-7-deoxy-7β,8β-methano-$\Delta^{12,13}$-iso-taxol;
2'-(triethylsilyl)-7-deoxy-7β,8β-methano-$\Delta^{12,13}$-iso-taxol;
2'-(t-butyldimethylsilyl)-7-deoxy-7β,8β-methano-$\Delta^{12,13}$-iso-taxol;
2'-(N,N-diethylaminopropionyl)-7-deoxy-7β,8β-methano-$\Delta^{12,13}$-iso-taxol;
2'-(N,N-dimethylglycyl)-7-deoxy-7β,8β-methano-$\Delta^{12,13}$-iso-taxol;
2'-(glycyl)-7-deoxy-7β,8β-methano-$\Delta^{12,13}$-iso-taxol;
2'-(L-alanyl)-7-deoxy-7β,8β-methano-$\Delta^{12,13}$-iso-taxol;
2'-(L-leucyl)-7-deoxy-7β,8β-methano-$\Delta^{12,13}$-iso-taxol;
2'-(L-isoleucyl)-7-deoxy-7β,8β-methano-$\Delta^{12,13}$-iso-taxol;
2'-(L-valyl)-7-deoxy-7β,8β-methano-$\Delta^{12,13}$-iso-taxol;
2'-(L-phenylalanyl)-7-deoxy-7β,8β-methano-$\Delta^{12,13}$-iso-taxol;
2'-(L-prolyl)-7-deoxy-7β,8β-methano-$\Delta^{12,13}$-iso-taxol;
2'-(L-lysyl)-7-deoxy-7β,8β-methano-$\Delta^{12,13}$-iso-taxol;
2'-(L-glutamyl)-7-deoxy-7β,8β-methano-$\Delta^{12,13}$-iso-taxol;
2'-(L-arginyl)-7-deoxy-7β,8β-methano-$\Delta^{12,13}$-iso-taxol;
7-deoxy-7β,8β-methano-$\Delta^{12,13}$-iso-taxotere;
N-debenzoyl-N-tetrahydrofuran-3-yloxycarbonyl-7-deoxy-7β,8β-methano-$\Delta^{12,13}$-iso-taxol;
N-debenzoyl-N-(1-adamantoyl)-7-deoxy-7β,8β-methano-$\Delta^{12,13}$-iso-taxol or
N-debenzoyl-N-phenylaminocarbonyl-7-deoxy-7β,8β-methano-$\Delta^{12,13}$-iso-taxol.

14. A pharmaceutical composition comprising an effective antitumor amount of at least one compound of the Formula I:

wherein:
$X^2$ is selected from the group consisting of
—H,
—$C_1$–$C_4$ alkyl,
—$C_1$–$C_3$ alkoxy,
halo,
—$C_1$–$C_3$ alkylthio,
-trifluoromethyl,
—$C_2$–$C_6$ dialkylamino,
benzyloxymethyl,
cyano,
azide ($N_3$),
or nitro;

$R_1$ is selected from the group consisting of
—$CH_3$,
—$C_6H_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-naphthyl, 2-naphthyl or 3,4-methylenedioxyphenyl;

$R_2$ is selected from the group consisting of —H, —NHC(O)H, —NHC(O)$C_1$–$C_{10}$alkyl, —NHC(O)phenyl, —NHC(O)phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, —NHC(O)C(CH$_3$)=CHCH$_3$, —NHC(O)OC(CH$_3$)$_3$, —NHC(O)OCH$_2$phenyl, —NH$_2$, —NHSO$_2$-4-methylphenyl, —NHC(O)(CH$_2$)$_3$COOH, —NHC(O)-4-(SO$_3$H)phenyl, —OH, —NHC(O)-1-adamantyl, —NHC(O)O-3-tetrahydrofuranyl, —NHC(O)O-4-tetrahydropyranyl, —NHC(O)CH$_2$C(CH$_3$)$_3$, —NHC(O)C(CH$_3$)$_3$, —NHC(O)OC$_1$–$C_{10}$alkyl, —NHC(O)NHC$_1$–$C_{10}$alkyl, —NHC(O)NHPh, —NHC(O)NHPh substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, or nitro, —NHC(O)$C_3$–$C_8$cycloalkyl, —NHC(O)OC(CH$_2$CH$_3$)$_2$CH$_3$, —NHC(O)OC(CH$_3$)$_2$CH$_2$Cl, —NHC(O)OC(CH$_3$)$_2$CH$_2$CH$_3$, phthalimido, —NHC(O)-1-phenyl-1-cyclopentyl, —NHC(O)-1-methyl-1-cyclohexyl, —NHC(S)NHC(CH$_3$)$_3$ or —NHC(O)NHC(CH$_3$)$_3$;

$R_3$ is selected from the group consisting of —H, —NHC(O)phenyl or —NHC(O)OC(CH$_3$)$_3$, with the overall proviso that one of $R_2$ and $R_3$ is —H but $R_2$ and $R_3$ are not both —H;

$R_4$ is —H or selected from the group consisting of —OH, —OAc (—OC(O)CH$_3$), —OC(O)OCH$_2$C(Cl)$_3$, —OCOCH$_2$CH$_2$NH$_3^+$HCOO$^-$, —NHC(O)phenyl, —NHC(O)OC(CH$_3$)$_3$, —OCOCH$_2$CH$_2$COOH and pharmaceutically acceptable salts thereof, —OCO(CH$_2$)$_3$COOH and pharmaceutically acceptable salts thereof, and —OC(O)—Z—C(O)—R', —OC(O)(CH$_2$)$_n$NR$^2$R$^3$, —OC(O)CH(R")NH$_2$, the residue of the amino acid proline, —OC(O)CH=CH$_2$, —C(O)CH$_2$CH$_2$C(O)NHCH$_2$CH$_2$SO$_3^-$Y$^+$, —OC(O)CH$_2$CH$_2$C(O)NHCH$_2$CH$_2$CH$_2$SO$_3^-$Y$^+$ wherein Y$^+$ is Na$^+$ or N$^+$(Bu)$_4$, —OC(O)CH$_2$CH$_2$C(O)OCH$_2$CH$_2$OH;

R$_5$ is —H or —OH, with the overall proviso that when R$_5$ is —OH, R$_4$ is —H and with the further proviso that when R$_{5n}$ is —H, R$_4$ is other than —H;

R$_6$ is —H:—H when R$_7$ is α-R$_{71}$:β-R$_{72}$ where one of R$_{71}$ and R$_{72}$ is —H and the other of R$_{71}$ and R$_{72}$ is —X$_7$ where X$_7$ is halo or azido (—N$_3$) and R$_8$ is —CH$_3$;

R$_6$ is —H:—H when R$_7$ is α-H:β-R$_{74}$ where R$_{74}$ and R$_8$ are taken together to form a cyclopropyl ring;

R$_6$ is R$_{65}$:R$_{66}$ when R$_7$ is R$_{75}$:R$_{76}$ where one of R$_{65}$ and R$_{66}$ is taken together with one of R$_{75}$ and R$_{76}$ to form a second bond between the carbon atoms to which they are attached and the other of R$_{65}$ and R$_{66}$ is —H, and the other of R$_{75}$ and R$_{76}$ is —H and where R$_8$ is —CH$_3$;

R$_6$ is —H:—H when R$_7$ is α-R$_{81}$:β-R$_{82}$ where one of R$_{81}$ and R$_{82}$ is —H and the other of R$_{81}$ and R$_{82}$ is —OH or —H and R$_8$ is —CH$_3$;

R$_6$ is —H:—H when R$_7$ is α-R$_{91}$:β-R$_{92}$ where one of R$_{91}$ and R$_{92}$ is —H and the other of R$_{91}$ and R$_{92}$ is —W where W is selected from the group consisting of —O—C$_1$–C$_6$alkyl, —O—C$_3$–C$_6$cycloalkyl, —O—(CH$_2$)$_n$phenyl where n is 1–6, —O—C(O)C$_1$–C$_{10}$alkyl, —O—C(O)phenyl, —O—C(O)phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)naphthyl, —O—C(O)naphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Ophenyl, —O—C(O)Ophenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)Onaphthyl, —O—C(O)Onaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OC$_1$–C$_{10}$alkyl, —O—C(O)NHC$_1$–C$_{10}$alkyl, —O—C(O)NHphenyl, —O—C(O)NHphenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)NHnaphthyl, —O—C(O)NHnaphthyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro, —O—C(O)OCH$_2$CHCl$_2$, —O—C(O)OCH$_2$CCl$_3$, —Si(R$^{16}$)$_3$, —O—CH$_2$—O—C$_1$-C$_6$ alkyl, —O—CH$_2$—O—(CH$_2$)$_n$phenyl where $_n$ is 1–3, —O—CH$_2$—O—(CH$_2$)$_n$phenyl substituted with one, 2 or 3 C$_1$–C$_4$ alkyl, C$_1$–C$_3$ alkoxy, halo, C$_1$–C$_3$ alkylthio, trifluoromethyl, C$_2$–C$_6$ dialkylamino, or nitro and where $_n$ is 1–3, —O—CH$_2$—O—CH$_2$—CX$_q$H$_{3-q}$ where $_q$=0–3 and X is halogen, and R$_8$ is —CH$_3$;

R$_{30}$ is —H, —OH, or —OC(O)CH$_3$; and pharmaceutically acceptable salts thereof when the compound contains either an acidic or basic functional group.

15. A compound according to claim 1 selected from the group consisting of 10-acetyl-7-deoxy-7-fluoro-Δ$^{12,13}$-iso-taxotere;
10-acetyl-7β,8β-methano-Δ$^{12,13}$-iso-taxotere;
10-acetyl-7-deoxy-Δ$^{6,7}$-Δ$^{12,13}$-iso-taxotere;
13-(N-Boc-β-phenyl isoserinyl)-Δ$^{12,13}$-iso-baccatin III (7);
10-deacetyl-13-(N-Boc-β-phenyl isoserinyl)-Δ$^{12,13}$-iso-baccatin III (8);
7-Troc-13-(N-Boc-β-phenyl isoserinyl)-Δ$^{12,13}$-iso-baccatin III (12);
2'-Troc-13-(N-Boc-β-phenyl isoserinyl)-7-deoxy-7-fluoro-Δ$^{12,13}$-iso-baccatin III (13);
2'-Troc-13-(N-Boc-β-phenylisoserinyl)-7-deoxy-7b,8b-methano-Δ$^{12,13}$-iso-baccatin III (14);
2'-Troc-13-(N-Boc-β-phenyl isoserinyl)-7-deoxy-Δ$^{6,7}$-Δ$^{12,13}$-iso-baccatin III (15);
13-(N-Boc-β-phenyl isoserinyl)-7-deoxy-7-fluoro-Δ$^{12,13}$-iso-baccatin III (16);
13-(N-Boc-β-phenyl isoserinyl)-7-deoxy-7b,8b-methano-Δ$^{12,13}$-iso-baccatin III (17);
13-(N-Boc-β-phenyl isoserinyl)-7-deoxy-Δ$^{6,7}$-Δ$^{12,13}$-iso-baccatin III (18);
7-TES-13-(N-(t-butylaminocarbonyl)-β-phenyl isoserinyl)-Δ$^{12,13}$-iso-baccatin III (32a);
13-(N-(t-butylaminocarbonyl)-β-phenyl isoserinyl)-Δ$^{12,13}$-iso-baccatin III (32b);
7-ethoxymethyl-13-(N-Boc-β-phenyl isoserinyl)-Δ$^{12,13}$-iso-baccatin III (41); and
7-methoxymethyl-13-(N-Boc-β-phenyl isoserinyl)-Δ$^{12,13}$-iso-baccatin III (66).

16. A compound according to claim 1 selected from the group consisting of

N-debenzoyl-N-tetrahydrofuran-3-yloxycarbonyl-7-deoxy-7β,8β-methano-Δ$^{12,13}$-iso-taxol;
N-debenzoyl-N-(1-adamantoyl)-7-deoxy-7β,8β-methano-Δ$^{12,13}$-iso-taxol;
N-debenzoyl-N-phenylaminocarbonyl-7-deoxy-7β,8β-methano-Δ$^{12,13}$-iso-taxol;
N-debenzoyl-N-t-butylaminocarbonyl-7-deoxy-7β,8β-methano-Δ$^{12,13}$-iso-taxol;
N-debenzoyl-N-(1-methyl-1-cyclohexylanoyl)-7-deoxy-7β,8β-methano-Δ$^{12,13}$-iso-taxol;
N-debenzoyl-N-(1-phenyl-1-cyclopentanoyl)-7-deoxy-7β,8β-methano-Δ$^{12,13}$-iso-taxol;
N-debenzoyl-N-phthalimido-7-deoxy-7β,8β-methano-Δ$^{12,13}$-iso-taxol;
N-debenzoyl-N-t-butylaminothiocarbonyl-7-deoxy-7β,8β-methano-Δ$^{12,13}$-iso-taxol;
N-debenzoyl-N-t-amyloxycarbonyl-7-deoxy-7β,8β-methano-Δ$^{12,13}$-iso-taxol;
N-debenzoyl-N-neopentyloxycarbonyl-7-deoxy-7β,8β-methano-Δ$^{12,13}$-iso-taxol;
N-debenzoyl-N-(2-chloro-1,1-dimethylethyl)oxycarbonyl-7-deoxy-7β,8β-methano-Δ$^{12,13}$-iso-taxol;
N-debenzoyl-N-(3-methyl-3-pentyl)oxycarbonyl-7-deoxy-7β,8β-methano-Δ$^{12,13}$-iso-taxol;
N-debenzoyl-N-tetrahydropyran-4-yloxycarbonyl-7-deoxy-7-fluoro-Δ$^{12,13}$-iso-taxol;
N-debenzoyl-N-pivaloyl-7-deoxy-7-fluoro-Δ$^{12,13}$-iso-taxol;
N-debenzoyl-N-n-hexylaminocarbonyl-7-deoxy-7-fluoro-Δ$^{12,13}$-iso-taxol;
N-debenzoyl-N-t-butylaminocarbonyl-7-deoxy-7-fluoro-Δ$^{12,13}$-iso-taxol;
N-debenzoyl-N-(1-methyl-1-cyclohexylanoyl)-7-deoxy-7-fluoro-Δ$^{12,13}$-iso-taxol;
N-debenzoyl-N-(1-phenyl-1-cyclopentanoyl)-7-deoxy-7-fluoro-Δ$^{12,13}$-iso-taxol;
N-debenzoyl-N-phthalimido-7-deoxy-7-fluoro-Δ$^{12,13}$-iso-taxol;

N-debenzoyl-N-t-butylaminothiocarbonyl-7-deoxy-7-fluoro-$\Delta^{12,13}$-iso-taxol;
N-debenzoyl-N-t-amyloxycarbonyl-7-deoxy-7-fluoro-$\Delta^{12,13}$-iso-taxol;
N-debenzoyl-N-neopentyloxycarbonyl-7-deoxy-7-fluoro-$\Delta^{12,13}$-iso-taxol;
N-debenzoyl-N-(2-chloro-1,1-dimethylyethyl)oxycarbonyl-7-deoxy-7-fluoro-$\Delta^{12,13}$-iso-taxol;
N-debenzoyl-N-(3-methyl-3-pentyl)oxycarbonyl-7-deoxy-7-fluoro-$\Delta^{12,13}$-iso-taxol;
N-debenzoyl-N-t-butylaminocarbonyl-7-deoxy-$\Delta^{6,7}$-$\Delta^{12,13}$-iso-taxol;
N-debenzoyl-N-(1-methyl-1-cyclohexylanoyl)-7-deoxy-$\Delta^{6,7}$-$\Delta^{12,13}$-iso-taxol;
N-debenzoyl-N-(1-phenyl-1-cyclopentanoyl)-7-deoxy-$\Delta^{6,7}$-$\Delta^{12,13}$-iso-taxol;
N-debenzoyl-N-phthalimido-7-deoxy-$\Delta^{6,7}$-$\Delta^{12,13}$-iso-taxol;
N-debenzoyl-N-t-butylaminothiocarbonyl-7-deoxy-$\Delta^{6,7}$-$\Delta^{12,13}$-iso-taxol;
N-debenzoyl-N-t-amyloxycarbonyl-7-deoxy-$\Delta^{6,7}$-$\Delta^{12,13}$-iso-taxol;
N-debenzoyl-N-neopentyloxycarbonyl-7-deoxy-$\Delta^{6,7}$-$\Delta^{12,13}$-iso-taxol;
N-debenzoyl-N-(2-chloro-1,1-dimethylyethyl)oxycarbonyl-7-deoxy-$\Delta^{6,7}$-$\Delta^{12,13}$-iso-taxol; or
N-debenzoyl-N-(3-methyl-3-pentyl)oxycarbonyl-7-deoxy-$\Delta^{6,7}$-$\Delta^{12,13}$-iso-taxol.

17. A compound according to claim 1 selected from the group consisting of

3'-desphenyl-3'-(2-furyl)-7-deoxy-7β,8β-methano-$\Delta^{12,13}$-iso-taxol;
3'-desphenyl-3'-(2-thienyl)-7-deoxy-7β,8β-methano-$\Delta^{12,13}$-iso-taxol;
3'-desphenyl-3'-(1-naphthyl)-7-deoxy-7β,8β-methano-$\Delta^{12,13}$-iso-taxol;
3'-desphenyl-3'-(2-naphthyl)-7-deoxy-7β,8β-methano-$\Delta^{12,13}$-iso-taxol;
3'-desphenyl-3'-(4-methoxyphenyl)-7-deoxy-7β,8β-methano-$\Delta^{12,13}$-iso-taxol;
3'-desphenyl-3'-(4-chlorophenyl)-7-deoxy-7β,8β-methano-$\Delta^{12,13}$-iso-taxol;
3'-desphenyl-3'-(4-bromophenyl)-7-deoxy-7β,8β-methano-$\Delta^{12,13}$-iso-taxol;
3'-desphenyl-3'-(3,4-methylenedioxyphenyl)-7-deoxy-7β,8β-methano-$\Delta^{12,13}$-iso-taxol;
3'-desphenyl-3'-(3,4-dimethoxyphenyl)-7-deoxy-7β,8β-methano-$\Delta^{12,13}$-iso-taxol;
3'-desphenyl-3'-(4-nitrophenyl)-7-deoxy-7β,8β-methano-$\Delta^{12,13}$-iso-taxol;
3'-desphenyl-3'-(4-fluorophenyl)-7-deoxy-7β,8β-methano-$\Delta^{12,13}$-iso-taxol;
N-debenzoyl-N-(4-bromobenzoyl)-7-deoxy-7β,8β-methano-$\Delta^{12,13}$-iso-taxol;
N-debenzoyl-N-(4-methylbenzoyl)-7-deoxy-7β,8β-methano-$\Delta^{12,13}$-iso-taxol;
N-debenzoyl-N-(4-t-butylbenzoyl)-7-deoxy-7β,8β-methano-$\Delta^{12,13}$-iso-taxol;
N-debenzoyl-N-(4-methoxybenzoyl)-7-deoxy-7β,8β-methano-$\Delta^{12,13}$-iso-taxol;
N-debenzoyl-N-(4-fluorobenzoyl)-3'-desphenyl-3'-(4-fluorophenyl)-7-deoxy-7β,8β-methano-$\Delta^{12,13}$-iso-taxol;
N-debenzoyl-N-(4-fluorobenzoyl)-7-deoxy-7β,8β-methano-$\Delta^{12,13}$-iso-taxol;
N-debenzoyl-N-(4-methylbenzoyl)-3'-desphenyl-3'-(4-chlorophenyl)-7-deoxy-7β,8β-methano-$\Delta^{12,13}$-iso-taxol;
N-debenzoyl-N-(4-chlorobenzoyl)-3'-desphenyl-3'-(4-fluorophenyl)-7-deoxy-7β,8β-methano-$\Delta^{12,13}$-iso-taxol;
N-debenzoyl-N-(4-bromobenzoyl)-3'-desphenyl-3'-(4-fluorophenyl)-7-deoxy-7β,8β-methano-$\Delta^{12,13}$-iso-taxol;
N-debenzoyl-N-(4-methylbenzoyl)-3'-desphenyl-3'-(4-fluorophenyl)-7-deoxy-7β,8β-methano-$\Delta^{12,13}$-iso-taxol;
N-debenzoyl-N-(4-fluorobenzoyl)-3'-desphenyl-3'-(4-methoxyphenyl)-7-deoxy-7β,8β-methano-$\Delta^{12,13}$-iso-taxol;
N-debenzoyl-N-(4-methylbenzoyl)-3'-desphenyl-3'-(4-methoxyphenyl)-7-deoxy-7β,8β-methano-$\Delta^{12,13}$-iso-taxol;
N-debenzoyl-N-(4-fluorobenzoyl)-3'-desphenyl-3'-(4-chlorophenyl)-7-deoxy-7β,8β-methano-$\Delta^{12,13}$-iso-taxol;
N-debenzoyl-N-(4-chlorobenzoyl)-3'-desphenyl-3'-(4-chlorophenyl)-7-deoxy-7β,8β-methano-$\Delta^{12,13}$-iso-taxol;
N-debenzoyl-N-(4-bromobenzoyl)-3'-desphenyl-3'-(4-chlorophenyl)-7-deoxy-7β,8β-methano-$\Delta^{12,13}$-iso-taxol;
N-debenzoyl-N-(4-t-butylbenzoyl)-3'-desphenyl-3'-(4-chlorophenyl)-7-deoxy-7β,8β-methano-$\Delta^{12,13}$-iso-taxol;
N-debenzoyl-N-(4-t-butylbenzoyl)-3'-desphenyl-3'-(4-fluorophenyl)-7-deoxy-7β,8β-methano-$\Delta^{12,13}$-iso-taxol;
N-debenzoyl-N-(4-chlorobenzoyl)-3'-desphenyl-3'-(4-methoxyphenyl)-7-deoxy-7β,8β-methano-$\Delta^{12,13}$-iso-taxol;
N-debenzoyl-N-(4-bromobenzoyl)-3'-desphenyl-3'-(4-methoxyphenyl)-7-deoxy-7β,8β-methano-$\Delta^{12,13}$-iso-taxol;
N-debenzoyl-N-(4-t-butylbenzoyl)-3'-desphenyl-3'-(4-methoxyphenyl)-7-deoxy-7β,8β-methano-$\Delta^{12,13}$-iso-taxol;
N-debenzoyl-N-(4-methoxybenzoyl)-3'-desphenyl-3'-(4-methoxyphenyl)-7-deoxy-7β,8β-methano-$\Delta^{12,13}$-iso-taxol;
3'-desphenyl-3'-(2-furyl)-7-deoxy-7-fluoro-$\Delta^{12,13}$-iso-taxol;
3'-desphenyl-3'-(2-thienyl)-7-deoxy-7-fluoro-$\Delta^{12,13}$-iso-taxol;
3'-desphenyl-3'-(2-naphthyl)-7-deoxy-7-fluoro-$\Delta^{12,13}$-iso-taxol;
3'-desphenyl-3'-(2-naphthyl)-7-deoxy-7-fluoro-$\Delta^{12,13}$-iso-taxol;
3'-desphenyl-3'-(4-methoxyphenyl)-7-deoxy-7-fluoro-$\Delta^{12,13}$-iso-taxol;
3'-desphenyl-3'-(4-chlorophenyl)-7-deoxy-7-fluoro-$\Delta^{12,13}$-iso-taxol;
3'-desphenyl-3'-(4-bromophenyl)-7-deoxy-7-fluoro-$\Delta^{12,13}$-iso-taxol;
3'-desphenyl-3'-(4-methylenedioxyphenyl)-7-deoxy-7-fluoro-$\Delta^{12,13}$-iso-taxol;
3'-desphenyl-3'-(3,4-dimethoxyphenyl)-7-deoxy-7-fluoro-$\Delta^{12,13}$-iso-taxol;
3'-desphenyl-3'-(4-nitrophenyl)-7-deoxy-7-fluoro-$\Delta^{12,13}$-iso-taxol;
3'-desphenyl-3'-(4-fluorophenyl)-7-deoxy-7-fluoro-$\Delta^{12,13}$-iso-taxol;
N-debenzoyl-N-(4-bromobenzoyl)-7-deoxy-7-fluoro-$\Delta^{12,13}$-iso-taxol;
N-debenzoyl-N-(4-methylbenzoyl)-7-deoxy-7-fluoro-$\Delta^{12,13}$-iso-taxol;
N-debenzoyl-N-(4-t-butylbenzoyl)-7-deoxy-7-fluoro-$\Delta^{12,13}$-iso-taxol;
N-debenzoyl-N-(4-methoxybenzoyl)-7-deoxy-7-fluoro-$\Delta^{12,13}$-iso-taxol;
N-debenzoyl-N-(4-fluorobenzoyl)-3'-desphenyl-3'-(4-fluorophenyl)-7-deoxy-7-fluoro-$\Delta^{12,13}$-iso-taxol;
N-debenzoyl-N-(4-fluorobenzoyl)-7-deoxy-7-fluoro-$\Delta^{12,13}$-iso-taxol;
N-debenzoyl-N-(4-methylbenzoyl)-3'-desphenyl-3'-(4-chlorophenyl)-7-deoxy-7-fluoro-$\Delta^{12,13}$-iso-taxol;

N-debenzoyl-N-(4-chlorobenzoyl)-3'-desphenyl-3'-(4-fluorophenyl)-7-deoxy-7-fluoro-$\Delta^{12,13}$-iso-taxol;
N-debenzoyl-N-(4-bromobenzoyl)-3'-desphenyl-3'-(4-fluorophenyl)-7-deoxy-7-fluoro-$\Delta^{12,13}$-iso-taxol;
N-debenzoyl-N-(4-methylbenzoyl)-3'-desphenyl-3'-(4-fluorophenyl)-7-deoxy-7-fluoro-$\Delta^{12,13}$-iso-taxol;
N-debenzoyl-N-(4-fluorobenzoyl)-3'-desphenyl-3'-(4-methoxyphenyl)-7-deoxy-7-fluoro-$\Delta^{12,13}$-iso-taxol;
N-debenzoyl-N-(4-methylbenzoyl)-3'-desphenyl-3'-(4-methoxyphenyl)-7-deoxy-7-fluoro-$\Delta^{12,13}$-iso-taxol;
N-debenzoyl-N-(4-fluorobenzoyl)-3'-desphenyl-3'-(4-chlorophenyl)-7-deoxy-7-fluoro-$\Delta^{12,13}$-iso-taxol;
N-debenzoyl-N-(4-chlorobenzoyl)-3'-desphenyl-3'-(4-chlorophenyl)-7-deoxy-7-fluoro-$\Delta^{12,13}$-iso-taxol;
N-debenzoyl-N-(4-bromobenzoyl)-3'-desphenyl-3'-(4-chlorophenyl)-7-deoxy-7-fluoro-$\Delta^{12,13}$-iso-taxol;
N-debenzoyl-N-(4-t-butylbenzoyl)-3'-desphenyl-3'-(4-chlorophenyl)-7-deoxy-7-fluoro-$\Delta^{12,13}$-iso-taxol;
N-debenzoyl-N-(4-t-butylbenzoyl)-3'-desphenyl-3'-(4-fluorophenyl)-7-deoxy-7-fluoro-$\Delta^{12,13}$-iso-taxol;
N-debenzoyl-N-(4-chlorobenzoyl)-3'-desphenyl-3'-(4-methoxyphenyl)-7-deoxy-7-fluoro-$\Delta^{12,13}$-iso-taxol;
N-debenzoyl-N-(4-bromobenzoyl)-3'-desphenyl-3'-(4-methoxyphenyl)-7-deoxy-7-fluoro-$\Delta^{12,13}$-iso-taxol;
N-debenzoyl-N-(4-t-butylbenzoyl)-3'-desphenyl-3'-(4-methoxyphenyl)-7-deoxy-7-fluoro-$\Delta^{12,13}$-iso-taxol;
N-debenzoyl-N-(4-methoxybenzoyl)-3'-desphenyl-3'-(4-methoxyphenyl)-7-deoxy-7-fluoro-$\Delta^{12,13}$-iso-taxol;
3'-desphenyl-3'-(2-furyl)-7-deoxy-$\Delta^{6,7}$-$\Delta^{12,13}$-iso-taxol;
3'-desphenyl-3'-(2-thienyl)-7-deoxy-$\Delta^{6,7}$-$\Delta^{12,13}$-iso-taxol;
3'-desphenyl-3'-(1-naphthyl)-7-deoxy-$\Delta^{6,7}$-$\Delta^{12,13}$-iso-taxol;
3'-desphenyl-3'-(2-naphthyl)-7-deoxy-$\Delta^{6,7}$-$\Delta^{12,13}$-iso-taxol;
3'-desphenyl-3'-(4-methoxyphenyl)-7-deoxy-$\Delta^{6,7}$-$\Delta^{12,13}$-iso-taxol;
3'-desphenyl-3'-(4-chlorophenyl)-7-deoxy-$\Delta^{6,7}$-$\Delta^{12,13}$-iso-taxol;
3'-desphenyl-3'-(4-bromophenyl)-7-deoxy-$\Delta^{6,7}$-$\Delta^{12,13}$-iso-taxol;
3'-desphenyl-3'-(3,4-methylenedioxyphenyl)-7-deoxy-$\Delta^{6,7}$-$\Delta^{12,13}$-iso-taxol;
3'-desphenyl-3'-(3,4-dimethoxyphenyl)-7-deoxy-$\Delta^{6,7}$-$\Delta^{12,13}$-iso-taxol;
3'-desphenyl-3'-(4-nitrophenyl)-7-deoxy-$\Delta^{6,7}$-$\Delta^{12,13}$-iso-taxol;
3'-desphenyl-3'-(4-fluorophenyl)-7-deoxy-$\Delta^{6,7}$-$\Delta^{12,13}$-iso-taxol;
N-debenzoyl-N-(4-bromobenzoyl)-7-deoxy-$\Delta^{6,7}$-$\Delta^{12,13}$-iso-taxol;
N-debenzoyl-N-(4-methylbenzoyl)-7-deoxy-$\Delta^{6,7}$-$\Delta^{12,13}$-iso-taxol;
N-debenzoyl-N-(4-t-butylbenzoyl)-7-deoxy-$\Delta^{6,7}$-$\Delta^{12,13}$-iso-taxol;
N-debenzoyl-N-(4-methoxybenzoyl)-7-deoxy-$\Delta^{6,7}$-$\Delta^{12,13}$-iso-taxol;
N-debenzoyl-N-(4-fluorobenzoyl)-3'-desphenyl-3'-(4-fluorophenyl)-7-deoxy-$\Delta^{6,7}$-$\Delta^{12,13}$-iso-taxol;
N-debenzoyl-N-(4-fluorobenzoyl)-7-deoxy-$\Delta^{6,7}$-$\Delta^{12,13}$-iso-taxol;
N-debenzoyl-N-(4-methylbenzoyl)-3'-desphenyl-3'-(4-chlorophenyl)-7-deoxy-$\Delta^{6,7}$-$\Delta^{12,13}$-iso-taxol;
N-debenzoyl-N-(4-chlorobenzoyl)-3'-desphenyl-3'-(4-fluorophenyl)-7-deoxy-$\Delta^{6,7}$-$\Delta^{12,13}$-iso-taxol;
N-debenzoyl-N-(4-bromobenzoyl)-3'-desphenyl-3'-(4-fluorophenyl)-7-deoxy-$\Delta^{6,7}$-$\Delta^{12,13}$-iso-taxol;
N-debenzoyl-N-(4-methylbenzoyl)-3'-desphenyl-3'-(4-fluorophenyl)-7-deoxy-$\Delta^{6,7}$-$\Delta^{12,13}$-iso-taxol;
N-debenzoyl-N-(4-fluorobenzoyl)-3'-desphenyl-3'-(4-methoxyphenyl)-7-deoxy-$\Delta^{6,7}$-$\Delta^{12,13}$-iso-taxol;

N-debenzoyl-N-(4-methylbenzoyl)-3'-desphenyl-3'-(4-methoxyphenyl)-7-deoxy-$\Delta^{6,7}$-$\Delta^{12,13}$-iso-taxol;
N-debenzoyl-N-(4-fluorobenzoyl)-3'-desphenyl-3'-(4-chlorophenyl)-7-deoxy-$\Delta^{6,7}$-$\Delta^{12,13}$-iso-taxol;
N-debenzoyl-N-(4-chlorobenzoyl)-3'-desphenyl-3'-(4-chlorophenyl)-7-deoxy-$\Delta^{6,7}$-$\Delta^{12,13}$-iso-taxol;
N-debenzoyl-N-(4-bromobenzoyl)-3'-desphenyl-3'-(4-chlorophenyl)-7-deoxy-$\Delta^{6,7}$-$\Delta^{12,13}$-iso-taxol;
N-debenzoyl-N-(4-t-butylbenzoyl)-3'-desphenyl-3'-(4-chlorophenyl)-7-deoxy-$\Delta^{6,7}$-$\Delta^{12,13}$-iso-taxol;
N-debenzoyl-N-(4-t-butylbenzoyl)-3'-desphenyl-3'-(4-fluorophenyl)-7-deoxy-$\Delta^{6,7}$-$\Delta^{12,13}$-iso-taxol;
N-debenzoyl-N-(4-chlorobenzoyl)-3'-desphenyl-3'-(4-methoxyphenyl)-7-deoxy-$\Delta^{6,7}$-$\Delta^{12,13}$-iso-taxol;
N-debenzoyl-N-(4-bromobenzoyl)-3'-desphenyl-3'-(4-methoxyphenyl)-7-deoxy-$\Delta^{6,7}$-$\Delta^{12,13}$-iso-taxol;
N-debenzoyl-N-(4-t-butylbenzoyl)-3'-desphenyl-3'-(4-methoxyphenyl)-7-deoxy-$\Delta^{6,7}$-$\Delta^{12,13}$-iso-taxol; and
N-debenzoyl-N-(4-methoxybenzoyl)-3'-desphenyl-3'-(4-methoxyphenyl)-7-deoxy-$\Delta^{6,7}$-$\Delta^{12,13}$-iso-taxol.

18. A compound of the formula

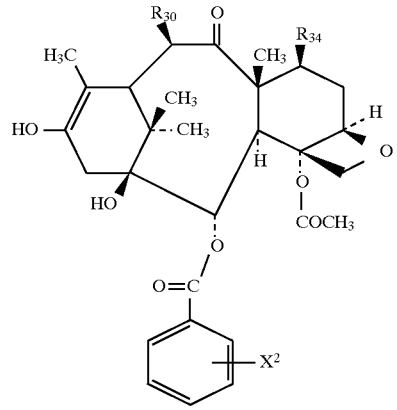

wherein $X_2$ is selected from the group consisting of
—H,
—$C_1$–$C_4$ alkyl,
—$C_1$–$C_3$ alkoxy,
halo,
—$C_1$–$C_3$ alkylthio,
-trifluoromethyl,
—$C_2$–$C_6$ dialkylamino,
benzyloxymethyl,
cyano,
azide ($N_3$),
or nitro; and
wherein $R_{30}$ and $R_{34}$, being the same or different, are selected from the group consisting of —OC(O)$C_1$–$C_6$alkyl, —OC(O)O$C_1$–$C_6$alkyl, —OC(O)OCH$_2$CX$_3$ where X is Halo, —OC(O)OCH$_2$CH$_2$Si($R_{20}$)$_3$ (where $R_{20}$ is $C_1$–$C_6$alkyl), or —OSi($R_{16}$)$_3$.

19. A compound according to claim 18 selected from the group consisting of
7-[O-2-(3-methylbutyl)dimethylsilyl]-iso-baccatin III;
7-(O-tri-n-butylsilyl)-iso-baccatin III;
7-(O-cyclohexyldimethylsilyl)-iso-baccatin III;
7-(O-i-propyldiethylsilyl)-iso-baccatin III; and
7-(O-cycloheptyldimethylsilyl)-iso-baccatin III.

20. A process of preparing

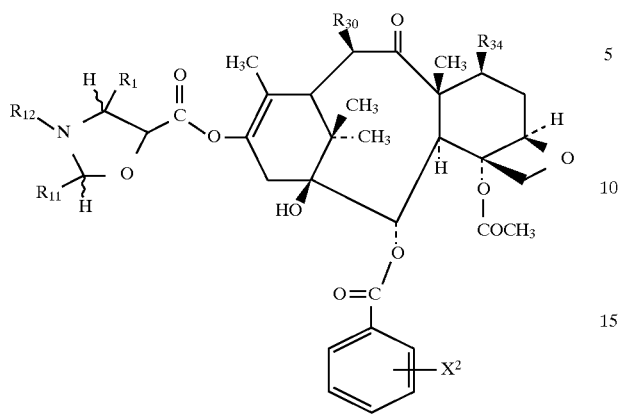

which comprises reacting an oxazolidine free acid of Formula 7

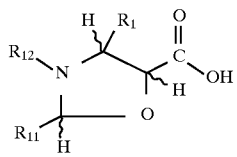

with a baccatin compound of Formula 8

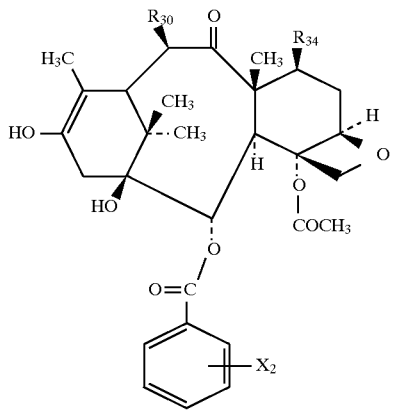

in the presence of a dehydrating agent;
  wherein $R_{30}$ and $R_{34}$, being the same or different, are selected from the group consisting of —OC(O)$C_1$-$C_6$alkyl, —OC(O)O$C_1$-$C_6$alkyl, —OC(O)OCH$_2$CX$_3$ where X is Halo, —OC(O)OCH$_2$CH$_2$Si($R_{20}$)$_3$ (where $R_{20}$ is $C_1$-$C_6$alkyl), or —OSi($R_{16}$)$_3$;
  $X^2$ is selected from the group consisting of
    —H,
    —$C_1$-$C_4$ alkyl,
    —$C_1$-$C_3$ alkoxy,
    halo,
    —$C_1$-$C_3$ alkylthio,
    -trifluoromethyl,
    —$C_2$-$C_6$ dialkylamino,
    benzyloxymethyl,
    cyano,
    azide (N$_3$),
    or nitro;
  $R_1$ is selected from the group consisting of
    —CH$_3$,
    —$C_6H_5$ or phenyl substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, hydroxy or nitro, 2-furyl, 2-thienyl, 1-naphthyl, 2-naphthyl or 3,4-methylenedioxyphenyl;
  $R_{11}$ is phenyl substituted with —(O$C_1$-$C_2$alkyl)$_n$ where n is 1 to 3; and
  $R_{12}$ is selected from the group consisting of —C(O)H, —C(O)$C_1$-$C_{10}$alkyl, —C(O)phenyl, —C(O)phenyl substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, hydroxy or nitro, —C(O)C(CH$_3$)=CHCH$_3$, —C(O)OC(CH$_3$)$_3$, —C(O)OCH$_2$phenyl, —SO$_2$-4-methylphenyl, —C(O)(CH$_2$)$_3$COOH, —C(O)-4-(SO$_3$H)phenyl, —C(O)-1-adamantyl, —C(O)O-3-tetrahydrofuranyl, —C(O)O-4-tetrahydropyranyl, —C(O)CH$_2$C(CH$_3$)$_3$, —C(O)C(CH$_3$)$_3$, —C(O)O$C_1$-$C_{10}$alkyl, —C(O)NH$C_1$-$C_{10}$alkyl, —C(O)NHPh substituted with one, 2 or 3 $C_1$-$C_4$ alkyl, $C_1$-$C_3$ alkoxy, halo, $C_1$-$C_3$ alkylthio, trifluoromethyl, $C_2$-$C_6$ dialkylamino, or nitro, or —C(O)$C_3$-$C_8$cycloalkyl, —C(O)C(CH$_2$CH$_3$)$_2$CH$_3$, —C(O)C(CH$_3$)$_2$CH$_2$Cl, —C(O)C(CH$_3$)$_2$CH$_2$CH$_3$, —C(O)-1-phenyl-1-cyclopentyl, —C(O)-1-methyl-1-cyclohexyl, —C(S)NHC(CH$_3$)$_3$, —NHC(O)NHC(CH$_3$)$_3$ or —C(O)NHPh.

21. A process of preparing

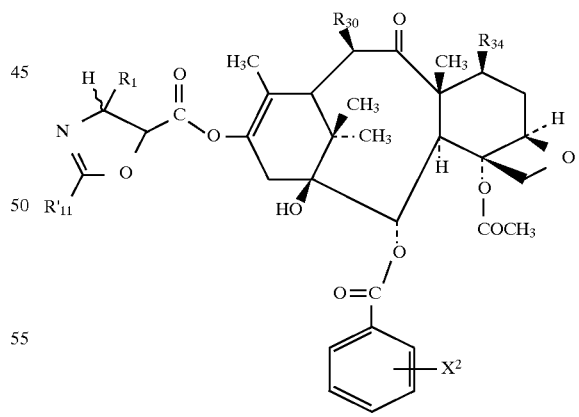

which comprises reacting an oxazoline free acid of Formula 7'

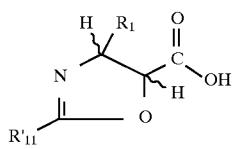

with a baccatin compound of Formula 8

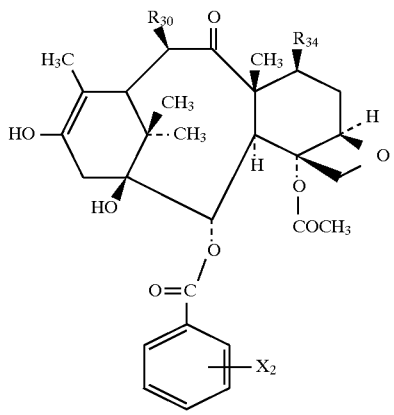

in the presence of a dehydrating agent;
wherein $R_{30}$ and $R_{34}$, being the same or different, are selected from the group consisting of —OC(O)$C_1$–$C_6$alkyl, —OC(O)O$C_1$–$C_6$alkyl, —OC(O)OCH$_2$CX$_3$ where X is Halo, —OC(O)OCH$_2$CH$_2$Si(R$_{20}$)$_3$ (where $R_{20}$ is $C_1$–$C_6$alkyl), or —OSi(R$_{16}$)$_3$;
$X^2$ is selected from the group consisting of
—H,
—$C_1$–$C_4$ alkyl,
—$C_1$–$C_3$ alkoxy,
halo,
—$C_1$–$C_3$ alkylthio,
-trifluoromethyl,
—$C_2$–$C_6$ dialkylamino,
benzyloxymethyl,
cyano,
azide (N$_3$),
or nitro;
$R_1$ is selected from the group consisting of
—CH$_3$,
—$C_6$H$_5$ or phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro, 2-furyl, 2-thienyl, 1-naphthyl, 2-naphthyl or 3,4-methylenedioxyphenyl; and
$R'_{11}$ is selected from the group consisting of
—$C_1$–$C_{10}$alkyl,
-phenyl,
-phenyl substituted with one, 2 or 3 $C_1$–$C_4$ alkyl, $C_1$–$C_3$ alkoxy, halo, $C_1$–$C_3$ alkylthio, trifluoromethyl, $C_2$–$C_6$ dialkylamino, hydroxy or nitro,
-1-adamantyl,
-3-tetrahydrofuranyl,
-4-tetrahydropyranyl, or
—CH$_2$C(CH$_3$)$_3$.

22. A compound according to claim 1 wherein $R_2$ is —NHC(O)NHC(CH$_3$)$_3$, $R_1$ is phenyl or substituted phenyl, $R_4$ is hydroxy, and $R_3$ and $R_5$ are —H.

23. A compound according to claim 1, namely N-debenzoyl-N-(t-butyl)aminocarbonyl-7-deoxy-$\Delta^{6,7}$-$\Delta^{12,13}$-iso-taxol.

* * * * *